United States Patent
Casimiro et al.

(10) Patent No.: US 12,239,735 B2
(45) Date of Patent: *Mar. 4, 2025

(54) LIPID NANOPARTICLES FOR DELIVERING MRNA VACCINES

(71) Applicant: SANOFI, Paris (FR)

(72) Inventors: Danilo Casimiro, Paris (FR); Sudha Chivukula, Paris (FR); Kirill Kalnin, Paris (FR); Timothy Plitnik, Paris (FR); Timothy Tibbitts, Paris (FR); Frank Derosa, Paris (FR); Anusha Dias, Paris (FR); Rebecca L. Goldman, Paris (FR); Hardip Rajeshbhai Gopani, Paris (FR); Shrirang Karve, Paris (FR); Asad Khanmohammed, Paris (FR); Priyal Patel, Paris (FR)

(73) Assignee: SANOFI, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/503,327

(22) Filed: Nov. 7, 2023

(65) Prior Publication Data

US 2024/0091154 A1    Mar. 21, 2024

Related U.S. Application Data

(63) Continuation of application No. 18/458,767, filed on Aug. 30, 2023, which is a continuation of application (Continued)

(30) Foreign Application Priority Data

Oct. 13, 2021 (EP) ..................................... 21315198

(51) Int. Cl.
*A61K 9/127* (2006.01)
*A61K 9/1272* (2025.01)
(Continued)

(52) U.S. Cl.
CPC .......... *A61K 9/1272* (2013.01); *A61K 39/145* (2013.01); *A61K 39/39* (2013.01);
(Continued)

(58) Field of Classification Search
None
See application file for complete search history.

(56) References Cited

U.S. PATENT DOCUMENTS 4,373,071 A    2/1983   Itakura
4,401,796 A    8/1983   Itakura
(Continued)

FOREIGN PATENT DOCUMENTS

EP    1664316 B1    8/2012
EP    2496700 B1    3/2017
(Continued)

OTHER PUBLICATIONS

Maria-Lucia Briuglia, Chiara Rotella, Amber McFarlane, and Dimitrios A. Lamprou. "Influence of cholesterol on liposome stability and on in vitro drug release." Drug Delivery and Translational Research, vol. 5, 2015, pp. 231-242. (Year: 2015).*
(Continued)

*Primary Examiner* — Isaac Shomer
(74) *Attorney, Agent, or Firm* — LATHROP GPM LLP; James H. Velema, Esq.; Michael J. Spellberg, Esq.

(57) ABSTRACT

Provided are novel lipid nanoparticles for delivering nucleic acids such as mRNA. Also provided are methods of making and using lipid nanoparticles for delivering nucleic acids such as mRNA.

45 Claims, 49 Drawing Sheets
Specification includes a Sequence Listing.

Related U.S. Application Data

No. 17/520,200, filed on Nov. 5, 2021, now Pat. No. 11,771,652.

(60) Provisional application No. 63/212,523, filed on Jun. 18, 2021, provisional application No. 63/110,965, filed on Nov. 6, 2020.

(51) Int. Cl.
*A61K 39/00* (2006.01)
*A61K 39/145* (2006.01)
*A61K 39/39* (2006.01)
*A61P 31/16* (2006.01)

(52) U.S. Cl.
CPC .......... *A61P 31/16* (2018.01); *A61K 2039/53* (2013.01); *A61K 2039/55555* (2013.01)

(56) References Cited

U.S. PATENT DOCUMENTS

| | | |
|---|---|---|
| 4,415,732 A | 11/1983 | Caruthers |
| 4,458,066 A | 7/1984 | Caruthers |
| 4,500,707 A | 2/1985 | Caruthers |
| 4,668,777 A | 5/1987 | Caruthers |
| 4,973,679 A | 11/1990 | Caruthers |
| 5,047,524 A | 9/1991 | Andrus |
| 5,132,418 A | 7/1992 | Caruthers |
| 5,153,319 A | 10/1992 | Caruthers |
| 5,262,530 A | 11/1993 | Andrus |
| 5,700,642 A | 12/1997 | Monforte |
| 5,744,335 A | 4/1998 | Wolff |
| 5,885,613 A | 3/1999 | Holland |
| 6,287,591 B1 | 9/2001 | Semple et al. |
| 6,428,324 B1 | 8/2002 | Parrington |
| 6,534,484 B1 | 3/2003 | Wheeler et al. |
| 6,815,432 B2 | 11/2004 | Wheeler et al. |
| 6,852,334 B1 | 2/2005 | Cullis et al. |
| 7,803,397 B2 | 9/2010 | Heyes |
| 8,058,069 B2 | 11/2011 | Yaworski et al. |
| 8,492,359 B2 | 7/2013 | Yaworski et al. |
| 8,822,668 B2 | 9/2014 | Yaworski et al. |
| 8,936,942 B2 | 1/2015 | Heyes |
| 9,006,417 B2 | 4/2015 | Yaworski et al. |
| 9,364,435 B2 | 6/2016 | Yaworski et al. |
| 9,404,127 B2 | 8/2016 | Yaworski et al. |
| 9,415,109 B2 | 8/2016 | Kumar et al. |
| 9,512,073 B2 | 12/2016 | Dong |
| 9,518,272 B2 | 12/2016 | Yaworski et al. |
| 9,758,795 B2 | 9/2017 | Cullis |
| 9,872,900 B2 | 1/2018 | Ciaramella et al. |
| 9,877,919 B2 | 1/2018 | Guild et al. |
| 9,878,042 B2 | 1/2018 | Yaworski et al. |
| 10,022,435 B2 | 7/2018 | Ciaramella et al. |
| 10,022,455 B2 | 7/2018 | De Rosa et al. |
| 10,041,091 B2 | 8/2018 | Cullis |
| 10,047,355 B2 | 8/2018 | Yin et al. |
| 10,087,247 B2 | 10/2018 | De Rosa et al. |
| 10,130,649 B2 | 11/2018 | De Rosa et al. |
| 10,137,087 B2 | 11/2018 | Guild et al. |
| 10,138,213 B2 | 11/2018 | De Rosa et al. |
| 10,143,758 B2 | 12/2018 | Guild et al. |
| 10,172,935 B2 | 1/2019 | Kallen et al. |
| 10,201,618 B2 | 2/2019 | Anderson et al. |
| 10,238,754 B2 | 3/2019 | Guild et al. |
| 10,350,303 B1 | 7/2019 | Guild et al. |
| 10,413,618 B2 | 9/2019 | Guild et al. |
| 10,463,751 B2 | 11/2019 | De Fougerolles et al. |
| 10,471,153 B2 | 11/2019 | De Rosa et al. |
| 10,493,167 B2 | 12/2019 | De Fougerolles et al. |
| 10,507,249 B2 | 12/2019 | Guild et al. |
| 10,583,203 B2 | 3/2020 | De Fougerolles et al. |
| 10,646,504 B2 | 5/2020 | De Rosa et al. |
| 10,695,444 B2 | 6/2020 | Anderson et al. |
| 10,709,779 B2 | 7/2020 | Ciaramella et al. |
| 10,772,975 B2 | 9/2020 | Bancel et al. |
| 11,771,652 B2 | 10/2023 | Casimiro et al. |
| 11,771,653 B2 * | 10/2023 | Casimiro ............ A61K 9/5123 424/450 |
| 2004/0142025 A1 | 7/2004 | Maclachlan et al. |
| 2005/0042229 A1 | 2/2005 | Yang et al. |
| 2006/0083780 A1 | 4/2006 | Heyes et al. |
| 2006/0134189 A1 | 6/2006 | Maclachlan et al. |
| 2006/0240554 A1 | 10/2006 | Chen et al. |
| 2007/0042031 A1 | 2/2007 | Maclachlan et al. |
| 2011/0244026 A1 | 10/2011 | Guild |
| 2013/0158021 A1 | 6/2013 | Dong et al. |
| 2014/0206753 A1 | 7/2014 | Guild |
| 2014/0271699 A1 | 9/2014 | Kwong et al. |
| 2015/0157565 A1 | 6/2015 | Heartlein |
| 2016/0032356 A1 | 2/2016 | Heartlein |
| 2016/0038432 A1 | 2/2016 | DeRosa |
| 2016/0151409 A1 | 6/2016 | DeRosa |
| 2016/0166710 A1 | 6/2016 | Baumhof |
| 2016/0235864 A1 | 8/2016 | Schlake |
| 2016/0256568 A1 | 9/2016 | Heyes et al. |
| 2016/0304883 A1 | 10/2016 | Grund |
| 2016/0367686 A1 * | 12/2016 | Anderson ............... A61P 3/06 |
| 2017/0029847 A1 | 2/2017 | Thess |
| 2018/0125989 A1 | 5/2018 | DeRosa |
| 2018/0153822 A1 | 6/2018 | Karve |
| 2018/0258423 A1 | 9/2018 | Dias et al. |
| 2018/0271970 A1 | 9/2018 | Ciaramella et al. |
| 2018/0311336 A1 | 11/2018 | Ciaramella et al. |
| 2019/0008948 A1 | 1/2019 | Ciaramella et al. |
| 2019/0015501 A1 | 1/2019 | Ciaramella et al. |
| 2019/0032087 A1 | 1/2019 | Cullis et al. |
| 2019/0336595 A1 | 11/2019 | Ciaramella et al. |
| 2019/0351048 A1 | 11/2019 | Rauch |
| 2020/0163878 A1 | 5/2020 | Baumhof et al. |
| 2020/0197508 A1 | 6/2020 | Bihi et al. |
| 2021/0052646 A1 | 2/2021 | Kuwae et al. |
| 2021/0214729 A1 | 7/2021 | Lemoine et al. |
| 2022/0142923 A1 | 5/2022 | Casimiro et al. |
| 2022/0378701 A1 | 6/2022 | Casimiro et al. |
| 2022/0347100 A1 | 11/2022 | Casimiro et al. |
| 2023/0043128 A1 | 2/2023 | Alefantis et al. |
| 2023/0302112 A1 | 9/2023 | Casimiro et al. |
| 2023/0310571 A1 | 10/2023 | Chan et al. |
| 2024/0091154 A1 * | 3/2024 | Casimiro ............... A61K 47/02 |
| 2024/0148651 A1 | 5/2024 | Casimiro et al. |
| 2024/0327847 A1 | 10/2024 | Cui et al. |

FOREIGN PATENT DOCUMENTS

| | | |
|---|---|---|
| EP | 2279254 B1 | 7/2017 |
| EP | 2506857 B1 | 2/2018 |
| EP | 2972360 B1 | 3/2018 |
| EP | 3310764 A1 | 4/2018 |
| EP | 3122878 B1 | 10/2018 |
| EP | 3318248 B1 | 4/2019 |
| EP | 2717893 B1 | 5/2019 |
| EP | 3336082 B1 | 4/2020 |
| EP | 3388834 B1 | 4/2020 |
| EP | 2994167 B1 | 5/2020 |
| WO | WO 2011/068810 A1 | 6/2001 |
| WO | WO 2005/007196 A2 | 1/2005 |
| WO | WO 2005/113782 A1 | 12/2005 |
| WO | WO 2009/127060 A1 | 10/2009 |
| WO | WO 2010/149743 A2 | 12/2010 |
| WO | WO 2011/005799 A2 | 1/2011 |
| WO | WO 2011/140627 A1 | 11/2011 |
| WO | WO 2012/075040 A2 | 6/2012 |
| WO | WO 2012/170889 A1 | 12/2012 |
| WO | WO 2013/063468 A1 | 5/2013 |
| WO | WO 2014/152774 A1 | 9/2014 |
| WO | WO 2014/186334 A1 | 11/2014 |
| WO | WO 2015/011633 A1 | 1/2015 |
| WO | WO 2015/061461 A1 | 4/2015 |
| WO | WO 2015/061467 A1 | 4/2015 |
| WO | WO 2015/130584 A2 | 9/2015 |
| WO | WO 2015/148247 A1 | 10/2015 |
| WO | WO 2015/164674 A1 | 10/2015 |
| WO | WO 2016/091391 A1 | 6/2016 |

(56) References Cited

FOREIGN PATENT DOCUMENTS

| | | | |
|---|---|---|---|
| WO | WO 2016/174271 A1 | 11/2016 | |
| WO | WO 2016/176330 A1 | 11/2016 | |
| WO | WO 2016/205691 A1 | 12/2016 | |
| WO | WO 2017/008076 A1 | 1/2017 | |
| WO | WO 2017/070620 A2 | 4/2017 | |
| WO | WO 2017/070626 A2 | 4/2017 | |
| WO | WO 2017/099823 A1 | 6/2017 | |
| WO | WO 2017/162265 A1 | 9/2017 | |
| WO | WO 2018/006052 A1 | 1/2018 | |
| WO | WO 2018/064755 A1 | 4/2018 | |
| WO | WO 2018/078053 A1 | 5/2018 | |
| WO | WO 2018/081480 A1 | 5/2018 | |
| WO | WO 2018/089540 A1 | 5/2018 | |
| WO | WO 2018/089790 A1 | 5/2018 | |
| WO | WO-2018089801 A1 * | 5/2018 | ........... A61K 38/177 |
| WO | WO 2018/107088 A2 | 6/2018 | |
| WO | WO 2018/119115 A1 | 6/2018 | |
| WO | WO 2018/161053 A1 | 9/2018 | |
| WO | WO 2018/170260 A1 | 9/2018 | |
| WO | WO 2018/172426 A1 | 9/2018 | |
| WO | WO 2018/187590 A1 | 10/2018 | |
| WO | WO 2018/189372 A1 | 10/2018 | |
| WO | WO 2018/232357 A1 | 12/2018 | |
| WO | WO 2019/036670 A2 | 2/2019 | |
| WO | WO 2019/141814 A1 | 7/2019 | |
| WO | WO 2019/148101 A1 | 8/2019 | |
| WO | WO 2019/152557 A1 | 8/2019 | |
| WO | WO 2019/232103 A1 | 12/2019 | |
| WO | WO 2019/246203 A1 | 12/2019 | |
| WO | WO 2020/023533 A1 | 1/2020 | |
| WO | WO 2020/047061 A1 | 3/2020 | |
| WO | WO 2020/056294 A1 | 3/2020 | |
| WO | WO 2020/061295 A1 | 3/2020 | |
| WO | WO 2020/097540 A1 | 5/2020 | |
| WO | WO 2020/219941 A1 | 10/2020 | |
| WO | WO 2021/016430 A1 | 1/2021 | |
| WO | WO 2021/080990 A1 | 4/2021 | |
| WO | WO 2021/080999 A1 | 4/2021 | |
| WO | WO 2021/123332 A1 | 6/2021 | |
| WO | WO 2021/155243 A1 | 8/2021 | |
| WO | WO-2021165543 A1 * | 8/2021 | ............ A61K 39/00 |
| WO | WO 2021/226436 A1 | 11/2021 | |
| WO | WO 2022/043551 A2 | 3/2022 | |
| WO | WO 2022/066916 A1 | 3/2022 | |
| WO | WO 2022/099003 A1 | 5/2022 | |
| WO | WO 2022/178196 A1 | 8/2022 | |
| WO | WO-2022221688 A1 * | 10/2022 | ......... C07D 295/088 |

OTHER PUBLICATIONS

U.S. Appl. No. 63/175,429 https://patentscope.wipo.int/search/docs2/PCT/WO2022221688/pdf/UVqD0zT6J3SZrpVSCywBHBn0iJchznGTIMtEwvUzZ4kSHGb25illx8Na8Ym7oGb2HOdAh-4HXb1n7r9Lun6LdAmfQ3cjLEjleiY3yg2IBnPwiyx54iqCTHERk4VgwRZe?docId=id00000069041581&filename=WO2022221688-PDOC-20221020-1581.pdf accessed Dec. 2, 2022 (Year: 2022).*
JN Israelachvili, S Marcelja, and RG Horn. "Physical principles of membrane organization." Quarterly Reviews of Biophysics, vol. 13(2), 1980, pp. 121-200. (Year: 1980).*
Takeshi Kuboyama et al. "Simplifying the Chemical Structure of Cationic Lipids for siRNA-Lipid Nanoparticles." ACS Medicinal Chemistry Letters, vol. 10, 2019, pp. 749-753. (Year: 2019).*
Linde Schoenmaker, Dominik Witzigmann, Jayesh A. Kulkarni, Rein Verbeke, Gideon Kersten, Wim Jiskoot, and Daan J.A. Crommelin. "mRNA-lipid nanoparticle COVID-19 vaccines: Structure and stability." International Journal of Pharmaceutics, vol. 601, 2021, Article 120586, pp. 1-13. (Year: 2021).*
Norbert Pardi et al. "Expression kinetics of nucleoside-modified mRNA delivered in lipid nanoparticles to mice by various routes." Journal of Controlled Release, vol. 217, 2015, pp. 345-351. (Year: 2015).*

Derek Lowe. "RNA Vaccines And Their Lipids." In the Pipeline (blog), https://www.science.org/content/blog-post/rna-vaccines-and-their-lipids originally published Jan. 11, 2021, 15 printed pages. (Year: 2021).*
Tam et al., "Advances in Lipid Nanoparticles for siRNA Delivery", Pharmaceutics, May 2013: 498-507. (Year: 2013).*
Acosta et al., "Brief History and Characterization of Enhanced Respiratory Syncytial Virus Disease", Clin Vaccine Immunol., 2015, 23(3): 189-195.
Agrawal et al., "Immunization with inactivated Middle East Respiratory Syndrome coronavirus vaccine leads to lung immunopathology on challenge with live virus", Hum Vaccin Immunother., 2016, 12(9): 2351-2356.
Argenziano et al., "Characterization and clinical course of 1000 patients with coronavirus disease 2019 in New York: retrospective case series", BMJ, 2020, 369: m1996.
Bernstein et al., "Phase 1 study of the safety and immunogenicity of a live, attenuated respiratory syncytial virus and parainfluenza virus type 3 vaccine in seronegative children", Pediatr Infect Dis J., 2012, 31(2): 109-114.
Biacchesi et al., "Infection of Nonhuman Primates with Recombinant Human Metapneumovirus Lacking the SH, G, or M2-2 Protein Categorizes Each as a Nonessential Accessory Protein and Identifies Vaccine Candidates", Journal of Virology, 2005, 79(19): 12608-12613.
Biacchesi et al., "Recombinant human Metapneumovirus lacking the small hydrophobic SH and/or attachment G glycoprotein: deletion of G yields a promising vaccine candidate", J Virol., 2004, 78(23): 12877-12887.
Bolles et al., "A double-inactivated severe acute respiratory syndrome coronavirus vaccine provides incomplete protection in mice and induces increased eosinophilic proinflammatory pulmonary response upon challenge", J Virol., 2011, 85(23): 12201-12215.
Bos et al., "Ad26 vector-based COVID-19 vaccine encoding a prefusion-stabilized SARS-CoV-2 Spike immunogen induces potent humoral and cellular immune responses", NPJ Vaccines, 2020, 5(91): 91.
Brunelle et al., "In vitro transcription from plasmid or PCR-amplified DNA", Methods Enzymol., 2013, 530: 101-114.
Buchholz et al., "Contributions of the structural proteins of severe acute respiratory syndrome coronavirus to protective immunity", PNAS USA, 2004, 101(26): 9804-9809.
Budker et al., "Protein/Amphipathic Polyamine Complexes Enable Highly Efficient Transfection with Minimal Toxicity", BioTechniques, 1997, 23(1): 139.
Bukreyev et al., "Mucosal immunisation of African green monkeys (Cercopithecus aethiops) with an attenuated parainfluenza virus expressing the SARS coronavirus spike protein for the prevention of SARS", Lancet, 2004, 363(9427): 2122-2127.
CDC (Centers for Disease Control and Prevention), "Scientific Brief: SARS-CoV-2 Transmission", May 7, 2021.
Chandrashekar et al., "SARS-CoV-2 infection protects against rechallenge in rhesus macaques", Science, 2020, 369(6505): 812-817.
Chang et al., "Human metapneumovirus (HMPV) binding and infection are mediated by interactions between the HMPV fusion protein and heparan sulfate", J Virol., 2012, 86(6): 3230-3243.
ClinicalTrials.gov, "A Study to Evaluate the Safety, Tolerability, Immunogenicity and Vaccine-like Viral Shedding of MEDI-534, Against Respiratory Syncytial Virus (RSV) and Parainfluenza Virus Type 3 (PIV3), in Healthy 6 to <24 Month-old Children and in 2 Month-old Infants", ClinicalTrials.gov Identifier: NCT00686075, May 29, 2008.
Corbett et al., "Evaluation of the mRNA-1273 Vaccine against SARS-CoV-2 in Nonhuman Primates", N Engl J Med., 2020, 383: 1544-1555.
Corbett et al., "SARS-CoV-2 mRNA vaccine design enabled by prototype pathogen preparedness", Nature, Oct. 22, 2020, 586: 567-571.
Corman et al., "Detection of 2019 novel coronavirus (2019-nCoV) by real-time RT-PCR", Euro Surveill., 2020, 25(3): 2000045.
Coudeville et al., "Relationship between haemagglutination-inhibiting antibody titres and clinical protection against influenza:

(56) References Cited

OTHER PUBLICATIONS development and application of a bayesian random-effects model", BMC Med Res Methodol., 2010, 10:18.

Coultas et al., "Respiratory syncytial virus (RSV): a scourge from infancy to old age", Thorax, 2019, 74: 986-993.

Dong et al., "Lipopeptide nanoparticles for potent and selective siRNA delivery in rodents and nonhuman primates", PNAS, 2014, 111(11): 3955-3960.

Dou et al., "Influenza A Virus Cell Entry, Replication, Virion Assembly and Movement", Front Immunol., Sep. 2018: 1581.

Draghici et al., "Synthetic Nucleic Acid Delivery Systems: Present and Perspectives", Journal of Medicinal Chemistry, 2015, 58: 4091-4130.

Durbin et al., "Recovery of infectious human parainfluenza virus type 3 from cDNA", Virology, 1997, 235(2): 323-332.

Edie et al., "Survey of Human Chromosome 21 Gene Expression Effects on Early Development in Danio rerio", G3 (Bethesda), 2018, 8(7): 2215-2223.

Espitia et al., "Duplex real-time reverse transcriptase PCR to determine cytokine mRNA expression in a hamster model of New World cutaneous leishmaniasis", BMC Immunol., Nov. 2010: 31.

Fenton et al., "Bioinspired Alkenyl Amino Alcohol Ionizable Lipid Materials for Highly Potent In Vivo mRNA Delivery", Adv Mater., 2016, 28(15): 2939-2943.

Fenton, "Design, synthesis, and biological evaluation of diketopiperazine based ionizable lipids for the in vivo delivery of messenger RNA", Jun. 2016, Massachusetts Institute of Technology, Department of Chemistry, 1 page abstract included.

Galloway et al., "Emergence of SARS-CoV-2 B.1.1.7 Lineage—United States, Dec. 29, 2020-Jan. 12, 2021", MMWR Morb Mortal Wkly Rep., 2021, 70(3): 95-99.

Gao et al., "A novel cationic liposome reagent for efficient transfection of mammalian cells", Biochem Biophys Res Comm., 1991, 179(1): 280-285.

Geall et al., "RNA: the new revolution in nucleic acid vaccines", Semin. Immunol., 2013, 25(2): 152-159.

He et al., "Temporal dynamics in viral shedding and transmissibility of COVID-19", Nat Med 26, 672-675 (2020).

Heald-Sargent et al., "Age-Related Differences in Nasopharyngeal Severe Acute Respiratory Syndrome Coronavirus 2 (SARS-CoV-2) Levels in Patients With Mild to Moderate Coronavirus Disease 2019 (COVID-19)", Jama Pediatr., 2020, 174(9): 902-903.

Hoffmann et al., "SARS-CoV-2 Cell Entry Depends on ACE2 and TMPRSS2 and Is Blocked by a Clinically Proven Protease Inhibitor", Cell, Mar. 5, 2020, 181(2): 271-280.e8.

Huff et al., "Asymptomatic transmission during the COVID-19 pandemic and implications for public health strategies", Clin Infect Dis., 2020, ciaa654.

International Search Report and Written Opinion for PCT International Patent Application No. PCT/IB2021/058250, mailed Feb. 11, 2022.

International Search Report and Written Opinion for PCT International Patent Application No. PCT/IB2022/055655, mailed Sep. 29, 2022.

International Search Report and Written Opinion for PCT International Patent Application No. PCT/IB2022/060639, mailed Jan. 23, 2023.

International Search Report and Written Opinion for PCT International Patent Application No. PCT/US2022/080555, mailed Apr. 25, 2023.

International Search Report and Written Opinion for PCT International Patent Application No. PCT/US2022/080588, mailed May 16, 2023.

Jayaraman et al., "Maximizing the potency of siRNA lipid nanoparticles for hepatic gene silencing in vivo", Angew Chem Int Ed., 2012, 51: 8529-8533.

Jorquera et al., "Insights into the antigenic advancement of influenza A(H3N2) viruses, 2011-2018", Scientific Reports, 2019, 9(2676), 2019.

Kalnin et al., "Immunogenicity and efficacy of mRNA COVID-19 vaccine MRT5500 in preclinical animal models", npj Vaccines, Jun. 2021: 61.

Karron et al., "Evaluation of a Live Attenuated Human Metapneumovirus Vaccine in Adults and Children", J Pediatric Infect Dis Soc., 2018, 7(1): 86-89.

Karron et al., "Evaluation of two chimeric bovine-human parainfluenza virus type 3 vaccines in infants and young children", Vaccine, 2012, 30(26): 3975-3981.

Karron et al., "Live-attenuated Vaccines Prevent Respiratory Syncytial Virus-associated Illness in Young Children", Am J Respir Crit Care Med., 2021, 203(5): 594-603.

Kirchdoerfer et al., "Stabilized coronavirus spikes are resistant to conformational changes induced by receptor recognition or proteolysis", Sci Rep., Aug. 2018: 15701.

Klibanov et al., "Amphipathic polyethyleneglycols effectively prolong the circulation time of liposomes", FEBS Letters, 1990, 268(1): 235-237.

Kozak, "An analysis of 5'-noncoding sequences from 699 vertebrate messenger RNAs", Nucleic Acids Res., 1987, 15(20): 8125-8148.

Krammer et al., "The human antibody response to influenza A virus infection and vaccination", Nat Rev Immunol., 2019, 19(6): 383-397.

Kuboyama et al., "Simplifying the Chemical Structure of Cationic Lipids for siRNA-Lipid Nanoparticles", ACS Medicinal Chemistry Letters, Oct. 2019: 749-753.

Lasic et al., "Gelation of liposome interior A novel method for drug encapsulation", FEBS Lett., 1992, 312: 255-258.

Le Nouen et al., "Intranasal pediatric parainfluenza virus-vectored SARS-CoV-2 vaccine candidate is protective in macaques", bioRxiv, Version 1, Preprint, May 23, 2022, doi:10.1101/2022.05.21.492923.

Liang et al., "Chimeric bovine/human parainfluenza virus type 3 expressing respiratory syncytial virus (RSV) F glycoprotein: effect of insert position on expression, replication, immunogenicity, stability, and protection against RSV infection", J Virol., 2014, 88(8): 4237-4250 (2014).

Liang et al., "Effects of Alterations to the CX3C Motif and Secreted Form of Human Respiratory Syncytial Virus (RSV) G Protein on Immune Responses to a Parainfluenza Virus Vector Expressing the Rsv G Protein", J Virol., 2019, 93(7): e02043-18.
Liang et al., "Enhanced Neutralizing Antibody Response Induced by Respiratory Syncytial Virus Prefusion F Protein Expressed by a Vaccine Candidate", J Virol., 2015, 89(18): 9499-9510.
Liang et al., "Improved Prefusion Stability, Optimized Codon Usage, and Augmented Virion Packaging Enhance the Immunogenicity of Respiratory Syncytial Virus Fusion Protein in a Vectored-Vaccine Candidate", J Virol., 2017, 91(15): e00189-17.
Liang et al., "Packaging and Prefusion Stabilization Separately and Additively Increase the Quantity and Quality of Respiratory Syncytial Virus (RSV)-Neutralizing Antibodies Induced by an RSV Fusion Protein Expressed by a Parainfluenza Virus Vector", J Virol., 2016, 90(21): 10022-10038.
Liguoro et al., "SARS-COV-2 infection in children and newborns: a systematic review", Eur J Pediatr., 2020, 179(7): 1029-1046.
Lindgren et al., "Corrigendum: Induction of Robust B Cell Responses After Influenza mRNA Vaccination Is Accompanied by Circulating Hemagglutinin-Specific ICOS+ PD-1+ CXCR3+ T Follicular Helper Cells", Front Immunol., Oct. 2019: 614.
Liu et al., "A single intranasal dose of a live-attenuated parainfluenza virus-vectored SARS-CoV-2 vaccine is protective in hamsters", PNAS USA, 2021, 118(50): e2019744118.
Liu et al., "Human parainfluenza virus type 3 expressing the respiratory syncytial virus pre-fusion F protein modified for virion packaging yields protective intranasal vaccine candidates", PLoS One, 2020, 15(2): e0228572.
Lowe, "RNA Vaccines And Their Lipids", published Jan. 11, 2021, pp. 1-15, Retrieved from url: https://www.science.org/content/blog-post/rna-vaccines-and-their-lipids.
Maier et al., "Biodegradable Lipids Enabling Rapidly Eliminated Lipid Nanoparticles for Systemic Delivery of RNAi Therapeutics", Mol Ther., 2013, 21(8): 1570-1578.

(56) References Cited

OTHER PUBLICATIONS

Mátés et al., "Molecular evolution of a novel hyperactive Sleeping Beauty transposase enables robust stable gene transfer in vertebrates", Nat Genet., 2009, 41(6): 753-761.
McLellan et al., "Structure of respiratory syncytial virus fusion glycoprotein in the postfusion conformation reveals preservation of neutralizing epitopes", J. Virol., 2011, 85(15): 7788-7796.
McLellan et al., "Structure of RSV Fusion Glycoprotein Trimer Bound to a Prefusion-Specific Neutralizing Antibody", Science, 2013, 340(6136): 1113-1117.
Meyer et al., "Aerosolized Ebola vaccine protects primates and elicits lung-resident T cell responses", J Clin Invest., 2015, 125(8): 3241-3255.
Mok et al., "An Alphavirus Replicon-Based Human Metapneumovirus Vaccine Is Immunogenic and Protective in Mice and Cotton Rats", Journal of Virology, Nov. 2008, (82(22): 11410-11418.
Mui et al., "Influence of Polyethylene Glycol Lipid Desorption Rates on Pharmacokinetics and Pharmacodynamics of siRNA Lipid Nanoparticles", Dec. 17, 2013, Molecular Therapy—Nucleic Acids, 2(12): e139, pp. 1-8.
Mullard, "COVID-19 vaccine development pipeline gears up", Lancet, 2020, 395: 1751-1752.
Munir et al., "Nonstructural proteins 1 and 2 of respiratory syncytial virus suppress maturation of human dendritic cells", J Virol., 2008, 82(17): 8780-8796.
NIH National Library of Medicine, National Center of Biotechnology Information, "Severe acute respiratory syndrome coronavirus 2 isolate SARS-CoV-2/human/USA/WA-CDC-02982586-001/2020, complete genome", GenBank MN985325.1, Nov. 8, 2021.
NIH National Library of Medicine, National Center of Biotechnology Information, "Severe acute respiratory syndrome coronavirus 2 isolate Wuhan-Hu-1, complete genome", GenBank: MN908947.3, Mar. 18, 2020.
Nishikawa, et al., "Nonviral vectors in the new millennium: delivery barriers in gene transfer", Hum Gene Ther., 2001, 12(8): 861-870.
Pallesen et al., "Immunogenicity and structures of a rationally designed prefusion MERS-CoV spike antigen", PNAS USA, 2017, 114(35): E7348-E7357.
Papa et al., "Furin cleavage of SARS-CoV-2 Spike promotes but is not essential for infection and cell-cell fusion", PLoS Pathog., 2021, 17(1): e1009246.
Pardi et al. "Expression kinetics of nucleoside-modified mRNA delivered in lipid nanoparticles to mice by various routes", Journal of Controlled Release, 2015, 217: 345-351.
Pardi et al., "Nucleoside-modified mRNA immunization elicits influenza virus hemagglutinin stalk-specific antibodies", Nature Communications, Aug. 22, 2018, 9(1): 3361.
Piccoli et al., "Mapping Neutralizing and Immunodominant Sites on the SARS-CoV-2 Spike Receptor-Binding Domain by Structure-Guided High-Resolution Serology", Cell, 2020, 183(4): 1024-1042.e21.
Pilaev et al., "Evaluation of pre- and post-fusion Human metapneumovirus F proteins as subunit vaccine candidates in mice", Vaccine, Feb. 24, 2020, 38(9): 2122-2127.
Rambaut et al., "A dynamic nomenclature proposal for SARS-CoV-2 lineages to assist genomic epidemiology", Nat Microbiol, 2020, 5(11): 1403-1407.
Reed et al., "A simple method of estimating fifty per cent endpoints", Am J Epidemiol., 1938, 27(3): 493-497.
Rimmelzwaan et al., "Correlates of protection: novel generation of influenza vaccines", Vaccine, 2008, 26(4): D41-D44.
Sahin, et al., "mRNA-based therapeutics—developing a new class of drugs", Nat. Rev. Drug Discov., 2014, 13: 759-780.
Sanchez-Felipe et al., "A single-dose live-attenuated YF17D-vectored SARS-CoV-2 vaccine candidate", Nature, 2021, 590(7845): 320-325.
Schmidt et al., "Bovine parainfluenza virus type 3 (BPIV3) fusion and hemagglutinin-neuraminidase glycoproteins make an important contribution to the restricted replication of BPIV3 in primates", J Virol., 2000, 74(19): 8922-8929.
Schoenmaker et al., "mRNA-lipid nanoparticle COVID-19 vaccines: Structure and stability", Int'l Journal of Pharmaceuticals, Apr. 2021, 601: 120586.
Schowalter et al., "Low-pH Triggering of Human Metapneumovirus Fusion: Essential Residues and Importance in Entry", Journal of Virology, 2009, 83(3): 1511-1522.
Semple et al., "Rational design of cationic lipids for siRNA delivery", Nat Biotechnol., 2010, 28(2): 172-176.
Shen et al., "Community Outbreak Investigation of SARS-CoV-2 Transmission Among Bus Riders in Eastern China", JAMA Intern Med, 2020, 180(12): 1665-1671.
Skiadopoulos et al., "Individual contributions of the human metapneumovirus F, G, and SH surface glycoproteins to the induction of neutralizing antibodies and protective immunity", Virology, 2006, 345(2): 492-501.
Sridhar et al., "Cellular immune correlates of protection against symptomatic pandemic influenza", Nat Med., 2013, 19(10): 1305-1312.
Sridhar et al., "Heterosubtypic T-Cell Immunity to Influenza in Humans: Challenges for Universal T-Cell Influenza Vaccines", Front Immunol., Jul. 2016: 195.
Subbarao et al., "Prior infection and passive transfer of neutralizing antibody prevent replication of severe acute respiratory syndrome coronavirus in the respiratory tract of mice", J Virol., 2004, 78(7): 3572-3577.
Suleyman et al., "Clinical Characteristics and Morbidity Associated With Coronavirus Disease 2019 in a Series of Patients in Metropolitan Detroit", JAMA Network Open, 2020, 3(6): e2012270.
Tam et al., "Advances in Lipid Nanoparticles for siRNA Delivery", Pharmaceutics, May 2013: 498-507.
Thess et al., "Sequence-engineered mRNA Without Chemical Nucleoside Modifications Enables an Effective Protein Therapy in Large Animals", Molecular Therapy, 2015, 23(9): 1456-1464.
Tseng et al., "Immunization with SARS coronavirus vaccines leads to pulmonary immunopathology on challenge with the SARS virus", PLoS One, 2012, 7(4): e35421.
Walls et al., "Structure, Function, and Antigenicity of the SARS-CoV-2 Spike Glycoprotein", Cell, 2020, 181(2): 281-292 e286.
Weissman, "mRNA transcript therapy", Expert Rev. Vaccines, 2015, 14: 265-281.
WHO (World Health Organization), "SARS-CoV-2 Variants", COVID-19—Global, Dec. 31, 2020.
Wölfel et al., "Virological assessment of hospitalized patients with COVID-2019", Nature, 2020, 581: 465-469.
Wrapp et al., "Cryo-EM structure of the 2019-nCoV spike in the prefusion conformation", Science, 2020, 367(6483): 1260-1263.
Wrapp et al., "Structural Basis for Potent Neutralization of Betacoronaviruses by Single-Domain Camelid Antibodies", Cell, May 28, 2020, 181(5): 1004-1015.e15.
Wright et al., "The absence of enhanced disease with wild type respiratory syncytial virus infection occurring after receipt of live, attenuated, respiratory syncytial virus vaccines", Vaccine, 2007, 25(42): 7372-7378.
Wrobel et al., "SARS-CoV-2 and bat RaTG13 spike glycoprotein structures inform on virus evolution and furin-cleavage effects", Nat Struct Mol Biol., 2020, 27: 763-767.
Wu et al., "A new coronavirus associated with human respiratory disease in China", Nature, 2020, 579: 265-269.
Yang et al., "Plasma IP-10 and MCP-3 levels are highly associated with disease severity and predict the progression of COVID-19", J Allergy Clin Immunol., 2020, 146(1): 119-127.e4.
Zachariah et al., "Epidemiology, Clinical Features, and Disease Severity in Patients With Coronavirus Disease 2019 (COVID-19) in a Children's Hospital in New York City, New York", JAMA Pediatr., 2020, 174(10): e202430.
Zachariah et al., "Symptomatic Infants Have Higher Nasopharyngeal SARS-CoV-2 Viral Loads but Less Severe Disease Than Older Children", Clin Infect Dis, 2020, 71, 2305-2306 (2020).
Zhou et al., "A pneumonia outbreak associated with a new coronavirus of probable bat origin", Nature, Feb. 3, 2020, 579: 270-273.
Zivcec et al., "Validation of assays to monitor immune responses in the Syrian golden hamster (*Mesocricetus auratus*)", J Immunol Methods., 2011, 368(1): 24-35.

(56) References Cited

OTHER PUBLICATIONS

U.S. Appl. No. 17/810,064 2022/0347100 U.S. Pat. No. 11,771,653, filed Jun. 30, 2022 Nov. 3, 2022 Oct. 3, 2023, Danilo Casimiro, Lipid Nanoparticles For Delivering mRNA Vaccines.

U.S. Appl. No. 18/458,767, filed Aug. 30, 2023, Danilo Casimiro, Lipid Nanoparticles For Delivering mRNA Vaccines.

U.S. Appl. No. 18/586,102 2024/0327847, filed Feb. 23, 2024 Oct. 3, 2024, Jianping Cui, Compositions and Methods for RNA Affinity.

U.S. Appl. No. 18/052,600 2023/0302112, filed Nov. 4, 2022 Sep. 28, 2023, Danilo Casimiro, Respiratory Syncytial Virus RNA Vaccine.

U.S. Appl. No. 18/741,976, filed Jun. 13, 2024, Vincent Pavot, Lyme Disease RNA Vaccine.

U.S. Appl. No. 17/520,200 2022/0142923 U.S. Pat. No. 11,771,652, filed Nov. 5, 2021 May 12, 2022 Oct. 3, 2023, Danilo Casimiro, Lipid Nanoparticles for Delivering mRNA Vaccines.

U.S. Appl. No. 17/810,055 2022/0378701, filed Jun. 30, 2022 Dec. 1, 2022, Danilo Casimiro, Lipid Nanoparticles for Delivering mRNA Vaccines.

U.S. Appl. No. 17/810,064 2022/0347100 U.S. Pat. No. 11,711,653, filed Jun. 30, 2022 Nov. 3, 2022 Oct. 3, 2023, Danilo Casimiro, Lipid Nanoparticles for Delivering mRNA Vaccines.

U.S. Appl. No. 18/458,767 2024/0148651, filed Aug. 30, 2023 May 9, 2024, Danilo Casimiro, Lipid Nanoparticles for Delivering mRNA Vaccines.

U.S. Appl. No. 17/843,445 2023/0043128, filed Jun. 17, 2022 Feb. 9, 2023, Tim Alefantis, Multivalent Influenza Vaccines.

U.S. Appl. No. 18/070,921 2023/0310571, filed Nov. 29, 2022 Oct. 5, 2023, Yvonne Chan, Human Metapneumovirus Vaccines.

U.S. Appl. No. 18/671,660, filed May 22, 2024, Yvonne Chan, Human Metapneumovirus Viral Vector-Based Vaccines.

U.S. Appl. No. 18/660,489, filed May 10, 2024, Emilie Danve-Chery, Combination Respiratory mRNA Vaccines.

August et al., "Safety and Immunogenicity of an mRNA-Based Human Metapneumovirus and Parainfluenza Virus Type 3 Combined Vaccine in Healthy Adults", Open Forum Infect Dis, Jul. 2022, 9(7): ofac206, Epublished May 1, 2022.

Comstedt et al., "The novel Lyme borreliosis vaccine VLA15 shows broad Protection against *Borrelia* species expressing six different OspA serotypes", PLOA One, Sep. 1, 2017, 12(9): e0184357.

Gipson et al., "Evaluation of Venezuelan Equine Encephalitis (VEE) replicon-based Outer surface protein A (OspA) vaccines in a tick challenge mouse model of Lyme disease", Vaccine, Sep. 8, 2003, 21(25-2): 3875-3884.

Iioka et al., "Efficient detection of RNA-protein interactions using tethered RNAs", Nucleic Acids Research, Apr. 2011, 39(8): e53.

International Search Report and Written Opinion for PCT International Patent Application No. PCT/EP2022/086341, mailed Mar. 13, 2023.

International Search Report and Written Opinion for PCT International Patent Application No. PCT/EP2024/063002 mailed Aug. 5, 2024.

International Search Report and Written Opinion for PCT International Patent Application No. PCT/IB2022/058234, mailed Jan. 17, 2023.

Leppek et al., "An optimized streptavidin-binding RNA aptamer for purification of ribonucleoprotein complexes identifies novel ARE-binding proteins", Nucleaic Acids Research, Jan. 2014, 42(2): e13.

Luke et al., "An OspA-based DNA vaccine protects mice against infection with Borrelia burgdorferi", J Infect Dis., Jan. 1997, 175(1): 91-97.

Pardi et al., "mRNA vaccines—a new era in vaccinology", Nature Reviews Drug Discovery, Jan. 12, 2018, 17: 261-279.

Schwendinger et al., "Evaluation of OspA Vaccination-Induced Serological Correlates of Protection against Lyme Borreliosis in a Mouse Model", PLOS One, Nov. 18, 2013, 8(11): e79022.

Tusup et al., "Design of in vitro Transcribed mRNA Vectors for Research and Therapy", Chimia (Aarau), May 29, 2019, 73(5): 391-394.

Uniprot KB, "Alignments OspA B31 and N40", Borreliella burgdorferi (strain ATCC 35210 / DSM 4680 / CIP 102532 / B31) (Borrelia burgdorferi) and Borreliella burgdorferi (strain N40) (Borrelia burgdorferi), Jan. 1, 2020, Retrieved from url: <https://www.uniprot.org/>.

Zhong et al., "Plasmid DNA and protein vaccination of mice to the outer surface protein A ofBorrelia burgdorferi leads to induction of T helper cells with specificity for a major epitope and augmentation of protective IgG antibodiesin vivo", Eur J Immunol., Nov. 1996, 26(11): 2749-2757.

\* cited by examiner

ATGAAAACCATATAATCGCGCTCTCATACATACTTTGCCTGTCTTTGCCCAAAAGATCCCTGGCAACGACAACTCAACCGGACGACCCTTTGCCTCTGCGGCCATCACGCCGT
GCCGAACGGCACTATCGTCAAGACCATCACAAACGACCATCGAAGTGACCATCGAAGCTGAGCTAGTGCAGAACTCCAGACAAGAACAACTGTAGCAGAGATTGCGATTCTCAC
ACCAAATCCTGGACGGAGAGAATTGTACCTTGATCGACGCGCTGTGGGGGACCCTGCTTCCCTCCGGGATTCCAGACAAGAACAAGAATGGGACCTTTTCGTGGAACGGAGC
AAGGCATACTCGAATTGCTACCCCTACGATGTGCCGCCTACTCGGGCGTCCTGAGCTTCTTCAGCCGCCTGAACTGGCTCACTCACCTCACCCTTCAACTACACCTACCCGG
GACCGGAGTCGACCATGCCGAACAAGGAACAATTCGACAAGCTCTACATTTGGGGTGCATCACCCGGGATGAAGCAGACAGACCCCATTCAAGATCGCGACATTCCATCGGAGGATCTCGATCTACTG
CACTGAACGTGACCACCGTGTCGCGACAGCCCTGATCCGAACATTGGAAGCAGACCGTATTCGCGACATTCGCAGCGGGAAGTCCTCCATCATGAGAA
GACGATTGTCAAGCCTGGCGACATCCGAGTGTATACACACTGGAATGCCAACTACAAAGCCATTCCAGATCAAGCCATCTTCGGGGATCTTCGCAGCCGCTATCCGGGATGCCACTCAGGCCGCGATTGACCAGA
GCGATGCCCCCTACGTTCAAACATTGGACCCTGCATGGTTGGTACGGTTTCAGACAACGAAGAATGTTCCAACCAGAATTCTCCGAAGTGGAGCCGCCGGGTGCAAGACCTGGAGAAGTAC
TCAACGGAAGGAAAGCTCAACAGATCCACCTTTGGAGCTCATTGGAAAGACCAGACGCGAAAATGCTTAAAGATCGTTTAAGATGCTTTAAGATGGGTCCAGATCAAGGGCCTGAGCTCATTGAGTGGTTCAGCAATGTGGAAGCCCTATCATACGGAACG
GTGGAGGACACTAAGAAGCAACTCCGGAAAACGCCTTGGAGCATGGAGAAATGCTTAACGATCAACAGATTCCAGATCAAGGGCCTGAGCTGAAGTCCGGCTACAAGATTGAGCTGTGAGTTCCC
TGAGAAAACTAAGAAGCAACTCCGGAAAACGCCTGGAGCATGGAGAAATGCTTAAGATCGTTCAGATCAAGGGCCTGTGAGCTGAAGTCCGGCTACAAGATTGAGCTGTGAGTTCC
AACTTACGACCATAACGTCTACCGGATGAAGCCCTGAACAACAGATTCCAGATCAAGGGCCTGTGAAGGGCAACATTAGTGCAACATATGCATATAA
TTCGCGATTCATGCTCTTGCTCTTGCCCTGCGTGGCCCTGCGT

| | | |
|---|---|---|
| MRT10279 | ATGAAAACCATATAATCGCGCTCTCATACATACTTTGCCTGTCTTTGCCCAAAAGATCCCT | |
| H3_WT | ATGAAGACTATCATTGCTTTGACTACATTCTATGTCTGTTTTCGCTCAAAAAATTCCT | |
| | ***** ** **** * ****** ** ** ***** * ** ***** | |

| | | |
|---|---|---|
| MRT10279 | GGCAACGACAACTCAACCGGACGACCCTTTGCCTCTGCGGCCATCACGCCGTGCCGAACGGCACT | |
| H3_WT | GGAAATGACAATAGCACGGCAACTGTGCCTTGGGCACCATGCCAACGCCAGTCAGTACCAAACGGAACG | |
| | ** ** ** ** ** ** ***** ** ** ** ** ***** ** | |

| | | |
|---|---|---|
| MRT10279 | ATCGTCAAGACCATCACAAACGACCGACTCGAAGC

```
                ** ***** **  ****  * ** ** ** ***** ** ***** ** ***** ** ***

MRT10279        TTTAATTGGACCGGAGTGACCCAGAATGGCACCTCGAGCGCCTGCATTCGGGGCTCCTCC
H3_WT           TTCAATTGGACTGGAGTCACTCAAAACGGAACAAGTTCTGCTTGCATAAGGGGATCTAGT
                ** ******** ***** ** ** ** ** **       ** *****  **** **

MRT10279        TCGAGCTTCTTCAGCCGCCTGAACTGGCTCACTCACCTCAACTACACCTACCCGGCACTG
H3_WT           AGTAGTTTCTTTAGTAGATTAAATTGGTTGACCCACTTAAACTACACATATCCAGCATTG
                ** ***** **  *  * ** *** * ** *** * ******** ** ** *** **

MRT10279        AACGTGACCATGCCGAACAAGGAACAATTCGACAAGCTCTACATTTGGGGGGTGCATCAC
H3_WT           AACGTGACTATGCCAAACAAGGAACAATTTGACAAATTGTACATTTGGGGGGTTCACCAC
                ******** ***** ************** *****  * ************** ** ***

MRT10279        CCGGGTACCGATAAGGACCAGATCTTCCTCTACGCCCAATCCTCGGGCCGGATCACCGTG
H3_WT           CCGGGTACGGACAAGGACCAAATCTTCCTGTATGCTCAATCATCAGGAAGAATCACAGTA
                ******** ** ******** ******** ** ** ***** ** **  * ***** **

MRT10279        TCCACTAAGCGCTCGCAGCAGGCCGTGATCCCGAACATTGGAAGCAGACCCCGCATTCGC
H3_WT           TCTACCAAAAGAAGCCAACAAGCTGTAATCCCAAATATCGGATCTAGACCCAGAATAAGG
                ** ** **  *    ** ** ** ** ***** ** ** ***   ****** * **  *

MRT10279        GACATTCCATCGAGGATCTCGATCTACTGGACGATTGTCAAGCCTGGCGACATCCTCCTC
H3_WT           GATATCCCTAGCAGAATAAGCATCTATTGGACAATAGTAAAACCGGGAGACATACTTTTG
                ** ** **    ** **    ***** ***** ** ** ** ** ** ***** **  *

MRT10279        ATTAACTCCACCGGGAACCTCATCGCCCCTCGGGGTTATTTCAAGATCCGCAGCGGGAAG
H3_WT           ATTAACAGCACAGGGAATCTAATTGCTCCTAGGGGTTACTTCAAAATACGAAGTGGGAAA
                ******  *** ***** ** ** ** *** ******* ***** ** ** ** *****

MRT10279        TCCTCCATCATGAGAAGCGATGCCCCCATTGGAAAGTGCAAGTCCGAGTGTATCACACCT
H3_WT           AGCTCAATAATGAGATCAGATGCACCCATTGGCAAATGCAAGTCTGAATGCATCACTCCA
                *** ** ******   ***** ******** ** ******** ** ** ***** **

MRT10279        AACGGAAGCATTCCCAATGACAAGCCATTCCAGAACGTGAACAGAATTACCTACGGAGCT
H3_WT           AATGGAAGCATTCCCAATGACAAACCATTCCAAAATGTAAACAGGATCACATACGGGGCC
                ** ******************* ******** ** ** ***** ** ** ***** **

MRT10279        TGCCCTCGCTACGTCAAACATTCGACCCTCAAGTTGGCGACTGGAATGCGCAACGTGCCG
H3_WT           TGTCCCAGATATGTTAAGCATAGCACTCTGAAATTGGCAACAGGAATGCGAAATGTACCA
                ** **  * ** ** ** ***    ** ** ** ***** ** ******** ** ** **

MRT10279        GAGAAGCAAACCCGGGGGATCTTCGGGGCTATCGCGGGATTCATCGAAAATGGATGGGAA
H3_WT           GAGAAACAAACTAGAGGCATATTTGGCGCAATAGCGGGTTTCATAGAAAATGGTTGGGAG
                ***** *****  * ** ** ** ** ** ** ***** ***** ******** *****
```

FIG. 5A (cont.)

```
MRT10279   GGAATGGTCGATGGTTGGTACGGTTTCAGACACCAGAACTCCGAGGGGCGGGGCCAGGCC
H3_WT      GGAATGGTGGATGGTTGGTACGGTTTCAGACACCAGAACTCCGAGGGGAAGAGGACAAGCA
           ******** *************************************** ** **

MRT10279   GCAGACCTGAAGTCCACTCAGGCCGCGATTGACCAGATCAACGAAAGCTCAACAGACTC
H3_WT      GCAGATCTCAAAAGCACTCAAGCAGCAGCAATCGATCAAATCAAATCAATGGGAAGCTGAATAGGTTG
           ***** ** **  ***** ***  **  *  **** **  ***** ** **     *

MRT10279   ATTGGAAAGACCAACGAAAAGTTCCACCAAATCGAAAAGGAATTCTCCGAAGTGGAGGGC
H3_WT      ATCGGAAAAACCAACGAGAAATTCATCAGATTGAAAAGAATTCTCAGAAGTAGAAGGA
           ** ***** ******** **  **  *   * ** ********* ***** ** ***

MRT10279   CGGGTGCAAGACCTGGAGAAGTACGTGGAGGACACTAAGATCGACCTTTGGAGCTATAAC
H3_WT      AGAGTTCAAGACCTTGAGAAATATGTTGAGGACACTAAAATAGATCTCTGGTCATACAAC
            *  ** ******* ***** * *** ********** *  *** ** *** ** ***

MRT10279   GCAGAACTCCTTGTGGCCCTGAAAAACCAGCACACCATCGACCTGACCGATTCAGAGATG
H3_WT      GCGGGAGCTTCTTGTTGCCCTGGAGAACCAACAACATACAACATTGATCTAACTGACTCAGAAATG
           ** * * * ***** ****** * ****   **  **  **  ** ** * ** ** ***

MRT10279   AACAAGCTCTCTTTGAGAAAACTAAGAACGCTTGAGGACAATGGGAAAT
H3_WT      AACAAACTGTTTGAAAAAAACAAAGAACAACAAATGTGACAACAATGCTGAGGAAAATGCTGAGGAAAT
           *****  * ** **  ***    ***  *  **  * * *****  ****** *******

MRT10279   GGATGCTTTAAGATCTACCACAAGTGCGACAACGCCTGCATTGAGTCATACGAACGAA
H3_WT      GGTTGTTTCAAAAATATACCACAAATGATGTGACATGTGACAATGCCTGCGGAATGACAATGAATGGAGAA
           ** ** ** *  *   *****   *     ** ** ** ***** **  *****

MRT10279   ACTTACGACCATAACGTCTACCGGGATGAAGCCCTGAACAACAGATTCCAGATCAAGGGC
H3_WT      ACTTATGACCACCAATGTGTACAGGGATGATCATTGAACAACCGGTTCCAGATCAAGGGA
           ***** ***** ** ** ** * *****    ** ****** *************

MRT10279   GTGGAGCTGAAGTCCGGCTACAAAGATTGGATCCTGTGGATTTCCTTCGCGATTTCATGC
H3_WT      GTTGAGCTGAAGTCAGGATCAGGATACAAAAGATTGGATCCATATGGATTCCTTGCCATATCATGT
           ** ****** *** **  ** ********** ****    ** ** * ****

MRT10279   TTCTTGCTCTGCGTGGCCCCTCCTGGGATTCATAATGTGGGCCCTGTCAGAAGGGCAACATT
H3_WT      TTTTTGCTTGTGTTGCTTTGTTGGGTTCATCATGTGGGCCTGCTGCCAAAAGGGCAACATT
           ** ***** * ** ** * **  ** ****  ** **** * ** ** *************

MRT10279   AGGTGCAACATATGCATATAA  (SEQ ID NO:2)
H3_WT      AGATGCAACATTGCATTTGA   (SEQ ID NO:3)
           ** ******** ****  *

FIG. 5A (cont.)
```

5' UTR
GGACAGAGAUCGCCUGGAGACCGCCAUCCACGCGCUGUUUGACCUCCAUAGAAGACACCGGGACCGAUCCAGCCUCCGCCGGGAACGCGGAUUCC
CCGUGCCAAGAGUGACUCACCGUCCUUGACACG

CDS (coding Sequence)
AUGAAAACCAUAAUCGCGCUCUCAUAUACAUUUGCCUGGUCUUUGCCCAAAAGAUCCUGGCAAGACACUCAACGCGACCCUUUGCCUCGGCCAUCACGCCGU
GCCGAACGGCACUAUCGUCAAGAGAAUGUACCUUGAUCGAACGCGUCCAUCGAGCGCUAGUGCAGAACCCCGCGAGAUCCAGCAACGCGAGAUUGCGAUUCCAC
ACCAAAUCCUGGACGGAGAGAAUUGUACCCCUACGAUGUGCCCAGUGCGAUCCGAGUGCUUUCCGCCGGGAUCCUGGAAUUCAAAAACGAGAAUUCGUGAACGGAGC
AAGGCAUACUCGAAUCGACCCCUAGCAUGCCGACUACGCCCUGGGGGUCGUCCGCCUCGGAGCUUCUCAGCGCCUGGCUCACUCAACUACACCUACCCGG
GACCGGAGUGACGUGACCAGAAUGGCCGGAACAUCGACAAGCAACAAUCGACAAGGAACAAUCGACAAGGCUCACACUCAACCUCACCCUUCUACGCCCAAUCC
CACUGAACGUGACCAGAAGCCCGAAGAACUUCACUCAGGCCCUGGAACCAAGCCUCGUGACCCGUCAAUUCGGGAGUGCAUCAUGGAAGCAGACCAGAUCCAUCCAGGAUCUCAGUACUG
UCGGCCGGAUUCAAGCCUGGCGACAUCCUCAUAACUCCCAUCGGGGGCUUAUUUCAAGACUCGAACACCGAGAAGUCCUCCAUCAUGAGAA
GCGAUGCCCCAUUGGAAUGUCAGUCCGUCCUCAAGGUGUAGGCGACGUUCAGAGACAGAAGCGAACCCGGGGUAUCCGGAUUCAUCGAGCUUGC
CCUCGCUACGUCAAACAUUCGAUGGGUUACGGCGUUCAGAGACAACGGUGAAAACGCGCAAACCCAGGCCGCGAGGGGCCAGGCCGCGAGCGCCGCUAUCCGGAUUGACCAGA
UGGAUGGGCAAGGAAGAGUGUCCACGGGAUCCAUCUCAACACAGAGAAUCGAAACGGAAUUCCACCCAAAUCGAAAGGAAAUCAGAGAAUCCAGCCAAGUCCCGCGAAGACCUGGAGAAGUAC
UCAACGGAAGACUCAACAGAUCGACACCUUUGGAGCUAUAACGCAGAACUCAGAAACCAGCACAACCAGCACACACAAGAUCCAGAUGGCUACCGUCGCCAUCAGGAACAAGCUCU
GUGGAGGACGAGAAGCCUGACACGACGACCAGAGGAUGUUAAGGGCCCUUGUGGCCCUGAGGACCAACAAGCCUGCACAAGCGCCAUAGAGUCCAUGGAUGGACGACGAACG
UGAGAAAACUAAGAAGAGACCUGAACUAAGCUCUCCUGCUGCCGGGAUGAAGGCCCUGAAGGGCCCUGUCAGAAGGCCUGCAAAGAUUGGAGAUCUAUGGACCAUAUAA
AACUUACGACCAUAAGCUCUCCCUCCUGCUGCCGGGAUGAAGGCCCUGAAGGGCCCUGUCAGAAGGCCUGCAACACAUUAGGUGCAACAAUGCAUAUAA
UUCGCGAUUUCAUGCGAUUCAUGCGAUUAAGCUCUCCUAUAUAAAAUUAAGUUGCAUC 3' UTR
CGGGUGGCAUCCCGUGACCUCCUCCCCCAGUGCCUGCUGACACCGGAAGUUGCCUGCCACCAGCCUGUCCUAUAAAAAUUAAGUUGCAUC + Poly A Tail (SEQ ID NO:4)

FIG. 5C

LIPID NANOPARTICLES FOR DELIVERING MRNA VACCINES

RELATED APPLICATIONS

This application is a continuation of U.S. patent application Ser. No. 18/458,767, filed Aug. 30, 2023, which is a continuation of U.S. patent application Ser. No. 17/520,200, filed Nov. 5, 2021, now U.S. Pat. No. 11,771,652, which claims the benefit of priority of U.S. Provisional Application No. 63/110,965, filed Nov. 6, 2020, U.S. Provisional Application No. 63/212,523, filed Jun. 18, 2021, and EP Priority Application No. 21315198.8, filed Oct. 13, 2021, the content of each incorporated by reference in their entirety for all purposes.

SEQUENCE LISTING

The instant application contains a Sequence Listing which has been submitted electronically in XML format and is hereby incorporated by reference in its entirety. Said XML file, created on Nov. 6, 2023, is named 747261_SA9-323CON2_ST26.xml and is 63,907 bytes in size.

BACKGROUND OF THE INVENTION

Messenger RNA (mRNA)-based vaccines provide a promising alternative to traditional subunit vaccines, which contain antigenic proteins derived from a pathogen. Antigenic proteins are usually recombinantly made and require bacterial fermentation and/or cell culture, as well as complex purification. Vaccines based on mRNA allow de novo expression of complex antigens in the vaccinated subject, which in turn allows proper post-translational modification and presentation of the antigen in its natural conformation. Unlike traditional technologies, the manufacture of mRNA vaccines does not require complex and costly bacterial fermentation, tissue culture, and purification processes. Moreover, once established, the manufacturing process for mRNA vaccines can be used for a variety of antigens, enabling rapid development and deployment of mRNA vaccines. Further, mRNA vaccines are inherently safe delivery vectors as they express the antigens only transiently and do not integrate into the host genome. Because antigens encoded by mRNAs are produced in vivo in the vaccinated individual, mRNA vaccines are especially effective in eliciting both humoral and T cell mediated immunity.

RNA, however, is unstable and subject to rapid degradation. There also are no natural cell surface receptors that facilitate cellular uptake of RNA. Indeed, development of mRNA vaccines has been hampered by inefficient in vivo delivery of mRNA. Thus, there remains a need to develop vaccine formulations that can improve mRNA delivery in vivo.

SUMMARY OF THE INVENTION

The present disclosure provides a pharmaceutical composition comprising nucleic acid molecules (e.g., mRNA molecules) encapsulated in lipid nanoparticles (LNPs), wherein each LNP comprises a cationic lipid at a molar ratio between 35% and 45%, a polyethylene glycol (PEG) conjugated (PEGylated) lipid at a molar ratio between 0.25% and 2.75%, a cholesterol-based lipid at a molar ratio between 20% and 35%, and a helper lipid at a molar ratio of between 25% and 35%, wherein all the molar ratios are relative to the total lipid content of the LNP. The composition may be used as a vaccine to elicit immune protection in subjects (e.g., human subjects) in need thereof.

In some embodiments, the cationic lipid is OF-02, cKK-E10, GL-HEPES-E3-E10-DS-3-E18-1, GL-HEPES-E3-E12-DS-4-E10, or GL-HEPES-E3-E12-DS-3-E14.

In some embodiments, the LNP comprises a cationic lipid at a molar ratio of 40%, a PEGylated lipid at a molar ratio of 1.5%, a cholesterol-based lipid at a molar ratio of 28.5%, and a helper lipid at a molar ratio of 30%.

In some embodiments, the cationic lipid is OF-02, cKK-E10, GL-HEPES-E3-E10-DS-3-E18-1, GL-HEPES-E3-E12-DS-4-E10, or GL-HEPES-E3-E12-DS-3-E14, the PEGylated lipid is dimyristoyl-PEG2000 (DMG-PEG2000), the cholesterol-based lipid is cholesterol, and/or the helper lipid is 1,2-dioleoyl-SN-glycero-3-phosphoethanolamine (DOPE). In particular embodiments, the LNP comprises OF-02, cKK-E10, GL-HEPES-E3-E10-DS-3-E18-1, GL-HEPES-E3-E12-DS-4-E10, or GL-HEPES-E3-E12-DS-3-E14 at a molar ratio of 40%, DMG-PEG2000 at a molar ratio of 1.5%, cholesterol at a molar ratio of 28.5%, and DOPE at a molar ratio of 30%.

In some embodiments, the LNP comprises 1-20, optionally 5-10 or 6-8, nucleic acid molecules. In some embodiments, the LNP comprises one or more mRNA molecules encoding an antigen (e.g., a viral antigen such as an influenza viral antigen, or a bacterial antigen).

In some embodiments, the LNP comprises two or more mRNA molecules, wherein each mRNA molecule encodes a different antigen, optionally wherein the different antigens are from the same pathogen or from different pathogens. In some embodiments, the composition comprises two or more LNPs, wherein each LNP comprises an mRNA encoding a different antigen, optionally wherein the different antigens are from the same pathogen or from different pathogens.

For example, the composition may comprise two, three, four, five, six, seven, eight, nine, or more mRNA molecules encoding (i) different hemagglutinin (HA) antigens, (ii) different neuraminidase (NA) antigens, or (iii) at least one HA antigen and at least one NA antigen.

In some embodiments, mRNA molecule comprises an open reading frame (ORF) encoding a respiratory syncytial virus (RSV) F protein antigen.

In some embodiments, the RSV F protein antigen comprises an amino acid sequence with at least 98% identity to SEQ ID NO: 16 or consists of an amino acid sequence of SEQ ID NO: 16.

In some embodiments, the RSV F protein antigen is a pre-fusion protein.

In some embodiments, the ORF is codon optimized.

In some embodiments, the mRNA molecule comprises at least one 5' untranslated region (5' UTR), at least one 3' untranslated region (3' UTR), and at least one polyadenylation (poly(A)) sequence.

In some embodiments, the mRNA comprises at least one chemical modification.

In some embodiments, at least 20%, at least 30%, at least 40%, at least 50%, at least 60%, at least 70%, at least 80%, at least 85%, at least 90%, at least 95%, or 100% of the uracil nucleotides in the mRNA are chemically modified.

In some embodiments, at least 20%, at least 30%, at least 40%, at least 50%, at least 60%, at least 70%, at least 80%, at least 85%, at least 90%, at least 95%, or 100% of the uracil nucleotides in the ORF are chemically modified.

In some embodiments, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

In some embodiments, the chemical modification is selected from the group consisting of pseudouridine, N1-methylpseudouridine, 5-methylcytosine, 5-methoxyuridine, and a combination thereof.

In some embodiments, the chemical modification is N1-methylpseudouridine.

In some embodiments, the mRNA comprises a nucleic acid sequence with at least 80% identity to a nucleic acid sequence set forth in SEQ ID NO: 17.

In some embodiments, the mRNA comprises a nucleic acid sequence with at least 80% identity to a nucleic acid sequence set forth in SEQ ID NO: 21.

In some embodiments, the mRNA comprises of the following structural elements:
(i) a 5' cap with the following structure:

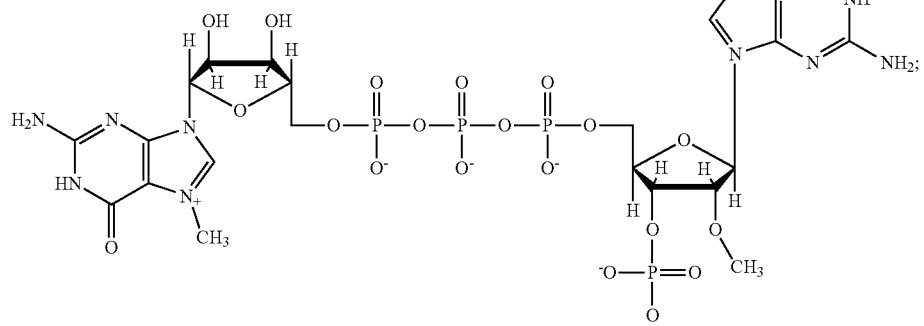

(ii) a 5' untranslated region (5' UTR) having the nucleic acid sequence of SEQ ID NO: 19;
(iii) a protein coding region having the nucleic acid sequence of SEQ ID NO: 17;
(iv) a 3' untranslated region (3' UTR) having the nucleic acid sequence of SEQ ID NO: 20; and
(v) a poly(A) tail.

In some embodiments, the LNP has an average diameter of 30-200 nm (e.g., 80-150 nm). In some embodiments, the composition comprises 1-10, optionally 1, mg/ml of the LNP. The composition may be formulated for intramuscular or intradermal injection and may comprise a phosphate-buffer saline. In some embodiments, the composition comprising trehalose, optionally at 10% (w/v) of the composition.

In another aspect, the present disclosure provides a method of preparing the LNP composition herein, comprising providing an aqueous buffered solution comprising the nucleic acid molecule, providing an amphiphilic solution comprising the cationic lipid, the PEGylated lipid, the cholesterol-based lipid, and the helper lipid, and mixing the aqueous buffered solution and the amphiphilic solution at a ratio of 5:1 to 3:1, optionally 4:1. The aqueous buffered solution may be, for example an acidic buffered solution (e.g., comprising 1 mM citrate and 150 mM sodium chloride with a pH of about 4.5). The amphiphilic solution may be, e.g., an ethanol solution.

In another aspect, the present disclosure provides a method of eliciting an immune response in a subject in need thereof, comprising administering to the subject, optionally intramuscularly, intranasally, intravenously, subcutaneously, or intradermally, a prophylactically effective amount of the present LNP composition. In some embodiments, the subject is treated with one or more (e.g., two) doses of the composition, each dose comprising 1-250, optionally 2.5, 5, 15, 45, or 135, μg of mRNA. The doses may be given at an interval of 2-24, optionally 4, 8, 12, 16, or 20 weeks, or one, two, three, four, five, or six months.

Also provided herein are use of the present composition for the manufacture of a medicament for use in treating a subject in need thereof, as well as the composition for use for use in treating a subject in need thereof.

The present disclosure also provides a kit comprising a container comprising a single-use or multi-use dosage of the present, optionally wherein the container is a vial or a pre-filled syringe or injector.

In another aspect, the disclosure provides a pharmaceutical composition comprising a mRNA molecule encapsulated in a lipid nanoparticle (LNP), wherein the LNP comprises:

a cationic lipid at a molar ratio between 35% and 45%,
a polyethylene glycol (PEG) conjugated (PEGylated) lipid at a molar ratio between 0.25% and 2.75%,
a cholesterol-based lipid at a molar ratio between 20% and 35%, and
a helper lipid at a molar ratio of between 25% and 35%,
wherein all the molar ratios are relative to the total lipid content of the LNP;
wherein the mRNA molecule comprises an open reading frame (ORF) encoding an antigen derived from influenza virus.

In another aspect, the disclosure provides a pharmaceutical composition comprising a mRNA molecule encapsulated in a lipid nanoparticle (LNP), wherein the LNP comprises:
a cationic lipid at a molar ratio between 35% and 45%,
a polyethylene glycol (PEG) conjugated (PEGylated) lipid at a molar ratio between 0.25% and 2.75%,
a cholesterol-based lipid at a molar ratio between 20% and 35%, and
a helper lipid at a molar ratio of between 25% and 35%,
wherein all the molar ratios are relative to the total lipid content of the LNP;
wherein the mRNA molecule comprises an open reading frame (ORF) encoding a respiratory syncytial virus (RSV) F protein antigen.

Other features, objects, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description

BRIEF DESCRIPTION OF THE DRAWINGS

FIGS. 5A-C show the MRT1400 mRNA encoding for influenza virus A/Singapore/INFIMH160019/2016 (Sing16; H3N2) HA hemagglutinin. FIG. 5A: an alignment of the wildtype (WT) gene and a codon-optimized gene (MRT10279) for the HA antigen. The sequence at the top corresponds to SEQ ID 25. The sequence in the alignment designated "MRT10279" corresponds to SEQ ID NO: 2. The sequence in the alignment designated "H3_WT" corresponds to SEQ ID NO: 3. FIG. 5B: the structure of the mRNA. FIG. 5C: the sequence of the mRNA (SEQ ID NO: 26).

FIG. 10B only shows study days −2 (baseline from pooled sera) and 42. First injection was given at study day 0 and second injection given at study day 28. Bars are geometric means and geometric standard deviations. Dashed line=lower limit of quantitation.

FIG. 16A shows the HAI titers reported as $Log_{10}$ for serum samples taken at study days 0, 14, 28, 42, 56, 92, and 107. FIG. 16B shows daily weights after intranasal challenge on day 93 with $4LD_{50}$ of A/Belgium/2009 H1N1 strain. Weights are presented as the percentage of weight lost from the day of challenge. Individual lines represent each animal.

mRNA. LNP formulations "Lipid A," "Lipid B," "Lipid C," "Lipid D," and "Lipid E" are shown. Bars represent means and standard deviations. The LNP compositions contain the cationic lipid, DMG-PEG2000, cholesterol, and DOPE, in this order, at a molar ratio of 40:1.5:28.5:30.

Figure 27:
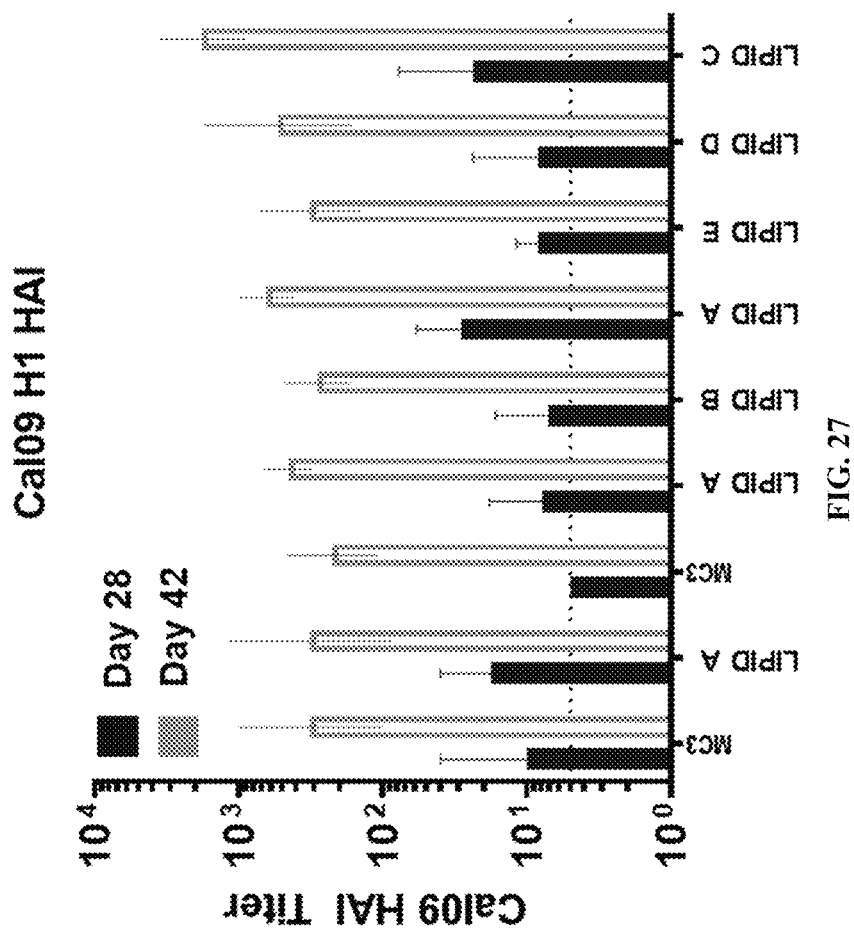

FIG. 27 depicts a graph showing Cal09 H1 HAI titers at day 28 and day 42 post injection with various LNP formulations of HA mRNA. LNP formulations "Lipid A," "Lipid B," "Lipid C," "Lipid D," and "Lipid E" are shown. Bars represent means and standard deviations. The LNP compositions contain the cationic lipid, DMG-PEG2000, cholesterol, and DOPE, in this order, at a molar ratio of 40:1.5:28.5:30.

Figure 28:
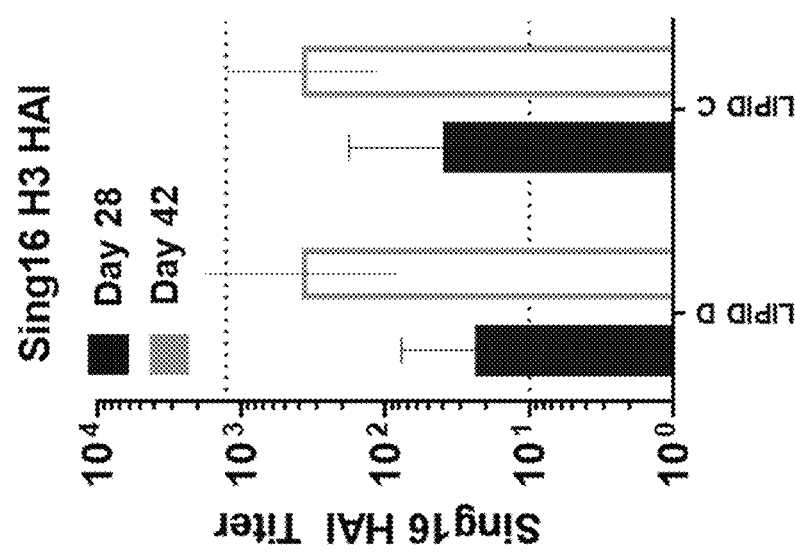

FIG. 28 depicts a graph showing Sing16 H3 HAI titers at day 28 and day 42 post injection with various LNP formulations of HA mRNA. LNP formulations "Lipid A," "Lipid B," "Lipid C," "Lipid D," and "Lipid E" are shown. Bars represent means and standard deviations. The LNP compositions contain the cationic lipid, DMG-PEG2000, cholesterol, and DOPE, in this order, at a molar ratio of 40:1.5:28.5:30.

Figure 29:
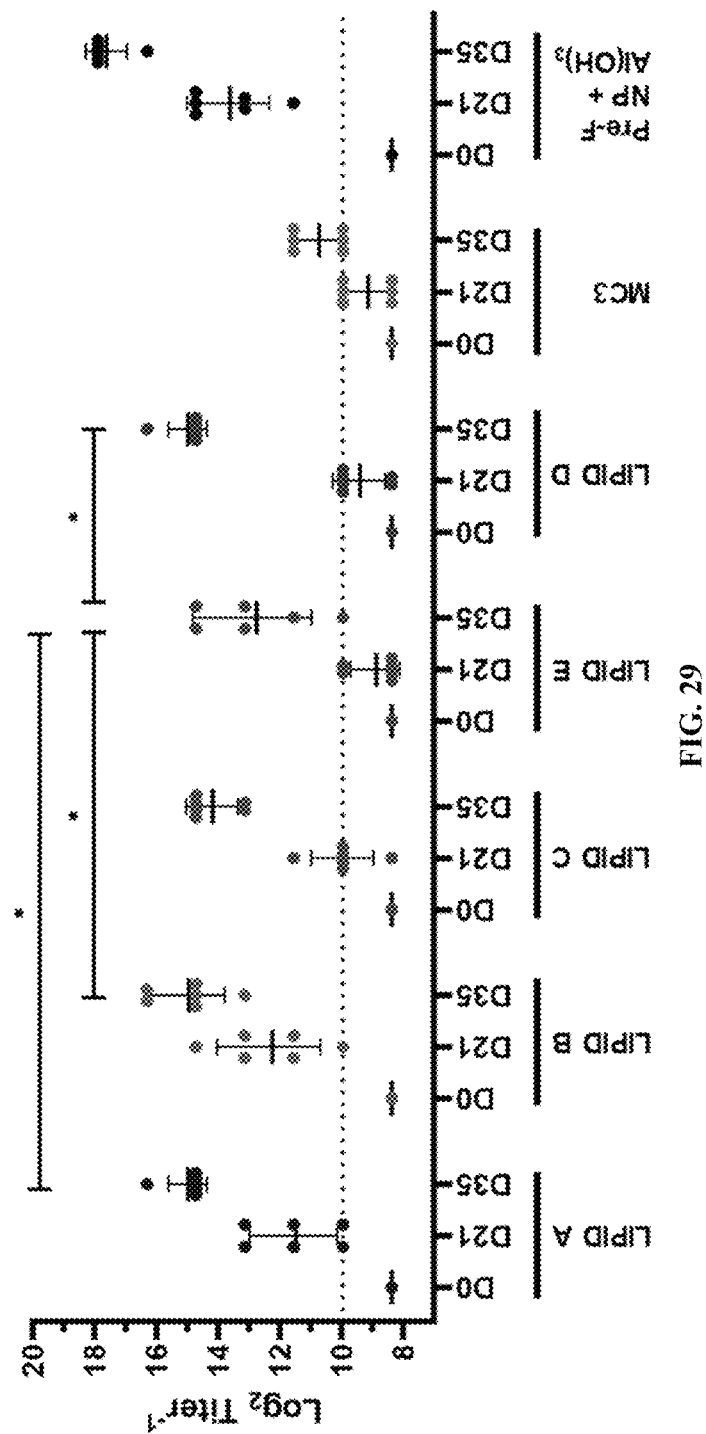

FIG. 29 depicts RSV F protein antibody titers in NHPs immunized with the FD3 F protein expressing mRNA. The mRNA was delivered with lipid nanoparticles (LNPs) containing one of several cationic lipids. The antibody titers were measured at day 0, 21, and 35 for each antigenic composition.

Figure 30:
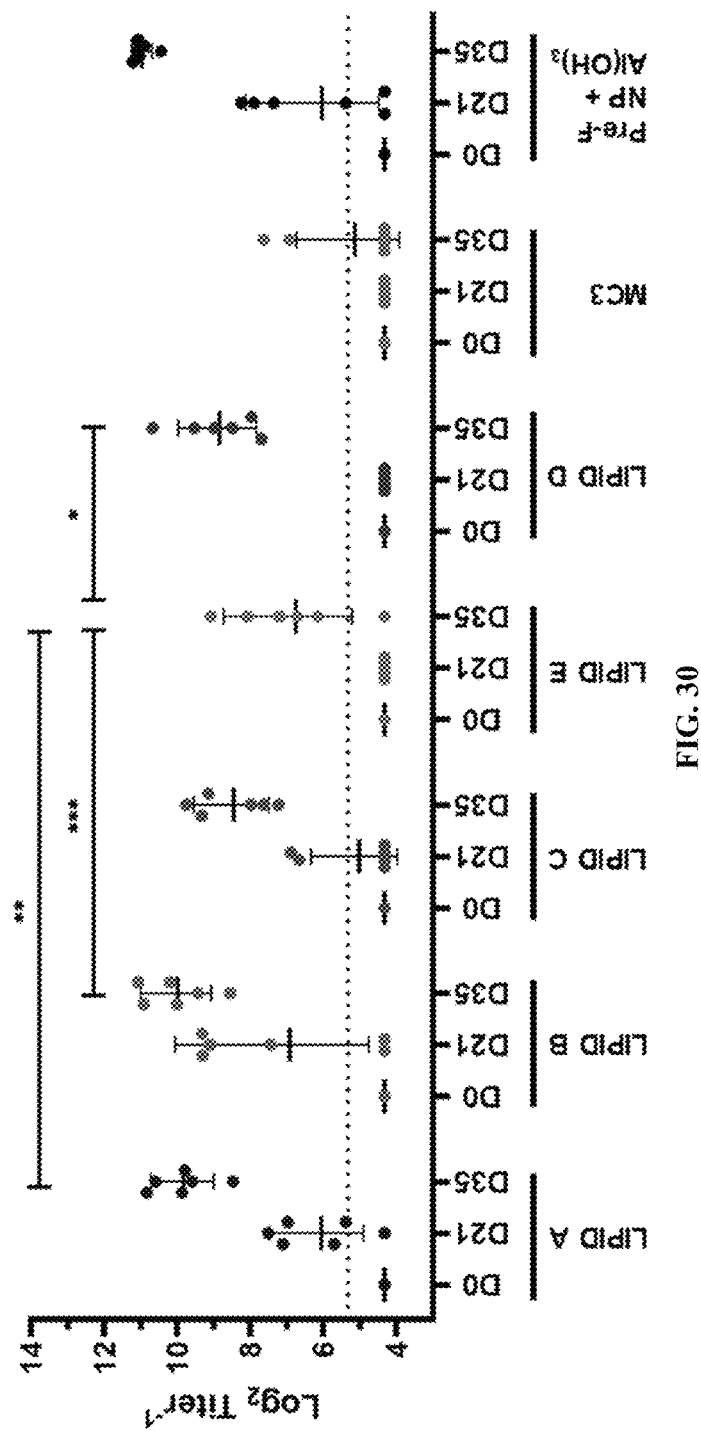

FIG. 30 depicts RSV neutralization titers in NHPs immunized with the FD3 F protein expressing mRNA. The mRNA was delivered with lipid nanoparticles (LNPs) containing one of several cationic lipids. The antibody titers were measured at day 0, 21, and 35 for each antigenic composition.

Figure 31:
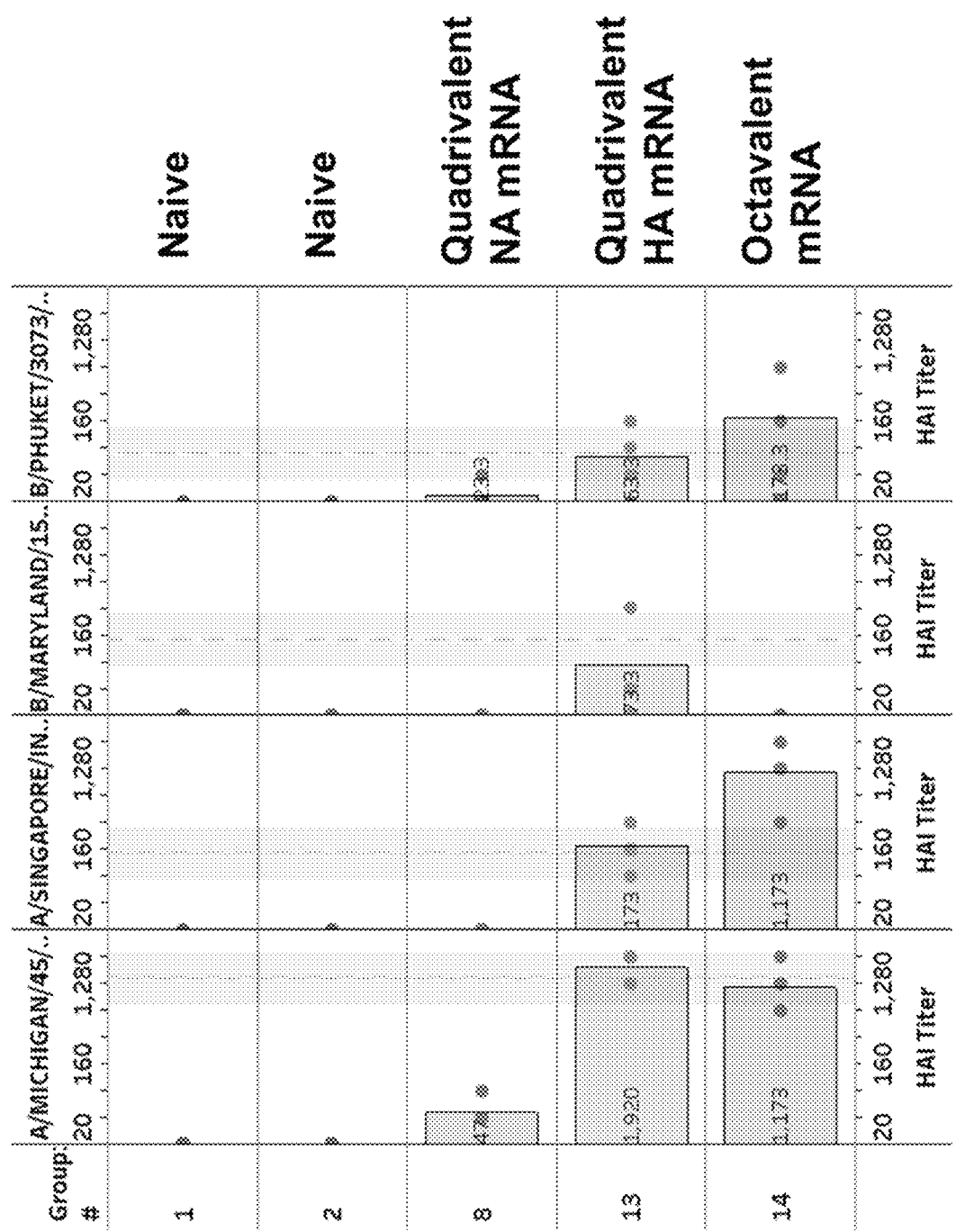

FIG. 31 depicts HAI titers for quadrivalent and octavalent mRNA-LNP vaccines administered to mice for 4 different influenza strains.

Figure 32:
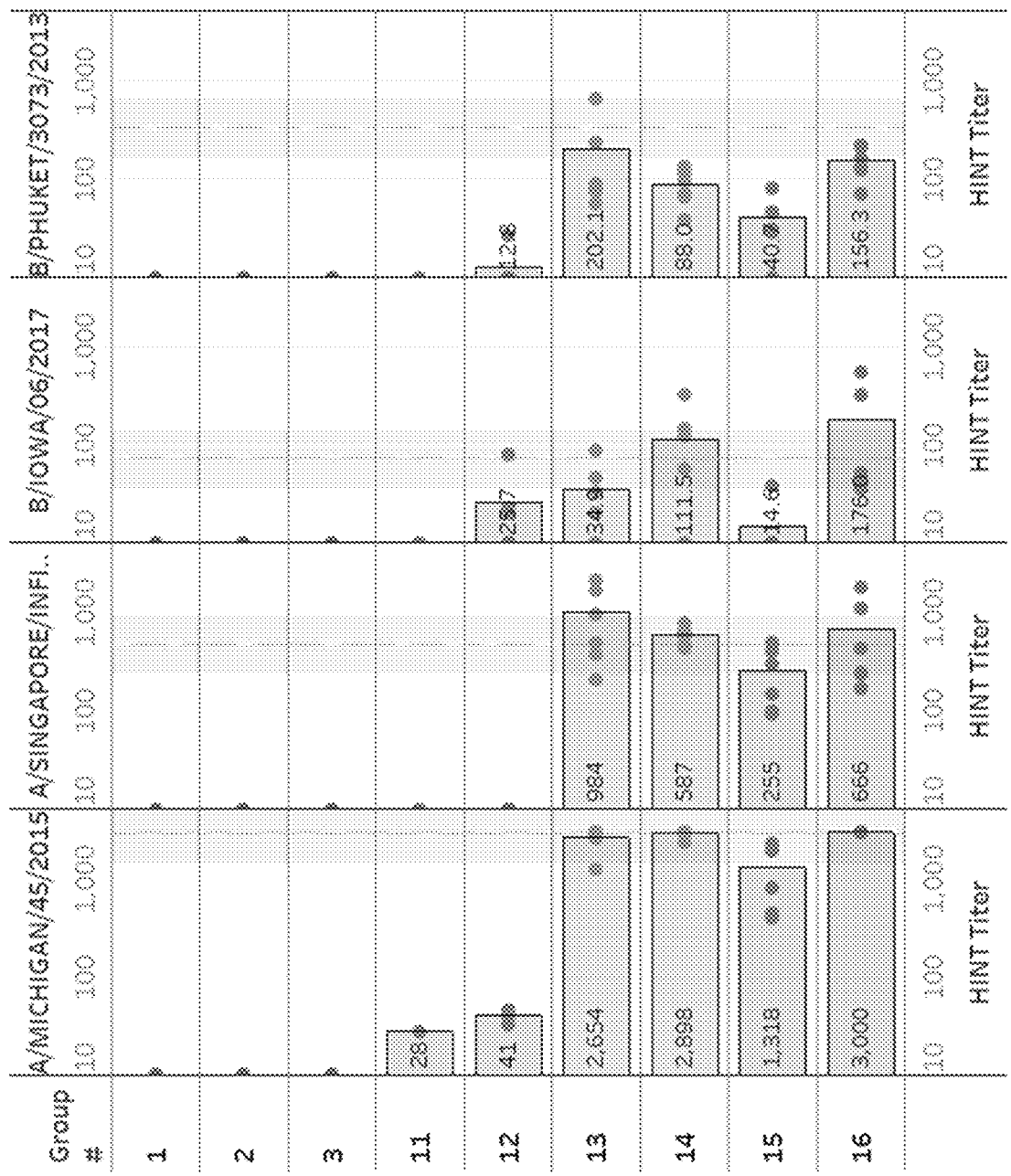

FIG. 32 depicts HINT values for quadrivalent and octavalent mRNA-LNP vaccines, administered to ferrets for 4 different influenza strains.

Figure 33:
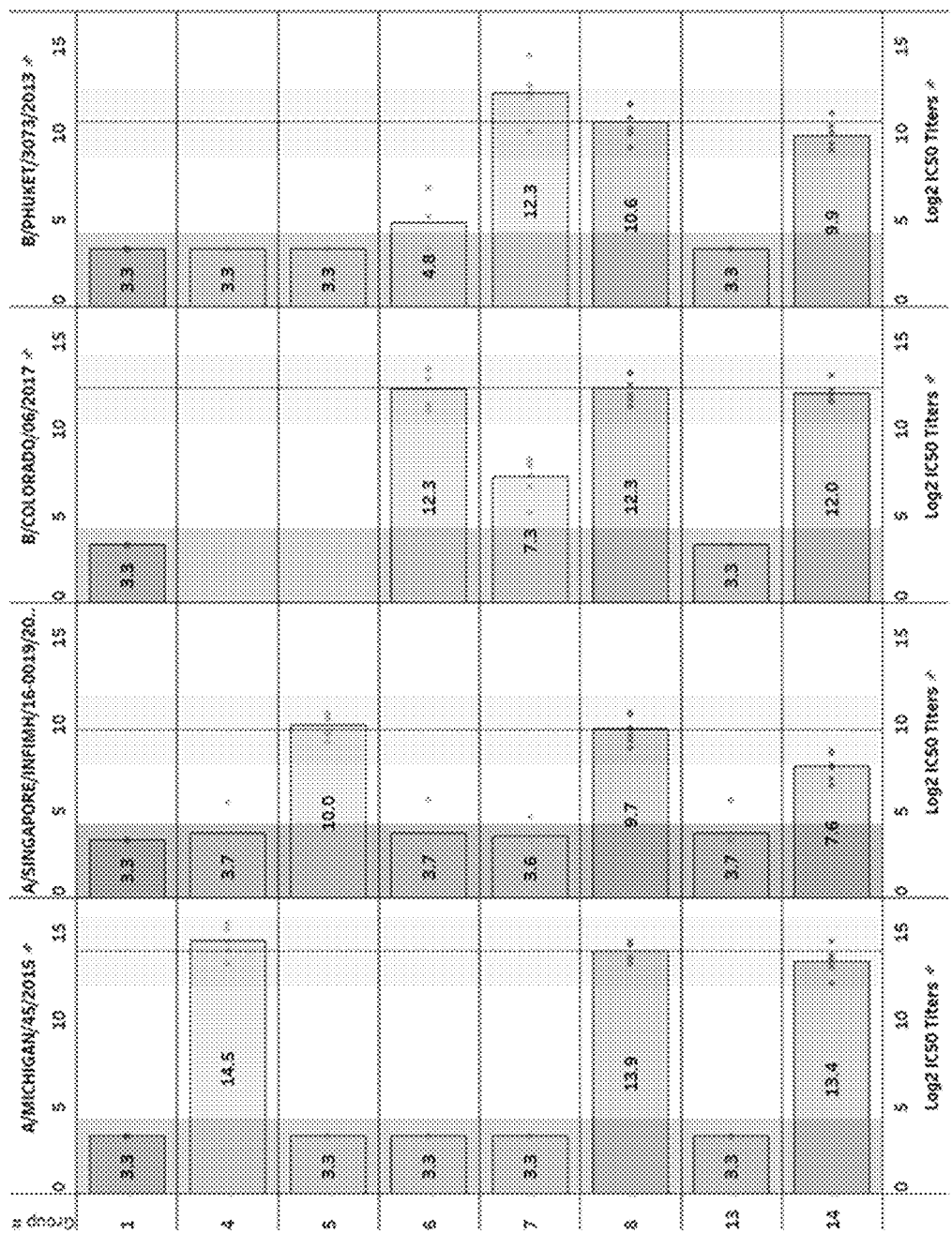

FIG. 33 depicts NAI titers for quadrivalent and octavalent mRNA-LNP vaccines, administered to mice for 4 different influenza strains.

Figure 34:
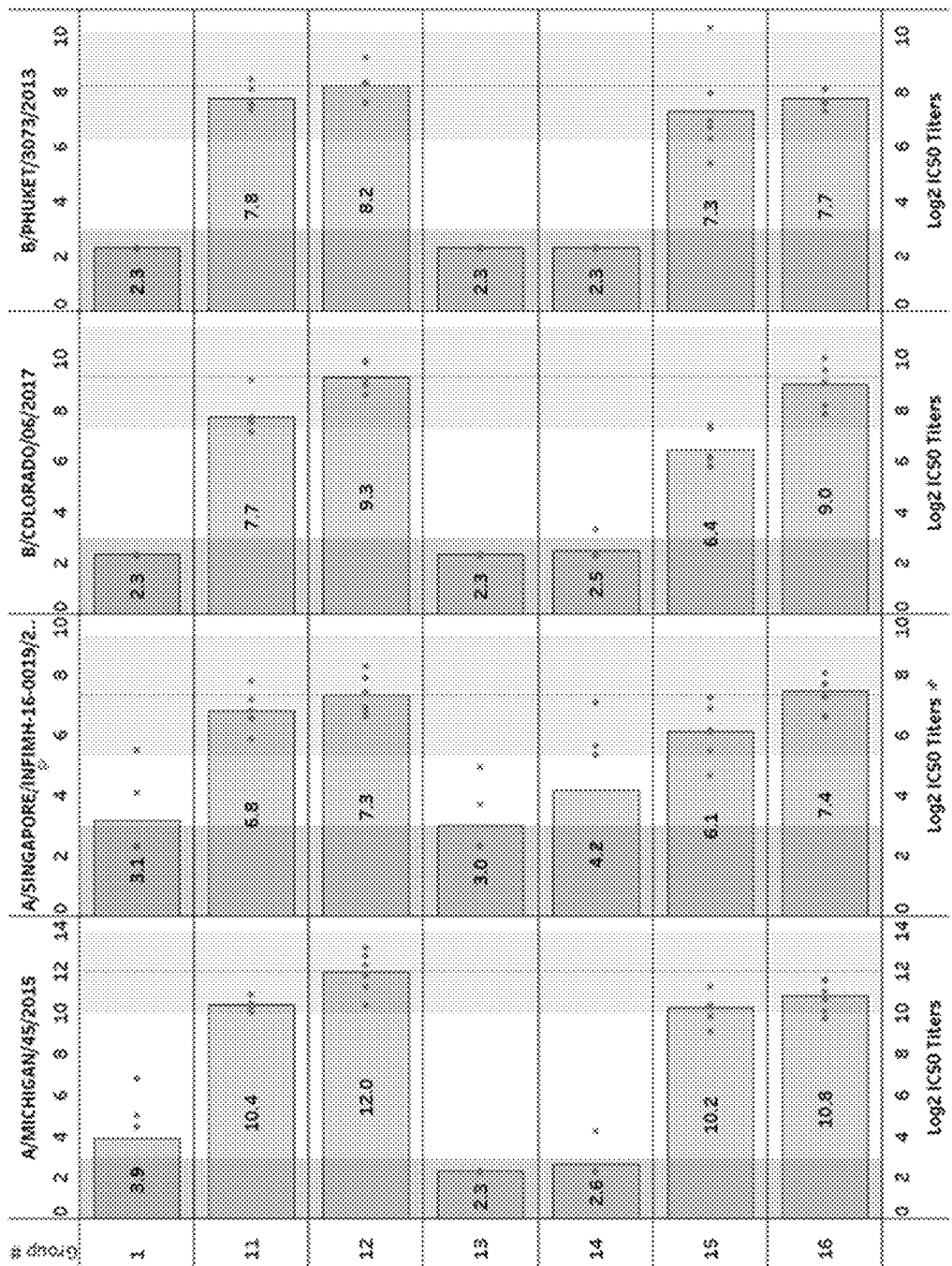

FIG. 34 depicts NAI titers for quadrivalent and octavalent mRNA-LNP vaccines, administered to ferrets for 4 different influenza strains. Samples were obtained on day 20 (D20) after the second dose of vaccine.

Figure 35:
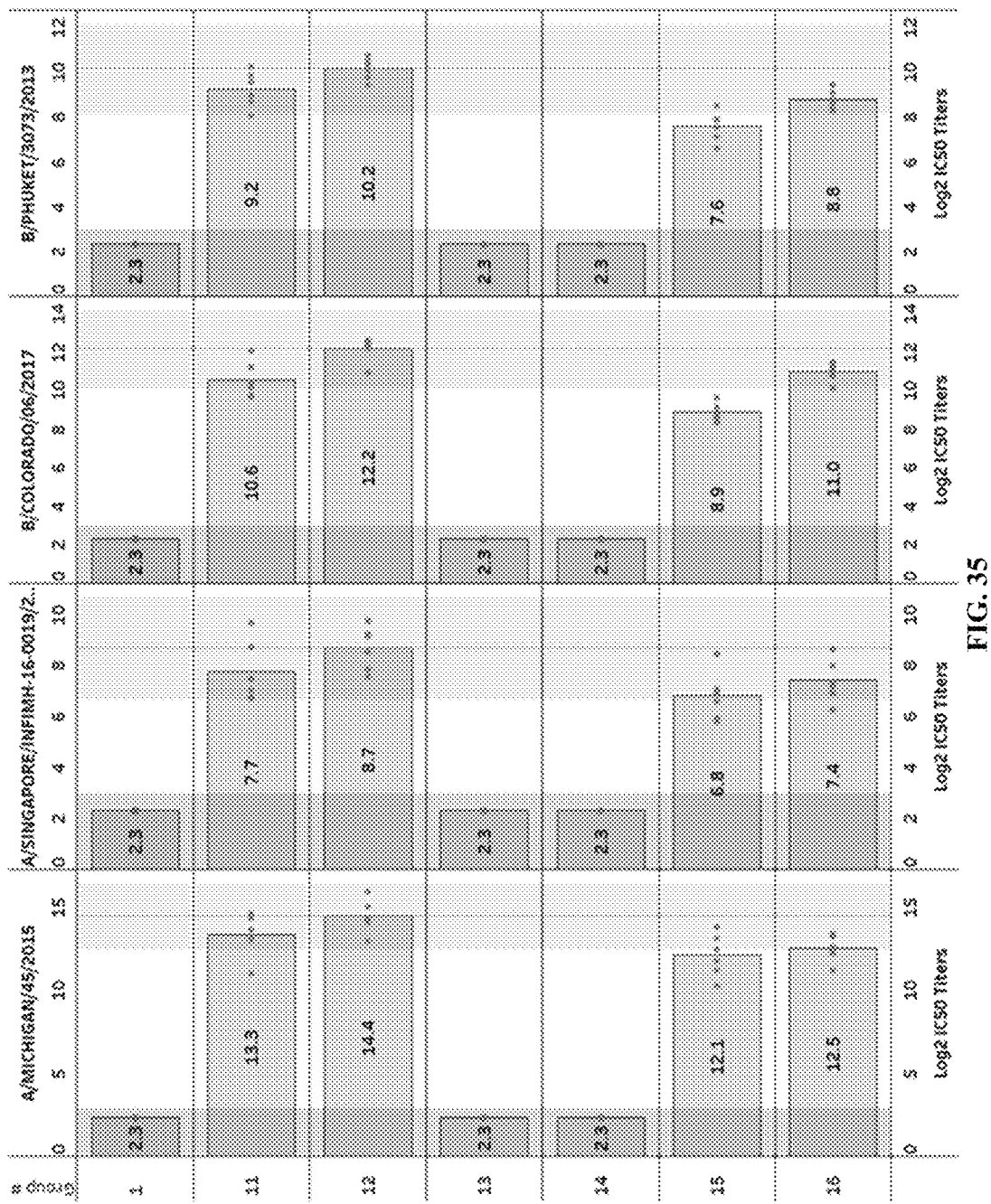

FIG. 35 depicts NAI titers for quadrivalent and octavalent mRNA-LNP vaccines, administered to ferrets for 4 different influenza strains. Samples were obtained on day 42 (D42) after the second dose of vaccine.

Figure 36:
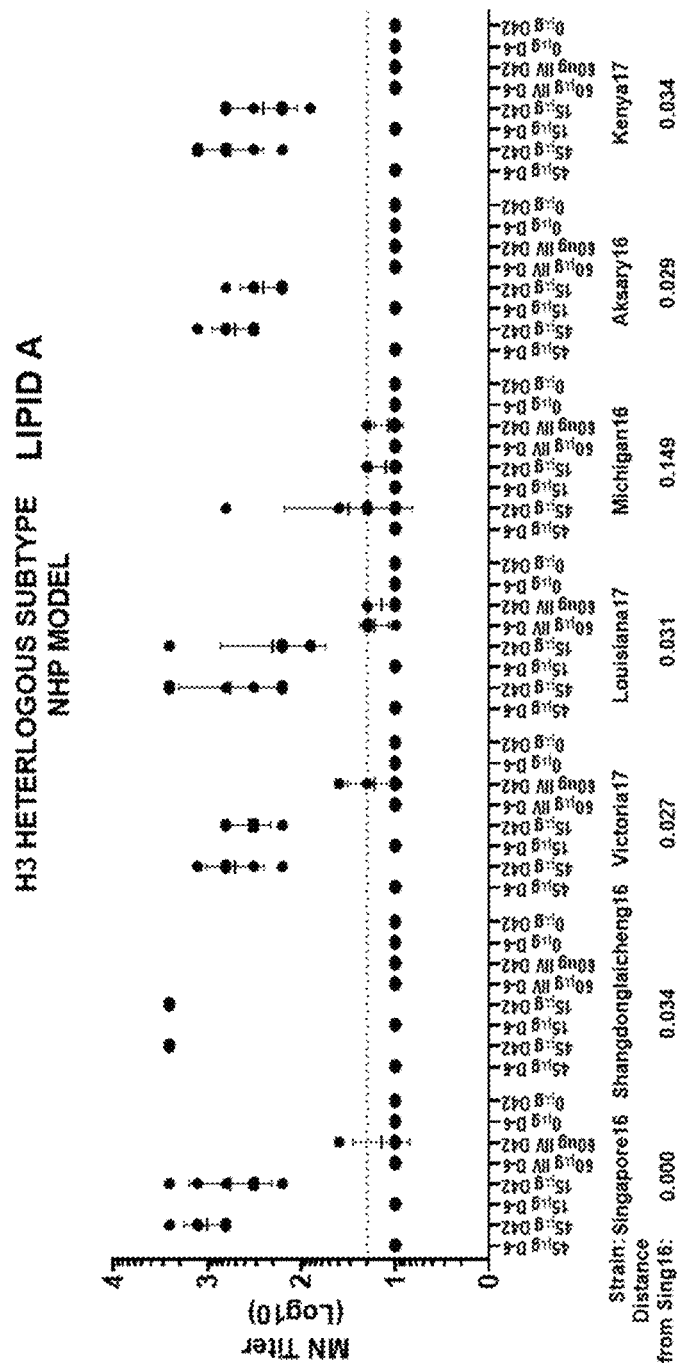

FIG. 36 depicts microneutralization titers for Sing16HA-encoding mRNA in a Lipid A LNP formulation, administered to NHPs at 15 µg and 45 µg doses. Samples were obtained on day 6 (D6) and day 42 (D42) after the second dose of vaccine.

Figure 37:
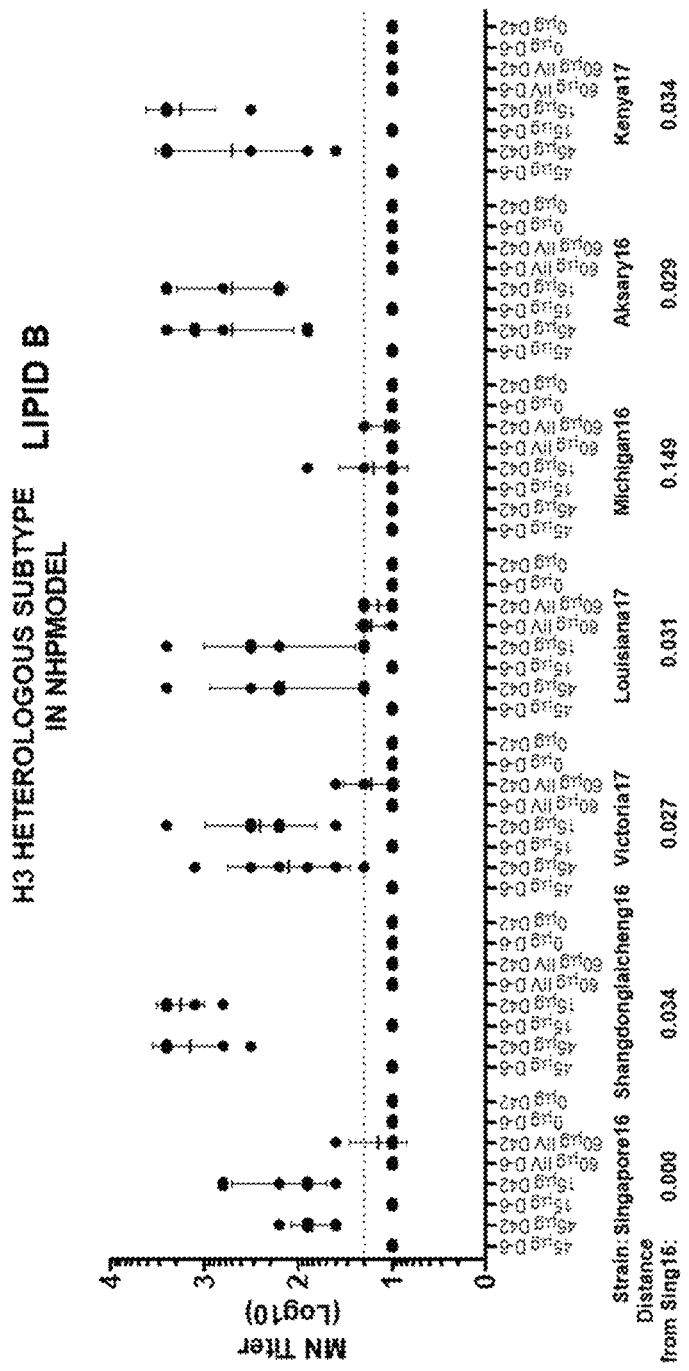

FIG. 37 depicts microneutralization titers for Sing16HA-encoding mRNA in a Lipid B LNP formulation, administered to NHPs at 15 µg and 45 µg doses. Samples were obtained on day 6 (D6) and day 42 (D42) after the second dose of vaccine.

DETAILED DESCRIPTION OF THE INVENTION

The present disclosure provides novel lipid nanoparticle (LNP) formulations for delivering mRNA vaccines in vivo and methods of making the vaccines. The LNPs are made of a mixture of four lipids: a cationic lipid, a polyethylene glycol (PEG)-conjugated lipid, a cholesterol-based lipid, and a helper lipid. The LNPs encapsulate mRNA molecules. The encapsulated mRNA molecules can be comprised of naturally-occurring ribonucleotides, chemically modified nucleotides, or a combination thereof, and can each or collectively code for one or more proteins.

The inventors have discovered the present formulations through screening combinatorial libraries of lipid components. The present LNPs encapsulate and protect the mRNA payload from degradation and facilitate cellular uptake of the encapsulated mRNA. The LNPs described herein have enhanced transfection efficiency, promote endosomal escape of the mRNA, and consequently have improved potency as demonstrated by enhanced expression in vivo and in vitro when compared to industrial formulations described in literature. For example, the LNPs disclosed herein have superior stability and/or potency profiles compared to known LNPs, e.g., heptatriaconta-6,9,28,31-tetraen-19-yl 4-(dimethylamino)butanoate (aka DLin-MC3-DMA or MC3; Semple et al., *Nat Biotechnol*. (2010) 28:172-6) or di((Z)-non-2-en-1-yl) 9-((4-(dimethylamino)butanoyl)oxy)heptadecanedioate (aka L319; Maier et al., *Mol Ther*. (2013) 21(8):1570-8). As further described below, the present formulations encapsulating an mRNA encoding hEPO, when delivered in vivo, led to high levels of erythropoietin circulating in blood at 6 hours and 24 hours, with an up to 12-fold increase, relative to the industrial standard, the MC3 LNP formulation. Similarly, high potency has been found with other mRNAs, such as those encoding influenza antigens, in both murine and non-human primate models.

The mRNA vaccines as formulated herein can be used to induce a balanced immune response comprising both cellular and humoral immunity. Because the advantages of the present LNP formulations are not sequence-specific, these formulations can be used to deliver mRNAs that encode a variety of antigens, allowing rapid deployment in epidemic or pandemic situations. Further, the present LNP-formulated mRNA vaccines are highly immunogenic and therefore provide significant dose sparing possibility.

I. Compositions of the Present Lipid Nanoparticles

The present LNPs comprise four categories of lipids: (i) an ionizable lipid; (ii) a PEGylated lipid; (iii) a cholesterol-based lipid, and (iv) a helper lipid.

A. Ionizable Lipids

An ionizable lipid facilitates mRNA encapsulation and may be a cationic lipid. A cationic lipid affords a positively charged environment at low pH to facilitate efficient encapsulation of the negatively charged mRNA drug substance.

In some embodiments, the cationic lipid is OF-02:

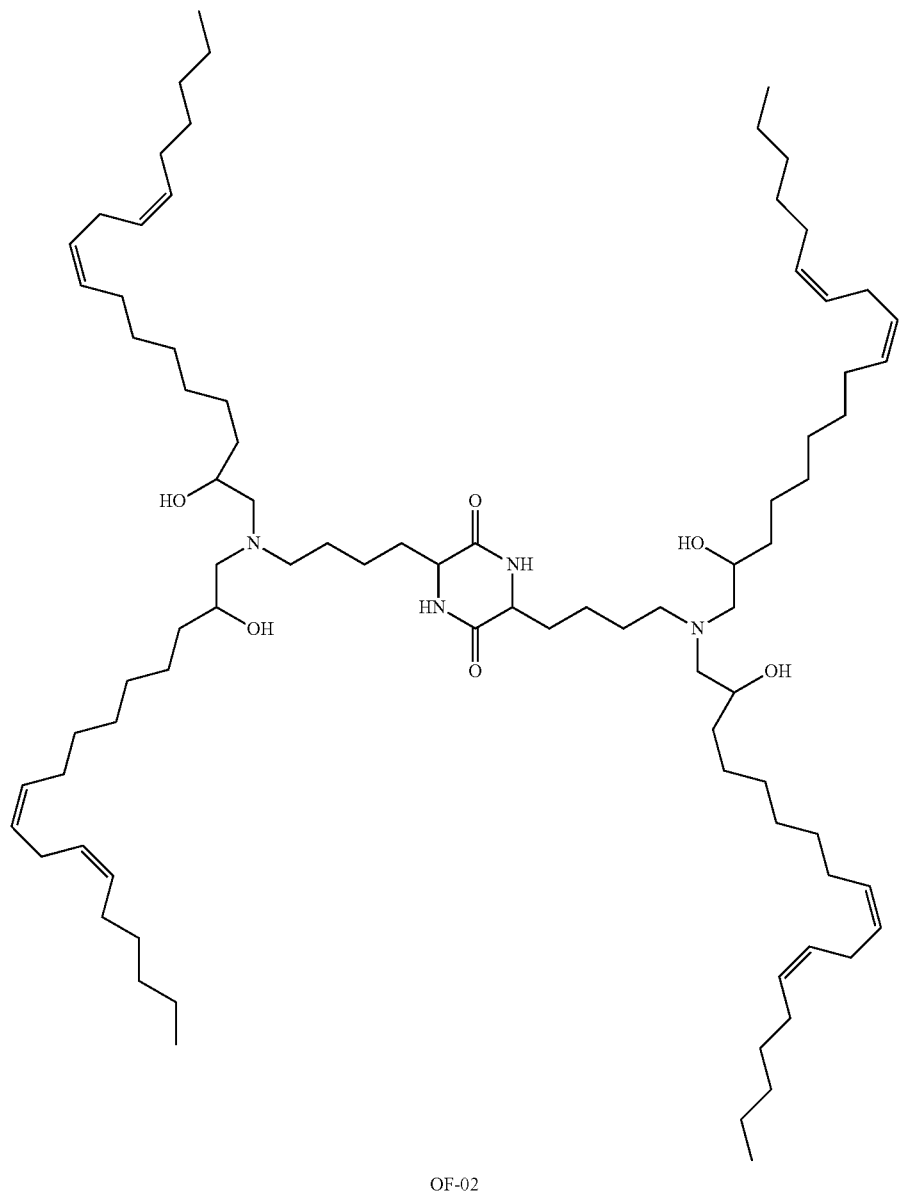

Formula (I)

OF-02

OF-02 is a non-degradable structural analog of OF-Deg-Lin. OF-Deg-Lin contains degradable ester linkages to attach the diketopiperazine core and the doubly-unsaturated tails, whereas OF-02 contains non-degradable 1,2-amino-alcohol linkages to attach the same diketopiperazine core and the doubly-unsaturated tails (Fenton et al., *Adv Mater.* (2016) 28:2939; U.S. Pat. No. 10,201,618). An exemplary LNP formulation herein, Lipid A, contains OF-2.

In some embodiments, the cationic lipid is cKK-E10 (Dong et al., *PNAS* (2014) 111(11):3955-60; U.S. Pat. No. 9,512,073):

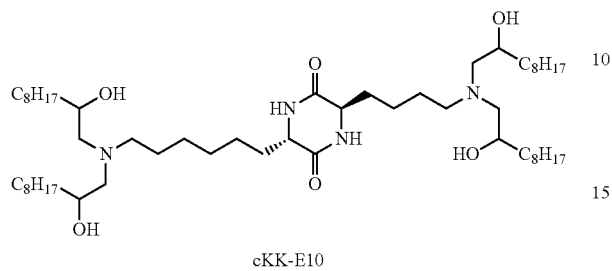

Formula (II)

cKK-E10

An exemplary LNP formulation herein, Lipid B, contains cKK-E10.

In some embodiments, the cationic lipid is GL-HEPES-E3-E10-DS-3-E18-1 (2-(4-(2-((3-(Bis((Z)-2-hydroxyoctadec-9-en-1-yl)amino)propyl)disulfaneyl)ethyl)piperazin-1-yl)ethyl 4-(bis(2-hydroxydecyl)amino)butanoate), which is a HEPES-based disulfide cationic lipid with a piperazine core, having the Formula III:

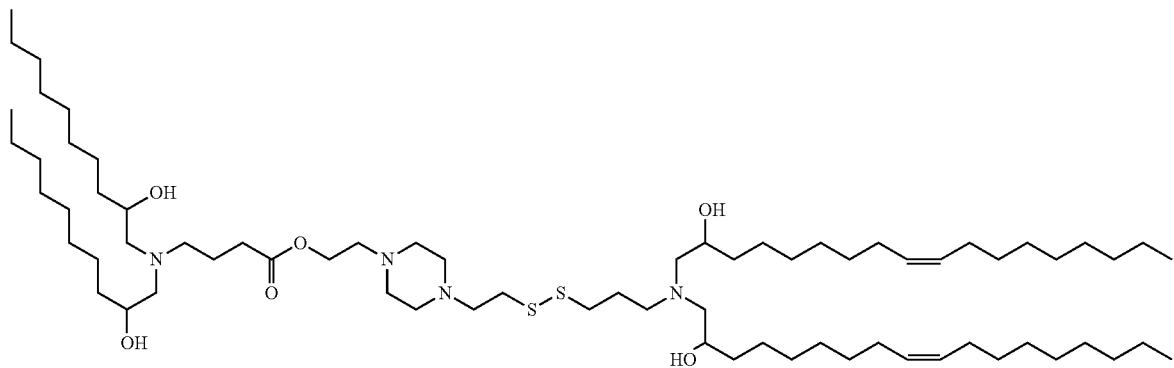

Formula (III)

An exemplary LNP formulation herein, Lipid C, contains GL-HEPES-E3-E10-DS-3-E18-1. Lipid C has the same composition as Lipid A or Lipid B but for the difference in the cationic lipid.

In some embodiments, the cationic lipid is GL-HEPES-E3-E12-DS-4-E10 (2-(4-(2-((3-(bis(2-hydroxydecyl)amino)butyl)disulfaneyl)ethyl)piperazin-1-yl)ethyl 4-(bis(2-hydroxydodecyl)amino)butanoate), which is a HEPES-based disulfide cationic lipid with a piperazine core, having the Formula IV:

Formula (IV)

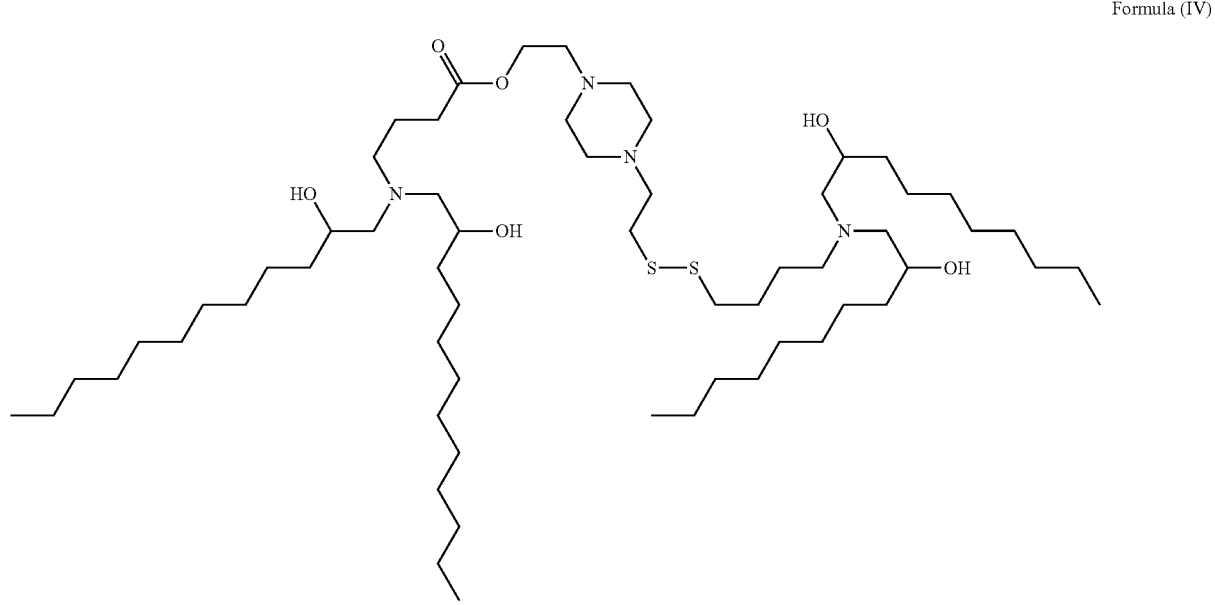 [SMILES: CCCCCCCCCCC(O)CN(CCCC(=O)OCCN1CCN(CCSSCCCCN(CC(O)CCCCCCCC)CC(O)CCCCCCCC)CC1)CC(O)CCCCCCCCCC]

An exemplary LNP formulation herein, Lipid D, contains GL-HEPES-E3-E12-DS-4-E10. Lipid D has the same composition as Lipid A or Lipid B but for the difference in the cationic lipid.

In some embodiments, the cationic lipid is GL-HEPES-E3-E12-DS-3-E14 (2-(4-(2-((3-(Bis(2-hydroxytetradecyl)amino)propyl)disulfaneyl)ethyl)piperazin-1-yl)ethyl 4-(bis(2-hydroxydodecyl)amino)butanoate), which is a HEPES-based disulfide cationic lipid with a piperazine core, having the Formula V:

Formula (V)

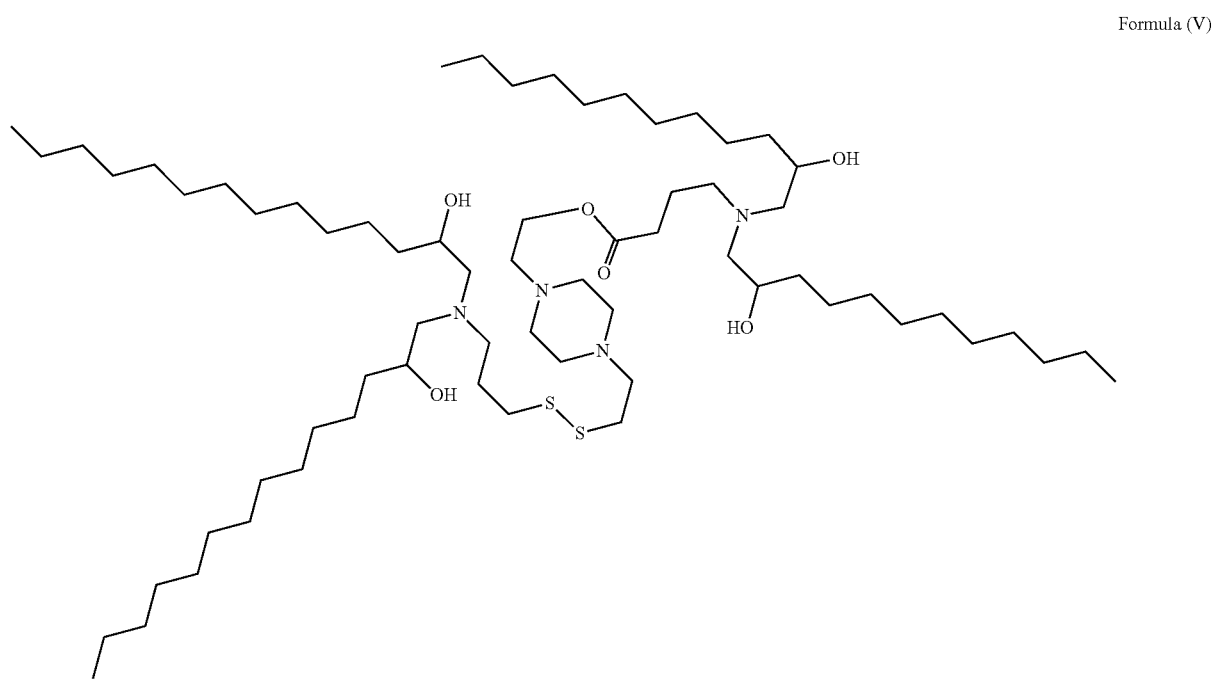 [SMILES: CCCCCCCCCCCCC(O)CN(CCCSSCCN1CCN(CCOC(=O)CCCN(CC(O)CCCCCCCCCC)CC(O)CCCCCCCCCC)CC1)CC(O)CCCCCCCCCCCC]

An exemplary LNP formulation herein, Lipid E, contains GL-HEPES-E3-E12-DS-3-E14. Lipid E has the same composition as Lipid A or Lipid B but for the difference in the cationic lipid.

The cationic lipids GL-HEPES-E3-E10-DS-3-E18-1 (III), GL-HEPES-E3-E12-DS-4-E10 (IV), and GL-HEPES-E3-E12-DS-3-E14 (V) can be synthesized according to the general procedure set out in Scheme 1:

Other cationic lipids that can be used include those described in Dong, supra; and U.S. Pat. No. 10,201,618.

B. PEGylated Lipids

The PEGylated lipid component provides control over particle size and stability of the nanoparticle. The addition of such components may prevent complex aggregation and

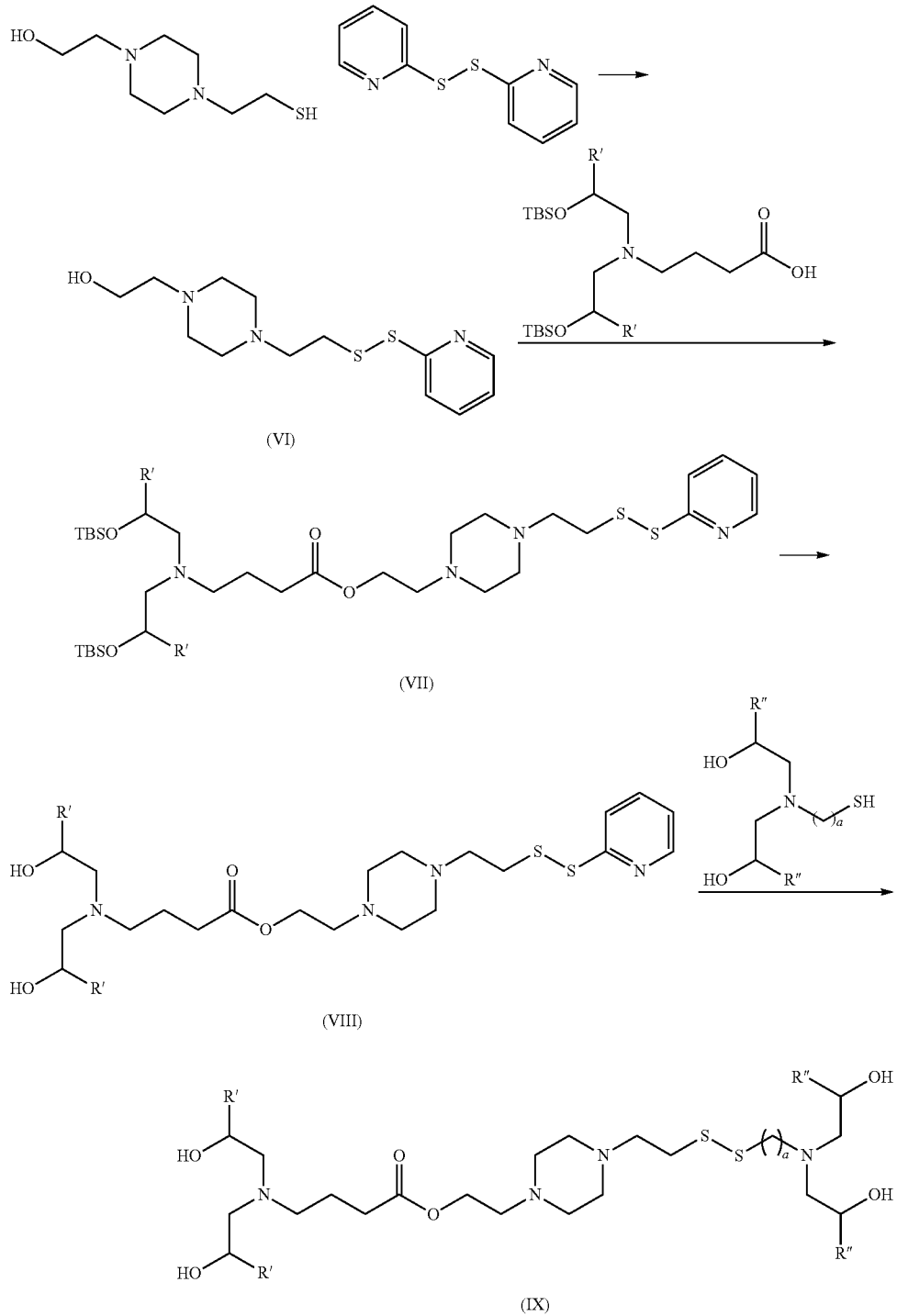

Scheme 1: General Synthetic Scheme for Lipids of Formulas (III), (IV), and (V)

provide a means for increasing circulation lifetime and increasing the delivery of the lipid-nucleic acid pharmaceutical composition to target tissues (Klibanov et al., *FEBS Letters* (1990) 268 (1):235-7). These components may be selected to rapidly exchange out of the pharmaceutical composition in vivo (see, e.g., U.S. Pat. No. 5,885,613).

Contemplated PEGylated lipids include, but are not limited to, a polyethylene glycol (PEG) chain of up to 5 kDa in length covalently attached to a lipid with alkyl chain(s) of $C_6$-$C_{20}$ (e.g., $C_8$, $C_{10}$, $C_{12}$, $C_{14}$, $C_{16}$, or $C_{18}$) length, such as a derivatized ceramide (e.g., N-octanoyl-sphingosine-1-[succinyl(methoxypolyethylene glycol)] (C8 PEG ceramide)). In some embodiments, the PEGylated lipid is 1,2-dimyristoyl-rac-glycero-3-methoxypolyethylene glycol (DMG-PEG); 1,2-distearoyl-sn-glycero-3-phosphoethanolamine-polyethylene glycol (DSPE-PEG); 1,2-dilauroyl-sn-glycero-3-phosphoethanolamine-polyethylene glycol (DLPE-PEG); or 1,2-distearoyl-rac-glycero-polyethelene glycol (DSG-PEG).

In particularly exemplary embodiments, the PEG has a high molecular weight, e.g., 2000-2400 g/mol. In some embodiments, the PEG is PEG2000 (or PEG-2K). In particular embodiments, the PEGylated lipid herein is DMG-PEG2000, DSPE-PEG2000, DLPE-PEG2000, DSG-PEG2000, or C8 PEG2000.

C. Cholesterol-Based Lipids

The cholesterol component provides stability to the lipid bilayer structure within the nanoparticle. In some embodiments, the LNPs comprise one or more cholesterol-based lipids. Suitable cholesterol-based lipids include, for example: DC-Choi (N,N-dimethyl-N-ethylcarboxamido-cholesterol), 1,4-bis(3-N-oleylamino-propyl)piperazine (Gao et al., *Biochem Biophys Res Comm.* (1991) 179:280; Wolf et al., *BioTechniques* (1997) 23:139; U.S. Pat. No. 5,744,335), imidazole cholesterol ester ("ICE"; WO 2011/068810), ß-sitosterol, fucosterol, stigmasterol, and other modified forms of cholesterol. In some embodiments, the cholesterol-based lipid used in the LNPs is cholesterol.

D. Helper Lipids

A helper lipid enhances the structural stability of the LNP and helps the LNP in endosome escape. It improves uptake and release of the mRNA drug payload. In some embodiments, the helper lipid is a zwitterionic lipid, which has fusogenic properties for enhancing uptake and release of the drug payload. Examples of helper lipids are 1,2-dioleoyl-SN-glycero-3-phosphoethanolamine (DOPE); 1,2-distearoyl-sn-glycero-3-phosphocholine (DSPC); 1,2-dioleoyl-sn-glycero-3-phospho-L-serine (DOPS); 1,2-dielaidoyl-sn-glycero-3-phosphoethanolamine (DEPE); and 1,2-dioleoyl-sn-glycero-3-phosphocholine (DPOC), dipalmitoylphosphatidylcholine (DPPC), 1,2-dilauroyl-sn-glycero-3-phosphocholine (DLPC), 1,2-Distearoylphosphatidylethanolamine (DSPE), and 1,2-dilauroyl-sn-glycero-3-phosphoethanolamine (DLPE).

Other exemplary helper lipids are dioleoylphosphatidylcholine (DOPC), dioleoylphosphatidylglycerol (DOPG), dipalmitoylphosphatidylglycerol (DPPG), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a combination thereof.

In particular embodiments, the helper lipid is DOPE. In further embodiments, the present LNPs comprise (i) a cationic lipid selected from OF-02, cKK-E10, GL-HEPES-E3-E10-DS-3-E18-1, GL-HEPES-E3-E12-DS-4-E10, or GL-HEPES-E3-E12-DS-3-E14; (ii) DMG-PEG2000; (iii) cholesterol; and (iv) DOPE.

E. Molar Ratios of the Lipid Components

The inventors have discovered that specific molar ratios of the above components are important for the LNPs' effectiveness in delivering mRNA. The molar ratio of the cationic lipid, the PEGylated lipid, the cholesterol-based lipid, and the helper lipid is A:B:C:D, where A+B+C+D=100%. In some embodiments, the molar ratio of the cationic lipid in the LNPs relative to the total lipids (i.e., A) is 35-45% (e.g., 38-42% such as 40%). In some embodiments, the molar ratio of the PEGylated lipid component relative to the total lipids (i.e., B) is 0.25-2.75% (e.g., 1-2% such as 1.5%). In some embodiments, the molar ratio of the cholesterol-based lipid relative to the total lipids (i.e., C) is 20-35% (e.g., 27-30% such as 28.5%). In some embodiments, the molar ratio of the helper lipid relative to the total lipids (i.e., D) is 25-35% (e.g., 28-32% such as 30%). In some embodiments, the (PEGylated lipid+cholesterol) components have the same molar amount as the helper lipid. In some embodiments, the LNPs contain a molar ratio of the cationic lipid to the helper lipid that is more than 1.

In particular embodiments, the LNPs contain a cationic lipid, a PEGylated lipid, a cholesterol-based lipid, and a helper lipid at a molar ratio of 40:1.5:28.5:30. In further specific embodiments, the LNPs contain (i) OF-02, cKK-E10, GL-HEPES-E3-E10-DS-3-E18-1, GL-HEPES-E3-E12-DS-4-E10, or GL-HEPES-E3-E12-DS-3-E14; (ii) DMG-PEG2000; (iii) cholesterol; and (iv) DOPE at 40:1.5:28.5:30.

To calculate the actual amount of each lipid to be put into an LNP formulation, the molar amount of the cationic lipid is first determined based on a desired N/P ratio, where N is the number of nitrogen atoms in the cationic lipid and P is the number of phosphate groups in the mRNA to be transported by the LNP. Next, the molar amount of each of the other lipids is calculated based on the molar amount of the cationic lipid and the molar ratio selected. These molar amounts are then converted to weights using the molecular weight of each lipid.

F. Active Ingredients of the LNPs

The active ingredient of the present LNP vaccine composition is an mRNA that encodes an antigen of interest. The antigen may be a polypeptide derived from a virus, for example, influenza virus, coronavirus (e.g., SARS-COV-1, SARS-COV-2, or MERS-related virus), Ebola virus, Dengue virus, human immunodeficiency virus (HIV), hepatitis A virus (HAV), hepatitis B virus (HBV), hepatitis C virus (HCV), herpes simplex virus (HSV), respiratory syncytial virus (RSV), rhinovirus, cytomegalovirus (CMV), zika virus, human papillomavirus (HPV), human metapneumovirus (hMPV), human parainfluenza virus type 3 (PIV3), Epstein-Barr virus (EBV), chikungunya virus, or respiratory syncytial virus (RSV).

The antigen also may be derived from a bacterium, for example, *Staphylococcus aureus, Moraxella* (e.g.,

*Moraxella catarrhalis*; causing otitis, respiratory infections, and/or sinusitis), *Chlamydia trachomatis* (causing *chlamydia*), *Borrelia* (e.g., *Borrelia burgdorferi* causing Lyme Disease), *Bacillus anthracis* (causing anthrax), *Salmonella typhi* (causing typhoid fever), *Mycobacterium tuberculosis* (causing tuberculosis), *Propionibacterium acnes* (causing acne), or non-typeable *Haemophilus influenzae*.

Where desired, the LNP or the LNP formulation may be multi-valent. In some embodiments, the LNP may carry mRNAs that encode more than one antigen, such as two, three, four, five, six, seven, eight, nine, ten, or more antigens, from the same or different pathogens. For example, the LNP may carry multiple mRNA molecules, each encoding a different antigen; or carry a polycistronic mRNA that can be translated into more than one antigen (e.g., each antigen-coding sequence is separated by a nucleotide linker encoding a self-cleaving peptide such as a 2A peptide). An LNP carrying different mRNA molecules typically comprises (encapsulate) multiple copies of each mRNA molecule. For example, an LNP carrying or encapsulating two different mRNA molecules typically carries multiple copies of each of the two different mRNA molecules.

In some embodiments, a single LNP formulation may comprise multiple kinds (e.g., two, three, four, five, six, seven, eight, nine, ten, or more) of LNPs, each kind carrying a different mRNA.

Examples of multi-valent LNP vaccines are those containing mRNAs encoding two or more antigens from the above-listed pathogens, such as LNP vaccines comprising mRNAs encoding polypeptides derived from influenza virus. In some embodiments, the multi-valent LNP vaccines contain mRNA molecules encoding polypeptides derived from two or more (e.g., three, four, five, six, seven, eight, nine, or ten) influenza viral proteins selected from hemagglutinin (e.g., hemagglutinin 1 (HA1) and hemagglutinin 2 (HA2)), neuraminidase (NA), nucleoprotein (NP), matrix protein 1 (M1), matrix protein 2 (M2), nonstructural protein 1 (NS1), and non-structural protein 2 (NS2). In further embodiments, the multi-valent LNP vaccines containing two or more (e.g., three, four five, six, seven, eight, or more) mRNA molecules encoding antigenic polypeptides derived from an HA protein, from an NA protein, and from both HA and NA proteins. In some embodiments, the mRNA molecules encoding antigenic polypeptides are derived from different influenza strains.

In certain embodiments, the composition may comprise one or more mRNA molecules encoding antigens of influenza A, B and C viruses. In one embodiment, the composition may comprise one or more mRNA molecules encoding HA and/or NA antigens of influenza A and influenza B viruses. In one embodiment, the HA antigens of influenza A viruses are selected from subtypes H1, H2, H3, H4, H5, H6, H7, H8, H9, H10, H11, H12, H13, H14, H15, H16, H17, and H18. In one embodiment, the NA antigens of influenza A viruses are selected from subtypes N1, N2, N3, N4, N5, N6, N7, N8, N9, N10, and N11. In one embodiment, the HA and NA antigens of Influenza B viruses are from the Influenza B/Yamagata lineage. In one embodiment, the HA and NA antigens of Influenza B viruses are from the Influenza B/Victoria lineage. In some embodiments, the one or more HA and NA antigens are from influenza virus strains recommended by the World Health Organization (WHO) in their annual recommendation for influenza vaccine formulations.

In certain embodiments, at least one of the one or more influenza virus proteins comprises an influenza virus HA protein and/or an influenza virus NA protein having a molecular sequence identified or designed from a machine learning model, and in certain embodiments, at least one of the one or more ribonucleic acid molecules encode one or more influenza virus proteins having a molecular sequence identified or designed from a machine learning model.

In certain embodiments, the composition comprises two, three, four, five, six, seven, eight, nine, or more mRNA molecules encoding (i) one or more HA antigens, (ii) one or more NA antigens, or (iii) a combination of one or more HA antigens and NA antigens.

In one embodiment, the composition comprises two, three, four, five, six, seven, eight, nine, or more mRNA molecules encoding (i) one or more HA antigens, (ii) one or more NA antigens, or (iii) a combination of one or more HA antigens and NA antigens, selected from H1N1, H3N2, H2N2, H5N1, H7N9, H7N7, H1N2, H9N2, H7N2, H7N3, H5N2, and H10N7 subtypes and/or B/Yamagata and B/Victoria lineages.

In one embodiment, the composition comprises one mRNA molecule encoding an H3 HA antigen, one mRNA molecule encoding an H1 HA antigen, one mRNA molecule encoding an HA antigen from the Influenza B/Yamagata lineage, and one mRNA molecule encoding an HA antigen from the Influenza B/Victoria lineage.

In one embodiment, the composition comprises one mRNA molecule encoding an H3 HA antigen, one mRNA molecule encoding an N2 NA antigen, one mRNA molecule encoding an H1 HA antigen, one mRNA molecule encoding an N1 NA antigen, one mRNA molecule encoding an HA antigen from the Influenza B/Yamagata lineage, one mRNA molecule encoding an NA antigen from the Influenza B/Yamagata lineage, one mRNA molecule encoding an HA antigen from the Influenza B/Victoria lineage, and one mRNA molecule encoding an NA antigen from the Influenza B/Victoria lineage.

In an embodiment, the composition comprises further comprise one or more mRNA molecules encoding a machine learning influenza virus HA having a molecular sequence identified or designed from a machine learning model, wherein the one or more machine learning influenza virus HA may be selected from an H1 HA, an H3 HA, an HA from a B/Victoria lineage, an HA from a B/Yamagata lineage, or a combination thereof.

When selecting one or more machine learning influenza virus HAs, any machine learning algorithm may be used. For example, envisioned herein are any of the machine learning algorithms and methods disclosed in PCT Application Nos. WO 2021/080990 A1, entitled Systems and Methods for Designing Vaccines, and WO 2021/080999 A1, entitled Systems and Methods for Predicting Biological Responses, both of which are incorporated by reference in their entireties herein.

The mRNA molecule may be unmodified (i.e., containing only natural ribonucleotides A, U, C, and/or G linked by phosphodiester bonds), or chemically modified (e.g., including nucleotide analogs such as pseudouridines (e.g., N-1-methyl pseudouridine), 2'-fluoro ribonucleotides, and 2'-methoxy ribonucleotides, and/or phosphorothioate bonds). The mRNA molecule may comprise a 5' cap and a polyA tail.

RSV F Protein:

Respiratory syncytial virus (RSV) is a negative-sense, single-stranded RNA virus belonging to the *Pneumoviridae* family. RSV can cause infection of the respiratory tract. RSV is an enveloped virus with a glycoprotein (G protein), small hydrophobic protein (SH protein), and a fusion protein (F protein) on the surface.

The RSV F protein is responsible for fusion of viral and host cell membranes and takes on at least three conformations (pre-fusion, intermediate, and post-fusion conformations). In the pre-fusion conformation (pre-fusion, Pre-F), the F protein exists in a trimeric form with the major antigenic site Ø exposed. Site Ø serves as a primary target of neutralizing antibodies produced by RSV-infected subjects (see, Coultas et al., Thorax. 74: 986-993. 2019; McLellan et al., Science. 340(6136): 1113-7. 2013). After binding to its target on the host cell surface, Pre-F undergoes a conformational change during which site Ø is no longer exposed. Pre-F transitions into a transient intermediate conformation, enabling the F protein to insert into the host cell membrane, leading to fusion of the viral and host cell membranes. A final conformational shift results in a more stable and elongated form of the protein (post-fusion, Post-F). Site II and Site IV of the F protein are specific to Post-F, while Site I is present in both the Pre-F and Post-F conformations (McLellan et al., J. Virol. 85(15): 7788-7796. 2011).

As used herein, the term "F protein" or "RSV F protein" refers to the protein of RSV responsible for driving fusion of the viral envelope with host cell membrane during viral entry.

As used herein, the term "RSV F polypeptide" or "F polypeptide" refers to a polypeptide comprising at least one epitope of F protein.

As used herein, the term "post-fusion" with respect to RSV F refers to a stable conformation of RSV F that occurs after merging of the virus and cell membranes.

As used herein, the term "pre-fusion" with respect to RSV F refers to a conformation of RSV F that is adopted before virus-cell interaction.

Provided herein are mRNA molecules that encode for antigenic RSV F polypeptides.

In some embodiments, the mRNA molecule comprises an open reading frame (ORF) encoding a respiratory syncytial virus (RSV) F protein antigen.

In some embodiments, the RSV F protein antigen comprises a sequence having at least 85%, 90%, 95%, 97%, 98%, 99%, or 99.5% identity to an amino acid sequence set forth in SEQ ID NO: 16.

In some embodiments, the RSV F protein antigen comprises an amino acid sequence with at least 98% identity to SEQ ID NO: 16 or consists of an amino acid sequence of SEQ ID NO: 16.

In some embodiments, the mRNA comprises a nucleic acid sequence with at least 80%, at least 85%, at least 90%, at least 91%, at least 92%, at least 93%, at least 94%, at least 95%, at least 96%, at least 97%, at least 98%, at least 99%, or 100% identity to the nucleic acid sequence set forth in SEQ ID NO: 17.

In some embodiments, the mRNA comprises a nucleic acid sequence with at least 80%, at least 85%, at least 90%, at least 91%, at least 92%, at least 93%, at least 94%, at least 95%, at least 96%, at least 97%, at least 98%, at least 99%, or 100% identity to the nucleic acid sequence set forth in SEQ ID NO: 21.

In some embodiments, the RSV F protein antigen is a pre-fusion protein.

In some embodiments, wherein the ORF is codon optimized.

In some embodiments, wherein the mRNA molecule comprises at least one 5' untranslated region (5' UTR), at least one 3' untranslated region (3' UTR), and at least one polyadenylation (poly(A)) sequence.

In some embodiments, the mRNA comprises at least one chemical modification.

In some embodiments, at least 20%, at least 30%, at least 40%, at least 50%, at least 60%, at least 70%, at least 80%, at least 85%, at least 90%, at least 95%, or 100% of the uracil nucleotides in the mRNA are chemically modified.

In some embodiments, at least 20%, at least 30%, at least 40%, at least 50%, at least 60%, at least 70%, at least 80%, at least 85%, at least 90%, at least 95%, or 100% of the uracil nucleotides in the ORF are chemically modified.

In some embodiments, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

In some embodiments, the chemical modification is selected from the group consisting of pseudouridine, N1-methylpseudouridine, 5-methylcytosine, 5-methoxyuridine, and a combination thereof. In some embodiments, the chemical modification is N1-methylpseudouridine.

In some embodiments, the mRNA comprises of the following structural elements:

(i) a 5' cap with the following structure:

(ii) a 5' untranslated region (5' UTR) having the nucleic acid sequence of SEQ ID NO: 19;
(iii) a protein coding region having the nucleic acid sequence of SEQ ID NO: 17;
(iv) a 3' untranslated region (3' UTR) having the nucleic acid sequence of SEQ ID NO: 20; and
(v) a poly(A) tail.

G. Buffer and Other Components

To stabilize the nucleic acid and/or LNPs (e.g., to prolong the shelf-life of the vaccine product), to facilitate administration of the LNP pharmaceutical composition, and/or to enhance in vivo expression of the nucleic acid, the nucleic acid and/or LNP can be formulated in combination with one or more carriers, targeting ligands, stabilizing reagents (e.g., preservatives and antioxidants), and/or other pharmaceutically acceptable excipients. Examples of such excipients are parabens, thimerosal, thiomersal, chlorobutanol, bezalkonium chloride, chelators (e.g., EDTA) and the like.

The LNP compositions of the present disclosure can be provided as a frozen liquid form or a lyophilized form. A variety of cryoprotectants may be used, including, without limitations, sucrose, trehalose, glucose, mannitol, mannose, dextrose, and the like. The cryoprotectant may constitute 5-30% (w/v) of the LNP composition. In some embodiments, the LNP composition comprises trehalose, e.g., at 5-30% (e.g., 10%) (w/v). Once formulated with the cryoprotectant, the LNP compositions may be frozen (or lyophilized and cryopreserved) at −20° C. to −80° C.

The LNP compositions may be provided to a patient in an aqueous buffered solution—thawed if previously frozen, or if previously lyophilized, reconstituted in an aqueous buffered solution at bedside. In particularly exemplary embodiments, the buffered solution is isotonic and suitable for e.g., intramuscular or intradermal injection. In some embodiments, the buffered solution is a phosphate-buffered saline (PBS).

II. RNA

The present LNP vaccine compositions of the disclosure may comprise an RNA molecule (e.g., mRNA) that encodes an antigen of interest. The RNA molecule of the present disclosure may comprise at least one ribonucleic acid (RNA) comprising an ORF encoding an antigen of interest. In certain embodiments, the RNA is a messenger RNA (mRNA) comprising an ORF encoding an antigen of interest. In certain embodiments, the RNA (e.g., mRNA) further comprises at least one 5' UTR, 3' UTR, a poly(A) tail, and/or a 5' cap.

II. A. 5' Cap

An mRNA 5' cap can provide resistance to nucleases found in most eukaryotic cells and promote translation efficiency. Several types of 5' caps are known. A 7-methylguanosine cap (also referred to as "m$^7$G" or "Cap-0"), comprises a guanosine that is linked through a 5'-5'-triphosphate bond to the first transcribed nucleotide.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp, (5'(A,G(5')ppp(5')A, and G(5')ppp(5')G. Additional cap structures are described in U.S. Publication No. US 2016/0032356 and U.S. Publication No. US 2018/0125989, which are incorporated herein by reference.

5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5')G (the ARCA cap); G(5')ppp(5')A; G(5')ppp(5')G; m7G(5')ppp(5')A; m7G(5')ppp(5')G; m7G(5')ppp(5')(2'OMeA)pG; m7G(5')ppp(5')(2'OMeA)pU; m7G(5')ppp(5')(2'OMeG)pG (New England BioLabs, Ipswich, MA; TriLink Biotechnologies). 5'-capping of modified RNA may be completed post-transcriptionally using a vaccinia virus capping enzyme to generate the Cap 0 structure: m7G(5')ppp(5')G. Cap 1 structure may be generated using both vaccinia virus capping enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase.

In certain embodiments, the mRNA of the disclosure comprises a 5' cap selected from the group consisting of 3'-O-Me-m7G(5')ppp(5')G (the ARCA cap), G(5')ppp(5')A, G(5')ppp(5')G, m7G(5')ppp(5')A, m7G(5')ppp(5')G, m7G(5')ppp(5')(2'OMeA)pG, m7G(5')ppp(5')(2'OMeA)pU, and m7G(5')ppp(5')(2'OMeG)pG.

In certain embodiments, the mRNA of the disclosure comprises a 5' cap of:

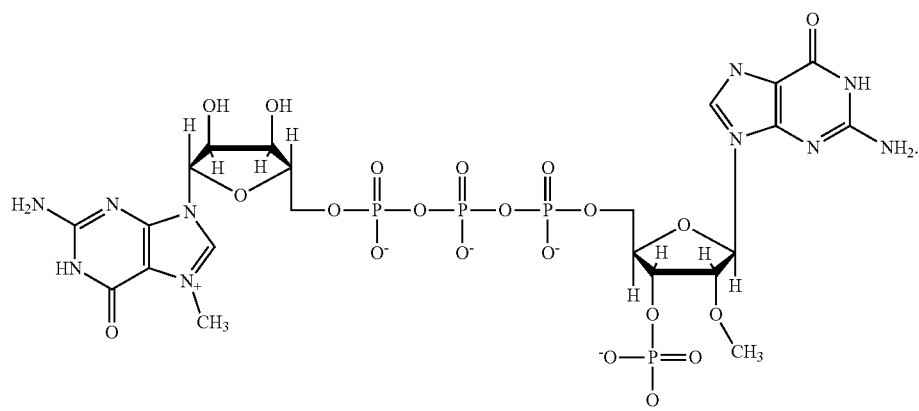

II. B. Untranslated Region (UTR)

In some embodiments, the mRNA of the disclosure includes a 5' and/or 3' untranslated region (UTR). In mRNA, the 5' UTR starts at the transcription start site and continues to the start codon but does not include the start codon. The 3' UTR starts immediately following the stop codon and continues until the transcriptional termination signal.

In some embodiments, the mRNA disclosed herein may comprise a 5' UTR that includes one or more elements that affect an mRNA's stability or translation. In some embodiments, a 5' UTR may be about 10 to 5,000 nucleotides in length. In some embodiments, a 5' UTR may be about 50 to 500 nucleotides in length. In some embodiments, the 5' UTR is at least about 10 nucleotides in length, about 20 nucleotides in length, about 30 nucleotides in length, about 40 nucleotides in length, about 50 nucleotides in length, about 100 nucleotides in length, about 150 nucleotides in length, about 200 nucleotides in length, about 250 nucleotides in length, about 300 nucleotides in length, about 350 nucleotides in length, about 400 nucleotides in length, about 450 nucleotides in length, about 500 nucleotides in length, about 550 nucleotides in length, about 600 nucleotides in length, about 650 nucleotides in length, about 700 nucleotides in length, about 750 nucleotides in length, about 800 nucleotides in length, about 850 nucleotides in length, about 900 nucleotides in length, about 950 nucleotides in length, about 1,000 nucleotides in length, about 1,500 nucleotides in length, about 2,000 nucleotides in length, about 2,500 nucleotides in length, about 3,000 nucleotides in length, about 3,500 nucleotides in length, about 4,000 nucleotides in length, about 4,500 nucleotides in length or about 5,000 nucleotides in length.

In some embodiments, the mRNA disclosed herein may comprise a 3' UTR comprising one or more of a polyadenylation signal, a binding site for proteins that affect an mRNA's stability of location in a cell, or one or more binding sites for miRNAs. In some embodiments, a 3' UTR may be 50 to 5,000 nucleotides in length or longer. In some embodiments, a 3' UTR may be 50 to 1,000 nucleotides in length or longer. In some embodiments, the 3' UTR is at least about 50 nucleotides in length, about 100 nucleotides in length, about 150 nucleotides in length, about 200 nucleotides in length, about 250 nucleotides in length, about 300 nucleotides in length, about 350 nucleotides in length, about 400 nucleotides in length, about 450 nucleotides in length, about 500 nucleotides in length, about 550 nucleotides in length, about 600 nucleotides in length, about 650 nucleotides in length, about 700 nucleotides in length, about 750 nucleotides in length, about 800 nucleotides in length, about 850 nucleotides in length, about 900 nucleotides in length, about 950 nucleotides in length, about 1,000 nucleotides in length, about 1,500 nucleotides in length, about 2,000 nucleotides in length, about 2,500 nucleotides in length, about 3,000 nucleotides in length, about 3,500 nucleotides in length, about 4,000 nucleotides in length, about 4,500 nucleotides in length, or about 5,000 nucleotides in length.

In some embodiments, the mRNA disclosed herein may comprise a 5' or 3' UTR that is derived from a gene distinct from the one encoded by the mRNA transcript (i.e., the UTR is a heterologous UTR).

In certain embodiments, the 5' and/or 3' UTR sequences can be derived from mRNA which are stable (e.g., globin, actin, GAPDH, tubulin, histone, or citric acid cycle enzymes) to increase the stability of the mRNA. For example, a 5' UTR sequence may include a partial sequence of a CMV immediate-early 1 (IE1) gene, or a fragment thereof, to improve the nuclease resistance and/or improve the half-life of the mRNA. Also contemplated is the inclusion of a sequence encoding human growth hormone (hGH), or a fragment thereof, to the 3' end or untranslated region of the mRNA. Generally, these modifications improve the stability and/or pharmacokinetic properties (e.g., half-life) of the mRNA relative to their unmodified counterparts, and include, for example, modifications made to improve such mRNA resistance to in vivo nuclease digestion.

Exemplary 5' UTRs include a sequence derived from a CMV immediate-early 1 (IE1) gene (U.S. Publication Nos. 2014/0206753 and 2015/0157565, each of which is incorporated herein by reference), or the sequence GGGAUCCUACC (SEQ ID NO: 22) (U.S. Publication No. 2016/0151409, incorporated herein by reference).

In various embodiments, the 5' UTR may be derived from the 5' UTR of a TOP gene. TOP genes are typically characterized by the presence of a 5'-terminal oligopyrimidine (TOP) tract. Furthermore, most TOP genes are characterized by growth-associated translational regulation. However, TOP genes with a tissue specific translational regulation are also known. In certain embodiments, the 5' UTR derived from the 5' UTR of a TOP gene lacks the 5' TOP motif (the oligopyrimidine tract) (e.g., U.S. Publication Nos. 2017/0029847, 2016/0304883, 2016/0235864, and 2016/0166710, each of which is incorporated herein by reference).

In certain embodiments, the 5' UTR is derived from a ribosomal protein Large 32 (L32) gene (U.S. Publication No. 2017/0029847, supra).

In certain embodiments, the 5' UTR is derived from the 5' UTR of an hydroxysteroid (17-b) dehydrogenase 4 gene (HSD17B4) (U.S. Publication No. 2016/0166710, supra).

In certain embodiments, the 5' UTR is derived from the 5' UTR of an ATP5A1 gene (U.S. Publication No. 2016/0166710, supra).

In some embodiments, an internal ribosome entry site (IRES) is used instead of a 5' UTR.

In some embodiments, the 5'UTR comprises a nucleic acid sequence set forth in SEQ ID NO: 19. In some embodiments, the 3'UTR comprises a nucleic acid sequence set forth in SEQ ID NO: 20. The 5' UTR and 3'UTR are described in further detail in WO2012/075040, incorporated herein by reference.

II. C. Polyadenylated Tail

As used herein, the terms "poly(A) sequence," "poly(A) tail," and "poly(A) region" refer to a sequence of adenosine nucleotides at the 3' end of the mRNA molecule. The poly(A) tail may confer stability to the mRNA and protect it from exonuclease degradation. The poly(A) tail may enhance translation. In some embodiments, the poly(A) tail is essentially homopolymeric. For example, a poly(A) tail of 100 adenosine nucleotides may have essentially a length of 100 nucleotides. In certain embodiments, the poly(A) tail may be interrupted by at least one nucleotide different from an adenosine nucleotide (e.g., a nucleotide that is not an adenosine nucleotide). For example, a poly(A) tail of 100 adenosine nucleotides may have a length of more than 100 nucleotides (comprising 100 adenosine nucleotides and at least one nucleotide, or a stretch of nucleotides, that are different from an adenosine nucleotide). In certain embodiments, the poly(A) tail comprises the sequence AAAAAAAAAAAAAAAAAAAAAAAAAAAAAAGCA UAUGACUAAAAAAAAAAAAAA AAAAAAAAA AAAAAAAAAAAAAAAAAAAAAAAAAAAAAAAA AAAAAAAAAA AA (SEQ ID NO: 23).

The "poly(A) tail," as used herein, typically relates to RNA. However, in the context of the disclosure, the term likewise relates to corresponding sequences in a DNA molecule (e.g., a "poly(T) sequence").

The poly(A) tail may comprise about 10 to about 500 adenosine nucleotides, about 10 to about 200 adenosine nucleotides, about 40 to about 200 adenosine nucleotides, or about 40 to about 150 adenosine nucleotides. The length of the poly(A) tail may be at least about 10, 50, 75, 100, 150, 200, 250, 300, 350, 400, 450, or 500 adenosine nucleotides.

In some embodiments where the nucleic acid is an RNA, the poly(A) tail of the nucleic acid is obtained from a DNA template during RNA in vitro transcription. In certain embodiments, the poly(A) tail is obtained in vitro by common methods of chemical synthesis without being transcribed from a DNA template. In various embodiments, poly(A) tails are generated by enzymatic polyadenylation of the RNA (after RNA in vitro transcription) using commercially available polyadenylation kits and corresponding protocols, or alternatively, by using immobilized poly(A)polymerases, e.g., using methods and means as described in WO2016/174271.

The nucleic acid may comprise a poly(A) tail obtained by enzymatic polyadenylation, wherein the majority of nucleic acid molecules comprise about 100 (+/−20) to about 500 (+/−50) or about 250 (+/−20) adenosine nucleotides.

In some embodiments, the nucleic acid may comprise a poly(A) tail derived from a template DNA and may additionally comprise at least one additional poly(A) tail generated by enzymatic polyadenylation, e.g., as described in WO2016/091391, incorporated herein by reference.

In certain embodiments, the nucleic acid comprises at least one polyadenylation signal.

In various embodiments, the nucleic acid may comprise at least one poly(C) sequence.

The term "poly(C) sequence," as used herein, is intended to be a sequence of cytosine nucleotides of up to about 200 cytosine nucleotides. In some embodiments, the poly(C) sequence comprises about 10 to about 200 cytosine nucleotides, about 10 to about 100 cytosine nucleotides, about 20 to about 70 cytosine nucleotides, about 20 to about 60 cytosine nucleotides, or about 10 to about 40 cytosine nucleotides. In some embodiments, the poly(C) sequence comprises about 30 cytosine nucleotides.

II. D. Chemical Modification

The mRNA disclosed herein may be modified or unmodified. In some embodiments, the mRNA may comprise at least one chemical modification. In some embodiments, the mRNA disclosed herein may contain one or more modifications that typically enhance RNA stability. Exemplary modifications can include backbone modifications, sugar modifications, or base modifications. In some embodiments, the disclosed mRNA may be synthesized from naturally occurring nucleotides and/or nucleotide analogues (modified nucleotides) including, but not limited to, purines (adenine (A) and guanine (G)) or pyrimidines (thymine (T), cytosine (C), and uracil (U)). In certain embodiments, the disclosed mRNA may be synthesized from modified nucleotide analogues or derivatives of purines and pyrimidines, such as, e.g., 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxy-acetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine.

In some embodiments, the disclosed mRNA may comprise at least one chemical modification including, but not limited to, pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

In some embodiments, the chemical modification is selected from the group consisting of pseudouridine, N1-methylpseudouridine, 5-methylcytosine, 5-methoxyuridine, and a combination thereof.

In some embodiments, the chemical modification comprises N1-methylpseudouridine.

In some embodiments, at least 20%, at least 30%, at least 40%, at least 50%, at least 60%, at least 70%, at least 80%, at least 85%, at least 90%, at least 95%, or 100% of the uracil nucleotides in the mRNA are chemically modified.

In some embodiments, at least 20%, at least 30%, at least 40%, at least 50%, at least 60%, at least 70%, at least 80%, at least 85%, at least 90%, at least 95%, or 100% of the uracil nucleotides in the ORF are chemically modified.

The preparation of such analogues is described, e.g., in U.S. Pat. Nos. 4,373,071, 4,401,796, 4,415,732, 4,458,066, 4,500,707, 4,668,777, 4,973,679, 5,047,524, 5,132,418, 5,153,319, 5,262,530, and 5,700,642.

II. E. mRNA Synthesis

The mRNAs disclosed herein may be synthesized according to any of a variety of methods. For example, mRNAs according to the present disclosure may be synthesized via in vitro transcription (IVT). Some methods for in vitro transcription are described, e.g., in Geall et al. (2013) Semin. Immunol. 25(2): 152-159; Brunelle et al. (2013) Methods Enzymol. 530:101-14. Briefly, IVT is typically performed with a linear or circular DNA template containing a promoter, a pool of ribonucleotide triphosphates, a buffer system that may include DTT and magnesium ions, an appropriate RNA polymerase (e.g., T3, T7, or SP6 RNA polymerase), DNase I, pyrophosphatase, and/or RNase inhibitor. The exact conditions may vary according to the specific application. The presence of these reagents is generally undesirable in a final mRNA product and these reagents can be considered impurities or contaminants which can be purified or removed to provide a clean and/or homogeneous mRNA that is suitable for therapeutic use. While mRNA provided from in vitro transcription reactions may be desirable in some embodiments, other sources of mRNA can be used according to the instant disclosure including wild-type mRNA produced from bacteria, fungi, plants, and/or animals.

III. Processes for Making the Present LNP Vaccines

The present LNPs can be prepared by various techniques presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion that results in the formation of MLVs. Unilamellar vesicles (ULV) can then be formed by homogenization, sonication or extrusion of the multilamellar vesicles. In addition, unilamellar vesicles can be formed by detergent removal techniques.

Various methods are described in US 2011/0244026, US 2016/0038432, US 2018/0153822, US 2018/0125989, and PCT/US2020/043223 (filed Jul. 23, 2020) and can be used to practice the present invention. One exemplary process entails encapsulating mRNA by mixing it with a mixture of lipids, without first pre-forming the lipids into lipid nanoparticles, as described in US 2016/0038432. Another exemplary process entails encapsulating mRNA by mixing pre-formed LNPs with mRNA, as described in US 2018/0153822.

In some embodiments, the process of preparing mRNA-loaded LNPs includes a step of heating one or more of the solutions to a temperature greater than ambient temperature, the one or more solutions being the solution comprising the pre-formed lipid nanoparticles, the solution comprising the mRNA and the mixed solution comprising the LNP-encapsulated mRNA. In some embodiments, the process includes the step of heating one or both of the mRNA solution and the pre-formed LNP solution, prior to the mixing step. In some embodiments, the process includes heating one or more of the solutions comprising the pre-formed LNPs, the solution comprising the mRNA and the solution comprising the LNP-encapsulated mRNA, during the mixing step. In some embodiments, the process includes the step of heating the LNP-encapsulated mRNA, after the mixing step. In some embodiments, the temperature to which one or more of the solutions is heated is or is greater than about 30° C., 37° C., 40° C., 45° C., 50° C., 55° C., 60° C., 65° C., or 70° C. In some embodiments, the temperature to which one or more of the solutions is heated ranges from about 25-70° C., about 30-70° C., about 35-70° C., about 40-70° C., about 45-70° C., about 50-70° C., or about 60-70° C. In some embodiments, the temperature is about 65° C.

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water or a buffer at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps. Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of, or greater than, about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

The process of incorporation of a desired mRNA into a lipid nanoparticle is referred to as "loading." Exemplary methods are described in Lasic et al., *FEBS Lett.* (1992) 312:255-8. The LNP-incorporated nucleic acids may be completely or partially located in the interior space of the lipid nanoparticle, within the bilayer membrane of the lipid nanoparticle, or associated with the exterior surface of the lipid nanoparticle membrane. The incorporation of an mRNA into lipid nanoparticles is also referred to herein as "encapsulation" wherein the nucleic acid is entirely or substantially contained within the interior space of the lipid nanoparticle.

Suitable LNPs may be made in various sizes. In some embodiments, decreased size of lipid nanoparticles is associated with more efficient delivery of an mRNA. Selection of an appropriate LNP size may take into consideration the site of the target cell or tissue and to some extent the application for which the lipid nanoparticle is being made.

A variety of methods known in the art are available for sizing of a population of lipid nanoparticles. Particularly exemplary methods herein utilize Zetasizer Nano ZS (Malvern Panalytical) to measure LNP particle size. In one protocol, 10 μl of an LNP sample are mixed with 990 μl of 10% trehalose. This solution is loaded into a cuvette and then put into the Zetasizer machine. The z-average diameter (nm), or cumulants mean, is regarded as the average size for the LNPs in the sample. The Zetasizer machine can also be used to measure the polydispersity index (PDI) by using dynamic light scattering (DLS) and cumulant analysis of the autocorrelation function. Average LNP diameter may be reduced by sonication of formed LNP. Intermittent sonication cycles may be alternated with quasi-elastic light scattering (QELS) assessment to guide efficient lipid nanoparticle synthesis.

In some embodiments, the majority of purified LNPs, i.e., greater than about 50%, 55%, 60%, 65%, 70%, 75%, 80%, 85%, 90%, 95%, 96%, 97%, 98%, or 99% of the LNPs, have a size of about 70-150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, substantially all (e.g., greater than 80 or 90%) of the purified lipid nanoparticles have a size of about 70-150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm).

In some embodiments, the LNPs in the present composition have an average size of less than 150 nm, less than 120 nm, less than 100 nm, less than 90 nm, less than 80 nm, less than 70 nm, less than 60 nm, less than 50 nm, less than 30 nm, or less than 20 nm.

In some embodiments, greater than about 70%, 75%, 80%, 85%, 90%, 95%, 96%, 97%, 98%, 99% of the LNPs in the present composition have a size ranging from about 40-90 nm (e.g., about 45-85 nm, about 50-80 nm, about 55-75 nm, about 60-70 nm) or about 50-70 nm (e.g., 55-65 nm) are particular suitable for pulmonary delivery via nebulization.

In some embodiments, the dispersity, or measure of heterogeneity in size of molecules (PDI), of LNPs in a pharmaceutical composition provided by the present invention is less than about 0.5. In some embodiments, an LNP has a PDI of less than about 0.5, less than about 0.4, less than about 0.3, less than about 0.28, less than about 0.25, less than about 0.23, less than about 0.20, less than about 0.18, less than about 0.16, less than about 0.14, less than about 0.12, less than about 0.10, or less than about 0.08. The PDI may be measured by a Zetasizer machine as described above.

In some embodiments, greater than about 75%, 80%, 85%, 90%, 95%, 96%, 97%, 98%, or 99% of the purified LNPs in a pharmaceutical composition provided herein encapsulate an mRNA within each individual particle. In some embodiments, substantially all (e.g., greater than 80% or 90%) of the purified lipid nanoparticles in a pharmaceutical composition encapsulate an mRNA within each individual particle. In some embodiments, a lipid nanoparticle has an encapsulation efficiency of between 50% and 99%; or greater than about 60, 65, 70, 75, 80, 85, 90, 92, 95, 98, or 99%. Typically, lipid nanoparticles for use herein have an encapsulation efficiency of at least 90% (e.g., at least 91, 92, 93, 94, or 95%).

In some embodiments, an LNP has a N/P ratio of between 1 and 10. In some embodiments, a lipid nanoparticle has a N/P ratio above 1, about 1, about 2, about 3, about 4, about 5, about 6, about 7, or about 8. In further embodiments, a typical LNP herein has an N/P ratio of 4.

In some embodiments, a pharmaceutical composition according to the present invention contains at least about 0.5 µg, 1 µg, 5 µg, 10 µg, 100 µg, 500 µg, or 1000 µg of encapsulated mRNA. In some embodiments, a pharmaceutical composition contains about 0.1 µg to 1000 µg, at least about 0.5 µg, at least about 0.8 µg, at least about 1 µg, at least about 5 µg, at least about 8 µg, at least about 10 µg, at least about 50 µg, at least about 100 µg, at least about 500 µg, or at least about 1000 µg of encapsulated mRNA.

In some embodiments, mRNA can be made by chemical synthesis or by in vitro transcription (IVT) of a DNA template. An exemplary process for making and purifying mRNA is described in Example 1. In this process, in an IVT process, a cDNA template is used to produce an mRNA transcript and the DNA template is degraded by a DNase. The transcript is purified by depth filtration and tangential flow filtration (TFF). The purified transcript is further modified by adding a cap and a tail, and the modified RNA is purified again by depth filtration and TFF.

The mRNA is then prepared in an aqueous buffer and mixed with an amphiphilic solution containing the lipid components of the LNPs. An amphiphilic solution for dissolving the four lipid components of the LNPs may be an alcohol solution. In some embodiments, the alcohol is ethanol. The aqueous buffer may be, for example, a citrate, phosphate, acetate, or succinate buffer and may have a pH of about 3.0-7.0, e.g., about 3.5, about 4.0, about 4.5, about 5.0, about 5.5, about 6.0, or about 6.5. The buffer may contain other components such as a salt (e.g., sodium, potassium, and/or calcium salts). In particular embodiments, the aqueous buffer has 1 mM citrate, 150 mM NaCl, pH 4.5.

An exemplary, nonlimiting process for making an mRNA-LNP composition is described in Example 1. The process involves mixing of a buffered mRNA solution with a solution of lipids in ethanol in a controlled homogeneous manner, where the ratio of lipids:mRNA is maintained throughout the mixing process. In this illustrative example, the mRNA is presented in an aqueous buffer containing citric acid monohydrate, tri-sodium citrate dihydrate, and sodium chloride. The mRNA solution is added to the solution (1 mM citrate buffer, 150 mM NaCl, pH 4.5). The lipid mixture of four lipids (e.g., a cationic lipid, a PEGylated lipid, a cholesterol-based lipid, and a helper lipid) is dissolved in ethanol. The aqueous mRNA solution and the ethanol lipid solution are mixed at a volume ratio of 4:1 in a "T" mixer with a near "pulseless" pump system. The resultant mixture is then subjected for downstream purification and buffer exchange. The buffer exchange may be achieved using dialysis cassettes or a TFF system. TFF may be used to concentrate and buffer-exchange the resulting nascent LNP immediately after formation via the T-mix process. The diafiltration process is a continuous operation, keeping the volume constant by adding appropriate buffer at the same rate as the permeate flow.

IV. Packaging and Use of the mRNA-LNP Vaccines

The mRNA-LNP vaccines can be packaged for parenteral (e.g., intramuscular, intradermal or subcutaneous) administration or nasopharyngeal (e.g., intranasal) administration. The vaccine compositions may be in the form of an extemporaneous formulation, where the LNP composition is lyophilized and reconstituted with a physiological buffer (e.g., PBS) just before use. The vaccine compositions also may be shipped and provided in the form of an aqueous solution or a frozen aqueous solution and can be directly administered to subjects without reconstitution (after thawing, if previously frozen).

Accordingly, the present disclosure provides an article of manufacture, such as a kit, that provides the mRNA-LNP vaccine in a single container, or provides the mRNA-LNP vaccine in one container and a physiological buffer for reconstitution in another container. The container(s) may contain a single-use dosage or multi-use dosage. The containers may be pre-treated glass vials or ampules. The article of manufacture may include instructions for use as well.

In particular embodiments, the mRNA-LNP vaccine is provided for use in intramuscular (IM) injection. The vaccine can be injected to a subject at, e.g., his/her deltoid muscle in the upper arm. In some embodiments, the vaccine is provided in a pre-filled syringe or injector (e.g., single-chambered or multi-chambered). In some embodiments, the vaccine is provided for use in inhalation and is provided in a pre-filled pump, aerosolizer, or inhaler.

The mRNA-LNP vaccines are administered to subjects in need thereof in a prophylactically effective amount, i.e., an amount that provides sufficient immune protection against a target pathogen for a sufficient amount of time (e.g., one year, two years, five years, ten years, or life-time). Sufficient immune protection may be, for example, prevention or alleviation of symptoms associated with infections by the pathogen. In some embodiments, multiple doses (e.g., two doses) of the vaccine are injected to subjects in need thereof to achieve the desired prophylactic effects. The doses (e.g., prime and booster doses) may be separated by an interval of e.g., 1 week, 2 weeks, 3 weeks, 4 weeks, one month, two months, three months, four months, five months, six months, one year, two years, five years, or ten years.

In some embodiments, a single dose of the mRNA-LNP vaccine contains 1-50 μg of mRNA (e.g., monovalent or multivalent). For example, a single dose may contain about 2.5 μg, about 5 μg, about 7.5 μg, about 10 μg, about 12.5 μg, or about 15 μg of the mRNA for intramuscular (IM) injection. In further embodiments, a multi-valent single dose of an LNP vaccine contains multiple (e.g., 2, 3, or 4) kinds of LNPs, each for a different antigen, and each kind of LNP has an mRNA amount of, e.g., 2.5 μg, about 5 μg, about 7.5 μg, about 10 μg, about 12.5 μg, or about 15 μg.

In another aspect, the present invention provides methods of immunizing a subject against one or more influenza viruses. The present invention further provides methods of eliciting an immune response against one or more influenza viruses in a subject. In some embodiments, the present methods comprise administering to the subject an effective amount of a composition described herein to a subject.

In various embodiments, the methods of immunizing provided herein elicit a broadly protective immune response against multiple epitopes within one or more influenza viruses. In various embodiments, the methods of immunizing provided herein elicit a broadly neutralizing immune response against one or more influenza viruses. In some embodiments, the immune response comprises an antibody response. Accordingly, in various embodiments, the composition described herein can offer broad cross-protection against different types of influenza viruses. In some embodiments, the composition offers cross-protection against avian, swine, seasonal, and/or pandemic influenza viruses. In some embodiments, the composition offers cross-protection against one or more influenza A, B, or C subtypes. In some embodiments, the composition offers cross-protection against multiple strains of influenza A H1-subtype viruses (e.g., H1N1), influenza A H3-subtype viruses (e.g., H3N2), influenza A H5-subtype viruses (e.g., H5N1), and/or influenza B viruses (e.g., Yamagata lineage, Victoria lineage).

In some embodiments, the methods of the invention are capable of eliciting an improved immune response against one or more seasonal influenza strains. Exemplary seasonal strains include, without limitation, A/Puerto Rico/8/1934, A/Fort Monmouth/1/1947, A/Chile/1/1983, A/Texas/36/1991, A/Singapore/6/1986, A/Beijing/32/1992, A/New Caledonia/20/1999, A/Solomon Islands/03/2006, A/Brisbane/59/2007, A(H3N2) virus antigenically like the cell-propagated prototype virus A/Victoria/361/2011, A/Beijing/262/95 (H1N1)-like virus, A/Brisbane/02/2018 (H1N1) pdm09-like virus, A/Brisbane/10/2007 (H3N2)-like virus, A/California/7/2004 (H3N2)-like virus, A/California/7/2009 (H1N1)-like virus, A/California/7/2009 (H1N1)pdm09-like virus, A/Cambodia/e0826360/2020 (H3N2)-like virus, A/Fujian/411/2002 (H3N2)-like virus, A/Fujian/411/2002 (H3N2)-like virus, A/Guangdong-Maonan/SWL1536/2019 (H1N1)pdm09-like virus-like virus, A/Hawaii/70/2019 (H1N1)pdm09-like virus-like virus, A/Hong Kong/2671/2019 (H3N2)-like virus, A/Hong Kong/45/2019 (H3N2)-like virus, A/Hong Kong/4801/2014 (H3N2)-like virus, A/Kansas/14/2017 (H3N2)-like virus, A/Michigan/45/2015 (H1N1)pdm09-like virus, A/Moscow/10/99 (H3N2)-like virus, A/New Caledonia/20/99 (H1N1)-like virus, A/Perth/16/2009 (H3N2)-like virus, A/Singapore/INFIMH-16-0019/2016 (H3N2)-like virus, A/Solomon Islands/3/2006 (H1N1)-like virus, A/South Australia/34/2019 (H3N2)-like virus, A/Switzerland/8060/2017 (H3N2)-like virus, A/Switzerland/9715293/2013 (H3N2)-like virus, A/Sydney/5/97 (H3N2)-like virus, A/Texas/50/2012 (H3N2)-like virus, A/Victoria/2570/2019 (H1N1)pdm09-like virus, A/Victoria/2570/2019 (H1N1)pdm09-like virus, A/Victoria/361/2011 (H3N2)-like virus, A/Wellington/1/2004 (H3N2)-like virus, A/Wisconsin/588/2019 (H1N1)pdm09-like virus, A/Wisconsin/588/2019 (H1N1)pdm09-like virus-like virus, A/Wisconsin/67/2005 (H3N2)-like virus, B/Beijing/184/93-like virus, B/Brisbane/60/2008-like virus, B/Colorado/06/2017-like virus (B/Victoria/2/87 lineage), B/Florida/4/2006-like virus, B/Hong Kong/330/2001-like virus, B/Malaysia/2506/2004-like virus, B/Massachusetts/2/2012-like virus, B/Phuket/3073/2013 (B/Yamagata lineage)-like virus, B/Phuket/3073/2013-like virus, B/Phuket/3073/2013-like virus (B/Yamagata/16/88 lineage), B/Shangdong/7/97-like virus, B/Shanghai/361/2002-like virus, B/Sichuan/379/99-like virus, B/Washington/02/2019 (B/Victoria lineage)-like virus, B/Washington/02/2019-like (B/Victoria lineage) virus, and B/Wisconsin/1/2010-like virus. In some embodiments, the methods of the invention are capable of eliciting an improved immune response against one or more pandemic influenza strains. Exemplary pandemic strains include, without limitation, A/California/07/2009, A/California/04/2009, A/Belgium/145/2009, A/South Carolina/01/1918, and A/New Jersey/1976. Pandemic subtypes include, in particular, the H1N1, H5N1, H2N2, H3N2, H9N2, H7N7, H7N3, H7N9 and H10N7 subtypes. In some embodiments, the methods of the invention are capable of eliciting an improved immune response against one or more swine influenza strains. Exemplary swine strains include, without limitation, A/New Jersey/1976 isolates and A/California/07/2009. In some embodiments, the methods of the invention are capable of eliciting an improved immune response against one or more avian influenza strains. Exemplary avian strains include, without limitation, H5N1, H7N3, H7N7, H7N9, and H9N2. Additional influenza pandemic, seasonal, avian and/or swine strains are known in the art.

In some embodiments, the present invention provides methods of preventing or treating influenza infections by administering the composition of the invention to a subject in need thereof. In some embodiments, the subject is suffering from or susceptible to an influenza infection. In some embodiments, a subject is considered to be suffering from an influenza infection if the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In various embodiments, the composition as described herein may be administered prior to or after development of one or more symptoms of influenza infection. In some embodiments, the composition is administered as a prophylactic. In such embodiments, the methods of the invention are effective in preventing or protecting a subject from influenza virus infection. In some embodiments, the composition of the present invention is used as a component of a seasonal and/or pandemic influenza vaccine or as part of an influenza vaccination regimen intended to confer long-lasting (multi-season) protection. In some embodiments, the composition of the presenting invention is used to treat the symptoms of influenza infection.

In some embodiments, the subject is a non-human mammal. In some embodiments, the subject is a farm animal or a pet (e.g., a dog, a cat, a sheep, cattle, and/or a pig). In some embodiments, the subject is a non-human primate. In some embodiments, the subject is an avian (e.g., a chicken, a duck, a goose and/or a turkey).

In some embodiments, the subject is a human. In certain embodiments, the subject is an adult, an adolescent, or an infant. In some embodiments, the human subject is younger than 6 months of age. In some embodiments, the human subject is 6 months of age or older, is 6 months through 35 months of age, is 36 months through 8 years of age, or is 9 years of age or older. In some embodiments, the human subject is an elderly aged 55 years or older, such as 60 years of age or older, or 65 years of age or older. Also contemplated by the present invention are the administration of the composition and/or performance of the methods of treatment in utero.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control. Generally, nomenclature used in connection with, and techniques of, cell and tissue culture, molecular biology, virology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art. As used herein, the term "approximately" or "about" as applied to one or more values of interest refers to a value that is similar to a stated reference value. In certain embodiments, the term refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context.

In order that this invention may be better understood, the following examples are set forth. These examples are for purposes of illustration only and are not to be construed as limiting the scope of the invention in any manner.

EXAMPLES

Example 1: Optimization of LNP Formulations

This Example describes a study in which a series of LNP formulations for mRNA vaccines was prepared from combinatorial libraries of various components. Rationally designed novel cationic lipids were synthesized. Altogether, more than 150 lipids and more than 430 formulations were tested. Human erythropoietin (hEPO) mRNA was used as a test mRNA. In the lead formulations described below, the mRNA was formulated into LNP using combinations of the cationic lipids and the three other lipids—helper lipids; cholesterol-based lipids; and PEGylated lipids—in various permutations of combinations.

The LNP formulations consisted of four lipid components—ionizable lipid, helper lipid DOPE, cholesterol, and PEGylated lipid DMG-PEG-2K. The PEGylated lipid molar fraction was held constant at 1.5%, while the ionizable lipid and the different helper lipids and their molar ratios were evaluated to identify the optimized ratios based on the hEPO screening studies.

Citrate buffer (1 mM citrate, 150 mM NaCl, pH 4.5) was used in the preparation of LNP formulation. mRNA solution added to the citrate buffer was mixed with the lipids in ethanol solution during the formulation process. The pH and the concentration of the buffer were selected to achieve the high rate of mRNA encapsulation in the LNP formulation.

The LNP formulation process included mixing the lipid ethanol solution and the mRNA citrate solution in a 'T' mixer using a pump system. The resultant solution was then subjected to buffer exchange using TFF/dialysis tubes. The concentration of the final formulation in 10% (w/v) trehalose was adjusted based on dosing needs.

Mouse in vivo expression of hEPO protein was used as a surrogate to measure the potency of the LNPs to delivery mRNA in vivo. In this study, a single dose of hEPO mRNA (0.1 µg) formulated in LNPs derived from various combinations of the components was injected into mice intramuscularly (IM). Serum collected at 6 hours and 24 hours after administration was tested for hEPO levels using ELISA. MC3 formulation, an industry benchmark, was used a reference for the calculation of fold-increase in hEPO expression (Angew, *Chem Int Ed*. (2012) 51:8529-33).

The level of hEPO expression seen for each LNP formulation indicated the formulation's ability to deliver mRNA into cells. The initial formulations included 2-dioleoyl-sn-glycero-3-phosphoethanolamine (DOPE; helper lipid), DMG-PEG2000, and cholesterol at the molar ratio of cationic lipid:DMG-PEG2000:cholesterol:DOPE at 40:1.5:28.5:30. These formulations were found to have robust potency when compared to MC3 formulations.

Further formulations were tested. Optimized formulations Lipid A LNP and Lipid B LNP are shown in Table 1. The mRNA in these formulations can be modified or unmodified and may encode an antigen derived from a virus such as influenza or SARS-COV-2.

TABLE 1

Composition of Exemplary LNP Formulations

| Components | | Function | Description |
| --- | --- | --- | --- |
| mRNA | | Active substance | mRNA Construct |
| lipid nanoparticle (LNP) | Cationic Lipid OF-02 (A) or cKK-E10 (B) | Delivery | Ionizable lipid, facilitates mRNA encapsulation |
| | DOPE | | Zwitterionic lipid, enhances uptake and release of drug payload |
| | Cholesterol | | Provides stability to lipid bilayer |
| | DMG-PEG-2K | | Provides control and stability to the lipid bilayer |
| Trehalose | | Excipient | Cryoprotectant |
| Water for Injection (WFI) | | Diluent | N/A |

In Table 1, the final dosing for a human vaccine would be dilution of the above final bulk product in phosphate-buffered saline (PBS) based on the intended single human dose. The WFI amount is calculated based upon nominal of final drug product. Trehalose content in the formulation corresponds to 10% (100 mg/mL) trehalose dihydrate, converted to an anhydrous basis using the ratio of the molecular weight values of anhydrous trehalose and trehalose dihydrate.

The molar ratios of lipid components in two optimized formulations—Lipid A and Lipid B LNP formulations—are shown in Table 2 (CL: cationic lipid).

TABLE 2

Molar Ratios of Lipid Components in Exemplary LNPs

| CL | LNP Code | Molar Ratios of CL:DMG-PEG2000:Cholesterol:DOPE |
| --- | --- | --- |
| OF-02 | Lipid A | 40:1.5:28.5:30 |
| cKK-E10 | Lipid B | 40:1.5:28.5:30 |

Figure 1A:
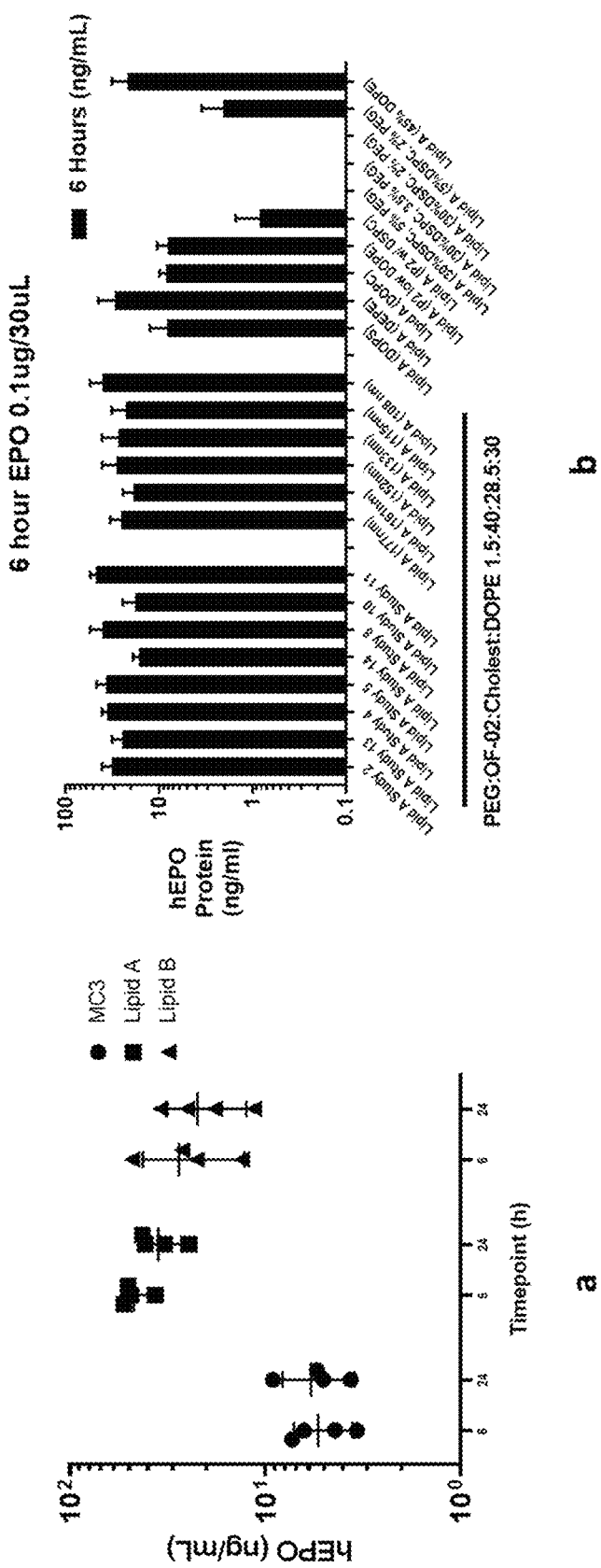
FIG. 1A is a pair of graphs showing the expression of human erythropoietin (hEPO) in mice treated with various LNP formulations of hEPO mRNA. Panel a): LNP formulations "Lipid A" and "Lipid B" compared to MC3. Bars represent means and standard deviations. Panel b): Formulation made with cationic lipid OF-02. PEG: DMG-PEG2000. Cholest: cholesterol. "Lipid A": LNP composition containing OF-02, DMG-PEG2000, cholesterol, and DOPE, in this order, at a molar ratio of 40:1.5:28.5:30, unless otherwise indicated. "Lipid B": LNP composition containing cKK-E10, DMG-PEG2000, cholesterol, and DOPE, in this order, at a molar ratio of 40:1.5:28.5:30.

As shown in Table 3 and FIG. 1A, the fold increase of hEPO expression for Lipid A and Lipid B compared to MC3 indicates the superiority of these LNPs over MC3 for the delivery of mRNA. In the table below, "P2" means PEG2000; "Times MC3" means the fold of increase over MC3; and "Std Dev" means standard deviation.

TABLE 3

In vivo Delivery of hEPO mRNA in Mice

| Study # | Cationic lipid | Formulation Composition | Times MC3 | Std Dev |
| --- | --- | --- | --- | --- |
| 1 | OF-02 (P2 low DOPE) | Cationic lipid:DMG-PEG2000:cholesterol:DOPE 40:3:27:30 | 1.74 | 0.97 |
| | OF-02 (P2 w/DSPC) | Cationic lipid:DMG-PEG2000:cholesterol:DSPC 50:1.5:38.5:10 | 0.18 | 0.17 |
| 2 | OF-02 | Cationic lipid:DMG-PEG2000:cholesterol:DOPE 40:1.5:28.5:30 | 5.04 | 1.79 |
| 3 | OF-02 (high DOPE) | Cationic lipid:DMG-PEG2000:cholesterol:DOPE 40:1.5:13.5:45 | 7.35 | 3.90 |
| 4 | OF-02 | Cationic lipid:DMG-PEG2000:cholesterol:DOPE 40:1.5:28.5:30 | 16.19 | 7.86 |
| 5 | OF-02 | Cationic lipid:DMG-PEG2000:cholesterol:DOPE 40:1.5:28.5:30 | 12.13 | 6.56 |
| 6 | cKK-E10 | Cationic lipid:DMG-PEG2000:cholesterol:DOPE 40:1.5:28.5:30 | 5.41 | 3.46 |
| 7 | cKK-E10 (DEPE) | Cationic lipid:DMG-PEG2000:cholesterol:DEPE 40:1.5:28.5:30 | 5.77 | 2.09 |
| 8 | OF-02 (177 nm) | Cationic lipid:DMG-PEG2000:cholesterol:DOPE 40:1.5:28.5:30 | 6.59 | 2.50 |
| | OF-02 (161 nm) | Cationic lipid:DMG-PEG2000:cholesterol:DOPE 40:1.5:28.5:30 | 4.94 | 1.75 |
| | OF-02 (153 nm) | Cationic lipid:DMG-PEG2000:cholesterol:DOPE 40:1.5:28.5:30 | 7.40 | 3.54 |
| | OF-02 (133 nm) | Cationic lipid:DMG-PEG2000:cholesterol:DOPE 40:1.5:28.5:30 | 7.15 | 3.86 |
| | OF-02 (115 nm) | Cationic lipid:DMG-PEG2000:cholesterol:DOPE 40:1.5:28.5:30 | 5.91 | 2.79 |
| | OF-02 (118 nm) | Cationic lipid:DMG-PEG2000:cholesterol:DOPE 40:1.5:28.5:30 | 10.54 | 4.38 |
| 9 | OF-02 (DSPC) | Cationic lipid:DMG-PEG2000:cholesterol:DSPC 40:5:25:30 | 0.00 | 0.00 |
| | OF-02 (DSPC) | Cationic lipid:DMG-PEG2000:cholesterol:DSPC 40:3.5:26.5:30 | 0.00 | 0.00 |
| | OF-02 (DSPC) | Cationic lipid:DMG-PEG2000:cholesterol:DSPC 40:2:28:30 | 0.00 | 0.00 |
| | OF-02 (DSPC) | Cationic lipid:DMG-PEG2000:cholesterol:DSPC 40:2:53:5 | 0.99 | 0.70 |
| 10 | OF-02 (DOPS) | Cationic lipid:DMG-PEG2000:cholesterol:DOPS 40:1.5:28.5:30 | 3.26 | 1.97 |
| | OF-02 (DEPE) | Cationic lipid:DMG-PEG2000:cholesterol:DEPE 40:1.5:28.5:30 | 11.83 | 6.89 |

TABLE 3-continued

In vivo Delivery of hEPO mRNA in Mice

| Study # | Cationic lipid | Formulation Composition | Times MC3 | Std Dev |
|---|---|---|---|---|
| | OF-02 (DOPC) | Cationic lipid:DMG-PEG2000:cholesterol:DOPC 40:1.5:28.5:30 | 3.32 | 1.20 |
| | OF-02 | Cationic lipid:DMG-PEG2000:cholesterol:DOPE 40:1.5:28.5:30 | 7.14 | 3.37 |
| 11 | cKK-E10 | Cationic lipid:DMG-PEG2000:cholesterol:DOPE 40:1.5:28.5:30 | 5.58 | 2.01 |
| | OF-02 (PD lot) | Cationic lipid:DMG-PEG2000:cholesterol:DOPE 40:1.5:28.5:30 | 8.81 | 3.22 |
| | cKK-E10 | Cationic lipid:DMG-PEG2000:cholesterol:DOPE 40:1.5:28.5:30 | 5.16 | 3.25 |

Figure 1B:
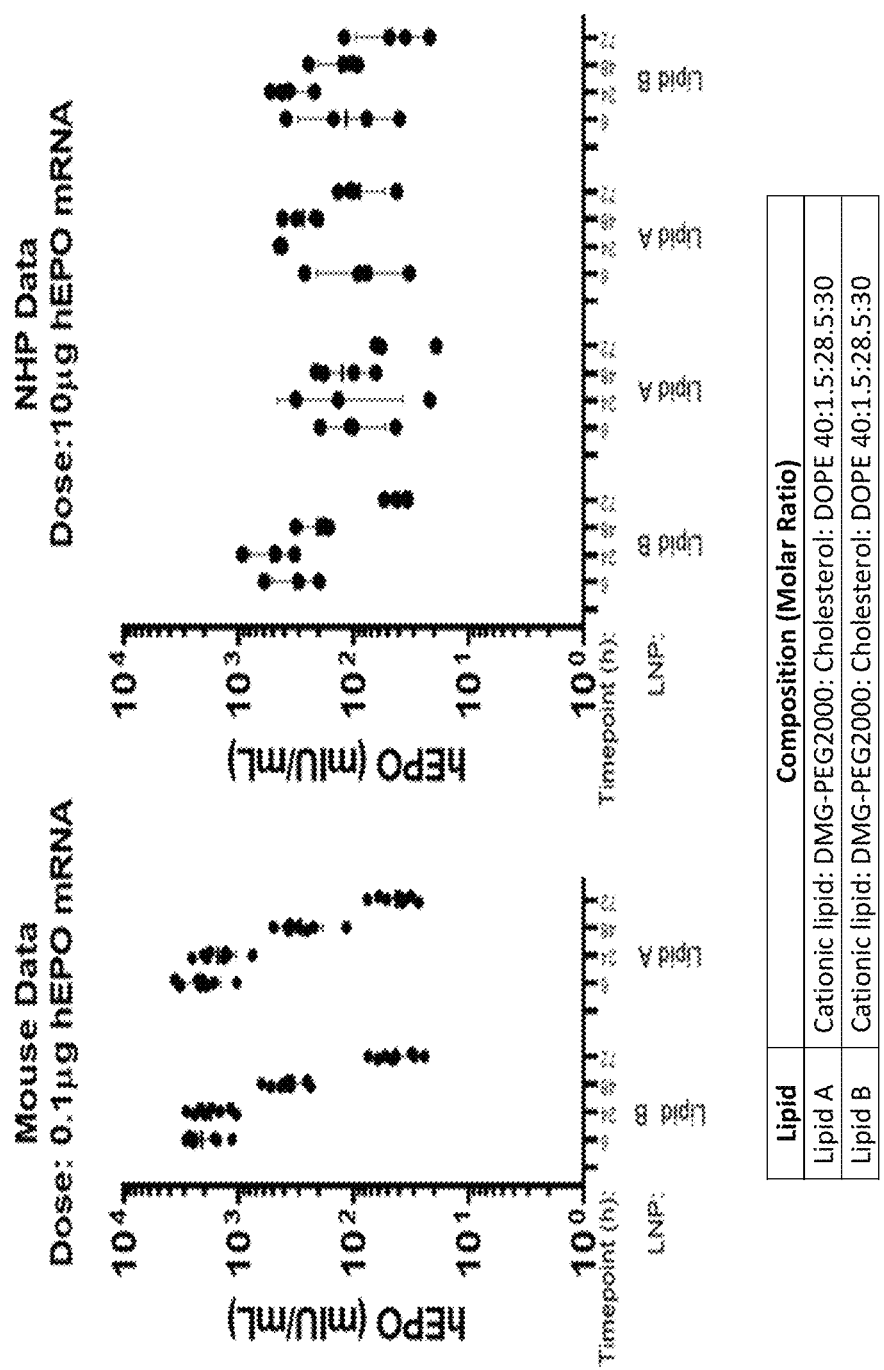
FIG. 1B is a pair of graphs showing expression of hEPO in mice and non-human primates (NHPs) using LNP formulations Lipid A and Lipid B.
Figure 2A:
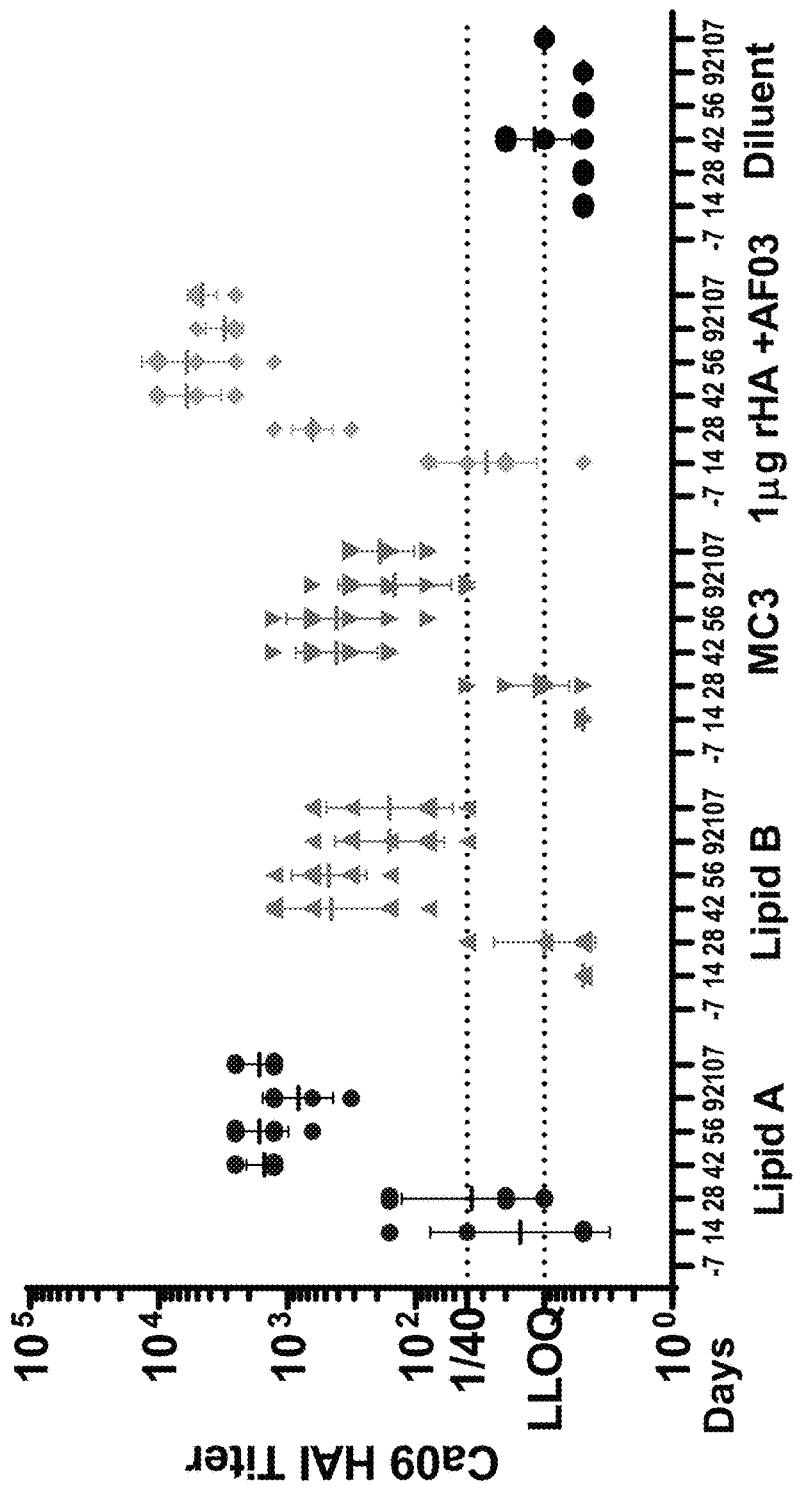
FIGS. 2A and 2B are a pair of graphs showing that Lipid A and Lipid B LNP formulations with mRNA encoding hemagglutinin (HA) of strain A/California/7/2009 (H1N1) (CA09) induced robust functional antibodies (FIG. 2A) and protected mice against death or severe weight loss (more than 20%) when challenged with a pandemic strain of influenza virus (FIG. 2B). Hemagglutinin inhibition (HAI) titers are reported as log 10 for serum samples taken at study days 0, 14, 28, 42, 56, 92, and 107. Bars are geometric means and geometric standard deviations. Daily weights were measured after intranasal challenge (day 93) with 4LD$_{50}$ of A/Belgium/2009 (H1N1) (Belgium09). Weights are presented as the percentage of weight lost from the day of challenge. Euthanasia occurred for mice losing more than 20% of their starting body weight and for all mice 14 days post-infection (day 107). rHA: recombinant hemagglutinin. AF03: an oil-in-water emulsion adjuvant. Diluent=PBS. LLOQ=lower limit of quantitation. 1/40=1/40 minimum target, which refers to HAI antibody titers associated with 50% reduction in the risk of influenza infection or disease in healthy adults (Coudeville et al., BMC Med Res Methodol. (2010) 10:18). Dashed line in FIG. 2B=20% weight loss cut off with respect to weight on the day of challenge.
Figure 2B:
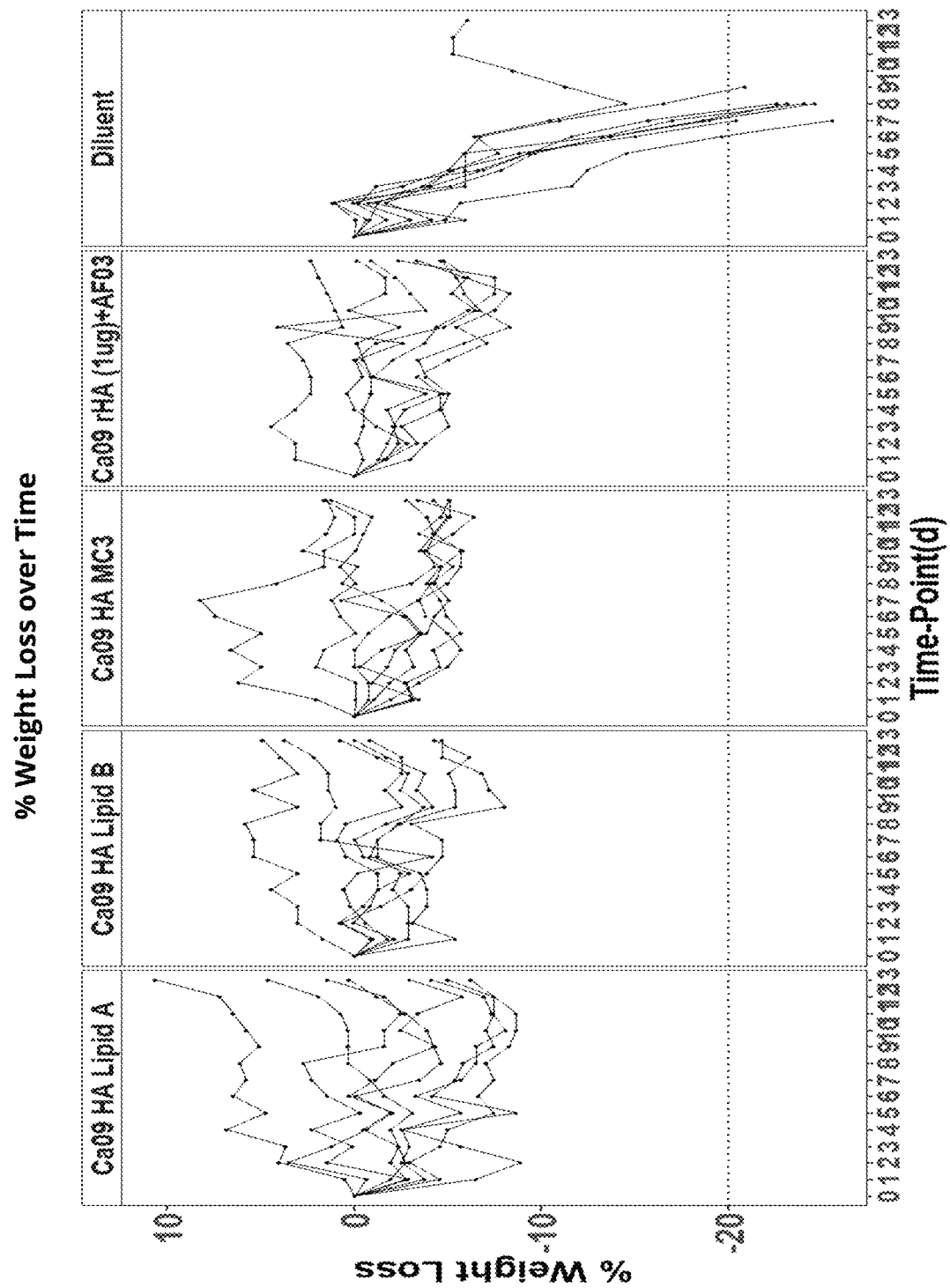

FIG. 1B shows hEPO expression in mice and non-human primates (NHPs) using LNPs Lipid A and Lipid B. A single dose of hEPO mRNA (0.1 µg for mice and 10 µg for NHPs) formulated with Lipid A or Lipid B was injected intramuscularly. Serum hEPO levels were quantified at 6, 24, 48, and 72 hours after administration using ELISA. The data show prolonged hEPO protein expression in vivo even beyond 4 days in mice and NHPs.

One of the key process parameters identified during optimization was the flow rate during initial mixing step. Formulations with different final LNP sizes (ranging from 108-177 nm) were prepared by changing these flow rates during mixing, allowing additional control on process and product attributes. The higher the flow rate, the smaller the particle size. When the flow rate reached 375 ml/min, producing an average LNP size of 108 nM, there was a markedly increased potency. The impact of size on potency of LNP was noted as a measure of fold increase in hEPO expression over MC3 as Table 4.

TABLE 4

LNP Size Optimization

| Formulation Lot# | Total Flow rate (ml/min) | Size (nm) | PDI | Encapsulation (%) | Cationic Lipid | Times MC3 |
|---|---|---|---|---|---|---|
| 1 | 250 | 108 | 0.077 | 99 | MC3 | 1.00 |
| 2 | 62.5 | 177 | 0.086 | 94 | OF-02 | 6.59 |
| 3 | 75 | 161 | 0.075 | 95 | OF-02 | 4.94 |
| 2-88 | 87.5 | 152 | 0.116 | 97 | OF-02 | 7.40 |
| 2-89 | 125 | 133 | 0.089 | 97 | OF-02 | 7.15 |
| 2-90 | 250 | 115 | 0.076 | 98 | OF-02 | 5.91 |
| 2-91 | 375 | 108 | 0.042 | 98 | OF-02 | 10.54 |

*PDI: polydispersity index.

The above screening data show that helper lipid DOPE was effective in promoting protein expression. The data also led to determination of the promising molar composition of the four lipids (OF-02 or cKK-E10:DMG-PEG-2K:cholesterol:DOPE=40:1.5:28.5:30). LNP formulations in 10% trehalose were characterized for all parameters including particle size, PDI, mRNA encapsulation, and mRNA integrity. All the tested batches showed the desired characteristics and stability in freeze/thaw cycling. The long-term stability of the formulation at −80° C. in 10% (w/v) trehalose was assessed. Lipid A and Lipid B formulations were shown to be highly stable.

Example 2: Influenza H1N1 LNP Vaccine Formulations

Figure 3A:
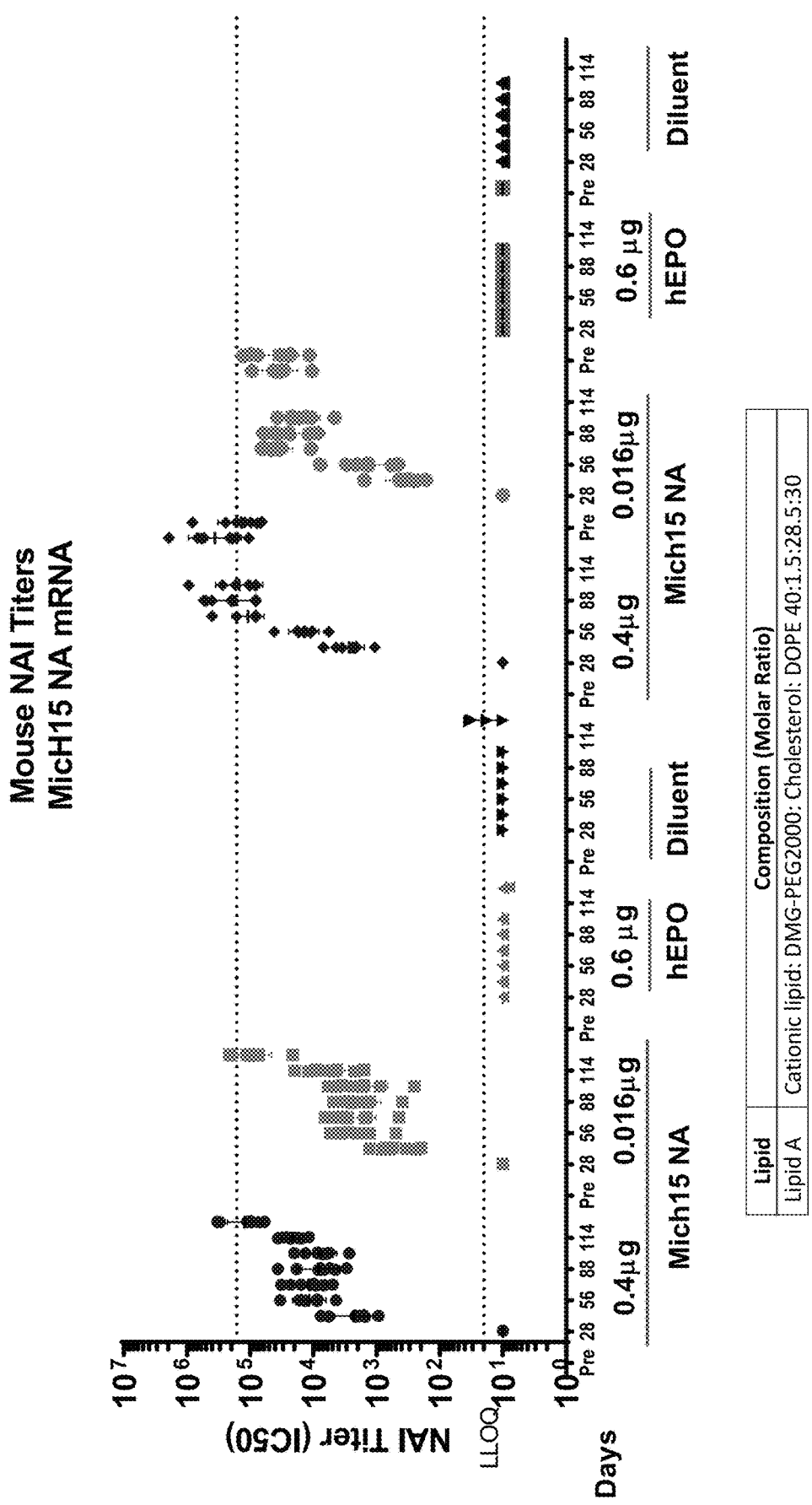
FIGS. 3A and 3B are a pair of graphs showing that A/Michigan/45/2015 (Mich15) neuraminidase (NA) mRNA formulated with Lipid A LNP induced robust functional antibodies (FIG. 3A) and protected mice against weight loss and death when challenged with a pandemic strain of influenza virus (FIG. 3B). Neuraminidase inhibition (NAI) titers are reported as log 10 for serum samples taken at study days 14, 28, 42, 56, 88, and 114. Daily weights were observed after intranasal challenge (day 89 for the one-dose groups or day 117 for the two-dose groups) with 4LD$_{50}$ of Belgium09. Weights are presented as the percentage of weight lost from the day of challenge. Euthanasia occurred for mice losing more than 20% of their starting body weight and for all mice 14 days post-infection (day 103 for the 1 dose groups or day 131 for the 2 dose groups). Bars are means and standard deviations. Upper dashed line in FIG. 3A=upper limit of quantitation. Lower dashed line in FIG. 3A=lower limit of quantitation. Dashed line in FIG. 3B=20% weight loss cut off with respect to weight on the day of challenge. mRNA dosed: 0.4 or 0.016 µg mRNA encoding Mich15 NA. Control: 0.6 µg mRNA encoding hEPO or diluent (PBS).
Figure 3B:
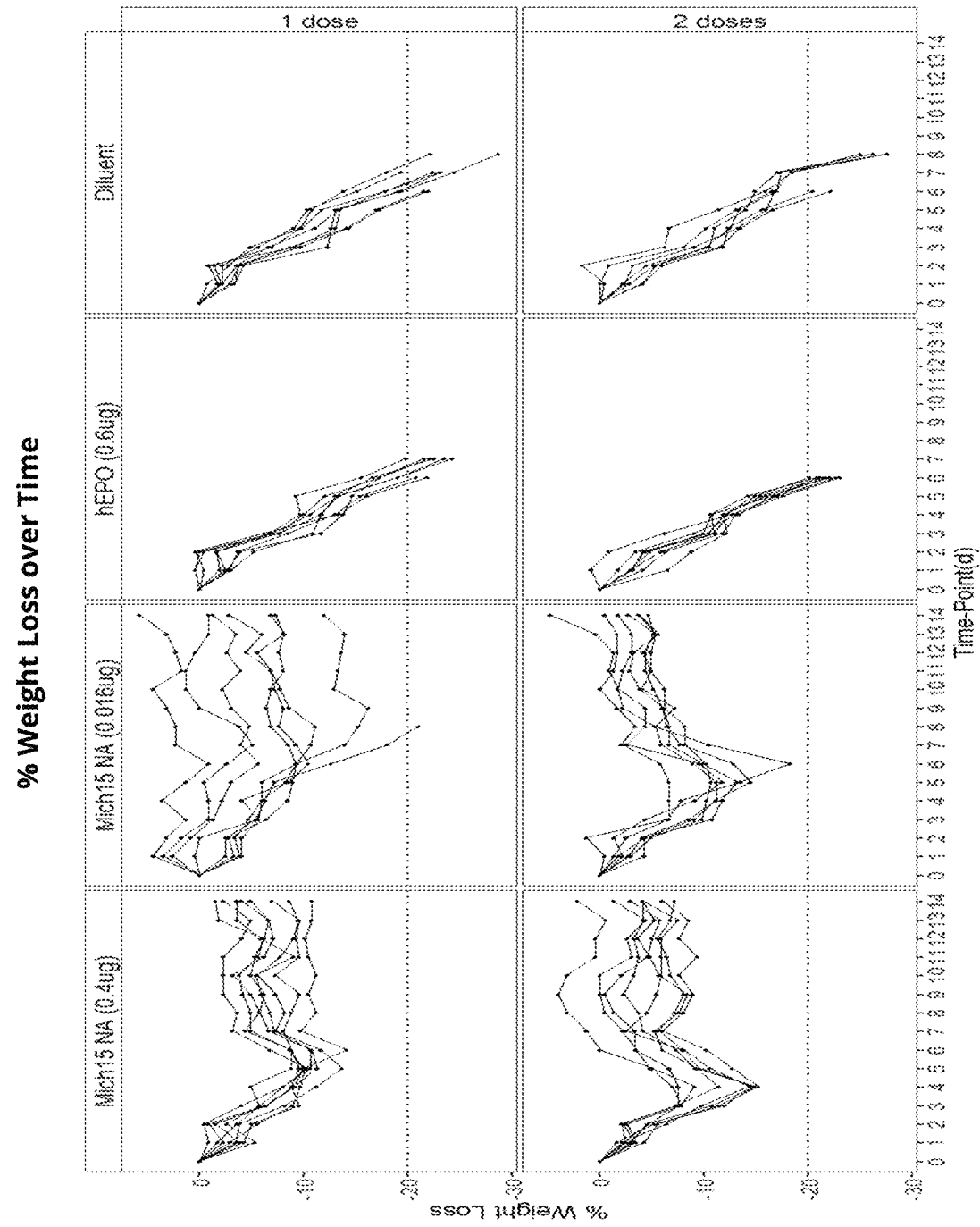

Influenza pandemics can occur when a novel influenza virus emerges in the human population. Such pandemics remain a major threat to public health, requiring vigilant attention and preparedness with countermeasures to be used in the event of sustained human-to-human spread of the virus. In the experiments described in this Example, hemagglutinin (HA) from a highly pathogenic H1N1 strain A/California/7/2009 (CA09), the cause of the 2009 flu pandemic, was used as a prototype antigen to evaluate the potency of mRNA vaccines prepared with LNP formulations of Lipid A and Lipid B.

The HA mRNA was prepared as described above. Citrate buffer (1 mM citrate, 150 mM NaCl, pH 4.5) was used in the preparation of the LNP compositions. A citrate buffer containing the mRNA was mixed with the lipids in ethanol solution during the formulation process. The pH and the concentration of the buffer were selected to achieve the high encapsulation rate of mRNA in the LNP formulations. The two solutions (mRNA in citrate buffer and lipids in ethanol solution) were mixed in a "T" mixer using a pump system, resulting in a homogeneous pulseless flow, wherein the lipids and the mRNA were mixed at a constant ratio throughout the process. This was critical to achieve a homogeneous formulation with the desired size and a low PDI, an indicator of a more homogeneous size distribution. This process resulted in high mRNA encapsulation, which is critical for achieving high potency. The resultant solution was then subjected to buffer exchange using TFF/dialysis tubes.

In a mouse study, efficacy of Lipid A and Lipid B CA09 HA formulations were assessed in a head-to-head comparison to MC3 LNP formulation as well as recombinant HA (rHA). CA09 (H1) HA mRNA (0.4 μg) formulated with different cationic lipids was injected intramuscularly into Balb/C mice (n=8) on day 0 (D0) and day 28 (D28). Immunogenicity of the vaccines, as indicated by HA inhibition (HAI) titers, is shown in FIG. 2A. The data show that two immunizations of Lipid A or Lipid B on day 0 (D0) and day 28 (D28) elicited high HAI titers and allowed complete protection of animals from homologous viral challenge (Belgium09 H1N1 virus) (FIG. 2B). During 14 days of post challenge observation, no obvious signs of morbidity (weight loss) were observed within the Lipid A and Lipid B treated groups, while a small number of animals within the recombinant protein control group demonstrated morbidity (FIG. 2B).

Similarly, mRNA encoding neuraminidase (NA) from the Mich15 influenza strain (Mich15 N1) was formulated with Lipid A and evaluated for its potency. Two doses (0.4 or 0.016 μg) of NA mRNA formulated with Lipid A were injected intramuscularly into Balb/c mice (n=8). The control groups (n=8) were injected with 0.6 μg of hEPO mRNA or with diluent. Half of the mice received only one injection (1 dose) on study day 0, while the other half received two injections (2 doses) given at study day 0 and day 28. The data show that this N1 Lipid A formulation elicited robust immune response, as indicated by NA inhibition (NAI) titers (FIG. 3A). The data further show that the mice treated with either one dose or two doses of the vaccine were protected from lethal viral challenge by Belgium09 H1N1 (FIG. 3B). The level of protection correlated with the NAI titers of vaccine treatment groups versus the negative control groups (hEPO and diluent).

Figure 4:
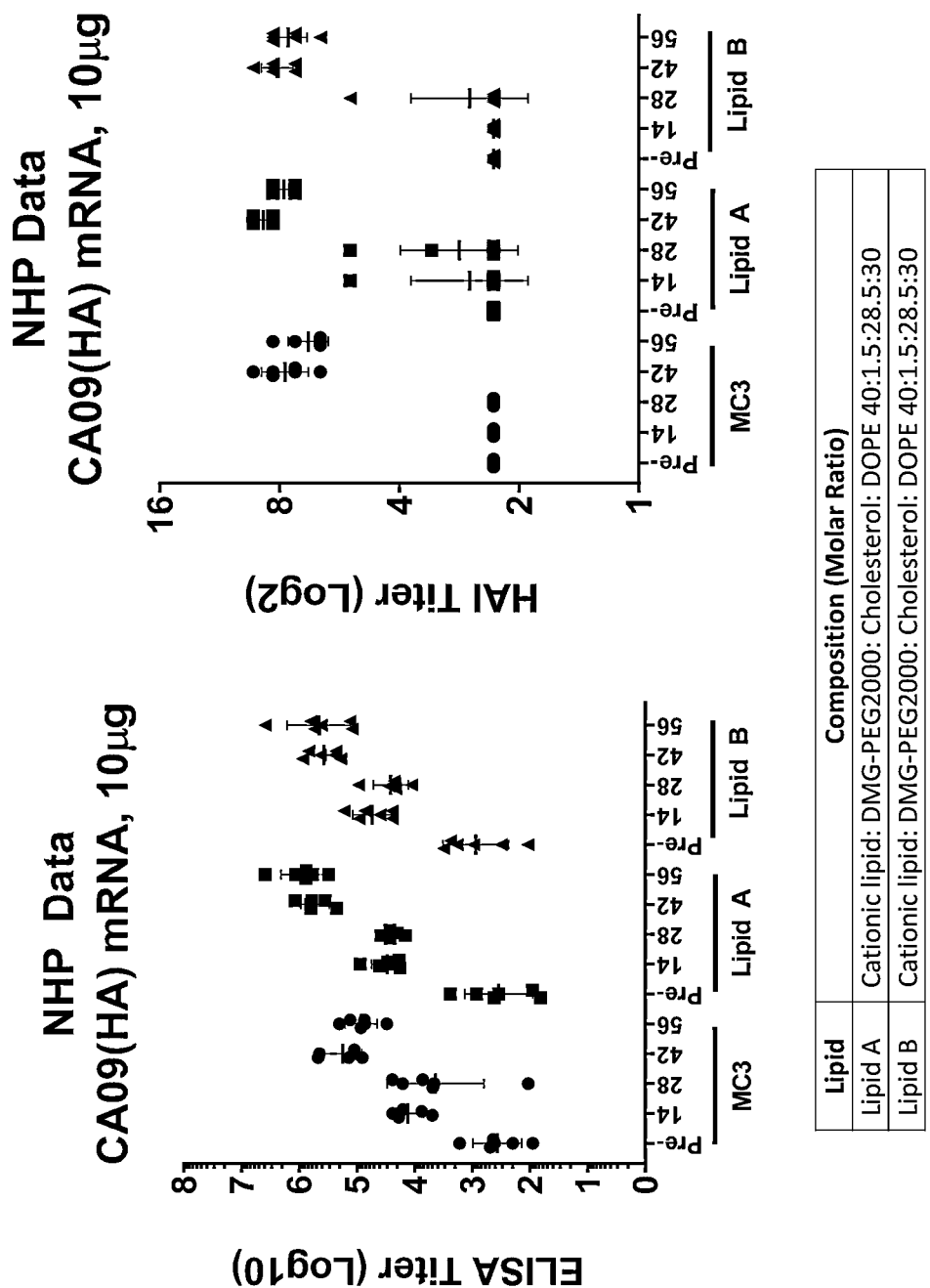
FIG. 4 is a graph showing that Lipid A and Lipid B LNP formulations with CA09 HA mRNA (10 µg) induced robust functional antibodies in cynomolgus macaque monkeys. HAI titers are reported as log 2 for serum samples taken at study days 0, 14, 28, 42, and 56.

The CA09 H1 mRNA formulated with the present LNPs was also tested in an NHP model. The mRNA (10 µg) was formulated with Lipid A and Lipid B, and injected intramuscularly into cynomolgus macaque monkeys (n=6) on study days 0 and 28. Detectable HAI priming by day 14 and a significant boost in HAI titer by day 28 for all LNPs were observed (FIG. 4, right panel). ELISA data also demonstrated significant priming over baseline by day 14 for all doses tested with a robust boost detected two weeks after the boost (FIG. 4, left panel). The results show that the present H1 mRNA formulations resulted in robust immune responses as indicated by HAI and endpoint ELISA titers.

Example 3: Influenza H3N2 LNP Vaccine Formulation

This Example describes experiments in which mRNA-LNP vaccine formulations for influenza strain Sing16 (H3N2) were evaluated for potency. One of the mRNAs used in these experiments is MRT1400. MRT1400 is a biosynthetic codon-optimized HA-H3 (influenza virus hemagglutinin, H3 subtype) messenger RNA (CO-HA-H3 mRNA) manufactured by in vitro transcription.

The protein sequence for influenza virus hemagglutinin, H3 subtype, is shown below:

```
                                            (SEQ ID NO: 1)
    MKTIIALSYI  LCLVFAQKIP  GNDNSTATLC  LGHHAVPNGT

IVKTITNDRI  EVTNATELVQ  NSSIGEICDS  PHQILDGENC

TLIDALLGDP  QCDGFQNKKW  DLFVERSKAY  SNCYPYDVPD

YASLRSLVAS  SGTLEFKNES  FNWTGVTQNG  TSSACIRGSS

SSFFSRLNWL  THLNYTYPAL  NVTMPNKEQF  DKLYIWGVHH

PGTDKDQIFL  YAQSSGRITV  STKRSQQAVI  PNIGSRPRIR

DIPSRISIYW  TIVKPGDILL  INSTGNLIAP  RGYFKIRSGK

SSIMRSDAPI  GKCKSECITP  NGSIPNDKPF  QNVNRITYGA

CPRYVKHSTL  KLATGMRNVP  EKQTRGIFGA  IAGFIENGWE

GMVDGWYGFR  HQNSEGRGQA  ADLKSTQAAI  DQINGKLNRL

IGKTNEKFHQ  IEKEFSEVEG  RVQDLEKYVE  DTKIDLWSYN

AELLVALENQ  HTIDLTDSEM  NKLFEKTKKQ  LRENAEDMGN

GCFKIYHKCD  NACIESIRNE  TYDHNVYRDE  ALNNRFQIKG

VELKSGYKDW  ILWISFAISC  FLLCVALLGF  IMWACQKGNI

RCNICI*
```

Figure 5B:
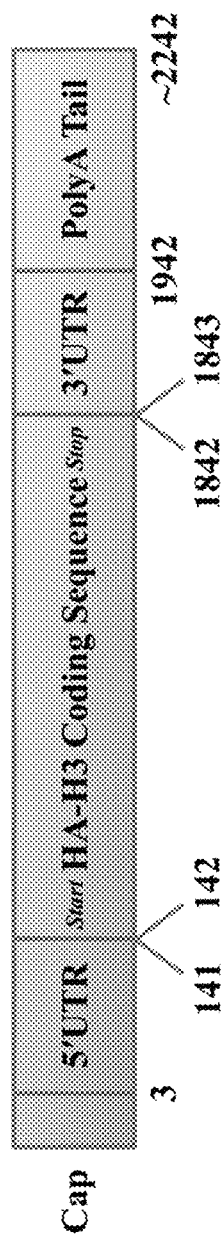

The coding sequence for this protein was codon-optimized. The codon-optimized sequence encoding the protein is shown in FIG. 5A (SEQ ID NO:2), where the wildtype sequence is shown as SEQ ID NO:3. The mRNA structure and sequence are shown in FIGS. 5B and 5C, respectively.

As shown in the figures, the HA-H3 mRNA coding sequence is flanked by 5' and 3' untranslated regions (UTRs) of 140 and 100 nucleotides, respectively. The biosynthetic HA-H3 mRNA also contains a 5' cap structure consisting of a 7-methyl guanosine (m7G) residue linked via an inverted 5'-5' triphosphate bridge to the first nucleoside of the 5' UTR, which is itself modified by 2'-O-ribose methylation. The 5' cap is essential for initiation of translation by the ribosome. The entire linear structure is terminated at the 3' end by a tract of approximately 100 to 500 adenosine nucleosides (polyA). The polyA region confers stability to the mRNA and is also thought to enhance translation. All of these structural elements are naturally occurring components used to promote the efficient translation of the HA-H3 mRNA.

A DNA plasmid was constructed for producing the codon-optimized mRNA sequence by in vitro transcription. In vitro transcription (IVT) reaction was carried out using RNA polymerase. The reaction mixes were precipitated. The precipitated RNA samples were loaded onto individual depth filtration cassette, washed with 80% ethanol and re-dissolved with recirculating water. A second aliquot of water was pumped through in a manner similar to the first step. This step was repeated one more time. The pooled eluates were subjected to ultrafiltration/diafiltration using a 50 kD hollow fiber TFF cassette. Each IVT TFF pool was then diluted in preparation for cap and tail reactions. Cap-tail reactions were precipitated and the RNA from the reaction was purified and collected as described above. The filtered mRNA was stored at −20° C. until use.

In these experiments, mRNA encoding Sing16 NA (N2) or Sing16 HA (H3; MRT1400 mRNA) antigens was formulated with Lipid A or Lipid B LNPs and injected intramuscularly into Balb/c mice (n=8) on D0 and D28 at 0.4 µg of mRNA per dose. For comparison, 1 µg of recombinant Sing16 H3 or Sing16 N2 protein with an oil-in-water emulsion adjuvant (AF03) was injected by the intramuscular route into Balb/c mice (n=8). Immune responses were measured by NAI and HAI assays.

Figure 6:
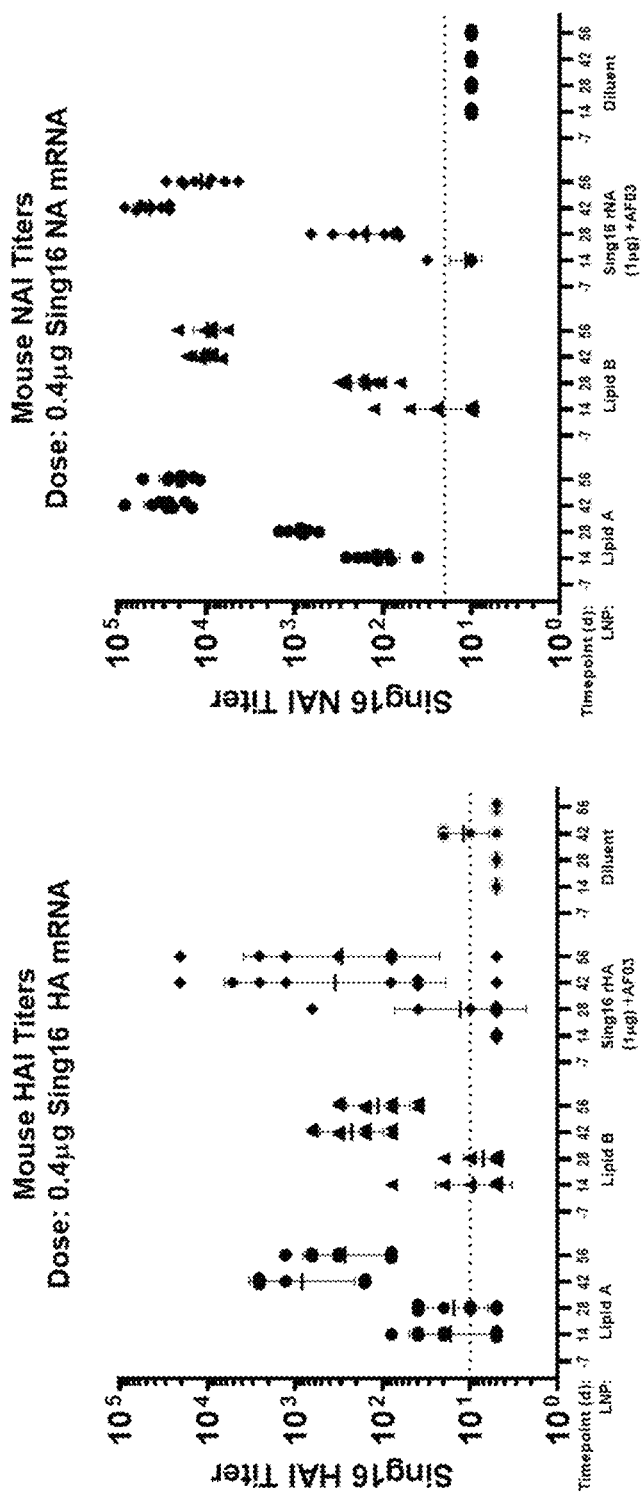
FIG. 6 is a pair of graphs showing that Lipid A and Lipid B LNP formulations with MRT1400 or NA mRNA induced robust functional antibodies in mice. First injection was given at study day 0 and second injection was given at study day 28. Left Panel: HAI titers are reported as log 10 for serum samples taken at study days 14, 28, 42, and 56. Right Panel: NAI titers are reported as log 10 for serum samples taken at study days 14, 28, 42, and 56. Bars are geometric means and geometric standard deviations. Dashed line=lower limit of quantitation.

The data show that animals immunized with NA (N2) mRNA demonstrated detectable NAI priming by day 14 and a significant boost in NAI titer by day 28 (FIG. 6, right panel). The data also show that HA Sing16 Lipid A and Lipid B formulations elicited robust HAI responses after boosting on day 28 (FIG. 6, left panel).

Figure 7A:
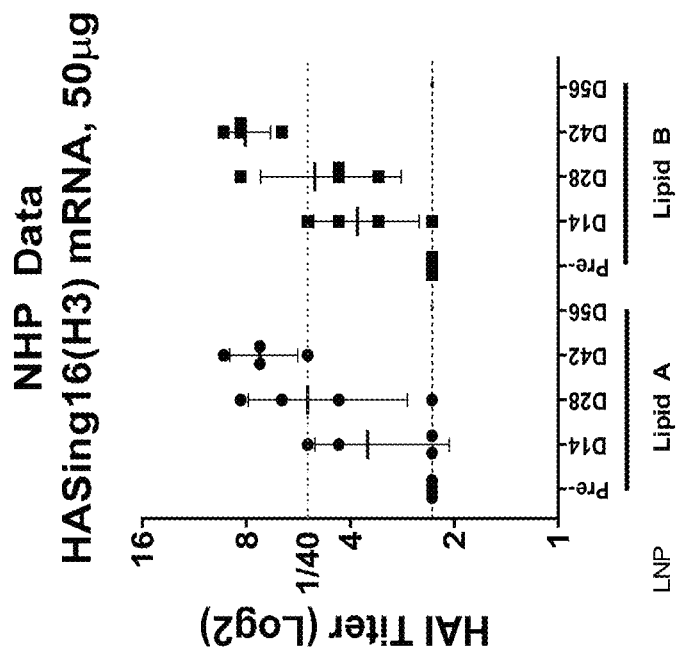
FIG. 7A is a graph showing that Lipid A and Lipid B LNP formulations with MRT 1400 induced robust functional antibodies in NHPs. HAI titers are reported as log 2 for serum samples taken at study days 0, 14, 28, 42, and 56. First injection was given at study day 0 and second injection was given at study day 28. Bars are means and standard deviations. Upper dashed line=1/40 minimum target. Lower dashed line=lower limit of detection.

Similarly, the Sing16 HA mRNA Lipid A and Lipid B vaccines were evaluated in non-human primates (NHPs), cynomolgus macaque monkeys (n=6). The HA Sing16 mRNA (50 µg) formulated with Lipid A or Lipid B was injected by the intramuscular route into the monkeys. The first injection was given at study day 0 and the second injection was given at study day 28. The data show that the vaccines elicited robust immune functional responses boosted on day 28 (FIG. 7A).

Figure 7B:
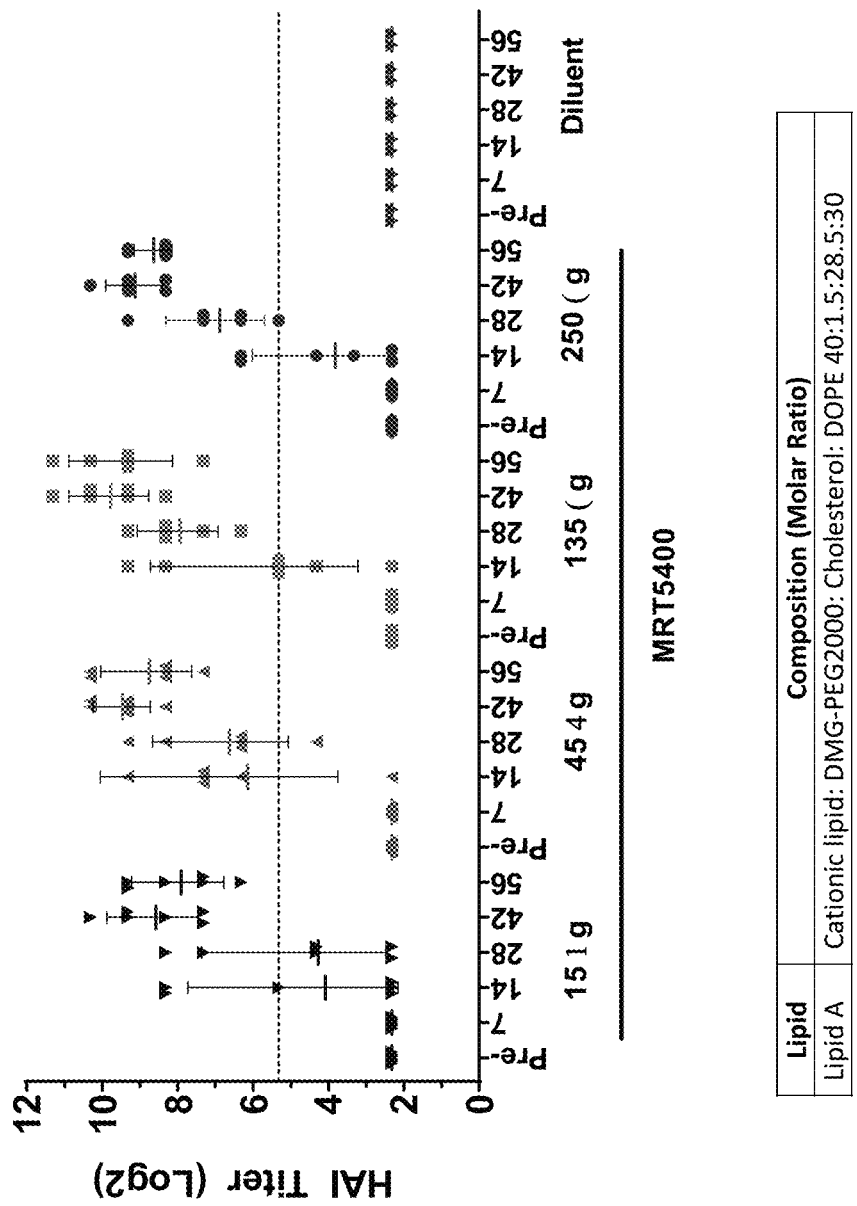
FIGS. 7B and 7C are a pair of graphs showing that a Lipid A LNP formulation (MRT5400) containing MRT1400 mRNA induced functional antibodies (FIG. 7B) and robust ELISA titers (FIG. 7C) in cynomolgus macaque monkeys at four dose levels: 15, 45, 135 and 250 µg of mRNA. HAI and ELISA titers are reported as log 2 for serum samples taken at study days 0, 14, 28, 42, and 56. First injection was given at study day 0 and second injection given at study day 28. Bars are means and standard deviations. Dash line=1/40 minimum target.
Figure 7C:
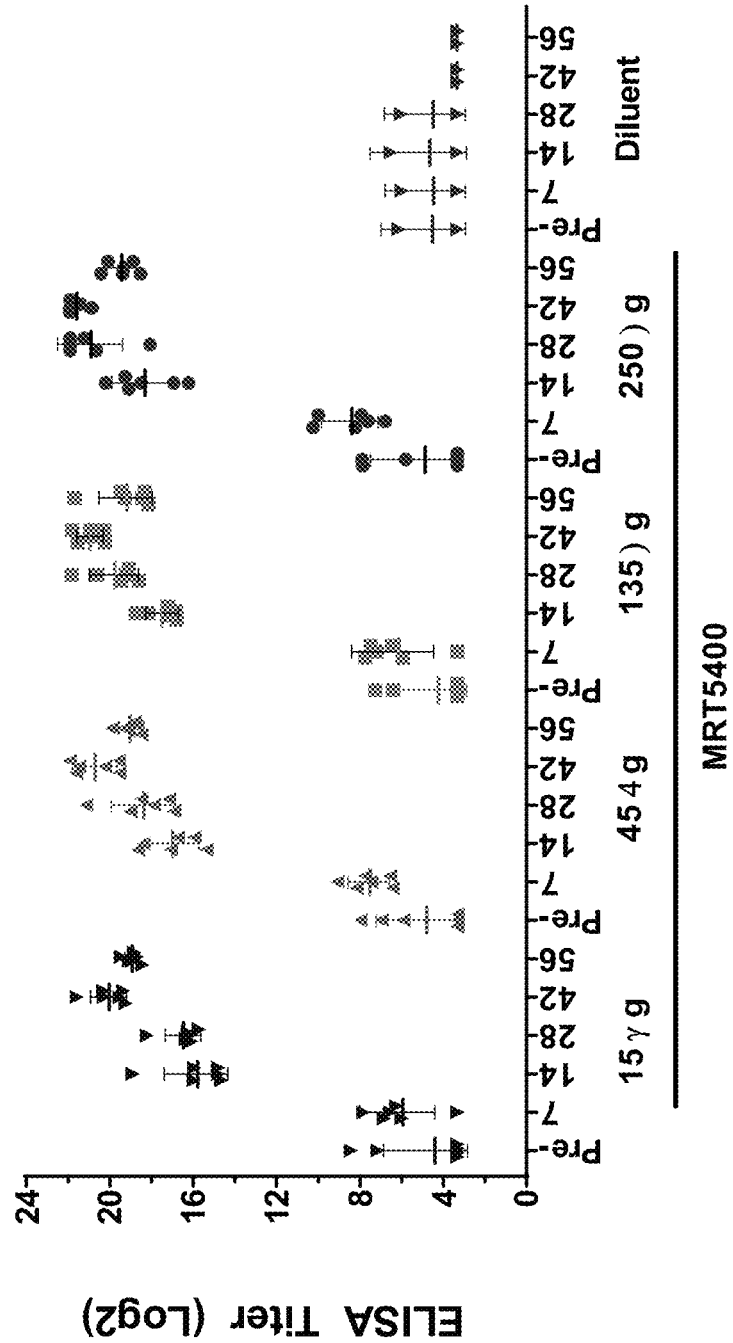

In addition, four dose levels of HA Sing16 mRNA formulated in Lipid A (i.e., MRT5400 vaccine)—15, 45, 135 and 250 µg—were evaluated in NHPs. The first immunization was given at study day 0 second immunization at study day 28. All NHPs demonstrated IgG binding and HAI titers for all doses tested with no differences in immune response between the various doses tested two weeks after the second injection at D42 (FIGS. 7B and 7C).

Figure 8A:
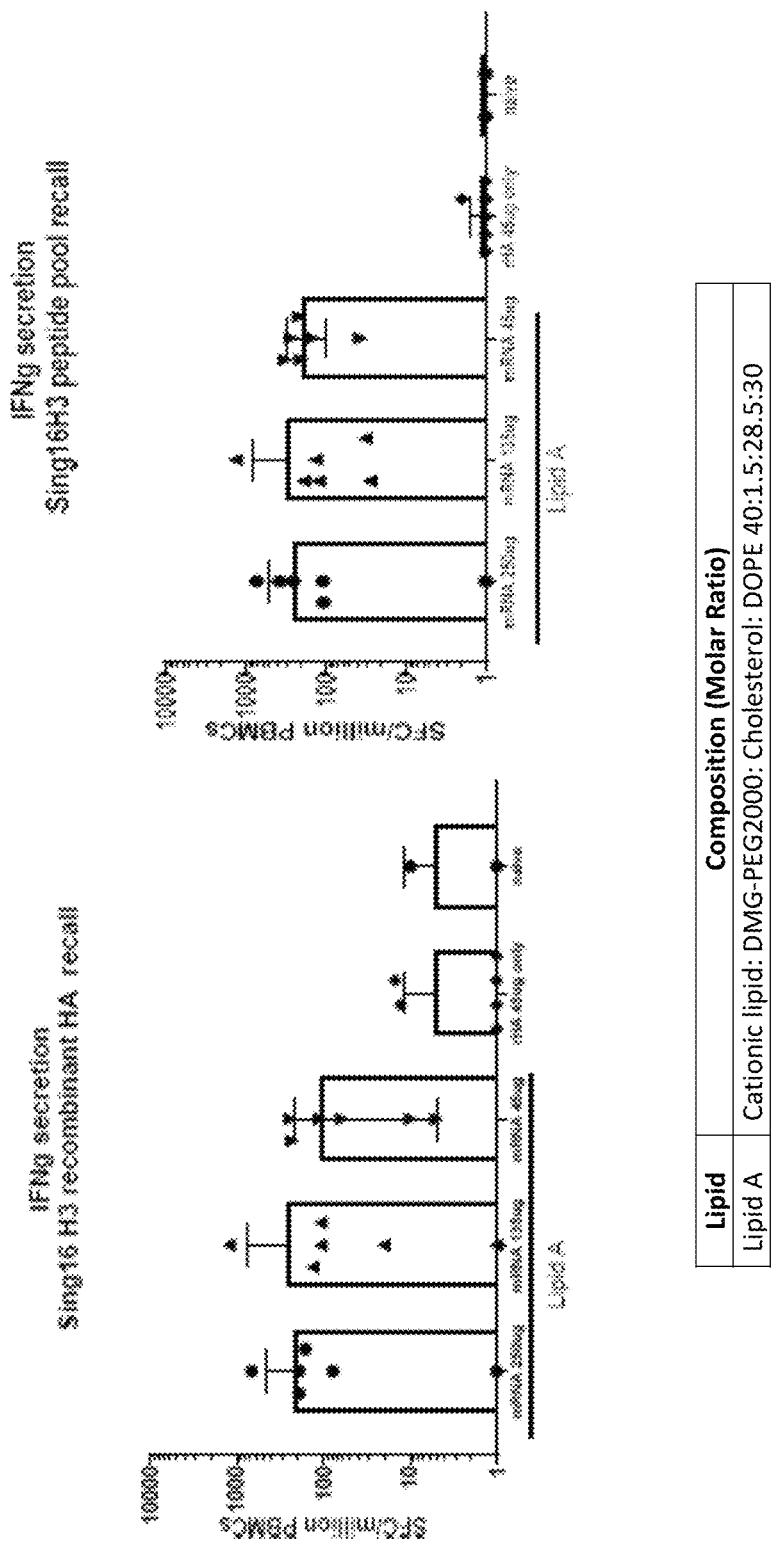
FIGS. 8A and 8B are panels of graphs showing the T cell cytokine response of cynomolgus macaques after a second vaccination with Lipid A LNP formulation MRT5400 in three dose level groups (250 µg, 135 µg, and 45 µg of mRNA). IFN-γ and IL-13 induced by re-stimulation with either the recombinant HA (rHA) protein (left panel) or the pooled peptides (right panel) were assessed in peripheral blood mononuclear cells (PMBC) on day 42 by ELISPOT assays. The frequencies of PBMC secreting IFN-γ (FIG. 8A) or IL-13 (FIG. 8B) were calculated as spots forming cells (SFC) per million PBMC. Each symbol represents an individual sample, and the bar represents the standard deviation.
Figure 8B:
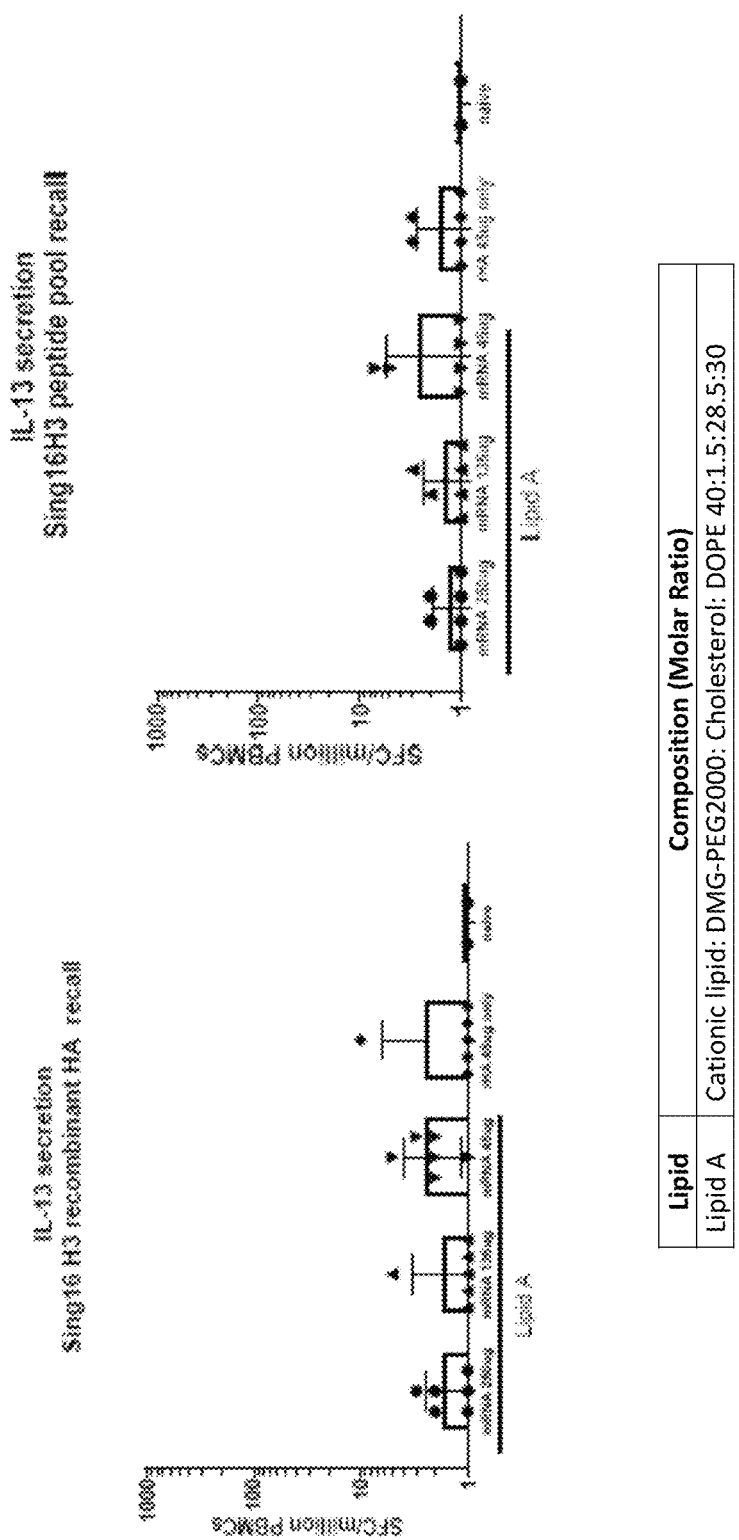

The Sing16 HA mRNA Lipid A vaccine was also evaluated for a T cell response in NHPs after the second vaccination. Peripheral blood mononuclear cells (PBMCs) were collected at day 42 and incubated overnight with either the Sing16 H3 recombinant protein or the peptide pools representing the entire HA open reading frame. Cytokines induced by the re-stimulation were assessed in ELISPOT assays. The frequencies of PBMC secreting IFN-γ, a Th1 cytokine (FIG. 8A), or IL-13, a Th2 cytokine (FIG. 8B) were calculated as spot-forming cells (SFC) per million PBMC. The majority of animals in the three dose level groups tested (250 µg, 135 µg, and 45 µg) demonstrated the presence of high frequency of IFN-γ secreting cells, with over 100 SFCs per million PBMCs (FIG. 8A). A dose-response was not observed, as the animals in the lower and higher dose level groups showed comparable frequencies of IFN-γ secreting cells. In contrast, the presence of IL-13 cytokine secreting cells was not detected in any of the groups tested and at any dose level (FIG. 8B). These data presented clear evidence for a Th1-biased cellular response and a lack of Th2 response to the HA antigen following vaccination in NHPs.

Example 4: Influenza LNP Vaccine Formulations with Modified mRNA

This Example describes experiments comparing the potency of vaccines containing unmodified (unmodified non-replicating or "UNR") and modified (modified non-replicating or "MNR") mRNA. UNR CA09 HA mRNA and MNR CA09 HA mRNA were prepared by in vitro transcription. In MNR, all uridines were replaced by pseudouridines.

Figure 9A:
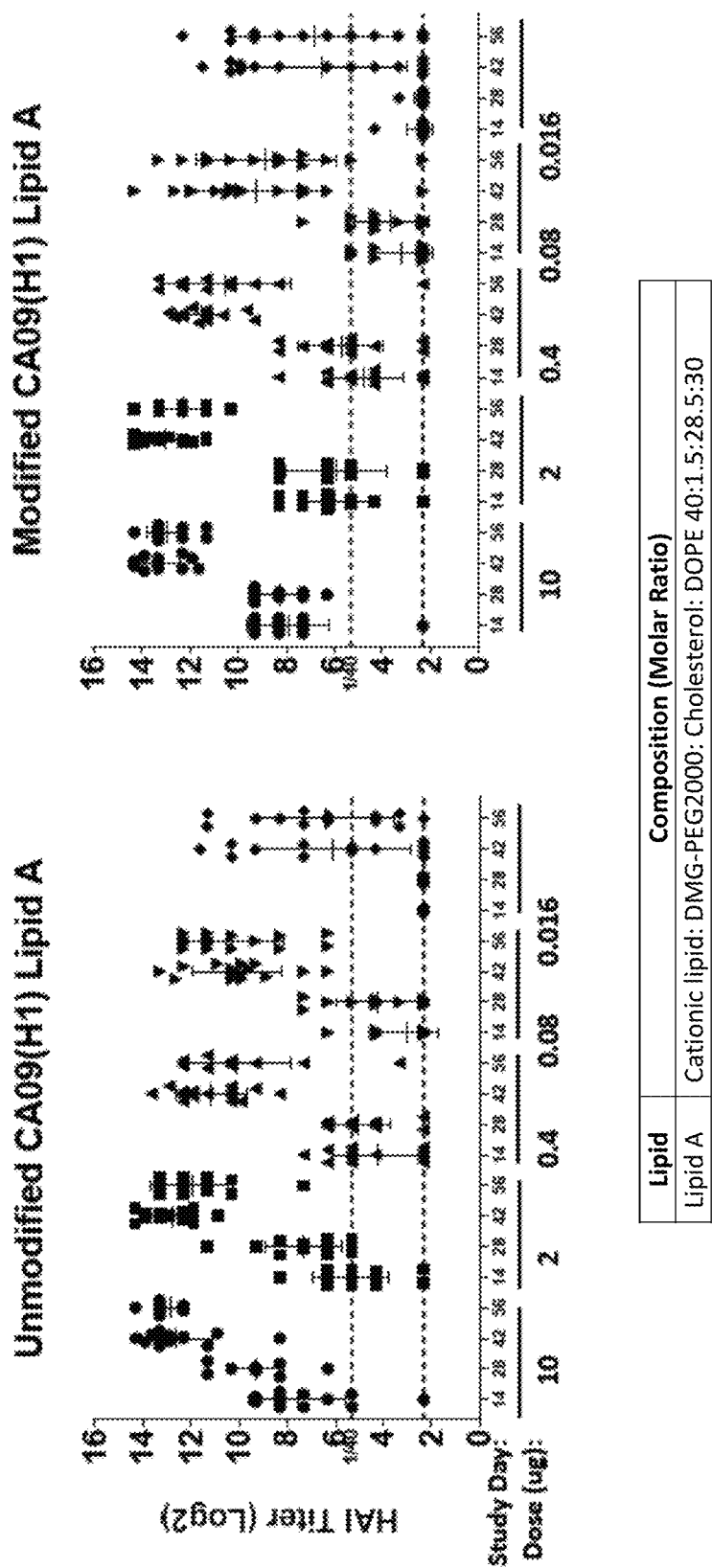
FIG. 9A is a pair of graphs showing that Lipid A LNP formulations containing modified and unmodified CA09 HA mRNA were comparable as indicated by HAI titers in vaccinated mice. HAI titers are reported as log 2 for serum samples taken at study days 14, 28, 42, and 56. First injection was given at study day 0 and second injection was given at study day 28. Bars are means and standard deviation. Upper dashed line=1/40 minimum target. Lower dashed line=lower limit of quantitation.
Figure 9B:
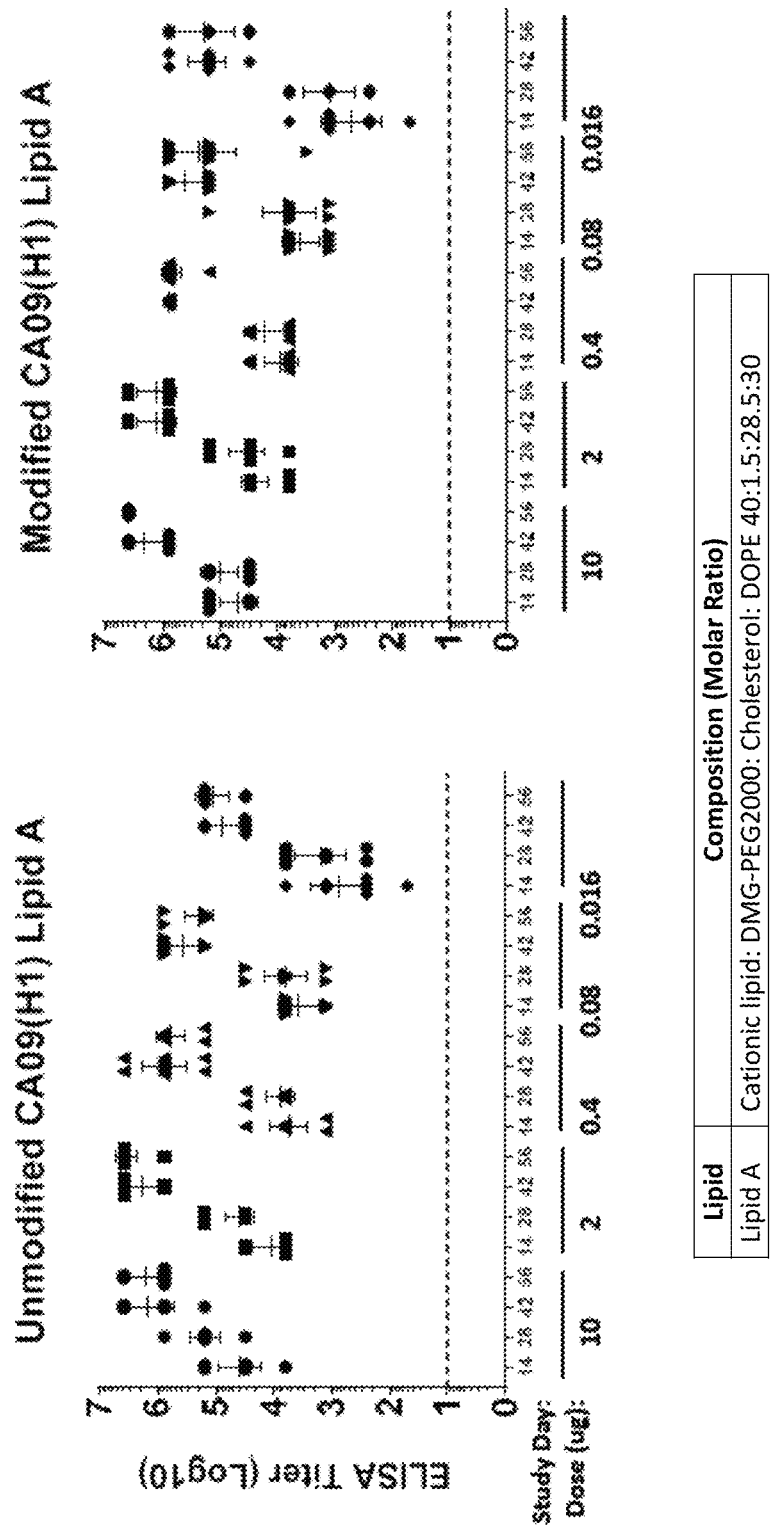
FIG. 9B is a pair of graphs showing that Lipid A LNP formulations containing modified and unmodified CA09 HA mRNA were comparable as indicated by ELISA titers in mice. Total IgG ELISA titers are reported as log 10 for serum samples taken at study days 14, 28, 42, and 56. First injection was given at study day 0 and second injection was given at study day 28. Dashed line=lower limit of quantitation.
Figure 10B:
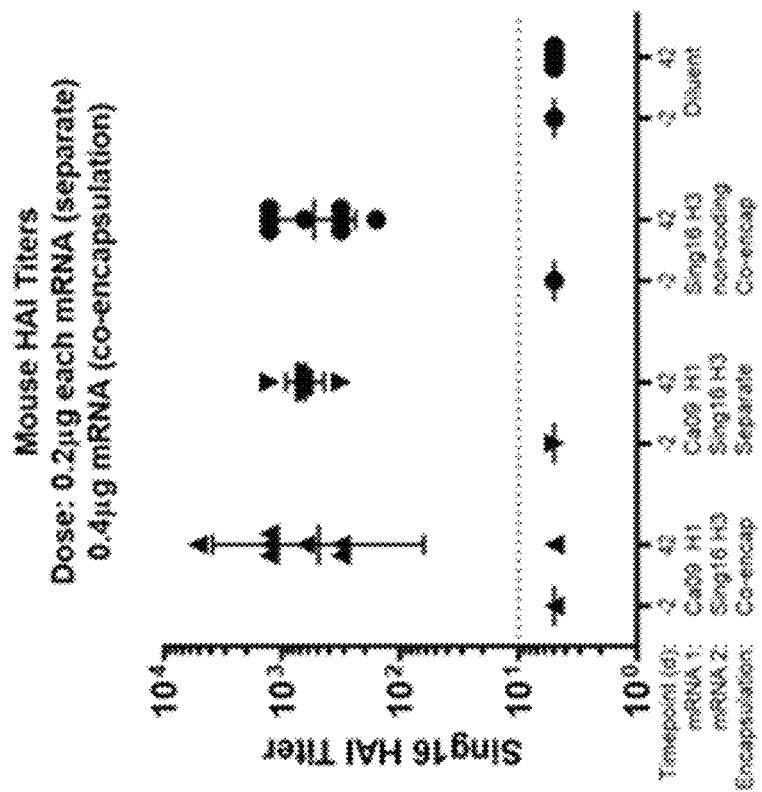
FIGS. 10A and 10B are a pair of graphs showing that bivalent Lipid A LNP formulations with CA09 HA mRNA and Sing16 HA mRNA induced robust functional antibodies as assessed by HAI titers (CA09 (FIG. 10A) and Sing16 (FIG. 10B)) in Balb/c mice at a dose of 0.4 µg of total mRNA. 0.4 µg mRNA was dosed as a co-encapsulated mRNA-LNP formulation, or each HA mRNA was separately administered with 0.2 µg going into each leg. Each HA mRNA was also co-encapsulated into a formulation with non-coding mRNA to control for total mRNA packing into the LNP. The diluent group received mRNA-LNP diluent buffer. HAI titers are reported for serum samples taken at study days −2 (baseline), 14, 28, and 42.
Figure 10A:
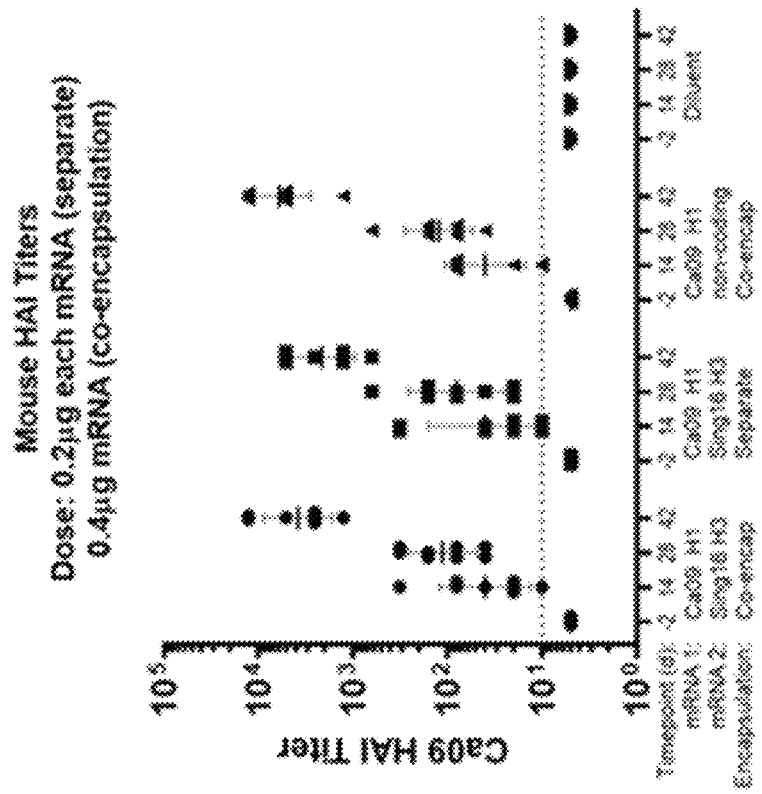

Five different doses (0.016, 0.08, 0.4, 2, and 10 µg) of CA09 HA mRNA (either modified or unmodified) formulated with Lipid A were injected by the intramuscular route into Balb/c mice (n=15). The data show that the LNP formulations increased the stability and delivery efficiency of naked mRNA (UNR), for the potency between UNR and MNR mRNA was comparable as indicated by HAI titers (FIG. 9A). ELISA data for Balb/c mice also demonstrated significant priming over baseline by day 14 for all doses tested (both UNR and MNR mRNAs), with a robust boost detected two weeks after the boost. The data also show that UNR and MNR mRNAs were comparable in eliciting ELISA titers (FIG. 9B).

In conclusion, the present dose titration study demonstrated that unmodified and modified CA09 HA mRNA formulated with Lipid A elicited statistically indistinguishable immune responses in Balb/c mice, as indicated by either HAI or by endpoint ELISA assay. Balb/c mice immunized with the four higher doses of UNR and MNR mRNA demonstrate detectable HAI priming by day 14 and a significant boost in HAI titer by day 42 for all doses. These day-14 priming titers represent both a dose effect and dose sparing potential for generating detectable titers over a 125-fold range. The second injection titers at the same dose range confirms the robustness of the immune response to this mRNA-LNP formulation. Similar results were also observed in non-human primates.

Example 5: Multi-Valent Influenza Vaccine LNP Formulation

This Example describes a study using a Lipid A-based LNP vaccine containing mRNA encoding CA09 HA (as described in Example 2) and mRNA encoding Sing16 HA (as described in Example 3).

More specifically, CA09 HA mRNA and Sing16 HA mRNA co-encapsulated in Lipid A were evaluated in Balb/c mice (n=8). mRNA-LNP was administered as two mRNAs co-encapsulated or dosed separately as singly encapsulated mRNAs. For both approaches, a total of 0.4 µg LNP formulation was injected into mice by intramuscular injection. The first injection was given at study day 0 and the second injection was given at study day 28. The data show that the vaccines elicited robust immune functional responses. There did not appear to be any difference between the two administration approaches. These data show that co-encapsulation did not cause hindrance or interference between the two mRNAs.

Example 6: Further Studies on Multi-Valent Influenza Vaccine LNP Formulations

A panel of unmodified mRNAs encoding CA09 HA, Sing16 HA, Sing16 NA, Mich15 NA, A/Perth/16/2009 Influenza virus (Perth09 NA), and reporter antigens of firefly luciferase (FF) and hEPO were prepared. LNP formulations for HA and NA mRNA-LNP preparation were then tested for expression in vitro, the immune responses in animals, and for potency in preclinical models. For the studies in this Example, all of the LNP formulations were the Lipid A formulation.

Materials and Methods mRNA-LNP Preparations mRNA transcripts encoding for hEPO, FF, CA09 HA, Sing16 HA, Mich15 NA, and Sing16 NA were synthesized by in vitro transcription employing RNA polymerase with a plasmid DNA template encoding the desired gene using unmodified nucleotides. The resulting purified precursor mRNA was reacted further via enzymatic addition of a 5' cap structure (Cap 1) and a 3' poly(A) tail of approximately 200 nucleotides in length as determined by gel electrophoresis and purified. All mRNA preparations were analyzed for purity, integrity, and percentage of Cap 1 before storage at −20° C. Preparation of mRNA/lipid nanoparticle (LNP) formulations was described above. Briefly, an ethanolic solution of a mixture of lipids (ionizable lipid, phosphatidylethanolamine, cholesterol and polyethylene glycol-lipid) at a fixed lipid and mRNA ratio were combined with an aqueous buffered solution of target mRNA at an acidic pH under controlled conditions to yield a suspension of uniform LNPs. Upon ultrafiltration and diafiltration into a suitable diluent system, the resulting nanoparticle suspensions were diluted to final concentration, filtered, and stored frozen at −80° C. until use. The mRNA-LNP formulations were characterized for size by dynamic light scattering, percentage encapsulation and were stored at −80° C. at 1 mg/mL until further use by dilution with suitable buffer. hEPO-LNPs and FF-LNPs were utilized to check level of expression of target protein in vivo.

Visualization of S-Proteins Expressed in HeLa Cells

Immunocytochemistry-immunofluorescence analysis of influenza NA and HA-proteins was performed in HeLa cells transfected with bivalent H3N2 (Sing16 HA and Perth09 NA) mRNAs LNPs) using method described previously (Kalnin et al., *npj Vaccines* (2021) 6:61). Cells were fixed in 4% paraformaldehyde and subjected antibody staining for HA (GeneTex GTX40258), NA, and ER marker Calnexin (Abcam ab22595) was performed. Images were captured on confocal microscope followed by image analysis for quantification of HA and NA colocalization to the ER, mean signal intensity, and percent of cell area.

Flow Cytometry

Human skeletal muscle cells (HskMCs, Lonza) were cultured in M199 (Life Technologies) supplemented with GlutaMAX (Life Technologies), streptomycin, penicillin (Gibco), and 20% heat inactivated FBS (VWR) at 37° C. with 5% $CO_2$. The cells were harvested by trypsinization, washed with PBS, and electroporated using human primary muscle cell transfection kit on Nucleofector 2b (Lonza) with 12 mg of mRNA per $10^6$ cells following manufacturer's electroporation program D-033. Post 24 hour harvested cells were fixed, permeabilized with Cytofix™/Perm (BD) and stained with CA09 HA (Immune Tech), Sing16 HA (30-2F11-F7-A5, GeneTex), Mich15 NA (6G6, Immune Tech) and Sing16 NA (40017-RP01, Sino Biologicals) specific Ab followed by PE conjugated goat anti-mouse IgG secondary Ab (Southern Biotech) or AF647 conjugated goat anti-rabbit IgG (Life Technologies). Then the antibody-labeled cells were acquired by Fortessa (BD) and the expression of each protein was analyzed by FlowJo™ (TreeStar).

Cryogenic Transmission Electron Microscopy

A PELCO easiGlow™ device was used to plasma-clean the grids prior to LNP sample application, and a Vitrobot Mark IV System (ThermoFisher) with the chamber held at 100% humidity and 18° C. was used for plunge freezing. A 3.0 µl droplet of LNP sample was dispensed onto 300 mesh R2/1 QUANTIFOIL® grids with carbon film and gold bars. Grids were blotted for 4 seconds, held in place for 10 seconds, and then immediately plunge frozen in liquid ethane for storage and transfer to a Krios microscope. Exposures were collected using a Titan Krios transmission electron microscope (ThermoFisher) equipped with a Bio-Quantum energy filter and K3 direct electron detector (Gatan) operating in counting mode. Calibrated physical pixel size at the detector was 1.38 Å, corresponding to 64,000× magnification. A total of 3,141 69-frame movie exposures were collected at a dose per frame of 1.045 e/Å2 with defocus between −0.5 to −1.7 µm. For each movie exposure, patch-based motion correction, binning of super-resolution pixels, and frame dose-weighting was performed using RELION-3.1.34. From corrected images, over 700 candidate particle coordinates were extracted. Subsequent data analysis was done with MATLAB R2019a with image processing toolbox.

Immunization of Mice and NHPs for Expression Studies

Groups of four cynomolgus macaques (NHPs) (male and female) and four to eight male BALB/c mice were administered intramuscularly either dose of 10 µg (NHP) or 1, 0.5, 0.1, and 0.05 µg (mice) with hEPO-LNP prepared in the same ratio as the one intended to be used for HA/NA mRNA-LNP formulations. Blood samples were taken pre-administration, and at 6 h, 24 h, 48 h, 72 h, and 96 h post administration to monitor for serum hEPO expression via an ELISA using R and D Systems, Quantikine® IVD® ELISA, Human Erythropoietin Immunoassay kit as per manufacturers protocol, and reported as final values of mIU/ml and ng/ml. Briefly, microplate wells, precoated with a mouse monoclonal antibody specific for EPO were incubated with specimen or standard. After removing excess specimen or standard, wells were incubated with a rabbit anti-EPO polyclonal antibody conjugated to horseradish peroxidase. During the second incubation, the antibody-enzyme conjugate bound to the immobilized EPO. Excess conjugate was removed by washing. A chromogen was added to the wells and was oxidized by the enzyme reaction to form a blue colored complex. The reaction was stopped by the addition of acid, which turned the blue to yellow. The amount of color generated was directly proportional to the amount of conjugate bound to the EPO antibody complex, which, in turn, was directly proportional to the amount of EPO in the specimen or standard. The absorbance of this complex was measured, and a standard curve was generated by plotting absorbance versus the concentration of the EPO standards. The EPO concentration of the unknown specimen was determined by comparing the optical density of the specimen to the standard curve. The standards used in this assay were recombinant hEPO calibrated against the Second International Reference Preparation (67/343), a urine-derived form of human erythropoietin.

Immunization of Mice and NHPs for Immunogenicity Studies

Groups of Balb/c mice (Mus musculus) as per the treatment group were immunized under isoflurane anesthesia with a dose of 0.05 mL of designated vaccine preparation or diluent via the IM route in the quadriceps, on day 0 in one hind leg and day 28 in the contralateral leg. Mice that lost more than 20% of their initial body weight and displayed severe clinical signs were euthanized after the veterinarian's assessment of the animal's health prior to the study termination.

Naïve male and female Mauritius origin Cynomolgus macaques (*Macaca fascicularis*) were selected for the study. Animals weighed >2 kg and were >2 years of age at the start of the study. Animals selected for the study underwent comprehensive physical examinations prior to assignment to the study. The pre-assignment assessment of health status included a hands-on veterinarian examination and blood sample collections for CBC analysis as applicable per NIRC SOPs. Animals were generally housed in pairs and acclimated for at least 3 days prior to the start of the study. Groups consisted of up to 6 animals per treatment group. All animals were immunized under ketamine HCl (10 mg/kg, IM) or telazol (4-8 mg/kg, IM) sedation with a dose of 0.5 ml of their respected vaccine preparation or diluent via the IM route in one forelimb of each animal, targeting the deltoid, on Study Day 0. Twenty-eight days after the first immunization took place, a second immunization was given to the animals in the contralateral limb.

Immunization of Mice and NHPs for Challenge Studies

Mice were inoculated with the challenge strain approximately 9-12 weeks after the last immunization. Vials of stock virus were thawed and diluted to the appropriate concentration in ice-cold sterile PBS. All mice were challenged with a total volume of 50 µl containing 105.54 $TCID_{50}$ of Belgium09 virus in PBS which equated to $4LD_{50}$. Virus challenge was performed inside the biosafety cabinet in an enhanced ABSL2 laboratory. Mice were first anesthetized with an IP injection of a Ketamine/Xylazine solution (50 mg/kg Ketamine and 5 mg/kg Xylazine), and then challenged IN (dropwise into both nostrils; 25 µl per nostril) with a total volume of 50 µl of influenza virus using a micropipette. Following the challenge procedure, mice were placed in dorsal recumbency and observed until recovery from anesthesia. Daily body weights were taken following H1N1 challenge. Any individual animal with a single observation >20% body weight loss was euthanized. The weight measurements were either recorded daily post challenge until euthanasia in the online database, Pristima® (Version 7.5.0 Build 8), or written on study specific working sheets.

Blood Collection

For mice, blood was collected via submandibular or orbital sinus bleeds (in-life bleed, pre-study and on study days 14, 28, and 42 approximately 200 µl) and cardiac puncture (terminal bleed, day 56) from all animals under sedation. Mice were bled on pre-study to obtain a base-line pre-immune serum sample and for pre-screening purposes. Processing of the serum, blood samples were collected into SST tubes and allowed to clot for 30 minutes to 1 hour at room temperature. The samples were then centrifuged 1000-1300 g for 5-10 minutes with brakes off. Serum was collected using a P200 pipettor, divided into two 0.5 ml cryovials, and stored at −20° C. All bleeds were documented on specimen collection and processing logs, indicating the time of sample collection and the technician responsible for performing the procedure. A portion of the serum samples were evaluated in the HAI or ELLA and ELISA assays for antibody titers.

NHPs were bled for serum isolation while under anesthesia administered intramuscularly using 10 mg/kg ketamine/1 mg/kg acepromazine (days −4, 2, 7, 14, 28, 30, 35, 42, 56, 90, and 180). The volume of blood withdrawn did not exceed established guidelines with respect to percentage of body weight and animal's physical condition. Blood was withdrawn from anesthetized NHPs using femoral venipuncture using a Vacutainer 21 ga×1" blood collection needle or Abbott Butterfly 23 ga×3/4" tubing attached to BD Vacutainer® SST™ gel tubes. Serum was isolated by spinning the tubes at room temperature at a speed of 1200× g for 10 minutes. Serum was then aliquoted into labeled cryovials (1 ml/vial) and stored at ≤−20° C. A portion of the serum samples were evaluated in the HAI or ELLA and ELISA assays for antibody titers. For PBMCs, NHPs were pre-bled before vaccination and again approximately 42-63 days after the first injection. For this purpose, blood was collected into BD Vacutainer® tubes containing heparin anticoagulant. Briefly, anticoagulated blood samples were diluted in PBS and subjected to gradient density centrifugation for 30 minutes at 400× g using Histopaque® separation solution (Sigma). The opaque interface containing mononuclear cells was then collected, washed three times in PBS using a low speed (250× g) centrifugation for the last centrifugation to reduce the number of platelets. The live vs. dead PBMC were enumerated using a Nexcelom Cellometer K2. The PBMC were cryopreserved in FBS with 10% DMSO using Mr. Frosty® freezing boxes. The boxes were placed immediately into a −80° C. freezer for 24 hours and then transferred for storage in a liquid nitrogen tank.

ELISA

The antibody ELISAs were performed using recombinantly produced Sing16 NA protein, Sing16 HA protein, or CA09 HA protein. The proteins were captured on 96 well high binding polystyrene plates at a concentration of 2 µg/ml in carbonate-bicarbonate buffer. The plates were covered and incubated overnight (16±4 hours) at 2-8° C. After overnight incubation, the antigen coated plates were washed 5 times with a washing buffer (PBS, 0.5% Tween20) and blocked with a blocking solution (10% BSA in PBS) for 60±30 minutes at room temperature. Test samples, naïve control, and the reference sample were diluted in a sample diluent (PBS 10% BSA 0.5% Tween 20) and added to wells in duplicates followed by incubation at room temperature for 90 minutes. Plates were washed 5 times with the washing buffer, and goat anti-mouse HRP for mouse sera or goat anti-monkey HRP for NHP sera was added at a dilution of 1:10,000. The plates were then incubated 30 minutes at room temperature and the excess HRP-IgG was washed with the washing buffer. Sure-Blue TMB substrate was added to each plate and the reaction was stopped after about 10 minutes with TMB stop solution. The plates were then read at 450 nm with a Thermo Labsystems Multiskan™ spectrophotometer. The anti-antigen (HA or NA) specific antibody titers were expressed as a reciprocal of the highest serum dilution with an absorbance value >0.3.

HAI Assay

HAI assays were performed using the Sing16 H3N2 and the CA09 H1N1 virus stocks (BIOQUAL, Inc.). Sera were treated with receptor-destroying enzyme (RDE) by diluting one-part serum with three parts enzyme and incubated overnight in a 37° C. water bath. Enzyme was inactivated by a 30-minute incubation period at 56° C. followed by addition of six parts PBS for a final dilution of 1/10. HAI assays were performed in V-bottom 96-well plates using four hemagglutinating units (HAU) of virus and 0.5% turkey RBC. The reference serum for each strain was included as a positive control on every assay plate. Each plate also included a back-titration to confirm the antigen dose (4 HAU/25 µl) as well as a negative control sample (PBS or naïve control serum). The HAI titer was determined as the highest dilution of serum resulting in complete inhibition of hemagglutination. Results were only valid for plates with the appropriate back-titration result (verifying 4 HAU/25 µl added) and a reference serum titer within 2-fold of the expected titer.

NAI Assay

The method for the enzyme-linked lectin assay (ELLA) assay was used to determine neuraminidase-inhibiting (NAI) antibody titers. The source of antigen (virus NA) was titrated, and a standard amount was selected for incubation with serial dilutions of serum. Titration of sera was performed with serial dilutions of sera (heat inactivated at 56° C. for 1 hour) and a standard amount of virus was added to duplicate wells of a fetuin-coated plate. This mixture was then incubated overnight (16-18 hours); the next day, HRP-conjugated peanut agglutinin PNA (diluted to 2.5 µg/ml) was added to the washed plate and incubated for 2 hours at room temperature. Substrate (ODP in sodium citrate) was added and incubated for 10 minutes to develop the color. And then stop buffer (IN sulfuric acid) was added to stop the reaction. Plates were scanned for absorbance at OD 490 nm. The reduction or absence of color relative to a viral control indicated inhibition of NA activity due to the presence of NA-specific antibodies. NAI titers ($IC_{50}$ values) were calculated from the OD readings and the results were graphed in GraphPad Prism. If ELLA titration curves did not allow a good fit to determine a reliable IC50 value, the samples were retested using a different dilution scheme to reach the 50% endpoint.

T Cell ELISPOT Assay

Complete medium (DMEM1640+10% heat-inactivated FCS) was prewarmed in a 37° C. water bath. PBMCs were quickly thawed in a 37° C. water bath and transferred dropwise to conical tubes with the prewarmed medium. The tubes were centrifuged at 1,500 rpm for 5 mins and the cells were resuspended and counted using a Guava cell counter. Monkey IFN-γ ELISPOT kit (Mabtech 3421M-4APW) and IL-13 ELISPOT kit (Mabtech 3470M-4APW) were used. Precoated plates provided by the kits were washed four times with sterile PBS and blocked with 200 µl of complete medium in 37° C. incubator for at least 30 minutes. Sing16 H3 peptides pool (Genscript Custom Order) (at 1 µg/ml of each peptide) were used as recall antigens in the assay. Two µg/ml of ConA (Sigma CAT #C5275) was used as a positive control. Fifty µl of recall antigens and 300,000 of PBMCs in 50 µl were added to each well for stimulation. The plates were placed in a 37° C., 5% $CO_2$ humidified incubator for 48 hours.

After the incubation, cells were removed, plates were washed 5 times with PBS, and 100 µl of 1 µg/ml biotinylated anti-IFN-γ or anti-IL-13 detection antibodies were added to each well in the plates. After a 2 hour incubation, the plates were washed 5 times with PBS and incubated with 100 µl of a 1:1000 dilution of streptavidin in each well for one hour at room temperature. Plates were developed with 100 µl of BCIP/NBT substrate solution until the spots emerged. Plates were rinsed by tap water, air-dried and scanned and counted using CTL ImmunoSpot® Reader (Cellular Technology Ltd.). The data was reported as spots forming cells (SFC) per million PBMCs.

Memory B Cell (MBC) ELISPOT Assay

Human IgG Single-Color memory B cell ELISPOT kit (CAT #NC1911372, CTL) was used per manufacturer's instruction to measure Sing16 H3-specific and total IgG+ antibody-secreting cells (ASCs). Differentiation of MBCs into ASCs was performed in PBMC using a stimulation cocktail provided by the kit. Briefly, frozen PBMCs were quickly thawed in a 37° C. water bath, mixed with DNase I (CAT #90083, Fisher Scientific) and transferred into the tube containing pre-warmed complete culture medium (CM) (RPMI 1640, (CAT #22400-089, Gibco) containing 10% FCS (CAT #SH30073.03, HyClone™), and 1% penicillin/streptomycin (CAT #P4333, Sigma) and centrifuged at 1,500 rpm for 5 minutes. Cell pellet was re-suspended in 5 ml of complete medium at $2 \times 10^6$ cells per ml and transferred to a T25 flask for 1 hour in 5% $CO_2$ incubator at 37° C. The volume of cell suspension was then adjusted to 6 ml and B-Poly-S was added at 1:1000 dilution. Cells were left in the $CO_2$ incubator for stimulation for 4 days. PVDF microplates supplied by the kit were pre-wetted with 70% ethanol, rinsed and coated overnight with 80 µl/well of either anti-human IgG capture Ab provided by the kit or Sing16/H3 recombinant protein at 4 µg/ml.

Cells were harvested after 4 days of stimulation, washed, and counted and adjusted to the designated concentration in the CM. Coated microplates were washed with PBS, blocked for 1 hour with the CM and emptied out. Cell suspension at 100 µl/well was added to the plates and incubated in $CO_2$ incubator at 37 C for 18 hrs. After washing, 80 µl/well of 1:400 diluted anti-human IgG biotin detection antibody was added to the plate and incubated at room temperature for 2 hours. Following washing, Streptavidin-AP at 1:1000 dilution was added to the plate at 80 µl/well for 1 hour. Freshly prepared Substrate solution was added and incubated at RT for 18 min. Plates were rinsed by tap water, air-dried and scanned and counted using CTL ImmunoSpot® Reader (Cellular Technology Ltd). For each individual animal the number of IgG+ and number of Sing16/H3-specific ASCs was calculated per million of PBMCs. The frequency of antigen-specific ASCs was calculated as % of antigen-specific ASCs to the total IgG+ ASCs. To assess assay background the negative control wells on every plate were coated with PBS (no background was detected).

Statistical Analysis

For estimating the $T_{max}$ of Radiance, a non-parametric method was used to estimate the $T_{max}$ of individual subject based on observed data. For estimating the half-life of Radiance, assuming exponential decay model for radiance after reaching the maximum value, a linear model was fitted to log transformed data per subject during the time course from the maximum radiance to decay to baseline (we estimate the baseline using the average of radiance in saline group). The half-life was estimated as the time point when the log radiance had reached the middle point between maximum and baseline values. For analysis of different readouts with results summarized as geometric mean, SE model based geometric means and SEs were estimated from a mixed effect model for repeated measures where the response was the log transformed readouts, vaccination was fixed effect and time was repeated measure; log-based means and SE estimates from the model were then back transformed to get geometric means and SEs. For weight change, over descriptive statistical analysis was used. Medians and ranges of each group of the maximum % body weight loss from baseline (Day 0) over time were reported to evaluate the worse scenarios; medians and ranges of each group of the % body weight change from baseline at the last observation were reported to evaluate the body weight recovery.

Antigen Sequences

The sequence of the Perth09 N2 antigen used here is:

(SEQ ID NO: 4)
MNPNQKIITIGSVSLTISTICFFMQIAILITTVTLHFKQYEFNSPPNNQVM

LCEPTIIERNITEIVYLTNTTIEKEICPKLAEYRNWSKPQCDITGFAPFSK

DNSIRLSAGGDIWVTREPYVSCDPDKCYQFALGQGTTLNNVHSNNTVRDRT

PYRTLLMNELGVPFHLGTKQVCIAWSSSSCHDGKAWLHVCITGDDKNATAS

FIYNGRLVDSVVSWSKEILRTQESECVCINGTCTVVMTDGSASGKADTKIL

FIEEGKIVHTSTLSGSAQHVEECSCYPRYPGVRCVCRDNWKGSNRPIVDIN

IKDHSIVSSYVCSGLVGDTPRKNDSSSSSHCLDPNNEEGGHGVKGWAFDDG

NDVWMGRTISEKSRLGYETFKVIEGWSNPKSKLQINRQVIVDRGNRSGYSG

IFSVEGKSCINRCFYVELIRGRKEETEVLWTSNSIVVFCGTSGTYGTGSWP

DGADINLMPI*

The sequence of the Mich15 N1 antigen used here is:

(SEQ ID NO: 5)
MNPNQKIITIGSICMTIGMANLILQIGNIISIWVSHSIQIGNQSQIETCNQ

SVITYENNTWVNQTYVNISNTNFAAGQSVVSVKLAGNSSLCPVSGWAIYSK

DNSVRIGSKGDVFVIREPFISCSPLECRTFFLTQGALLNDKHSNGTIKDRS

PYRTLMSCPIGEVPSPYNSRFESVAWSASACHDGINWLTIGISGPDSGAVA

VLKYNGIITDTIKSWRNNILRTQESECACVNGSCFTIMTDGPSDGQASYKI

FRIEKGKIIKSVEMKAPNYHYEECSCYPDSSEITCVCRDNWHGSNRPWVSF

NQNLEYQMGYICSGVFGDNPRPNDKTGSCGPVSSNGANGVKGFSFKYGNGV

WIGRTKSISSRKGFEMIWDPNGWTGTDNKFSIKQDIVGINEWSGYSGSFVQ

HPELTGLDCIRPCFWVELIRGRPEENTIWTSGSSISFCGVNSDTVGWSWPD

GAELPFTIDK*

The sequence of the Sing16 H3 antigen used here is:

(SEQ ID NO: 6)
MKTIIALSYILCLVFAQKIPGNDNSTATLCLGHHAVPNGTIVKTITNDRIE

VTNATELVQNSSIGEICDSPHQILDGENCTLIDALLGDPQCDGFQNKKWDL

FVERSKAYSNCYPYDVPDYASLRSLVASSGTLEFKNESFNWTGVTQNGTSS

ACIRGSSSSFFSRLNWLTHLNYTYPALNVTMPNKEQFDKLYIWGVHHPGTD

KDQIFLYAQSSGRITVSTKRSQQAVIPNIGSRPRIRDIPSRISIYWTIVKP

GDILLINSTGNLIAPRGYFKIRSGKSSIMRSDAPIGKCKSECITPNGSIPN

DKPFQNVNRITYGACPRYVKHSTLKLATGMRNVPEKQTRGIFGAIAGFIEN

GWEGMVDGWYGFRHQNSEGRGQAADLKSTQAAIDQINGKLNRLIGKTNEKF

HQIEKEFSEVEGRVQDLEKYVEDTKIDLWSYNAELLVALENQHTIDLTDSE

MNKLFEKTKKQLRENAEDMGNGCFKIYHKCDNACIESIRNETYDHNVYRDE

ALNNRFQIKGVELKSGYKDWILWISFAISCFLLCVALLGFIMWACQKGNIR

CNICI*

The sequence of the Sing16 N2 antigen used here is:

(SEQ ID NO: 7)
MNPNQKIITIGSVSLTISTICFFMQIAILITTVTLHFKQYEFNSPPNNQVM

LCEPTIIERNITEIVYLTNTTIEKEICPKPAEYRNWSKPQCGITGFAPFSK

DNSIRLSAGGDIWVTREPYVSCDPDKCYQFALGQGTTLNNVHSNNTVRDRT

PYRTLLMNELGVPFHLGTKQVCIAWSSSSCHDGKAWLHVCITGDDKNATAS

FIYNGRLIDSVVSWSKDILRTQESECVCINGTCTVVMTDGNATGKADTKIL

FIEEGKIVHTSKLSGSAQHVEECSCYPRYPGVRCVCRDNWKGSNRPIVDIN

IKDHSIVSSYVCSGLVGDTPRKNDSSSSSHCLNPNNEEGGHGVKGWAFDDG

NDVWMGRTINETSRLGYETFKVVEGWSNPKSKLQINRQVIVDRGDRSGYSG

IFSVEGKSCINRCFYVELIRGRKEETEVLWTSNSIVVFCGTSGTYGTGSWP

DGADLNLMHI*

The sequence of the CA09 H1 antigen used here is:

(SEQ ID NO: 24)
MKAILVVLLYTFATANADTLCIGYHANNSTDTVDTVLEKNVTVTHSVNL

LEDKHNGKLCKLRGVAPLHLGKCNIAGWILGNPECESLSTASSWSYIVE

TPSSDNGTCYPGDFIDYEELREQLSSVSSFERFEIFPKTSSWPNHDSNK

GVTAACPHAGAKSFYKNLIWLVKKGNSYPKLSKSYINDKGKEVLVLWGI

HHPSTSADQQSLYQNADAYVFVGSSRYSKKFKPEIAIRPKVRDREGRMN

YYWTLVEPGDKITFEATGNLVVPRYAFAMERNAGSGIIISDTPVHDCNT

TCQTPKGAINTSLPFQNIHPITIGKCPKYVKSTKLRLATGLRNIPSIQS

RGLFGAIAGFIEGGWTGMVDGWYGYHHQNEQGSGYAADLKSTQNAIDEI

TNKVNSVIEKMNTQFTAVGKEFNHLEKRIENLNKKVDDGFLDIWTYNAE

LLVLLENERTLDYHDSNVKNLYEKVRSQLKNNAKEIGNGCFEFYHKCDN

TCMESVKNGTYDYPKYSEEAKLNREEIDGVKLESTRIYQILAIYSTVAS

SLVLVVSLGAISFWMCSNGSLQCRICI*

The sequence of the HA strain A/California/7/2009 (H1N1) (CA09) antigen mRNA open reading frame (ORF) used here is:

(SEQ ID NO: 8)
AUGAAAGCUAUCCUGGUCGUCUUGCUGUAUACUUUCGCCACUGCCAACG

CCGACACCCUGUGUAUCGGUUACCACGCGAACAACUCCACCGACACUGU

GGACACCGUGCUCGAAAAGAACGUGACCGUGACUCAUUCUGUGAAUCUG

CUCGAGGACAAGCACAACGGAAAGUUGUGCAAGCUGCGCGGAGUGGCAC

CGCUGCACCUUGGAAAGUGCAACAUUGCCGGAUGGAUCCUGGGAAACCC

GGAGUGCGAAAGCCUGAGCACCGCGUCCUCAUGGUCCUACAUCGUGGAA

ACCCCGUCCUCUGACAACGGCACCUGUUACCCCGGCGAUUUCAUCGACU

ACGAAGAACUGCGGGAGCAGCUGUCCUCCGUGUCCUCGUUUGAACGCUU

CGAGAUUUUCCCUAAGACCUCCAGCUGGCCUAAUCACGAUAGCAACAAG

GGCGUGACGGCAGCCUGCCCGCACGCCGGAGCAAAGUCAUUCUACAAGA

AUCUGAUUUGGCUCGUGAAGAAAGGGAACUCAUACCCCAAGCUGUCCAA

GUCGUACAUCAACGACAAGGGAAAGGAAGUGCUCGUGCUCUGGGGGAUC

CACCACCCAUCCACCUCCGCCGACCAGCAGAGCCUGUACCAGAACGCCG

AUGCUUACGUGUUUGUGGGGUUCCAGCCGGUACUCCAAGAAGUUCAAGCC

UGAAAUCGCGAUCAGGCCUAAAGUCCGGGACCGCGAGGGCCGCAUGAAC

UACUACUGGACUCUCGUGGAGCCUGGAGACAAGAUCACCUUCGAGGCCA

CCGGAAAUCUCGUGGUGCCACGCUACGCUUUCGCCAUGGAACGGAACGC

CGGAAGCGGCAUCAUCAUUAGCGAUACUCCUGUGCAUGACUGUAACACC

ACGUGCCAGACACCCAAGGGCGCCAUCAACACCAGCCUGCCGUUUCAAA

ACAUCCAUCCCAUUACCAUUGGGAAGUGCCCCAAAUACGUCAAGUCCAC

CAAGCUGAGGCUGGCGACCGGACUGCGGAACAUUCCGAGCAUCCAGUCG

AGAGGCCUGUUCGGUGCCAUCGCGGGAUUCAUCGAGGGCGGCUGGACUG

GAAUGGUGGACGGUUGGUACGGGUAUCACCACCAAAACGAACAGGGAUC

AGGCUACGCGGCCGAUUUGAAGUCCACCCAGAACGCCAUUGAUGAAAUC

ACCAACAAGGUCAACUCCGUGAUUGAGAAGAUGAAUACUCAAUUCACCG

CCGUGGGCAAAGAAUUCAAUCACCUGGAGAAGAGAAUAGAGAACCUGAA

CAAGAAGGUCGACGACGGGUUCCUCGACAUCUGGACCUAUAACGCCGAG

UUGCUCGUGCUGCUGGAAAACGAACGGACCCUGGACUAUCACGACUCGA

ACGUGAAGAACCUGUACGAGAAAGUCCGCUCGCAACUGAAGAACAACGC

CAAGGAAAUCGGAAAUGGUUGCUUCGAGUUCUACCAUAAGUGCGACAAC

ACUUGCAUGGAGUCCGUGAAGAACGGCACUUACGAUUACCCCAAGUACU

CCGAAGAGGCUAAACUUAACCGGGAAGAGAUCGAUGGCGUGAAGCUCGA

GUCCACCAGAAUCUACCAGAUUCUCGCCAUCUACUCGACUGUGGCAUCG

AGCCUCGUCCUUGUCGUGUCCUGGGGGCCAUUUCAUUCUGGAUGUGCU

CCAACGGGUCCCUGCAGUGCCGGAUUUGCAUCUAA

The sequence of the A/Michigan/45/2015 (Mich15) neuraminidase (NA) antigen mRNA open reading frame (ORF) used here is:

(SEQ ID NO: 9)
AUGAACCCAAACCAGAAAAUCAUCACGAUUGGCUCGAUUUGCAUGACCA

UUGGAAUGGCGAACCUUAUCCUCCAAAUUGGCAACAUUAUCUCGAUCUG

GGUCAGCCACUCGAUCCAGAUCGGCAACCAAUCCCAGAUUGAAACUUGC

AACCAGAGCGUGAUUACUUACGAAAACAACACGUGGGUGAACCAGACUU

ACGUCAAUAUUAGCAACACUAACUUCGCCGCUGGGCAGAGCGUCGUCAG

CGUGAAGCUCGCCGGAAAUUCCUCGCUCUGCCCCGUGUCCGGCUGGGCG

AUCUACAGCAAGGAUAACAGCGUCCGGAUUGGUAGCAAGGGCGACGUUU

UCGUGAUCCGCGAACCCUUCAUAUCAUGCUCCCCGCUCGAAUGUCGCAC

GUUCUUCCUGACCCAAGGCGCCCUGCUGAACGACAAGCACUCCAAUGGC

ACUAUCAAGGAUCGGAGCCCUUACCGGACCUUGAUGUCCUGCCCUAUUG

GAGAAGUGCCUUCACCAUAUAACUCGCGCUUUGAAAGCGUGGCUUGGUC

AGCCUCCGCCUGCCAUGACGGGAUUAACUGGCUGACCAUUGGCAUAAGC
GGCCCCGAUUCCGGCGCCGUGGCCGUCCUGAAGUACAACGGGAUCAUCA
CCGACACCAUUAAGUCCUGGCGCAACAACAUCCUGAGGACCCAGGAGUC
CGAGUGCGCGUGCGUGAACGGGUCCUGCUUUACCAUCAUGACCGACGGA
CCGUCCGACGGUCAAGCCUCGUACAAGAUCUUCCGGAUCGAGAAGGAA
AGAUCAUCAAGAGCGUGGAGAUGAAGGCCCCGAACUACCACUACGAGGA
AUGUUCAUGCUAUCCCGACUCGUCCGAGAUUACUUGCGUGUGCCGCGAC
AAUUGGCACGGAUCCAACAGGCCGUGGGUCAGCUUCAACCAGAACCUUG
AAUACCAGAUGGGAUACAUUUGCAGCGGAGUGUUCGGGGACAACCCUCG
CCCGAACGACAAGACCGGAUCGUGUGGGCCCGUGUCCUCCAACGGCGCA
AACGGCGUCAAGGGAUUUUCCUUCAAAUACGGGAACGGGUCUGGAUCG
GACGGACCAAGAGCAUUUCAAGCAGAAAGGGAUUCGAGAUGAUUUGGGA
CCCGAACGGCUGGACUGGUACCGAUAACAAAUUCAGCAUCAAGCAGGAC
AUCGUGGAAUUAACGAGUGGUCCGGUUACUCCGGGAGCUUCGUGCAGC
AUCCCGAACUCACUGGACUGGACUGCAUUCGGCCGUGCUUUUGGGUGGA
AUUGAUCCGGGCAGACCUGGAGGAACACGAUUUGGACCUCCGGCUCC
UCGAUCUCGUUCUGCGGAGUGAACUCCGACACCGUGGGAUGGUCCUGGC
CCGACGGUGCAGAGCUGCCCUUCACCAUUGAUAAGUAA

The sequence of the A/Singapore.INFIMH160019/2016 (Sing16; H3N2) HA hemagglutinin antigen mRNA open reading frame (ORF) used here is:

(SEQ ID NO: 10)
AUGAAAACCAUAAUCGCGCUCUCAUACAUACUUUGCCUGGUCUUUUGCCC
AAAAGAUCCCUGGCAACGACAACUCAACCGCGACCCUUUGCCUCGGCCA
UCACGCCGUGCCGAACGGCACUAUCGUCAAGACCAUCACAAACGACCGC
AUCGAAGUGACCAACGCGACUGAGCUAGUGCAGAACUCCAGCAUUGGAG
AGAUUUGCGAUUCUCCACACCAAAUCCUGGACGGAGAGAAUUGUACCUU
GAUCGACGCGCUGCUGGGGAUCCGCAGUGCGACGGAUUCCAGAACAAG
AAAUGGGACCUUUUCGUGGAACGGAGCAAGGCAUACUCGAAUUGCUACC
CCUACGAUGUGCCCGACUACGCCUCGCUGCGGUCCUUGGUCGCUUCCUC
CGGGACCCUGGAAUUCAAAAACGAGAGCUUUAAUUGGACCGGAGUGACC
CAGAAUGGCACCUCGAGCGCCUGCAUUCGGGGCUCCUCCUCGAGCUUCU
UCAGCCGCCUGAACUGGCUCACUCACCUCAACUACACCUACCCGGCACU
GAACGUGACCAUGCCGAACAAGGAACAAUUCGACAAGCUCUACAUUUGG
GGGGUGCAUCACCCGGGUACCGAUAAGGACCAGAUCUUCCCUCUACGCCC
AAUCCUCGGGCCGGAUCACCGUGUCCACUAAGCGCUCGCAGCAGGCCGU
GAUCCCGAACAUUGGAAGCAGACCCCGCAUUCGCGACAUUCCAUCGAGG
AUCUCGAUCUACUGGACGAUUGUCAAGCCUGGCGACAUCCUCCUCAUUA
ACUCCACCGGGAACCUCAUCGCCCCUCGGGGUUAUUUCAAGAUCCGCAG
CGGGAAGUCCUCCAUCAUGAGAAGCGAUGCCCCCAUUGGAAAGUGCAAG
UCCGAGUGUAUCACACCUAACGGAAGCAUUCCCAAUGACAAGCCAUUCC

AGAACGUGAACAGAAUUACCUACGGAGCUUGCCCUCGCUACGUCAAACA
UUCGACCCUCAAGUUGGCGACUGGAAUGCGCAACGUGCCGGAGAAGCAA
ACCCGGGGGAUCUUCGGGGCUAUCGCGGGAUUCAUCGAAAAUGGAUGGG
AAGGAAUGGUCGAUGGUUGGUACGGUUUCAGACACCAGAACUCCGAGGG
GCGGGGCCAGGCCGCAGACCUGAAGUCCACUCAGGCCGCGAUUGACCAG
AUCAACGGAAAGCUCAACAGACUCAUUGGAAAGACCAACGAAAAGUUCC
ACCAAAUCGAAAAGGAAUUCUCCGAAGUGGAGGGCCGGGUGCAAGACCU
GGAGAAGUACGUGGAGGACACUAAGAUCGACCUUUGGAGCUAUAACGCA
GAACUCCUUGUGGCCCUGGAAAACCAGCACACCAUCGACCUGACCGAUU
CAGAGAUGAACAAGCUCUUUGAGAAAACUAAGAAGCAACUCCGGGAAAA
CGCUGAGGACAUGGGAAAUGGAUGCUUUAAGAUCUACCACAAGUGCGAC
AACGCCUGCAUUGAGUCCAUACGGAACGAAACUUACGACCAUAACGUCU
ACCGGGAUGAAGCCCUGAACAACAGAUUCCAGAUCAAGGGCGUGGAGCU
GAAGUCCGGCUACAAAGAUUGGAUCCUGUGGAUUUCCUUCGCGAUUUCA
UGCUUCUUGCUCUGCGUGGCCCUCCUGGGAUUCAUAAUGUGGGCCUGUC
AGAAGGGCAACAUUAGGUGCAACAUAUGCAUAUAA

The sequence of the Perth/16/2009 (H3N2) NA antigen mRNA open reading frame (ORF) used here is:

(SEQ ID NO: 11)
AUGAACCCUAACCAGAAGAUCAUCACAAUUGGAAGCGUGUCCCUGACCA
UUUCGACGAUUUGCUUCUUCAUGCAAAUCGCGAUCUUGAUUACCACCGU
CACCCUGCAUUUCAAGCAAUACGAAUUCAACUCCCCGCCAAACAACCAA
GUCAUGCUCUGCGAGCCCACCAUCAUCGAACGCAACAUCACCGAGAUCG
UGUACCUUACCAACACUACCAUCGAAAAGGAGAUUUGCCCCAAGUUGGC
CGAAUACCGGAACUGGAGCAAGCCCCAGUGUGACAUCACGGGAUUUGCG
CCAUUCAGCAAGGAUAACUCGAUCAGACUUUCCGCCGGGGGCGACAUUU
GGGUCACUCGGGAGCCUUACGUGAGCUGCGACCCGGACAAGUGCUACCA
AUUCGCACUCGGACAGGGUACCACCCUGAACAACGUCCAUAGCAACAAC
ACCGUGCGCGAUAGAACCCCGUACCGCACCCUCCUCAUGAACGAACUGG
GAGUGCCGUUCCACUUGGGAACCAAACAAGUCUGCAUUGCAUGGUCCUC
CUCCUCCUGCCACGACGGCAAAGCCUGGCUUCACGUUUGCAUCACCGGC
GACGACAAGAAUGCGACGGCCUCCUUCAUAUACAAUGGUAGACUCUGUGG
AUAGCGUGGUGUCAUGGUCCAAGGAAAUUCUCAGGACUCAGGAGUCAGA
GUGCGUGUGCAUCAACGGGACUUGCACUGUCGUGAUGACCGACGGAUCG
GCCUCCGGAAAGGCCGACACUAAGAUCCUCUUCAUCGAGGAGGGAAAGA
UCGUGCACACUUCUACCCUGAGCGGCUCGGCUCAGCAUGUCGAAGAGUG
CUCGUGCUACCCCCGGUAUCCCGGGGUCCGCUGCGUGUGCCGGGACAAU
UGGAAAGGCUCAAACCGCCCCAUCGUGGACAUUAACAUCAAGGACCACU
CCAUCGUGAGCUCCUACGUAUGCAGCGGGCUGGUCGGGGAUACCCCGCG
GAAGAACGAUUCCUCGUCCUCCUCCCACUGCCUGGACCCUAACAACGAA

-continued

GAGGGAGGCCACGGAGUGAAGGGAUGGGCUUUUGACGAUGGCAACGACG

UGUGGAUGGGCAGGACUAUUUCCGAAAAGUCCCGGCUGGGAUACGAAAC

CUUCAAGGUCAUCGAGGGCUGGUCCAACCCGAAGUCAAAGCUCCAGAUC

AACCGCCAGGUCAUCGUGGAUAGGGGCAAUAGAUCCGGCUACUCCGGGA

UCUUCAGCGUGGAAGGGAAGUCCUGCAUUAACCGAUGCUUCUACGUGGA

ACUCAUUCGGGGUCGGAAGGAGGAAACCGAAGUGCUGUGGACUUCGAAC

UCAAUCGUGGUGUUUUGUGGGACCUCCGGAACUUACGGAACUGGGUCCU

GGCCUGACGGUGCCGACAUCAACCUUAUGCCGAUCUAA

The sequence of the A/Wisconsin/588/2019 antigen mRNA open reading frame (ORF) used here is:

(SEQ ID NO: 12)
AUGAAAGCCAUCCUUGUUGUCAUGCUGUACACAUUCACCACCGCAAAUG

CGGAUACCCUGUGUAUCGGCUACCACGCAAAUAAUUCCACCGACACCGU

UGAUACCGUCCUGGAAAAGAACGUGACAGUGACUCACAGCGUCAAUCUC

CUUGAGGAUAAACAUAAUGGCAAGCUGUGCAAGCUGAGAGGCGUGGCUC

CCCUGCAUCUGGGAAAGUGCAACAUCGCUGGUUGGAUCCUCGGGAACCC

AGAGUGUGAGUCCCUCUCAACCGCACGGUCUUGGUCAUACAUCGUGGAG

ACUAGCAAUUCAGACAACGGCACAUGCUACCCCGGUGACUUCAUUAACU

ACGAGGAGCUGAGAGAACAGCUGAGUUCCGUGUCAUCCUUCGAGAGAUU

CGAAAUCUUCCCCAAAACCUCCUCCUGGCCCAAUCAUGACUCCGACAAU

GGAGUGACAGCCGCUUGUCCCCACGCCGGUGCCAAGAGUUUCUAUAAGA

ACCUCAUCUGGCUGGUGAAAAAGGGCAAGUCCUAUCCCAAAAUUAACCA

GACCUACAUUAACGAUAAGGGGAAAGAAGUCCUGGUCCUGUGGGGGAUA

CACCACCCCCCUACCAUCGCCGACCAGCAGUCUCUGUAUCAGAACGCCG

ACGCCUACGUGUUCGUGGGUACCAGCCGUUAUAGUAAAAAGUUCAAGCC

AGAAAUUGCCACCAGACCUAAGGUGCGCGACCAGGAGGGCCGCAUGAAC

UACUACUGGACCCUGGUGGAACCUGGCGACAAGAUUACAUUCGAGGCCA

CUGGGAACCUGGUGGCACCCAGAUACGCCUUUACAAUGGAACGGGAUGC

UGGGAGCGGAAUCAUUAUCUCCGAUACCCCUGUCCACGACUGCAAUACU

ACCUGUCAGACCCCAGAAGGCGCUAUCAAUACCUCUCUGCCUUUCCAAA

ACGUGCACCCUAUCACUAUCGGGAAAUGUCCCAAGUAUGUGAAAAGCAC

CAAACUGCGCCUGGCAACCGGUCUGAGAAAUGUGCCCUCCAUCCAGUCC

CGCGGCUUGUUCGGUGCAAUCGCUGGCUUUAUCGAGGGUGGCUGGACUG

GAAUGGUCGAUGGCUGGUACGGCUACCAUCACCAGAACGAGCAGGGGUC

CGGGUAUGCUGCCGACCUGAAAAGCACUCAGAACGCCAUCGAUAAAAUC

ACUAACAAGGUGAACUCCGUGAUCGAAAAGAUGAAUACACAGUUCACAG

CAGUUGGCAAGGAGUUCAACCACCUGGAAAAACGGAUAGAGAACCUGAA

UAAGAAAGUCGAUGAUGGCUUUCUGGACAUCUGGACUUACAAUGCCGAG

CUGCUGGUGCUCCUGGAAAACGAGCGGACACUGGAUUAUCACGACUCAA

ACGUGAAGAACCUGUAUGAAAAGGUGCGUAACCAGCUGAAAAACAACGC

CAAGGAAAUCGGCAAUGGCUGUUUCGAAUUUUACCACAAGUGUGAUAAU

ACCUGUAUGGAGAGCGUUAAGAACGGGACUUACGACUACCCAAAAUACA

GCGAGGAGGCCAAGCUGAACCGGGAGAAGAUCGACGGCGUCAAACUCGA

CUCCACUAGAAUAUACCAGAUUCUCGCCAUCUAUAGCACAGUGGCAUCA

AGUCUCGUCCUGGUGGUGUCACUGGGGAGCCAUCAGCUUUUGGAUGUGCA

GCAAUGGAUCCCUCCAGUGUAGGAUCUGCAUCUAA

The sequence of the A/Tasmania/503/2020 antigen mRNA open reading frame (ORF) used here is:

(SEQ ID NO: 13)
AUGAAGACCAUCAUCGCUCUGUCCUACAUCCUGUGCCUGGUGUUUGCUC

AGAAAAUCCCCGGGAAUGACAAUUCCACUGCCACUCUCUGCCUGGGCCA

UCAUGCCGUGCCAAAUGGAACCAUUGUCAAGACUAUAACAAAUGACCGC

AUCGAAGUGACCAACGCUACCGAGCUGGUUCAGAACAGCAGUAUUGGAG

AAAUCUGCGAUUCCCCACACCAGAUACUGGAUGGCGGCAACUGCACCCU

GAUCGACGCACUGCUGGGUGACCCUCAGUGCGACGGAUUUCAGAAUAAG

GAGUGGGACCUUUUCGUUGAGCGCAGCAGAGCCAAUAGCAACUGCUACC

CGUACGACGUGCCGGAUUACGCCAGUCUUCGAAGCCUGGUCGCAUCCAG

CGGGACACUGGAGUUUAAGAAUGAGUCCUUUAAUUGGACAGGCGUGAAG

CAGAACGGGACUAGCAGCGCAUGCAUUCGGGGCAGUAGCUCAUCCUUCU

UUAGCCGACUGAACUGGCUGACCCACCUCAACUACACAUACCCCGCACU

GAAUGUGACUAUGCCAAACAAAGAACAGUUUGACAAACUGUACAUCUGG

GGAGUGCACCAUCCUAGCACAGACAAGGACCAGAUCAGCCUGUUUGCCC

AGCCCAGCGGCAGGAUUACCGUGUCCACAAAACGGUCACAGCAAGCCGU

GAUCCCUAAUAUUGGAUCCCGCCCCCGGAUAAGGGACAUCCCUAGUCGC

AUCAGUAUCUACUGGACCAUCGUGAAGCCCGGAGAUAUCUUGCUCAUCA

AUAGCACUGGCAACCUCAUUGCCCCCAGGGGCUAUUUUAAGAUCAGAAG

CGGCAAGUCCAGCAUUAUGCGCAGCGACGCACCCAUUGGCAAGUGCAAG

UCCGAGUGCAUCACUCCUAAUGGGUCCAUCCCAAACGACAAGCCAUUCC

AAAAUGUCAACAGAAUCACCUACGGGGCUUGCCCCCGCUACGUGAAGCA

GAGUACACUGAAACUGGCCACCGGGAUGCGCAACGUGCCCGAGAAGCAA

ACUAGAGGCAUCUUUGGAGCUAUCGCUGGCUUCAUUGAGAAUGGCUGGG

AGGGUAUGGUGGACGGCUGGUACGGAUUCCGCCACCAGAAUAGCGAAGG

CAGAGGCCAGGCAGCAGACUUGAAGUCCACCCAGGCCGCCAUUGAUCAG

AUCAACGGCAAACUGAAUCGGCUUAUUGGAAAAACAAACGAGAAGUUCC

AUCAGAUUGAGAAGGAGUUUAGCGAGGUGGAGGGCCGCGUGCAGGAUCU

GGAAAAGUACGUUGAAGACACCAAGAUCGACCUGUGGUCAUACAAUGCA

GAGCUGCUCGUUGCCCUGGAAAAUCAGCACACAAUUGACCUUACAGACU

CCGAAAUGAAUAAGCUCUUUGAAAAGACCAAGAAGCAGCUGCGCGAGAA

CGCCGAGGAUAUGGGGAACGGUUGUUUUAAGAUCUACCACAAGUGUGAC

AACGCCUGCAUUGGGUCCAUCCGAAAUGAAACAUACGACCACAACGUGU

AUAGAGAUGAGGCCCUGAACAACCGAUUCCAGAUUAAGGGAGUCGAGCU

-continued
GAAGAGUGGCUAUAAGGACUGGAUCCUGUGGAUCUCAUUCGCCAUGUCA

UGCUUCCUUCUGUGUAUUGCUCUGCUCGGCUUCAUCAUGUGGGCUUGCC

AGAAAGGCAAUAUCCGGUGCAACAUCUGCAUCUAA

The sequence of the B/Washington/02/2019 antigen mRNA open reading frame (ORF) used here is:

(SEQ ID NO: 14)
AUGAAAGCAAUCAUAGUGCUGCUGAUGGUGGUGACUAGCAAUGCCGAUC

GGAUCUGCACCGGCAUCACUUCCAGUAACAGCCCUCAUGUGGUCAAAAC

CGCCACACAGGGCGAGGUGAACGUGACCGGAGUGAUUCCACUGACAACU

ACACCAACGAAGAGUCACUUCGCCAACCUGAAGGGCACCGAAACACGAG

GCAAGCUCUGCCCCAAGUGUCUGAAUUGCACCGACCUGGACGUCGCUUU

GGGCCGCCCUAAAUGUACCGGCAAAAUACCUUCCGCCAGAGUGUCCAUC

CUGCACGAGGUGCGCCCCGUGACCUCCGGGUGUUUUCCCAUAAUGCACG

ACCGCACUAAAAUCCGCCAGCUGCCCAAUCUUCUGAGGGGGUACGAACA

UGUCAGGCUGUCCACUCACAACGUGAUCAACGCAGAAGACGCCCCCGGA

AGGCCUUAUGAGAUUGGAACCAGUGGGUCCUGCCCAAACAUUACCAACG

GCAACGGCUUCUUCGCCACUAUGGCCUGGGCCGUGCCAAAGAACAAGAC

CGCCACCAACCCCCUGACAAUUGAAGUCCCUUACAUCUGCACAGAGGGA

GAGGAUCAGAUCACCGUGUGGGGUUUCACUCUGAUAACGAAACUCAGA

UGGCCAAGCUGUACGGGGAUUCUAAACCCCAGAAGUUCACCAGUAGCGC

UAACGGGGUGACCACCCAUUAUGUGUCUCAGAUCGGAGGUUUCCCAAAU

CAGACCGAGGACGGCGGACUGCCCCAGUCUGGAAGGAUCGUAGUGGACU

AUAUGGUGCAGAAGAGUGGAAAAACCGGCACCAUUACCUAUCAGCGCGG

CAUACUGCUGCCACAGAAGGUGUGGUGUGCUUCCGGCAGGUCCAAGGUU

AUCAAAGGGUCCCUCCCCCUGAUCGGCGAAGCAGAUUGUCUGCACGAGA

AGUACGGCGGACUGAAUAAGAGCAAACCCUACUACACCGGAGAACACGC

UAAGGCAAUUGGGAAUUGUCCGAUCUGGGUGAAGACGCCCCUGAAACUG

GCCAAUGGCACAAAAUACCGGCCCCCCGCUAAGCUGCUGAAGGAACGGG

GGUUCUUCGGCGCCAUAGCCGGCUUUCUGGAGGGAGGCUGGGAGGGCAU

GAUAGCCGGGUGGCACGGCUACACUUCCCAUGGGCUCACGGGGUGGCU

GUGGCCGCCGACCUGAAGUCUACGCAGGAAGCUAUCAACAAAAUCACUA

AGAACCUGAACAGCCUGUCGGAAUUGGAGGUCAAGAAUCUGCAGCGGCU

GAGCGGCGCCAUGGAUGAGCUGCACAAUGAGAUCCUGGAGCUUGACGAG

AAGGUCGAUGAUCUUCGGGCCGAUACAAUUAGUAGCCAAAUUGAGUUGG

CCGUGCUGCUCAGCAACGAAGGCAUAAUCAACAGCGAGGACGAGCACCU

CCUGGCUCUGGAGAGAAAGCUGAAGAAGAUGCUCGGCCCUAGCGCAGUU

GAGAUCGGAAACGGCUGCUUCGAAACCAAGCACAAGUGCAACCAGACCU

GCCUGGACAGGAUCGCGGCAGGAACAUUCGACGCUGGGGAAUUCAGCCU

CCCCACCUUCGACAGCCUGAACAUCACAGCCGCCAGUCUGAAUGAUGAC

GGACUGGAUAACCAUACCAUCCUGCUGUACUACUCUACCGCUGCUUCCU

CCCUGGCCGUGACAUUGAUGAUCGCAAUCUUUGUGGGUUUAUAUGGUGAG

CCGAGACAACGUCAGUUGCAGUAUCUGCCUUUAA

The sequence of the B/Phuket/3073/2013 antigen mRNA open reading frame (ORF) used here is:

(SEQ ID NO: 15)
AUGAAAGCCAUCAUUGUGCUGCUGAUGGUUGUUACAAGCAACGCCGACC

GCAUCUGCACCGGGAUUACAAGCAGCAAUAGCCCUCACGUGGUGAAGAC

AGCAACACAGGGAGAGGUGAACGUGACCGGCGUGAUUCCACUGACAACC

ACCCCAACUAAAUCUUACUUUGCAAACCUGAAAGGGACACGGACCAGAG

GAAAGCUGUGCCCUGAUUGCCUGAAUUGCACAGACCUGGACGUGGCCCU

GGGCAGACCAAUGUGCGUGGGCACUACACCAAGCGCCAAGGCCUCCAUC

CUCCAUGAGGUGCGGCCCGUGACUUCUGGAUGUUUCCCCAUUAUGCACG

ACAGAACCAAGAUUAGACAGCUGCCAAACCUGCUCCGCGGCUACGAGAA

AAUUCGCCUGUCUACACAGAAUGUGAUCGACGCCGAGAAGGCUCCAGGA

GGACCAUACAGACUGGGGACUUCUGGCAGCUGCCCUAACGCCACCUCUA

AGAUCGGGUUCUUCGCAACCAUGGCUUGGGCCGUGCCUAAAGACAAUUA

CAAGAAUGCCACCAAUCCACUGACUGUCGAGGUGCCAUAUAUUUGCACA

GAGGGGGAGGACCAGAUCACUGUGUGGGGCUUUCAUAGCGAUAAUAAGA

CUCAGAUGAAGUCUCUCUACGGCGACUCUAACCCUCAGAAGUUCACCUC

CUCUGCCAACGGGGUGACAACACACUACGUGUCCCAGAUCGGGGACUUU

CCUGACCAGACCGAGGAUGGAGGACUGCCUCAGUCUGGACGCAUCGUGG

UGGACUAUAUGAUGCAGAAGCCUGGGAAGACCGGCACUAUCGUGUACCA

GAGGGGCGUGCUGCUGCCCAAAAGGUGUGGUGUGCCUCCGGAAGAAGC

AAAGUGAUUAAGGGAUCCCUGCCUCUGAUUGGGGAGGCCGAUUGCCUGC

AUGAAGAGUAUGGAGGGCUGAACAAGUCCAAGCCAUACUAUACAGGAAA

GCACGCAAAAGCCAUCGGCAACUGUCCCAUCUGGGUCAAAACUCCUCUG

AAGCUGGCCAACGGCACCAAAUACCGCCCUCCAGCCAAGCUGCUGAAAG

AACGCGGAUUCUUCGGCGCCAUUGCAGGGUUUCUGGAAGGAGGCUGGGA

GGGCAUGAUUGCUGGAUGGCACGGAUAUACCUCUCACGGCGCUCACGGG

GUGGCCGUGGCCGCCGAUCUGAAGUCCACACAGGAGGCAAUUAACAAGA

UCACCAAGAAUCUGAAUUCACUGUCCGAGCUCGAAGUGAAAAACCUGCA

GCGCCUGUCCGGCGCCAUGGACGAGCUGCACAAUGAAAUCCUGGAGCUG

GACGAGAAGGUGGACGACCUGCGGGCUGACACUAUCAGCAGCCAGAUCG

AGCUGGCAGUGCUGCUGAGCAAUGAGGGCAUCAUCAACUCAGAAGACGA

ACACCUCCUGGCACUGGAAAGGAAACUCAAGAAGAUGCUGGGCCCCUCC

GCAGUGGACAUUGGGAACGGCUGUUUCGAAACCAAGCAUAAGUGUAACC

AGACUUGUCUGGAUAGGAUCGCAGCAGGAACCUUCAACGCCGGCGAAUU

UUCUCUGCCAACAUUUGACUCCCUGAACAUCACAGCUGCAUCCCUGAAC

GACGACGGACUGGACAAUCACACCAUCCUGCUGUACUACUCUACUGCCG

-continued
CUAGCUCCCUGGCCGUGACCCUGAUGCUGGCCAUCUUCAUCGUGUACAU

GGUUUCCAGGGAUAACGUGUCUUGUAGCAUUUGCCUGUAA

Results mRNA Antigen Preparation, Characterization, and Expression mRNAs coding for the full-length codon-optimized HA and NA for the various influenza strains were synthesized enzymatically using unmodified ribonucleotides. All mRNA preparations had >95% of 5' Cap1 and showed a single homogenous peak on capillary electrophoresis. mRNA-LNP formulations were prepared by mixing the various lipid components with mRNA under controlled conditions and at fixed ratios. All mRNA-LNPs exhibited >95% encapsulation with uniform hydrodynamic radius ranging from 95-105 nm and a poly dispersity index (PDI) of 0.060-0.136 as shown in Table 5.

TABLE 5

Attributes of LNP Formulations Used in Mouse Preclinical Testing

| LNP | Size (nm) | PDI | % Encapsulation |
|---|---|---|---|
| CA09 HA | 97.54 | 0.117 | 95.2 |
| Sing16 HA | 103.2 | 0.068 | 97.3 |
| Sing16 NA | 105.8 | 0.128 | 96.5 |
| Mich15 NA | 103.3 | 0.136 | 97.4 |

Cryo-electron microscopy (Cryo-TEM) of the CA09 HA mRNA-LNP images showed uniform spherical particles with a multi-lamellar inner core structure. The lamellarity of the solid core structure analyzed further with Fourier Transform, indicated a 3.7 nm periodicity between layers. The uniform morphology of the particles seen in the micrographs are indicative of homogenous LNP preparations with proper assembly of the LNPs.

Antigen expression was confirmed with flow cytometry by transiently transfecting human skeletal muscle cells (HskMCs) with the unencapsulated mRNA constructs of CA09 HA, Sing16 HA, Sing16 NA, or Mich15 NA, and stained with protein-specific antibodies for analysis. High levels of HA and NA expression from HskMCs were observed, confirming proper assembly and trafficking of native form HA trimers and NA tetramers upon expression in muscle cells. To study the subcellular localization of expressed HA and NA proteins, HeLa cells were transfected with bivalent H3N2 LNP and proteins were visualized by immunostaining and confocal microscopy. While NA signal indicated strong colocalization in ER (about 90%), HA was found to colocalize moderately (25%) with ER when permeabilized cells were stained with antibodies for corresponding proteins and calnexin, an endoplasmic reticulum (ER) marker. This is consistent with the understanding that nascent NA and HA proteins are translocated to ER for assembly (Dou et al., Front Immunol. (2018) 9:1581).

Figure 11:
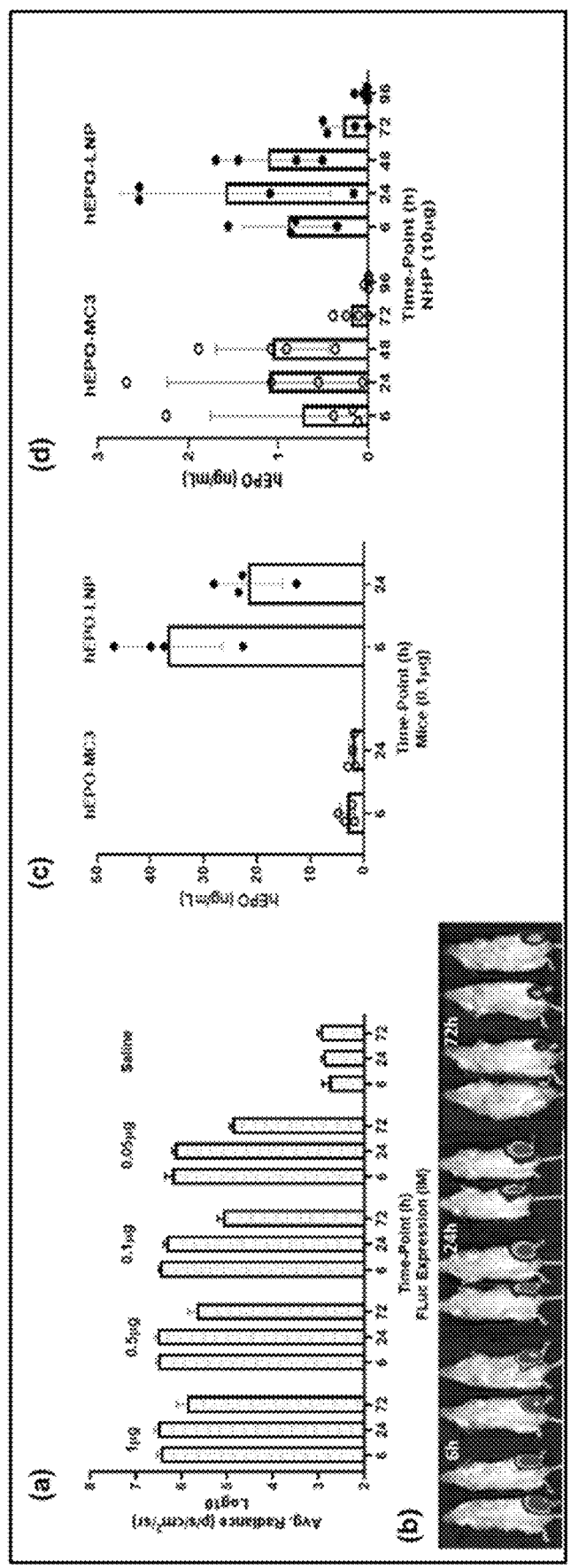
FIG. 11 shows the functional verification of mRNA-LNP Formulations. Panel (a) is a graph showing the expression of firefly (FF) luciferase in BALB/c mice: a single dose of Luciferase FF mRNA-LNP (5, 1, 0.1, 0.05 µg) was injected in mice (n=4) by IM route. Luciferin (3 mg) was injected at the time of whole animal imaging, using IVIS Spectrum, Perkin Elmer recording bioluminescence intensity. Images of whole animal average radiance at 6, 24, 48 and 72 h after injection were taken. Radiance recorded for 1, 0.5, 0.1 and 0.05 µg dose administrations of Luc mRNA-LNP are shown in the graph. Panel (b) shows whole animal images indicating total flux of luminescence, at 6 to 72 hours. Total flux of luminescence in groups of mice (n=4) receiving 0.1 µg dose of FF-LNP are shown. Panel (c) shows the expression of hEPO in BALB/c mice. A single dose of hEPO mRNA-LNP (0.1 µg) was injected in BALB/c mice by IM route. hEPO expression was quantified in serum at 6 hours and 24 hours after administration using ELISA. Bars represent means and standard deviations. Panel (d) shows the expression of hEPO in NHP. A single dose of hEPO mRNA-LNP (10 µg) was injected in Cynomolgus macaques by IM route. hEPO expression was quantified in serum at 6, 24, 48, 72, and 96 hours after administration, using ELISA. Bars represent means and standard deviations.

The efficiency of delivery of mRNA by LNPs and selection of optimal formulation parameters was evaluated using reporter mRNA expression (Thess et al., Molecular Therapy (2015) 23(1):S55). A single dose of either 0.05, 0.1, 1, 5, µg of unmodified FF-LNP formulations was administered intramuscularly (IM) in mice. Luciferase activity, measured by average bioluminescence, indicated sustained expression from mRNA construct which peaked at 6 hours post injection and detectable beyond 72 hours at all doses (FIG. 11, panel (a)). The high-level mRNA-mediated protein expression was further verified with hEPO at a single 0.1 µg dose in mice and 10 µg in non-human primate (NHP). The study was intended to compare LNP, using standard LNP Dlin-MC3-DMA25 formulation as a control. Serum hEPO quantified by ELISA demonstrated maximum expression at 6 h with approximately 12-fold higher erythropoietin expressed with hEPO-LNP compared to hEPO-MC3 (FIG. 11, panel (c)). Both hEPO-LNP and hEPO-MC3 showed similar expression kinetics in NHPs, detectable from 6 hours to 72 hours (FIG. 11, panel (d)). The results confirmed the utility of the present LNP formulation for efficient delivery of mRNA for expression both in vitro and in vivo.

Immunogenicity of HA (H1, H3) and NA (N1, N2) mRNA-LNP in Mice

Figure 12:
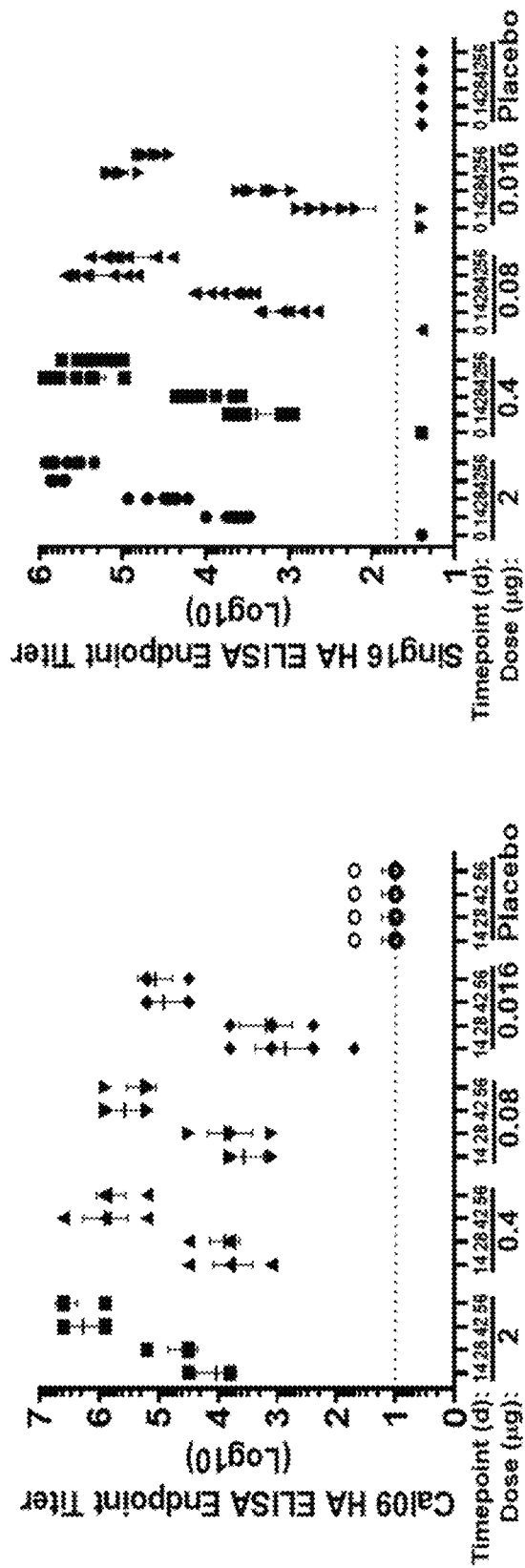
FIG. 12 shows the serological evaluation of HA mRNA-LNP vaccine in mice. BALB/c mice (n=8 per group) were immunized twice IM, 4 weeks apart with 2, 0.4, 0.08, and 0.016 µg of either Cal09 HA mRNA-LNP or Sing16 HA mRNA-LNP. ELISA titers recorded for sera collected at days 14, 28, 42, 56 against CA09 (Cal09) H1N1 influenza virus recombinant HA (left panel) and Sing16 H3N2 influenza virus recombinant HA (right panel) are shown.
Figure 13:
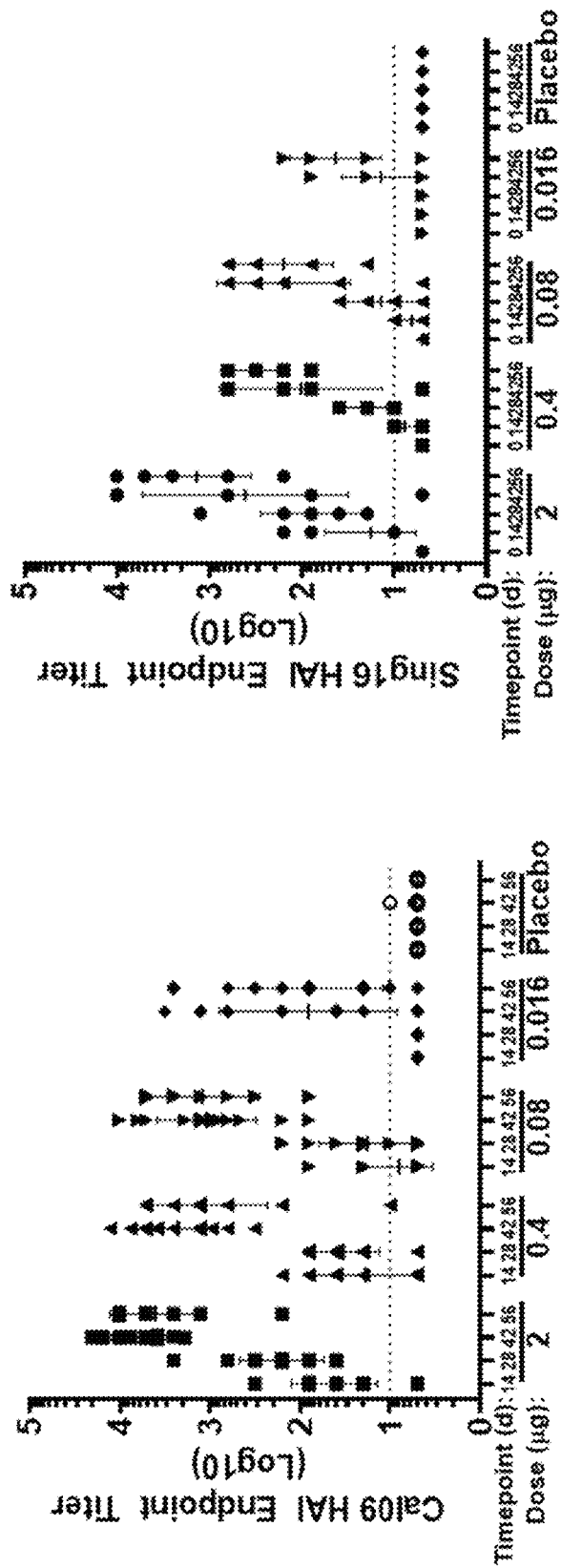
FIG. 13 shows the serological evaluation of HA mRNA-LNP vaccine in mice. BALB/c mice (n=8 per group) were immunized twice IM, 4 weeks apart with 2, 0.4, 0.08 and 0.016 µg of either CA09 HA mRNA-LNP or Sing16 HA mRNA-LNP. $Log_{10}$ HAI titers recorded against CA09 H1N1 influenza virus (left panel) and Sing16 H3N2 influenza virus (right panel) are shown.

Natural history and vaccine studies have shown that antibodies to influenza HA and NA have antiviral function and both antigens are considered important for effective influenza vaccines (Krammer et al., Nat Rev Immunol. (2019) 19(6):383-97). Unmodified CA09 HA-LNP and Sing16 HA-LNP mRNA vaccines were evaluated in BALB/c mice (n=8) in a two-dose regimen at 2, 0.4, 0.08, or 0.016 µg mRNA-LNP administered at 4-week apart schedule. Recombinant HA (rHA) antigens of the same strain were used to evaluate the total IgG responses in ELISAs. HA-specific antibodies were detected in all groups after a single dose, but the titers peaked at day 42 after the second dose (FIG. 12). To measure functional antibodies, hemagglutination inhibition (HAI) response was evaluated against the homologous strains, CA09 and Sing16. Although the HAI titers after a first dose could be observed for the 2 µg dose of CA09-LNP and Sing16-LNP treatment groups with GMTs of 160 and GMT 70 at day 28 respectively, a more profound increase in HAI titers were observed after second dose. At day 42 GMT titers were 80 and 2200 for the 0.016 µg and 0.4 µg groups respectively in the CA09-HA-LNP and 14 and 100 for the 0.016 µg and 0.4 µg groups respectively in the Sing16 HA-LNP groups (FIG. 13).

Figure 14:
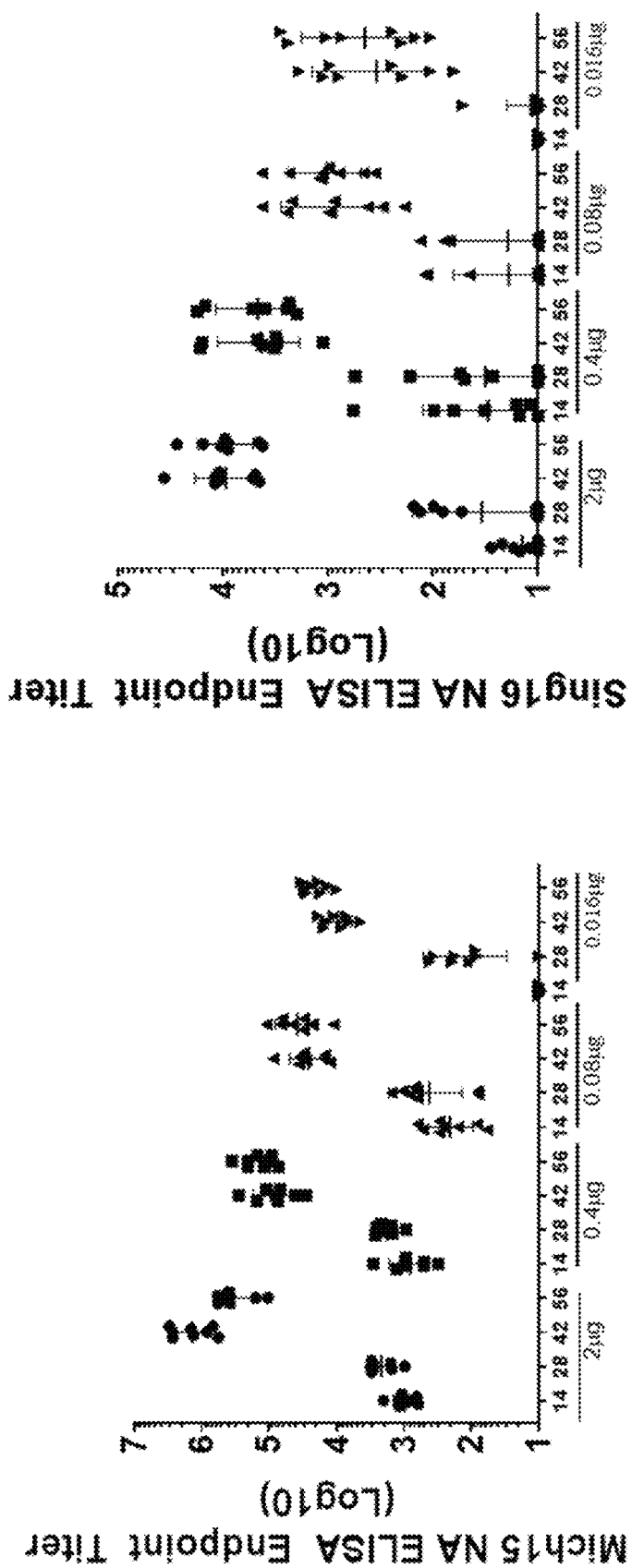
FIG. 14 shows the serological evaluation of NA mRNA-LNP vaccine in mice. BALB/c mice (n=8 per group) were immunized twice IM 4 weeks apart with 2, 0.4, 0.08, and 0.016 µg of either Mich15 NA mRNA-LNP or Sing16 NA mRNA-LNP. Total IgG titers recorded for sera collected at days 0, 14, 28, 42, 56 against Mich15 N1 influenza virus recombinant NA (left panel) and Sing16 N2 virus recombinant NA (right panel) are shown
Figure 15:
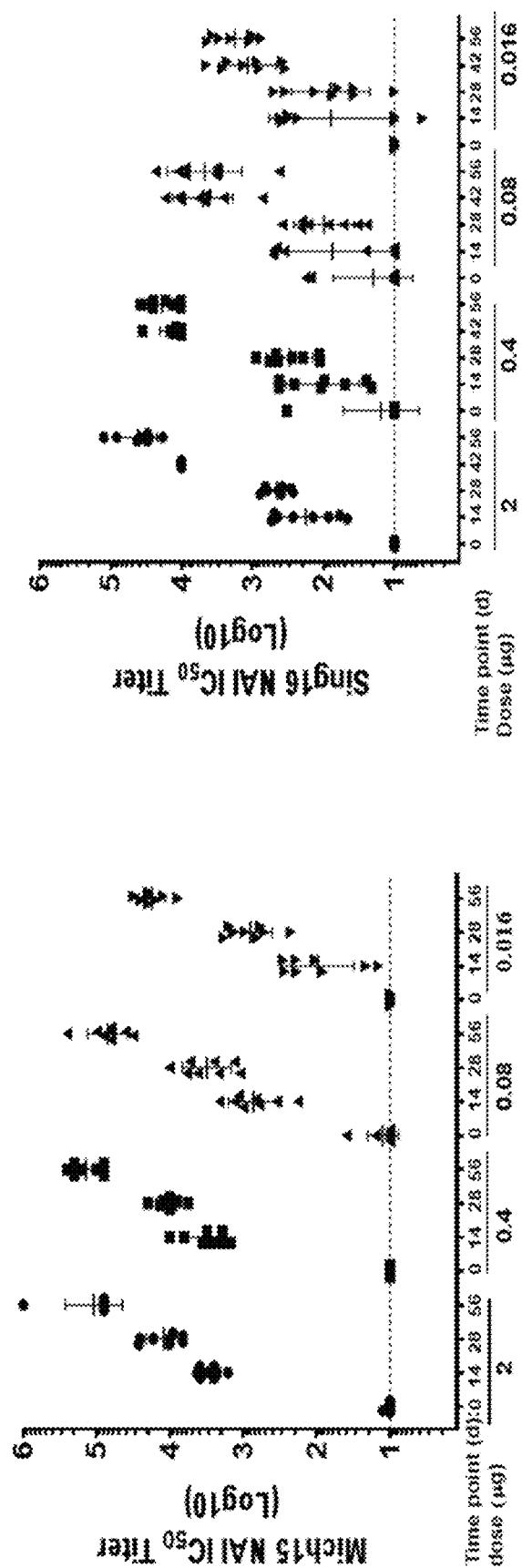
FIG. 15 shows the serological evaluation of NA mRNA-LNP vaccine in mice. BALB/c mice (n=8 per group) were immunized twice IM 4 weeks apart with 2, 0.4, 0.08 and 0.016 µg of either Mich15 NA mRNA-LNP or Sing16 NA mRNA-LNP. $Log_{10}$ NAI (ELLA) titers recorded for sera against Mich2015 (N1): A/Mallard/Sweden/2002 (H6) chimeric influenza virus (left panel) and Sing16 (N2): A/Mallard/Sweden/2002 (H6) chimeric virus (right panel) are shown.

Similarly, for testing anti-NA responses, mice were immunized with 2, 0.4, 0.08, or 0.016 µg of Sing16 NA-LNP or Mich15 NA-LNP. ELISA with recombinant NA antigens were conducted to assess the total IgG responses induced by either Mich15 NA-LNP or Sing16 NA-LNP formulations. Animals developed high antibody binding responses after a single dose, with a marked increase in NA binding antibodies post second dose at day 42 (FIG. 14). Enzyme-linked lectin assay (ELLA) was used as a surrogate for functional antibody titers for Neuraminidase inhibition (NAI) activity against H6N1 or H6N2 chimeric viruses. Although two doses of the vaccine substantially increased the functional antibody response as compared to a single dose, encouraging NAI titers with GMTs 800 and GMT 60 were recorded at day 28 after a single dose even with low dose of 0.016 µg of Mich15 NA-LNP and Sing16 NA-LNP, respectively. At day 42, the GMT titers between the 0.4 µg and 0.016 µg, were 900 and 10200 respectively in the Sing16 NA-LNP group indicating a dose-dependent response with titers reaching above ULOQ in case of Mich15 NA-LNP (FIG. 15).

Protection from Viral Challenge in Mice

Figure 16B:
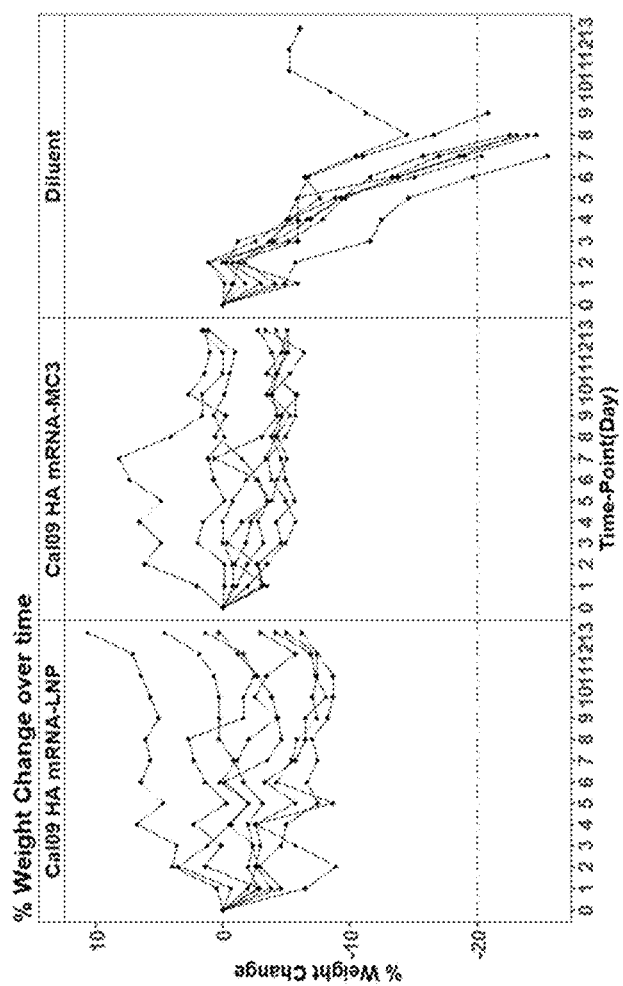
FIGS. 16A and 16B show the protective efficacy of CA09 HA mRNA-LNP vaccine in mice after lethal A/Belgium/2009 H1N1 virus challenge. Mice (n=8) received two IM doses of CA09 HA mRNA-LNP (0.4 µg each) on day 0 and day 28. Control animals received two IM doses of diluent on day 0 and day 28.
Figure 16A:
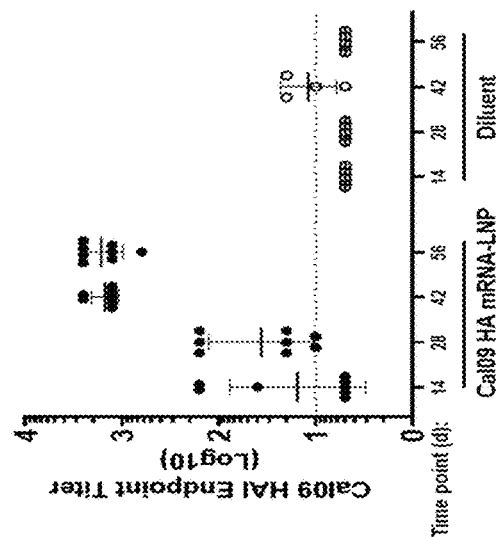

To test the efficacy of the mRNA vaccine in mouse influenza virus challenge model, we inoculated BALB/c mice with 0.4 µg of CA09 HA-LNP IM at week 0 and 4, along with a negative control group with two doses of LNP diluent buffer. HAI titers for vaccine group serum samples at study days 0, 14, 28, 42, 56, 92, and 107 demonstrated robust immune response with GMT of 1660 and 1:830 at day 56 and day 92 respectively (FIG. 16A). At day 93, all mice were challenged intranasally with Belgium09 virus, homologous to CA09, at four times the dose which can cause 50% lethal outcome (4×LD$_{50}$). All mice in the vaccine group survived the challenge with no mortality, and some mild morbidity marked by transient weight loss of less than 5% (FIG. 16B). However, those in the diluent control group suffered significant and rapid weight loss which led to high mortality rate (90%) by day 9. These results demonstrated high efficacy of HA-based MRT formulations in a lethal mouse influenza challenge model.

Figure 17A:
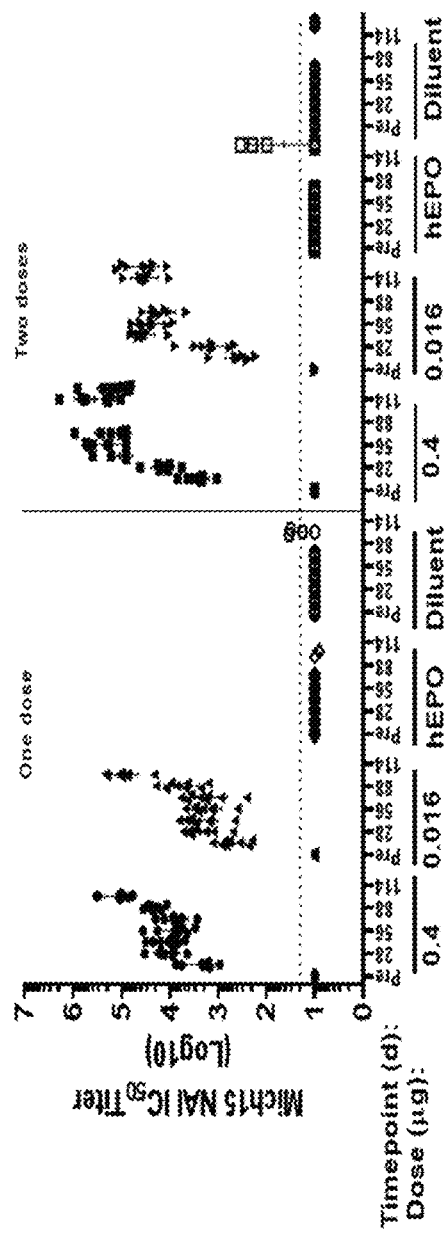
FIGS. 17A-B show the protective efficacy of a single dose of unmodified Mich15 NA mRNA-LNP in mice after lethal A/Belgium/2009 H1N1 virus challenge. Mice (n=16) were injected by the IM route with 0.4 µg or 0.016 µg of Mich15 NA mRNA-LNP.
Figure 17B:
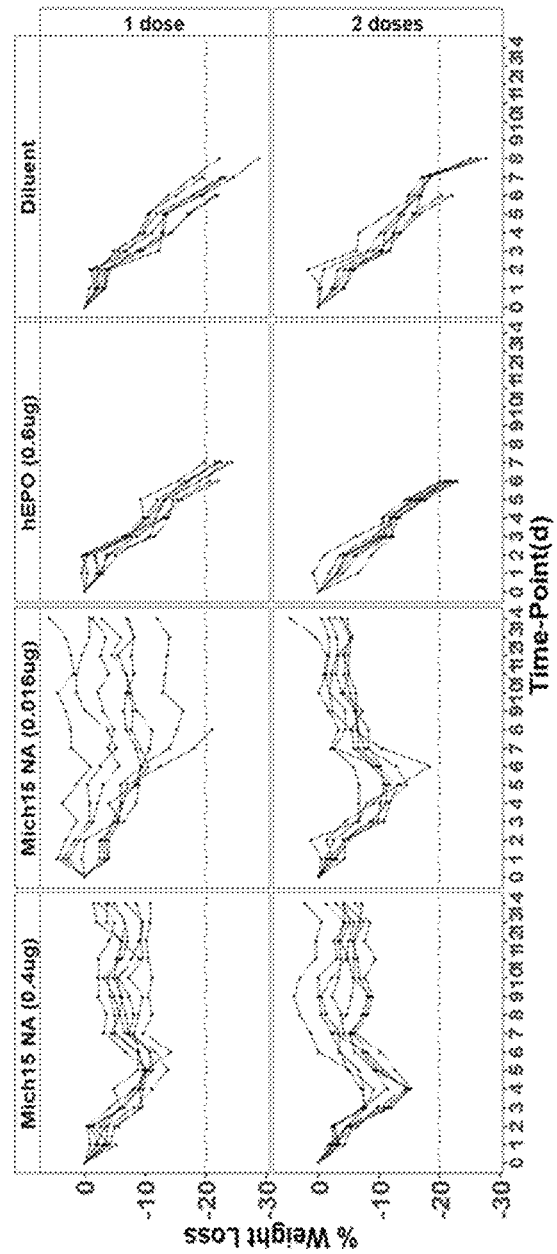

To assess protective efficacy of NA-based MRT vaccines, we conducted an analogous challenge experiment in BALB/c mice. Since the Mich15 NA-LNP vaccine elicited robust NAI titers after a single immunization in naïve mice (FIG. 16A), we evaluated one or two dosing regimens with administrations of 0.4 or 0.016 μg of Mich15 NA-LNPs over a 4-week interval. The control groups were vaccinated at the same regimens, receiving either 0.6 μg hEPO-LNP or diluent buffer. Robust NAI titers were observed after a single administration with GMTs of 14,000 NAI for 0.4 μg and 1,800 NAI for 0.016 μg of Mich15 NA-LNP recorded at day 28 (FIG. 17A). After the second immunization at day 42, NAI titers rose to 108,000 NAI for 0.4 μg and 37,000 NAI for 0.016 μg groups. After more than 12 weeks post vaccination regimens, all groups were challenged with 4×LD$_{50}$ of Belgium09 H1N1 virus. Individual weight changes from baseline over time by treatment groups are graphed in FIG. 17B. All mice in the two control groups suffered significant morbidity, and all animals had to be euthanized due to >20% weight loss by day 8 post-infection. Remarkably, all animals except one in the vaccine groups survived the challenge in the single dose 0.016 μg group, indicating high protective efficacy against death even after a single dose of as low as 0.016 μg of Mich15 NA-LNP. The higher dose (0.4 μg) demonstrated overall higher protection, however, in contrast to HA-immunization, NA vaccination was not sufficient to protect against weight loss as vaccinated animals demonstrated median weight loss of 10% of initial body weight, consistent with observations reported for other NA vaccines. Body weight recoveries were observed for vaccinated groups resulting in an average final weight change of 2.7% at the low dose and 4.8% weight gain for the higher dose, as compared to baseline. Overall, the results demonstrated that a single low-dose MRT NA-LNP vaccination can elicit functional antibodies measurable for blocking influenza NA activity and sufficient to confer protection against lethal challenge in mice.

Immunogenicity of HA (H3) mRNA-LNP in NHP

Figure 18:
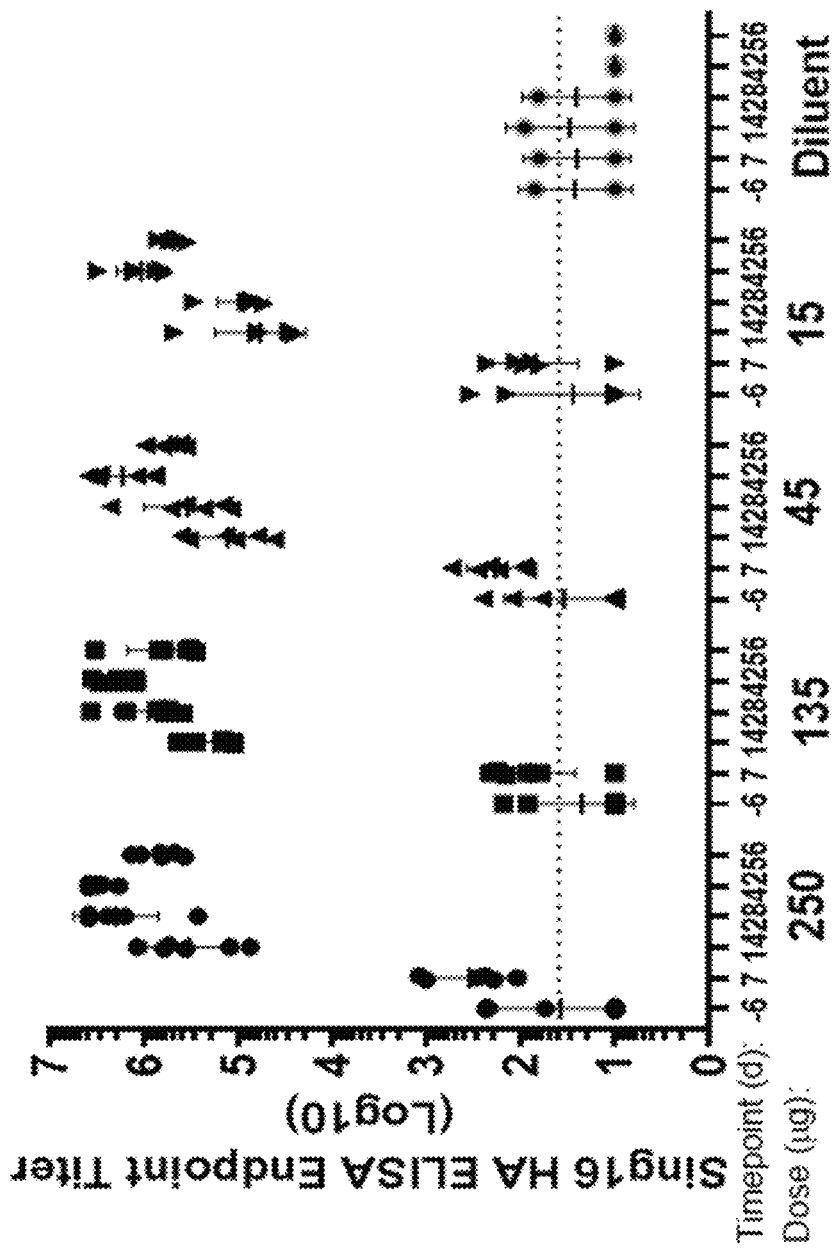
Figures 19A, 19B:
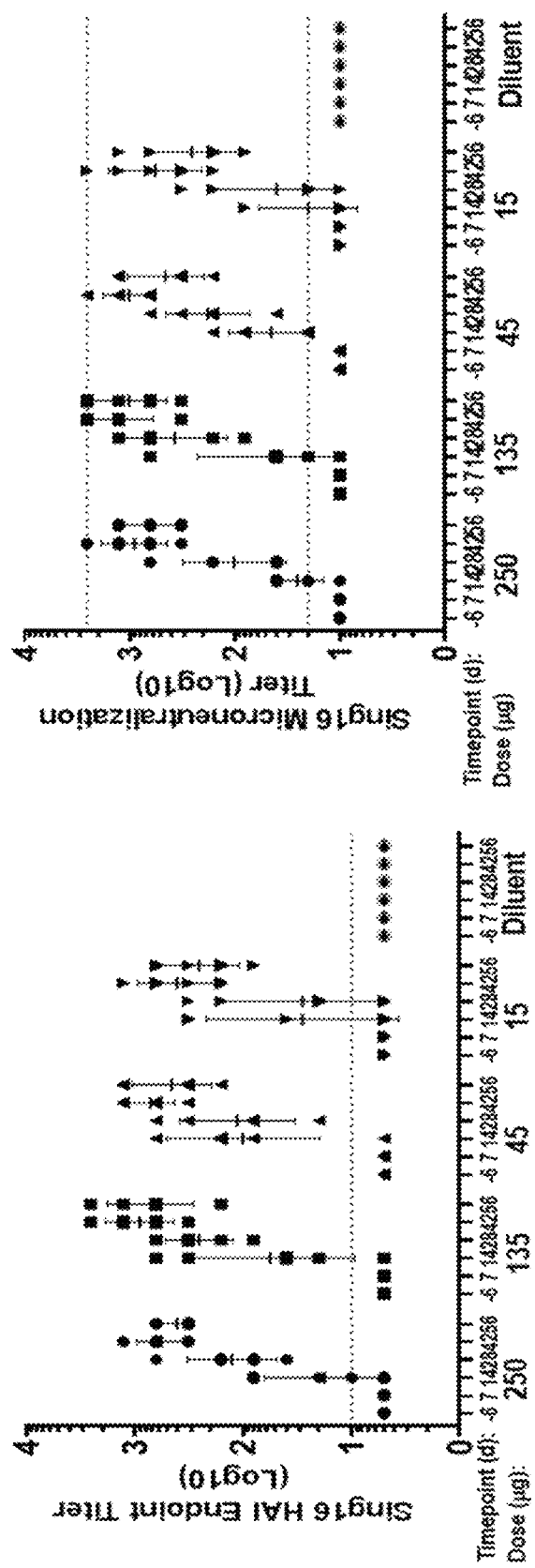

To evaluate immunogenicity of the mRNA-LNP in NHP, a dose range study covering 15, 45, 135, and 250 μg of Sing16 HA-LNP was performed in NHPs. After the first immunization, all vaccinated NHPs developed antibodies reactive to recombinant HA protein as noted in ELISA (FIG. 18). Further boosting of titers was observed post second dose. Surprisingly, the 15 μg dose induced only 1.8-fold lower ELISA titers than the 135 μg dose level (95% CI 1.0, 3.6), suggesting a dose saturation close to 15 μg level. Robust HAI antibodies were induced in all dose groups on day 42 and GMTs recorded were 400 for 15 μg, 700 for 45 μg, 900 for 135 μg and 570 for 250 μg. At day 42, the fold increase in GMT titers with 95% CI was 2.2-fold (1.0; 5.0) between the 135 μg and 15 μg and was 1.3-fold (0.6; 2.8) between the 135 μg and 45 μg treatment groups indicating that despite the observed trend towards higher titers with increasing dose, the difference between groups was minimal (FIG. 19A). The neutralization potency assessed by microneutralization (MN) assay (FIG. 19B) showed a better trend for dose effect with GMTs on D28 of 40 for 15 μg, 180 for 45 μg, 300 and for 135 μg.

Figure 20B:
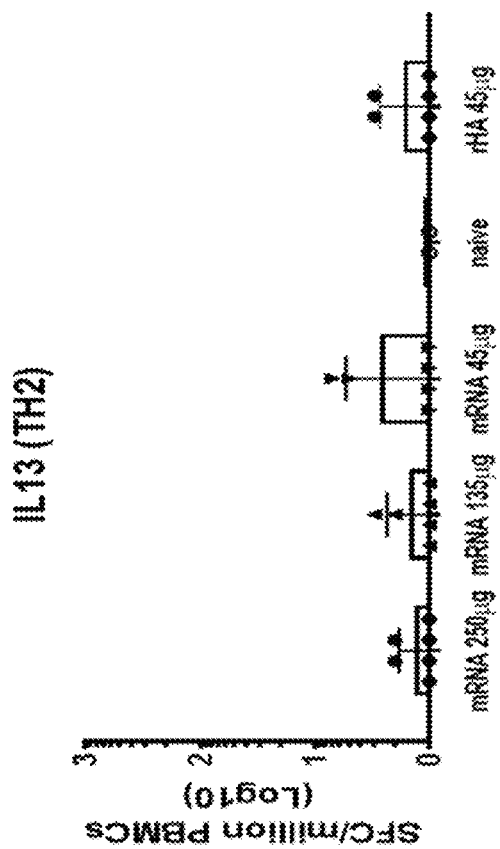
Figure 20A:
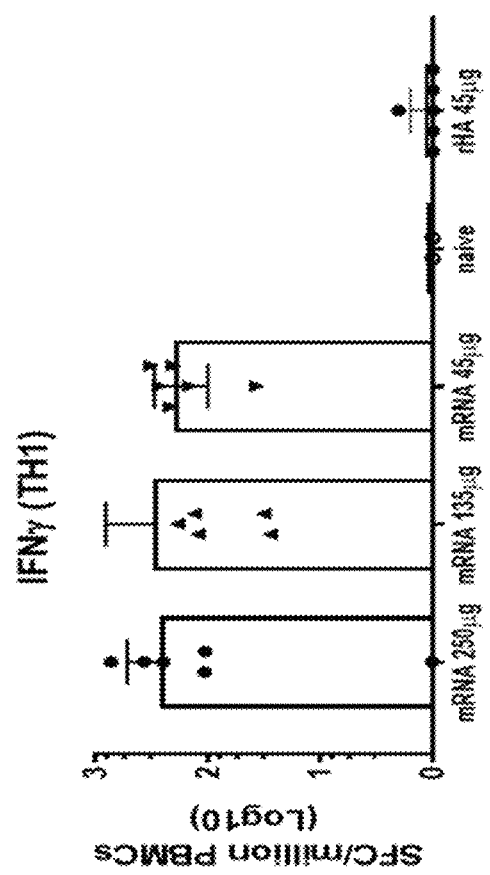

Since T cells have been shown effective in reducing viral load and limiting disease severity in animal models (Rimmelzwaan et al., *Vaccine* (2008) 26(4):D41-D44; Sridhar et al., *Nat Med.* (2013) 19(10): 1305-12; Sridhar et al., *Front Immunol.* (2016) 7:195), we evaluated recall T cells in the NHPs vaccinated with 45, 135, 250 μg of Sing16 HA-LNP or with 45 μg of recombinant HA. PBMCs collected at day 42 were evaluated in IFN-γ (Th1 cytokine) and IL-13 (Th2 cytokine) ELISPOT assay with recall stimulation with pooled overlapping peptides spanning the entire sequence of the Sing16 HA. All vaccinated animals except one in 250 μg group developed IFN-γ secreting cells, ranging from 28 to 1328 spot-forming cells (SFC) per million PBMCs (FIG. 20A). Notably, a dose-response was not observed, and the lower and higher dose level groups of animals showed comparable frequencies of IFN-γ secreting cells. In contrast, all animals in the control group immunized with the recombinant Sing16 HA protein demonstrated absence of IFN-γ producing cells. The presence of IL-13 cytokine secreting cells was either not detected or very low in all the groups tested (FIG. 20B). The data suggest that Sing16 HA-LNP induced strong Th1-biased cellular responses in NHPs, comparable to that seen with MRT5500 (Kalnin et al., supra), a SARS-COV-2 vaccine currently under development.

Figure 21:
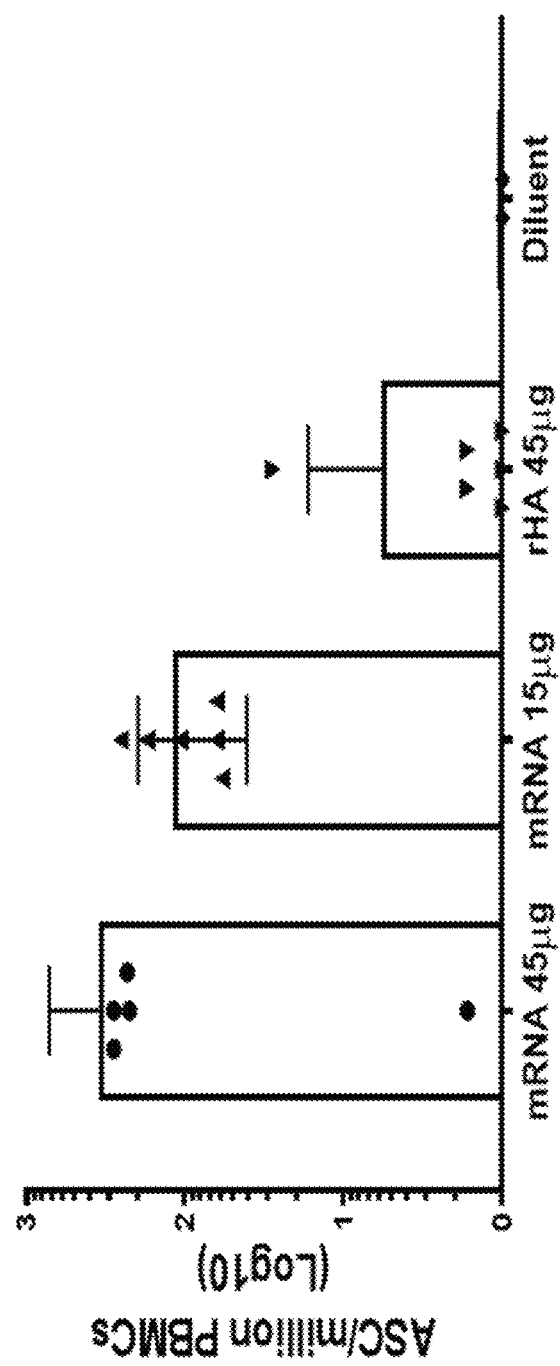

To investigate frequency of memory B cells (MBCs) in NHPs after immunization with Sing16 HA-LNP, an ELISPOT assay was developed to quantify antigen-specific MBCs as a readout of humoral immune memory. On day 180, PBMCs were collected from the NHPs immunized with 45 μg or 15 μg of the Sing16 HA mRNA-LNP formulations or with a recombinant HA as a comparator at a 45 μg dose. A 4-day polyclonal stimulation of PBMCs that is optimized to drive memory B cells to antibody secreting cells (ASC) was performed, and the stimulated PBMCs were plated in an antigen-specific ELISPOT where the frequency of antigen-specific ASCs could be determined. Antigen-specific memory B cells were then quantified as a percentage of total IgG+ memory B cells. Antigen-specific memory B cells were detected in all animals and their frequency was ranging from 1 to 5% for the 45 μg dose group and 0.3 to 1.5% for the 15 μg dose group. In the rHA immunized animals, the memory B cell responses appeared to be markedly lower as antigen-specific memory B cells were undetectable in five out of six animals (FIG. 21). It was concluded that Sing16 HA-LNP, like other mRNA vaccines, elicits a population of anti-HA specific memory B cells that promise to prolong immunity (Lindgren et al., *Front Immunol.* (2019) 10:614).

Multivalent Influenza Virus Antigens

Figure 22:
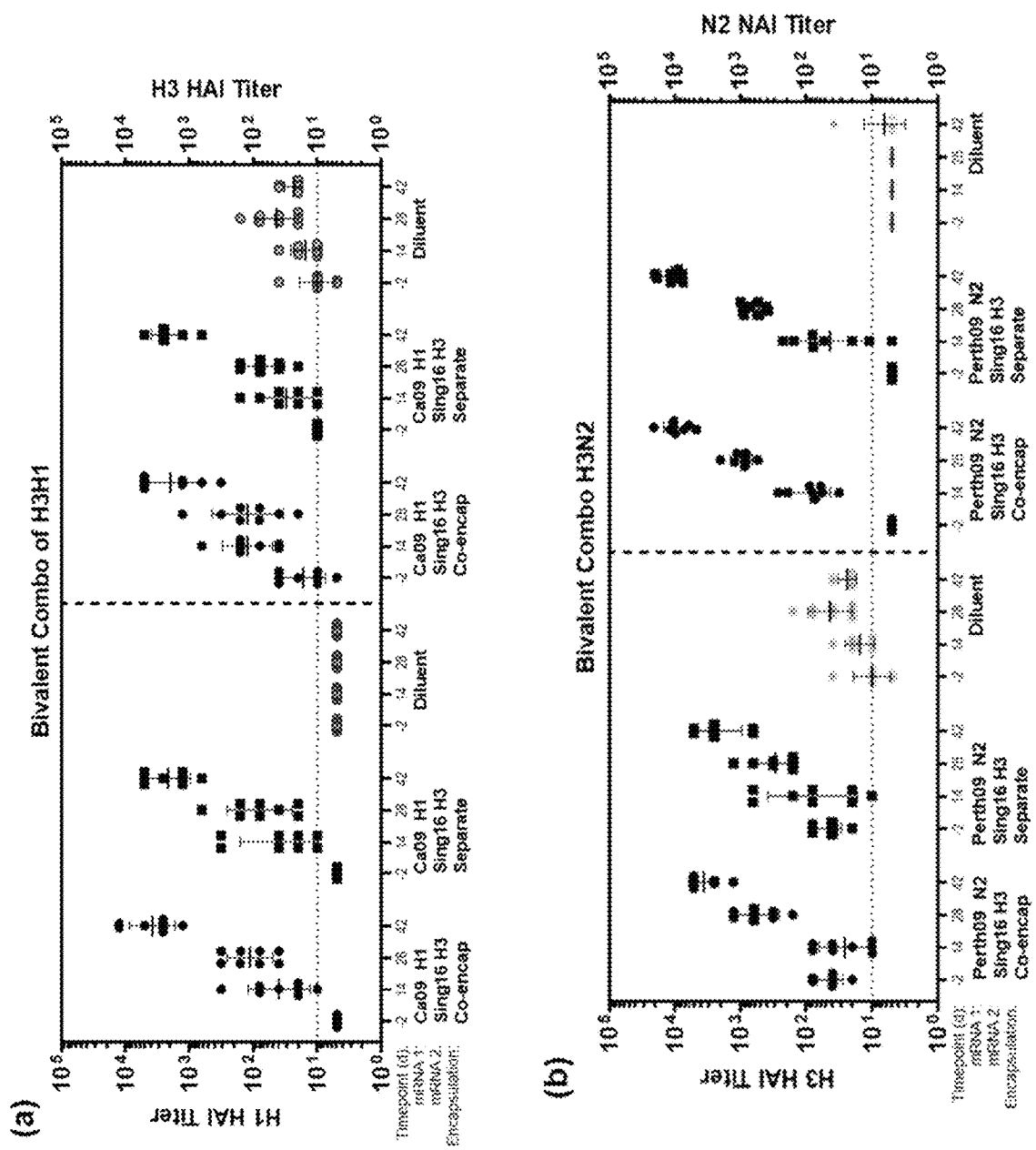
Figure 22:
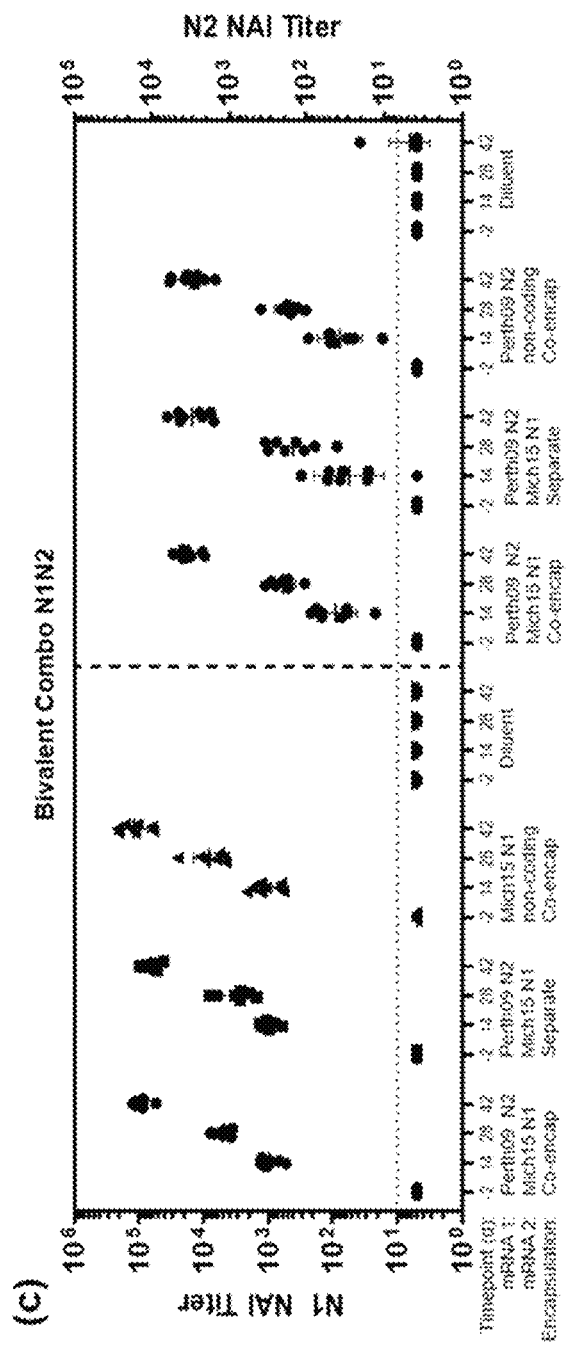

An advantage of mRNA-LNP platform is the flexibility of LNP encapsulation for multiple mRNA antigen constructs. However, this potential needs to be tested to address the concern of antigenic interference. To explore the combinations of influenza antigens, co-encapsulated HA and NA mRNA were formulated in LNPs as bivalent formulations containing 0.2 μg each of mRNA in an H3H1, H3N2, or N1N2 combination or with the monovalent containing 0.2 μg of each corresponding antigen. These formulations were administered in mice to determine any antigenic interference on immunogenicity by comparing the functional titers of the individual antigen in bivalent vs. monovalent formulations (FIG. 22, panels (a)-(c) and Table 6).

TABLE 6

Frequency of Antigen-Specific Memory B Cells in NHPs Vaccinated with H3 mRNA-LNP Vaccine

| Animal group | Animal ID | PBMCs/ well of Ag-Specific IgG | Spot # of Ag-Specific IgG/million PBMCs | PBMCs/ Well of Total IgG | Spot # of Total IgG/ million PBMCs | % of Ag-Specific IgG to Total IgG |
|---|---|---|---|---|---|---|
| H3 mRNA-LNP (45 μg) | 1 | $3 \times 10^5$ | 1082 | $5 \times 10^3$ | 21700 | 5.0 |
| | 2 | $3 \times 10^5$ | 232 | $5 \times 10^3$ | 6100 | 3.8 |
| | 3 | $3 \times 10^5$ | 282 | $5 \times 10^3$ | 11700 | 2.4 |
| | 4 | $3 \times 10^5$ | 2 | $5 \times 10^3$ | 100 | 2.0 |
| | 5 | $3 \times 10^5$ | 283 | $5 \times 10^3$ | 8700 | 3.3 |
| | 6 | $3 \times 10^5$ | 225 | $5 \times 10^3$ | 22800 | 1.0 |
| H3 mRNA-LNP (15 μg) | 1 | $3 \times 10^5$ | 63 | $5 \times 10^3$ | 21600 | 0.3 |
| | 2 | $3 \times 10^5$ | 58 | $5 \times 10^3$ | 11300 | 0.5 |
| | 3 | $3 \times 10^5$ | 253 | $5 \times 10^3$ | 17300 | 1.5 |
| | 4 | $3 \times 10^5$ | 173 | $5 \times 10^3$ | 17300 | 1.0 |
| | 5 | $3 \times 10^5$ | 63 | $5 \times 10^3$ | 9300 | 0.7 |
| | 6 | $3 \times 10^5$ | 107 | $5 \times 10^3$ | 19300 | 0.6 |
| rHA (45 μg) | 1 | $3 \times 10^5$ | 2 | $5 \times 10^3$ | 19800 | 0.0 |
| | 2 | $3 \times 10^5$ | 28 | $5 \times 10^3$ | 14300 | 0.2 |
| | 3 | $3 \times 10^5$ | 2 | $5 \times 10^3$ | 17000 | 0.0 |
| | 4 | $3 \times 10^5$ | 0 | $5 \times 10^3$ | 7900 | 0.0 |
| | 5 | $3 \times 10^5$ | 0 | $5 \times 10^3$ | 21600 | 0.0 |
| | 6 | $3 \times 10^5$ | 0 | $5 \times 10^3$ | 14600 | 0.0 |
| Diluent | 1 | $3 \times 10^5$ | 0 | $5 \times 10^3$ | 30900 | 0.0 |
| | 2 | $3 \times 10^5$ | 0 | $5 \times 10^3$ | 7100 | 0.0 |

In the H1H3 combo, between the co-encapsulated and separately administered vaccines, no statistically significant difference (p=0.2584) irrespective of the time points was observed for HAI titers and no significant difference (p=0.8389) at D42 was observed for H3 titers. In the case of H3N2 combo, the NA component of the vaccine elicited high neutralizing antibodies in combination with the HA component, demonstrating lack of HA dominance. Between the co-encapsulated and separately administered vaccines, no statistically significant difference (p=0.2960), irrespective of the time points, was observed for H3 titers, and no significant difference (p=0.0904) at D42 was observed for N2 titers. Likewise, the N1N2 combo was not statistically significantly different (p=0.3899) for N2. N1 titers at day 42 for co-encapsulated and separately administered vaccines were above limit of quantification. Combination of N2N1, H3H1, or H3N2 thus generated antibody titers equivalent to individual LNPs separately formulated.

Quadrivalent formulations of co-encapsulated H1, N1, H3, and/or N2 mRNA were further explored. These formulations were tested in NHPs in total 10 μg composed of 2.5 μg each of influenza antigen mRNA and filling amount of noncoding mRNA (nc mRNA) if needed in combinations, resulting in quadrivalent (H1N1H3N2), bivalent (H1N1 or H3N2), or monovalent (H1, H3, N1, or N2) LNPs (Table 7).

Figure 23:
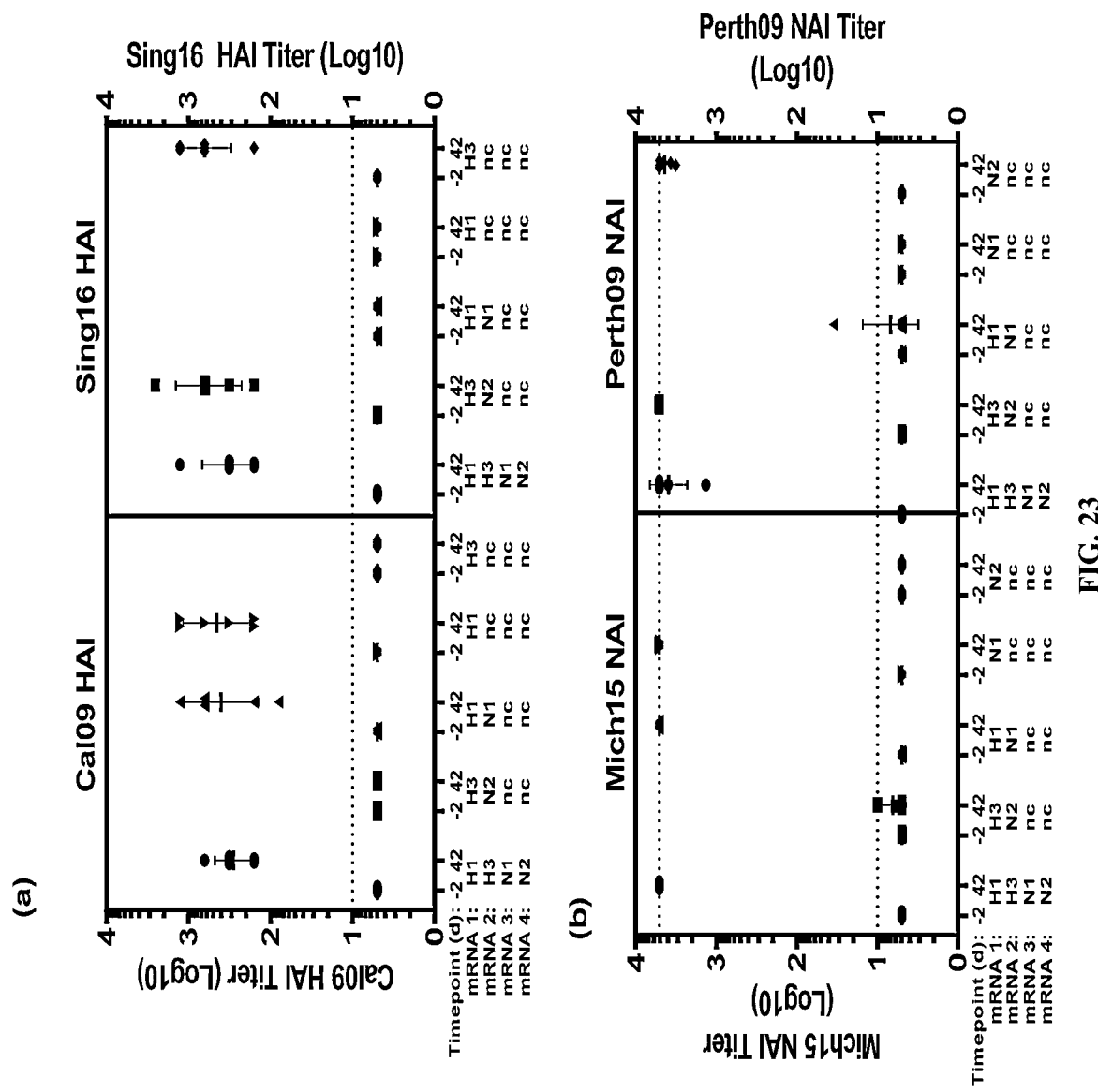

HAI titers to H1 or H3, or NAI titers to N1 or N2 were compared between the monovalent formulations vs. bivalent or quadrivalent formulations (FIG. 23). On day 42, the HAI titers to H1 of the quadrivalent group were comparable when analyzed with that of the H1 monovalent group (p=0.9054, t-test, unpaired, two-tailed) or H1N1 bivalent group (p=0.8002). Similarly, the H3 HAI titers of the quadrivalent group was comparable when analyzed with that of the H3 monovalent group (p=0.2504) or H3N2 bivalent group (p=0.5894). The NAI titers to N1 were almost identical in groups of animals vaccinated with N1 monovalent mRNA or H1N1 bivalent mRNA or the quadrivalent H1N1H3N2 mRNA formulations. Likewise, there was no difference in N2 NAI titers between the N2 monovalent mRNA (p=0.8485) or H3N2 bivalent mRNA (0.4545) with the quadrivalent H1N1H3N2 mRNA formulations.

Overall, these findings indicate that co-encapsulated or combination multivalent vaccines of HA/NA mRNA-LNPs at this dose level could efficiently deliver all four antigens without any concern for antigenic interference and all antigens were as immunogenic as in the formulation when these antigens were delivered singularly.

TABLE 7

Bivalent Combination of Influenza Virus in Mouse Study

| Group | N | mRNA1 | mRNA2 | LNP | mRNA dose (μg) | Description | CA09 HAI | Sing16 HAI | Mich15 NAI | Perth09 NAI |
|---|---|---|---|---|---|---|---|---|---|---|
| 1 | 8 | Sing16 | Perth09 | Yes | 0.2, 0.2 | Coformulated | | x | | x |
| 2 | 8 | H3 | N2 | | | Separate | | x | | x |
| 3 | 8 | CA09 | Sing16 | | | Coformulated | x | x | | |
| 4 | 8 | H1 | H3 | | | Separate | x | x | | |
| 5 | 8 | Mich15 | Perth09 | | | Coformulated | | | x | x |
| 6 | 8 | N1 | N2 | | | Separate | | | x | x |
| 7 | 8 | Diluent | — | — | 0 | single | x | x | x | x |

Example 7: Additional LNP Formulations

Figure 24:
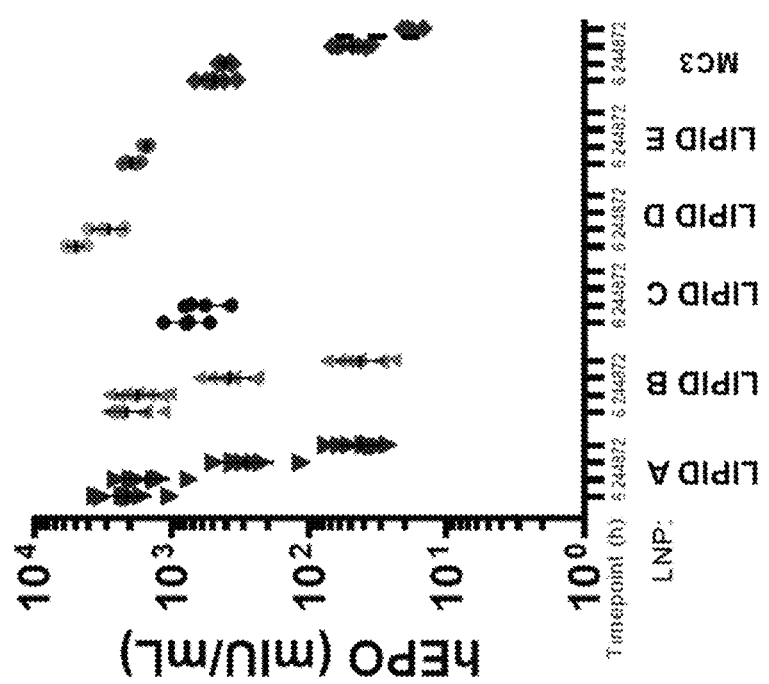

Additional LNP formulations for mRNA vaccines were prepared, designated Lipid C (containing cationic lipid GL-HEPES-E3-E10-DS-3-E18-1), Lipid D (containing cationic lipid GL-HEPES-E3-E12-DS-4-E10), and Lipid E (containing cationic lipid GL-HEPES-E3-E12-DS-3-E14). Human erythropoietin (hEPO) mRNA was used as a test mRNA. Expression of hEPO was measured by ELISA from samples taken from mice injected with the LNPs. Samples were taken 6 hours, 24 hours, 48 hours, and 72 hours after injection. As show in FIG. 24, hEPO expression was consistently higher at all time points with LNP formulations Lipid A, Lipid B, Lipid C, Lipid D, and Lipid E, compared to a control LNP formulation containing cationic lipid MC3.

Table 8 below summarizes the results relative to a control LNP containing the MC3 cationic lipid.

TABLE 8

Levels of hEPO from LNP formulations Lipid A-E relative to MC3.

| LNP Formulation | Fold higher hEPO at 6 hours (compared to MC3) | STDEV |
|---|---|---|
| Lipid A | 10.35 | 4.15 |
| Lipid B | 5.62 | 1.34 |
| Lipid D | 7.78 | 2.79 |
| Lipid E | 6.17 | 1.57 |

Figure 25:
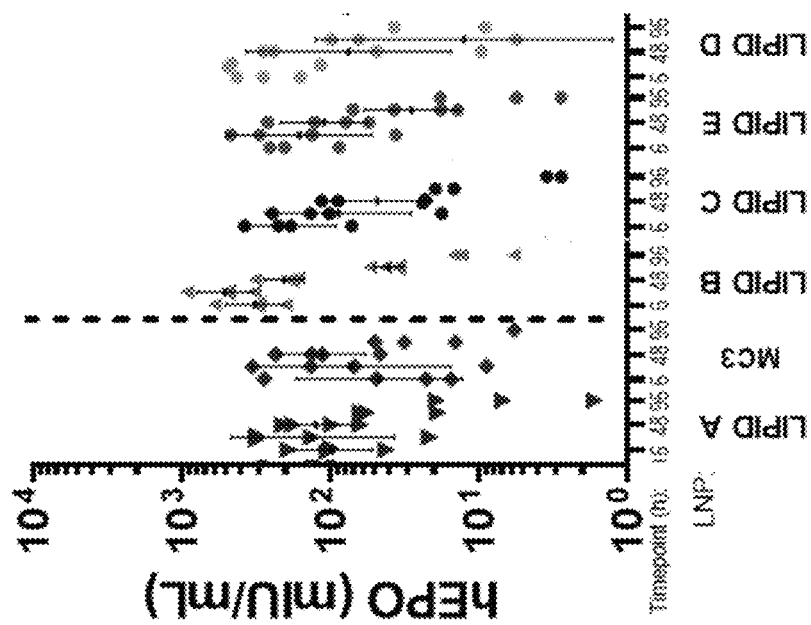

The same hEPO mRNA-LNP formulations were next tested in non-human primates (NHPs). Samples were taken at 6 hours, 48 hours, and 96 hours after injection. As shown in FIG. 25, each LNP formulation produced levels of hEPO comparable to the MC3 control formulation.

Figure 26:
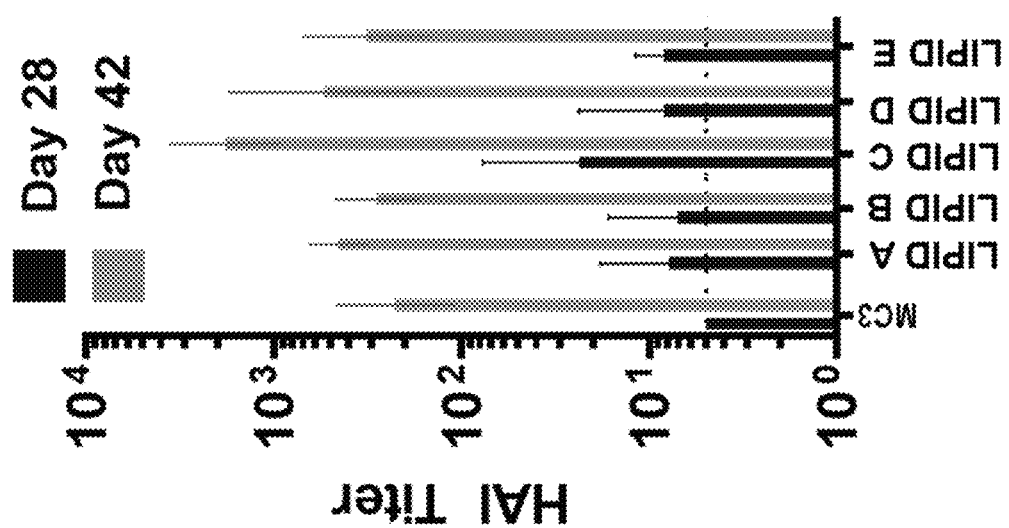

Influenza HA-encoding mRNA-LNP formulations were also tested in NHPs. NHPs were administered the LNP formulations at 10 µg via intramuscular injection and samples were taken at say 28 and day 42 post injection. HAI titers were measured as described above. As shown in FIG. 26, each LNP formulation produced HAI titers comparable to or higher than the MC3 control formulation.

The same experiment as shown in FIG. 26 was performed while measuring HAI titers with the Cal09 H1 influenza antigen. As shown in FIG. 27, each LNP formulation produced HAI titers comparable to or higher than the MC3 control formulation.

As shown in FIG. 28, HAI titers with the Sing16 H3 antigen were elevated for LNP formulations Lipid C and Lipid D.

Example 8: Respiratory Syncytial Virus (RSV) F Protein-Encoding mRNA LNP Formulations The effect of different cationic lipids in the LNP were tested for the LNP-encapsulated RSV F protein mRNA. Lipid formulations of Lipid A, Lipid B, Lipid C, Lipid D, and Lipid E were tested. Each LNP was composed of 40% of one of the five cationic lipids, 30% phospholipid DOPE, 1.5% PEGylated lipid DMG-PEG2000, and 28.5% cholesterol. An LNP with the cationic lipid MC3 was also used, considered an industry benchmark (Jayaraman et al. Angew Chem Int Ed. 51:8529-33. 2012).

The F protein tested was designated FD3, and corresponds to a pre-fusion RSV F protein. The amino acid sequence for FD3 is recited below.

FD3:
(SEQ ID NO: 16)
MELLILKANAITTILTAVTFCFASGQNITEEFYQSTCSAVSKGYLSALR

TGWYTSVITIELSNIKENKCNGTDAKVKLIKQELDKYKNAVTELQLLMG

SGNVGLGGAIASGVAVSKVLHLEGEVNKIKSALLSTNKAVVSLSNGVSV

LTFKVLDLKNYIDKQLLPILNKQSCSISNPETVIEFQQKNNRLLEITRE

FSVNAGVTTPVSTYMLTNSELLSLINDMPITNDQKKLMSNNVQIVRQQS

YSIMSIIKEEVLAYVVQLPLYGVIDTPCWKLHTSPLCTTNTKNGSNICL

TRTDRGWYCDNAGNVSFFPQAETCKVQSNRVFCDTMNSRTLPSEVNLCN

VDIFNPKYDCKIMTSKTDVSSSVITSLGAIVSCYGKTKCTASNKNRGII

KTFSNGCDYVSNKGVDTVSVGNTLYYVNKQEGKSLYVKGEPIINFYDPL

VFPSDEFDASISQVNELINQSLAFINQSDELLHNVNAGKSTTNIMITTI

IIVIIVILLSLIAVGLLLYCKARSTPVTLSKDQLSGINNIAFSN

The mRNA molecule described herein comprises an open reading frame (ORF) encoding an RSV F protein antigen, at least one 5' untranslated region (5' UTR), at least one 3' untranslated region (3' UTR), and at least one polyadenylation (poly(A)) sequence. The mRNA further comprises a 5' cap with the following structure:

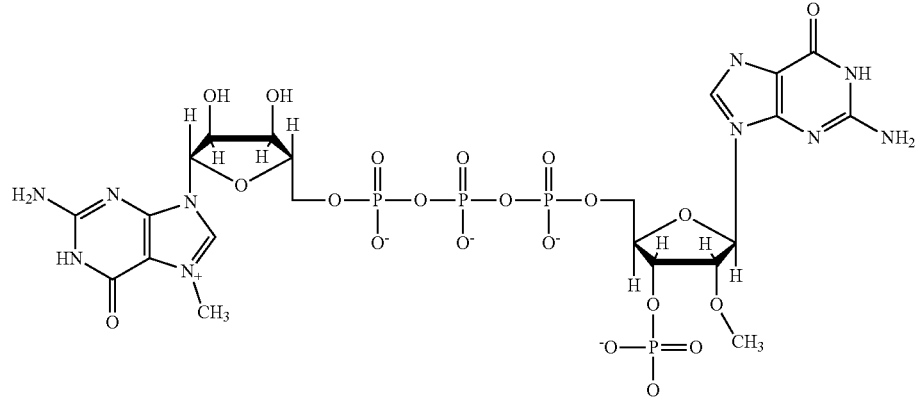

The nucleic acid sequence for the mRNA open reading frame (ORF) encoding the RSV F protein is recited below.

The nucleic acid sequences for the DNA template encoding the RSV F protein is recited below.

```
FD3 mRNA ORF:
                                          (SEQ ID NO: 17)
AUGGAACUGCUGAUCCUCAAAGCCAACGCAAUCACCACCAUUCUCACCG

CUGUGACCUUCUGCUUCGCAUCGGGGCAGAACAUCACUGAAGAGUUUUA

CCAGAGCACUUGCAGCGCGGUGUCAAAGGGUUACCUUUCCGCACUGCGG

ACCGGAUGGUACACUUCCGUGAUCACCAUUGAGCUCAGCAACAUCAAGG

AAAACAAGUGCAAUGGCACCGACGCCAAGGUCAAGCUGAUCAAACAAGA

ACUGGACAAGUACAAGAACGCCGUGACAGAAUUGCAGCUCCUGAUGGGA

UCCGGAAACGUCGGUCUGGGCGGAGCCAUCGCGAGUGGAGUGGCUGUGU

CCAAGGUCUUGCACCUCGAGGGAGAAGUGAACAAGAUCAAGUCCGCGCU

GCUGUCAACGAACAAGGCCGUGGUGUCCCUGUCUAACGGCGUCAGCGUG

CUGACGUUCAAGGUCCUGGACCUGAAGAAUUACAUUGACAAGCAGCUGC

UGCCCAUCCUCAACAAGCAAUCCUGCUCCAUCUCCAACCCCGAAACCGU

GAUCGAGUUCCAGCAGAAGAACAACCGCCUGCUGGAAAUUACUCGCGAG

UUCUCUGUGAAUGCCGGCGUGACCACCCCUGUGUCCACCUACAUGCUGA

CCAACUCCGAGCUUCUCUCCCUUAUCAAUGACAUGCCUAUCACGAACGA

CCAGAAGAAGCUGAUGUCGAACAACGUGCAGAUUGUGCGGCAGCAGUCA

UACAGCAUCAUGUCGAUCAUCAAGGAAGAAGUGCUGGCGUACGUGGUGC

AACUCCCGCUGUACGGCGUCAUCGAUACCCCGUGCUGGAAGCUGCACAC

CUCGCCUUUGUGUACCACCAACACCAAGAACGGAUCCAACAUCUGCUUA

ACCCGGACUGAUCGGGGUUGGUACUGCGACAACGCCGGGAAUGUUUCGU

UCUUCCCACAAGCCGAGACUUGUAAAGUGCAGUCAAACAGAGUGUUCUG

UGACACCAUGAACUCGAGAACCCUGCCCAGCGAAGUGAACCUGUGUAAC

GUCGACAUCUUUAACCCAAAAUACGAUUGCAAGAUUAUGACCAGCAAAA

CCGACGUGUCCUCCUCCGUGAUAACAAGCCUGGGGGCGAUUGUGUCAUG

CUACGGAAAGACUAAGUGCACCGCCUCGAACAAGAACCGCGGCAUCAUU

AAGACUUUCUCGAAUGGUUGCGACUAUGUGUCCAACAAGGGCGUGGAUA

CUGUGUCAGUCGGGAAUACUCUUUACUACGUGAACAAGCAGGAGGGGAA

AAGCCUCUACGUGAAGGGAGAGCCUAUUAUCAACUUUUACGAUCCGCUG

GUGUUCCCGUCCGACGAAUUCGACGCCAGCAUCAGCCAAGUCAACGAGC

UGAUUAACCAGUCCCUCGCCUUCAUCAACCAAUCCGACGAGCUCCUGCA

UAACGUGAACGCCGGAAAGUCCACCACCAACAUCAUGAUCACUACUAUU

AUCAUCGUGAUCAUCGUCAUCCUGCUGAGCCUGAUUGCUGUGGGCCUGU

UGCUGUAUUGCAAAGCCAGGUCCACCCCGGUCACCCUGUCGAAGGAUCA

GCUGUCCGGAAUCAACAACAUUGCCUUCUCCAACUAA
```

```
FD3 DNA:
                                          (SEQ ID NO: 18)
ATGGAACTGCTGATCCTCAAAGCCAACGCAATCACCACCATTCTCACCG

CTGTGACCTTCTGCTTCGCATCGGGGCAGAACATCACTGAAGAGTTTTA

CCAGAGCACTTGCAGCGCGGTGTCAAAGGGTTACCTTTCCGCACTGCGG

ACCGGATGGTACACTTCCGTGATCACCATTGAGCTCAGCAACATCAAGG

AAAACAAGTGCAATGGCACCGACGCCAAGGTCAAGCTGATCAAACAAGA

ACTGGACAAGTACAAGAACGCCGTGACAGAATTGCAGCTCCTGATGGGA

TCCGGAAACGTCGGTCTGGGCGGAGCCATCGCGAGTGGAGTGGCTGTGT

CCAAGGTCTTGCACCTCGAGGGAGAAGTGAACAAGATCAAGTCCGCGCT

GCTGTCAACGAACAAGGCCGTGGTGTCCCTGTCTAACGGCGTCAGCGTG

CTGACGTTCAAGGTCCTGGACCTGAAGAATTACATTGACAAGCAGCTGC

TGCCCATCCTCAACAAGCAATCCTGCTCCATCTCCAACCCCGAAACCGT

GATCGAGTTCCAGCAGAAGAACAACCGCCTGCTGGAAATTACTCGCGAG

TTCTCTGTGAATGCCGGCGTGACCACCCCTGTGTCCACCTACATGCTGA

CCAACTCCGAGCTTCTCTCCCTTATCAATGACATGCCTATCACGAACGA

CCAGAAGAAGCTGATGTCGAACAACGTGCAGATTGTGCGGCAGCAGTCA

TACAGCATCATGTCGATCATCAAGGAAGAAGTGCTGGCGTACGTGGTGC

AACTCCCGCTGTACGGCGTCATCGATACCCCGTGCTGGAAGCTGCACAC

CTCGCCTTTGTGTACCACCAACACCAAGAACGGATCCAACATCTGCTTA

ACCCGGACTGATCGGGGTTGGTACTGCGACAACGCCGGGAATGTTTCGT

TCTTCCCACAAGCCGAGACTTGTAAAGTGCAGTCAAACAGAGTGTTCTG

TGACACCATGAACTCGAGAACCCTGCCCAGCGAAGTGAACCTGTGTAAC

GTCGACATCTTTAACCCAAAATACGATTGCAAGATTATGACCAGCAAAA

CCGACGTGTCCTCCTCCGTGATAACAAGCCTGGGGGCGATTGTGTCATG

CTACGGAAAGACTAAGTGCACCGCCTCGAACAAGAACCGCGGCATCATT

AAGACTTTCTCGAATGGTTGCGACTATGTGTCCAACAAGGGCGTGGATA

CTGTGTCAGTCGGGAATACTCTTTACTACGTGAACAAGCAGGAGGGGAA

AAGCCTCTACGTGAAGGGAGAGCCTATTATCAACTTTTACGATCCGCTG

GTGTTCCCGTCCGACGAATTCGACGCCAGCATCAGCCAAGTCAACGAGC

TGATTAACCAGTCCCTCGCCTTCATCAACCAATCCGACGAGCTCCTGCA

TAACGTGAACGCCGGAAAGTCCACCACCAACATCATGATCACTACTATT

ATCATCGTGATCATCGTCATCCTGCTGAGCCTGATTGCTGTGGGCCTGT

TGCTGTATTGCAAAGCCAGGTCCACCCCGGTCACCCTGTCGAAGGATCA

GCTGTCCGGAATCAACAACATTGCCTTCTCCAACTAA
```

The nucleic acid sequences for the 5'UTR and 3'UTR are recited below.

5'UTR:
(SEQ ID NO: 19)
GGACAGAUCGCCUGGAGACGCCAUCCACGCUGUUUUGACCUCCAUAGAA

GACACCGGGACCGAUCCAGCCUCCGCGGCCGGGAACGGUGCAUUGGAAC

GCGGAUUCCCCGUGCCAAGAGUGACUCACCGUCCUUGACACG

3'UTR:
(SEQ ID NO: 20)
CGGGUGGCAUCCCUGUGACCCCUCCCCAGUGCCUCUCCUGGCCCUGGAA

GUUGCCACUCCAGUGCCCACCAGCCUUGUCCUAAUAAAAUUAAGUUGCA

UC

The nucleic acid sequences for the full-length mRNA encoding the RSV F protein is recited below.

FD3 mRNA:
(SEQ ID NO: 21)
GGACAGAUCGCCUGGAGACGCCAUCCACGCUGUUUUGACCUCCAUAGAA

GACACCGGGACCGAUCCAGCCUCCGCGGCCGGGAACGGUGCAUUGGAAC

GCGGAUUCCCCGUGCCAAGAGUGACUCACCGUCCUUGACACGAUGGAAC

UGCUGAUCCUCAAAGCCAACGCAAUCACCACCAUUCUCACCGCUGUGAC

CUUCUGCUUCGCAUCGGGGCAGAACAUCACUGAAGAGUUUUACCAGAGC

ACUUGCAGCGCGGUGUCAAAGGGUUACCUUUCCGCACUGCGGACCGGAU

GGUACACUUCCGUGAUCACCAUUGAGCUCAGCAACAUCAAGGAAAACAA

GUGCAAUGGCACCGACGCCAAGGUCAAGCUGAUCAAACAAGAACUGGAC

AAGUACAAGAACGCCGUGACAGAAUUGCAGCUCCUGAUGGGAUCCGGAA

ACGUCGGUCUGGGCGGAGCCAUCGCGAGUGGAGUGGCUGUGUCCAAGGU

CUUGCACCUCGAGGGAGAAGUGAACAAGAUCAAGUCCGCGCUGCUGUCA

ACGAACAAGGCCGUGGUGUCCCUGUCUAACGGCGUCAGCGUGCUGACGU

UCAAGGUCCUGGACCUGAAGAAUUACAUUGACAAGCAGCUGCUGCCCAU

CCUCAACAAGCAAUCCUGCUCCAUCUCCAACCCCGAAACCGUGAUCGAG

UUCCAGCAGAAGAACAACCGCCUGCUGGAAAUUACUCGCGAGUUCUCUG

UGAAUGCCGGCGUGACCACCCCUGUGUCCACCUACAUGCUGACCAACUC

CGAGCUUCUCUCCCUUAUCAAUGACAUGCCUAUCACGAACGACCAGAAG

AAGCUGAUGUCGAACAACGUGCAGAUUGUGCGGCAGCAGUCAUACAGCA

UCAUGUCGAUCAUCAAGGAAGAAGUGCUGGCGUACGUGGUGCAACUCCC

GCUGUACGGCGUCAUCGAUACCCCGUGCUGGAAGCUGCACACCUCGCCU

UUGUGUACCACCAACACCAAGAACGGAUCCAACAUCUGCUUAACCCGGA

CUGAUCGGGGUUGGUACUGCGACAACGCCGGGAAUGUUUCGUUCUUCCC

ACAAGCCGAGACUUGUAAAGUGCAGUCAAACAGAGUGUUCUGUGACACC

AUGAACUCGAGAACCCUGCCCAGCGAAGUGAACCUGUGUAACGUCGACA

UCUUUAACCCAAAAUACGAUUGCAAGAUUAUGACCAGCAAAACCGACGU

GUCCUCCUCCGUGAUAACAAGCCUGGGGGCGAUUGUGUCAUGCUACGGA

AAGACUAAGUGCACCGCCUCGAACAAGAACCGCGGCAUCAUUAAGACUU

-continued
UCUCGAAUGGUUGCGACUAUGUGUCCAACAAGGGCGUGGAUACUGUGUC

AGUCGGGAAUACUCUUUACUACGUGAACAAGCAGGAGGGGAAAAGCCUC

UACGUGAAGGGAGAGCCUAUUAUCAACUUUUACGAUCCGCUGGUGUUCC

CGUCCGACGAAUUCGACGCCAGCAUCAGCCAAGUCAACGAGCUGAUUAA

CCAGUCCCUCGCCUUCAUCAACCAAUCCGACGAGCUCCUGCAUAACGUG

AACGCCGGAAAGUCCACCACCAACAUCAUGAUCACUACUAUUAUCAUCG

UGAUCAUCGUCAUCCUGCUGAGCCUGAUUGCUGUGGGCCUGUUGCUGUA

UUGCAAAGCCAGGUCCACCCCGGUCACCCUGUCGAAGGAUCAGCUGUCC

GGAAUCAACAACAUUGCCUUCUCCAACUAACGGGUGGCAUCCCUGUGAC

CCCUCCCCAGUGCCUCUCCUGGCCCUGGAAGUUGCCACUCCAGUGCCCA

CCAGCCUUGUCCUAAUAAAAUUAAGUUGCAUC

LNP-RSV FD3 mRNA compositions were administered to NHPs. Groups of 6 cynomolgus macaques were administered a 5 μg dose of mRNA encapsulated with the above LNPs, or a 10 μg dose of an RSV Pre-F NP subunit control vaccine adjuvanted with $Al(OH)_3$, by intramuscular (IM) injection on D0 and D21. Monkeys were bled prior to each vaccine administration as well as at two weeks post-last vaccination (D35). As shown in FIG. 29, all tested cationic lipids effectively induced the production of anti-RSV F protein antibodies to a similar level as a Pre-F NP with an aluminum adjuvant.

As shown in FIG. 30, all tested cationic lipids generated effective RSV neutralization titers to a similar level as a Pre-F NP with an aluminum adjuvant.

The cumulative results of FIG. 29 and FIG. 30 are shown below in Table 9 and Table 10.

TABLE 9

Magnitude of immune response

| LNP Formulation | Neutralization Titer | Fold vs. MC3 |
|---|---|---|
| LIPID A | 9.86 | 23.43 |
| LIPID B | 10.03 | 26.35 |
| LIPID C | 8.509 | 9.18 |
| LIPID E | 6.929 | 3.07 |
| LIPID D | 8.894 | 11.99 |
| MC3 | 5.308 | 1.00 |
| Pre-F NP | 10.97 | 50.56 |

TABLE 10

Quality of immune response

| Cationic Lipid | Antibody Titer | Neutralization Titer | Antibody Titer/ Neutralization Titer ratio |
|---|---|---|---|
| LIPID A | 15.58 | 9.86 | 52.71 |
| LIPID B | 15.56 | 10.03 | 46.21 |
| LIPID C | 14.67 | 8.51 | 71.51 |
| LIPID E | 13.27 | 6.93 | 81.01 |
| LIPID D | 14.71 | 8.89 | 56.49 |
| MC3 | 11.3 | 5.31 | 63.56 |
| Pre-F NP | 17.59 | 10.97 | 98.36 |

A better quality of an immune response is demonstrated with a lower value for the antibody titer/neutralization titer ratio. Here, the LNP formulation Lipid B demonstrated the best quality of immune response, while all LNP formulations demonstrated a superior quality of immune response compared to the non-mRNA vaccine, Pre-F NP, and several were better than the industry benchmark LNP formulation of MC3.

Example 9: SARS-COV-2 Spike (S) Protein-Encoding mRNA LNP Formulations

LNP Formulations with SARS-COV-2 Spike (S) Protein-Encoding mRNA:

An LNP formulation containing a SARS-COV-2 S protein-encoding mRNA was administered to human subjects. The subjects were administered an LNP of formulation Lipid B. The unmodified mRNA encoded a SARS-COV-2 S protein mutated to remove the furin cleavage site and to mutate residues 986 and 987 to proline. The subjects were administered the LNP-SARS-COV-2 vaccine under clinical trial protocol for NCT04798027, described below.

This was a sequential group prevention study consisting of a sentinel cohort followed by the Full Enrollment Cohort. There were 3 dose levels (up to 25 participants 18-49 years of age for each dose level) in the Sentinel Cohort, which was done in an open-label fashion with stepwise safety evaluation for each dose level and each vaccination. All sentinel participants received 2 vaccinations, 21 days apart. For the Full Enrollment Cohort, participants were stratified into 2 age groups based on age at enrollment: the younger adult age group (140 participants 18-49 years of age) and the older adult age group (168 participants ≥ 50 years of age). The Full Enrollment Cohort 1 (Groups 1 to 4) received a single injection of study intervention while participants in Cohort 2 (Groups 5 to 8) received 2 vaccinations (to be given 21 days apart). The route of administration for all groups was intramuscular (IM).

Experimental: Group 1—1 injection of SARS-COV-2 mRNA vaccine formulation 1 at Day 1.

Experimental: Group 2—1 injection of SARS-COV-2 mRNA vaccine formulation 2 at Day 1.

Experimental: Group 3—1 injection of SARS-COV-2 mRNA vaccine formulation 3 at Day 1.

Placebo Comparator: Group 4—1 injection of placebo (0.9% normal saline) at Day 1.

Experimental: Group 5—2 injections of SARS-COV-2 mRNA vaccine formulation 1 at Day 1 and Day 22.

Experimental: Group 6—2 injections of SARS-COV-2 mRNA vaccine formulation 2 at Day 1 and Day 22.

Experimental: Group 7—2 injections of SARS-COV-2 mRNA vaccine formulation 3 at Day 1 and Day 22.

Placebo Comparator: Group 8—2 injections of placebo (0.9% normal saline) at Day 1 and Day 22.

Results from the study showed neutralizing antibody seroconversion (defined as 4-fold increase vs baseline) in 91% to 100% of study participants, two weeks after a second injection, across all 3 dosages tested. No safety concern has been observed and the tolerability profile is comparable to that of other unmodified mRNA SARS-COV-2 vaccines.

Example 10: Further Studies on Quadrivalent or Octavalent Influenza Vaccine LNP Formulations HAI titers and NAI titers were measured from mice administered various multivalent LNP-influenza mRNA vaccines. HAI titers were measured against influenza strains A/Michigan/45/2015, A/SINGAPORE/INFIMH160019/2016, B/Maryland/15/2016 BX69A, and B/Phuket/3073/2013. NAI titers were measured against influenza strains A/Michigan/45/2015, A/SINGAPORE/INFIMH160019/2016, B/Colorado/06/201, and B/Phuket/3073/2013.

The HAI titers and NAI titers were compared against mice receiving mono- or quadrivalent HA or NA mRNA vaccines.

Mice were injected with a prime vaccine on day 0 and a booster vaccine of the same dosage on Day 21. Blood was collected on days 1, 20, 22, and 35. For monovalent compositions containing mRNA encoding HA or NA antigens, mRNA encoding each of the following individually was used: H1, H3, HA from a B/Victoria lineage, and HA from a B/Yamagata lineage (specifically from strains A/Michigan/45/2015; A/Singapore/Infimh160019/2016; B/Maryland/15/2016; and B/Phuket/3037/2013). Quadrivalent vaccine compositions containing mRNA encoding each of N1, N2, NA from a B/Victoria lineage and NA from a B/Yamagata lineage, and each of H1, H3, HA from a B/Victoria lineage and HA from a B/Yamagata lineage (specifically from strains A/Michigan/45/2015; A/Singapore/Infimh160019/2016; B/Colorado/06/2017; and B/Phuket/3037/2013) were also prepared. Finally, an octavalent vaccine composition containing mRNA encoding each of H1, H3, HA from a B/Victoria lineage, HA from a B/Yamagata lineage, each of N1, N2, NA from a B/Victoria lineage and NA from a B/Yamagata lineage (specifically from strains A/Michigan/45/2015; A/Singapore/Infimh160019/2016; B/Colorado/06/2017; and B/Phuket/3037/2013) was prepared and administered as an octavalent vaccine. Each mRNA for all compositions was added in an amount of 0.4 μg/strain. For each group, n=6 mice.

An overview of each experimental group is recited below in Table 11.

TABLE 11

Overview of experimental groups for multivalent influenza vaccines in mice

| Group # | N | Prime (D 0)/boost (D 21) – NA mRNA | Dose mRNA NA (μg per strain) | Prime (D 0)/boost (D 21) – HA (together with NA) | Dose rHA (μg per strain) | Adjuvant (rHA) |
|---|---|---|---|---|---|---|
| 1 | 6 | LNP diluent | — | — | — | — |
| 3 | 6 | NA mRNA-LNP (N2 Perth) | 0.4 | — | — | — |
| 4 | 6 | NA mRNA-LNP (N1) | 0.4 | — | — | — |
| 5 | 6 | NA mRNA-LNP (N2) | 0.4 | — | — | — |
| 6 | 6 | NA mRNA-LNP (NV) | 0.4 | — | — | — |
| 7 | 6 | NA mRNA-LNP (NY) | 0.4 | — | — | — |
| 8 | 6 | NA mRNA-LNP (N1, N2, BV, BY) | 0.4 | — | — | — |
| 9 | 6 | — | — | HA mRNA-LNP (H1) | 0.4 | — |
| 10 | 6 | — | — | HA mRNA-LNP (H3) | 0.4 | — |

TABLE 11-continued Overview of experimental groups for multivalent influenza vaccines in mice

| Group # | N | Prime (D 0)/boost (D 21) – NA mRNA | Dose mRNA NA (µg per strain) | Prime (D 0)/boost (D 21) – HA (together with NA) | Dose rHA (µg per strain) | Adjuvant (rHA) |
|---|---|---|---|---|---|---|
| 11 | 6 | — | — | HA mRNA-LNP (BV) | 0.4 | — |
| 12 | 6 | — | — | HA mRNA-LNP (BY) | 0.4 | — |
| 13 | 6 | — | — | HA mRNA-LNP (H1, H3, BV, BY) | 0.4 | — |
| 14 | 6 | NA mRNA-LNP (N1, N2, BV, BY) | 0.4 | HA mRNA-LNP (H1, H3, BV, BY) | 0.4 | — |

As shown in FIG. 31, octavalent mRNA-LNP formulations led to HAI titers within 4-fold of the quadrivalent for 3 out of 4 influenza strains.

An overview of the NAI titer results for each of the groups above is shown in FIG. 33. The octavalent mRNA-LNP formulations led to NAI titers comparable to the quadrivalent mRNA-LNP formulations.

Thus, the data demonstrate that an octavalent vaccine was capable of inducing robust HA and NA immune responses and that the presence of the immunodominant HA from four different influenza strains does not appear to suppress or interfere with the anti-NA immune response.

High content imaging-based neutralization test (HINT) titers for HA and NAI titers were additionally measured from ferrets administered various multivalent LNP-influenza mRNA vaccines. The HINT assay is described in further detail in Jorquera et al. (Scientific Reports. 9: 2676. 2019), incorporated herein by reference. HINT titers were measured against influenza strains A/Michigan/45/2015, A/SINGAPORE/INFIMH160019/2016, B/IOWA/06/2017, and B/Phuket/3073/2013. NAI titers were measured against influenza strains A/Michigan/45/2015, A/SINGAPORE/INFIMH160019/2016, B/Colorado/06/201, and B/Phuket/3073/2013.

Ferrets used to assess multivalent vaccine immunogenicity were vaccinated twice 21 days apart with (1) a mixture of four mRNAs encoding NA antigens (N1, N2, BvNA, and ByNA), (2) a mixture of four mRNAs encoding HA antigens (H1, H3, BvHA, and ByHA), or (3) a mixture of four mRNAs encoding NA antigens (N1, N2, BvNA, and ByNA) and four mRNAs encoding HA antigens (H1, H3, BvHA, and ByHA), as shown below in Table 12. Each HA includes HA from one of the following four strains: A/Michigan/45/2015 (H1); A/Singapore/Infimh-16-0019/2016 (H3); B/Iowa/06/2017 (B/Victoria lineage); and B/Phuket/3073/2013 (B/Yamagata lineage). All antigens were administered at a 1:1 ratio.

An overview of each experimental group is recited below in Table 12.

All ferrets were bled under sedation (isoflurane) at baseline, one day before or just before booster, at booster vaccination, and two weeks after challenge as required. Sera samples (stored at −20° C. until required) were tested by ELLA to assess NAI activity. Additionally, the hemagglutinin inhibition assay (HAI) was undertaken to assess antibody responses to hemagglutinin antigens following multivalent vaccination.

TABLE 12

Overview of experimental groups for multivalent influenza vaccines in ferrets

| Group # | N | Prime (D 0)/boost (D 21) - NA | Prime (D 0)/boost (D 21) - HA | Dose (µg per strain) | Adjuvant |
|---|---|---|---|---|---|
| 1 | 6 | PBS | PBS | 0 | — |
| 11 | 6 | NA mRNA-LNP (N1, N2, BV, BY) | — | 1 | — |
| 12 | 6 | NA mRNA-LNP (N1, N2, BV, BY) | — | 15 | — |
| 13 | 6 | — | HA mRNA-LNP (H1, H3, BV, BY) | 1 | — |
| 14 | 6 | — | HA mRNA-LNP (H1, H3, BV, BY) | 15 | — |
| 15 | 6 | NA mRNA-LNP (N1, N2, BV, BY) | HA mRNA-LNP (H1, H3, BV, BY) | 1 | — |
| 16 | 6 | NA mRNA-LNP (N1, N2, BV, BY) | HA mRNA-LNP (H1, H3, BV, BY) | 15 | — |

An overview of the HINT results for each of the groups above is shown in FIG. 32. The octavalent mRNA-LNP formulations led to HINT titers comparable to the quadrivalent mRNA-LNP formulations.

An overview of the NAI titer results for each of the groups above is shown in FIG. 34 (day 20) and FIG. 35 (day 42). The octavalent mRNA-LNP formulations led to NAI titers comparable to the quadrivalent mRNA-LNP formulations. This was true from the day 20 and day 42 samples.

Example 11: Functional Antibody Titers to Influenza Heterologous Subtype Strains Recorded with mRNA in Lipid A or Lipid B LNP Formulations To evaluate immunogenicity of the mRNA-LNP in NHP, 0, 15, 45, µg of Sing16 HA-encoding mRNA encapsulated in either Lipid A or Lipid B LNP formulation (encoding for HA A/Singapore/INFIMH-16-0019/2016) were immunized. Naïve male and female Mauritius origin Cynomolgus macaques (*Macaca fascicularis*) were used. Animals weighed >2 kg and were >2 years of age at the start of the studies. Groups consisted of up to 6 animals per treatment group and were vaccinated in 0.5 mL of their respected vaccine dose or diluent via the IM route in one forelimb of each animal, targeting the deltoid, on Study Day 0. Twenty-eight days after the first immunization took place, a second immunization was given to the animals in the contralateral limb. A quadrivalent egg-derived inactivated influenza vaccine (IIV) containing the A/Singapore/INFIMH-16-0019/2016 (H3N2) strain was used as a comparator.

Influenza assays were performed using the A/Singapore/INFIMH-16-0019/2016 (H3N2) virus stocks from BIOQUAL, Inc. Additional breadth testing by HAI was performed using the following H3N1 virus stocks: A/Shandoglaicheng/1763/2016, A/Louisiana/13/2017, A/Kenya/105/2017, A/Victoria/746/2017, and A/Michigan/84/2016, A/Aksaray/4048/2016. These include strains from both 3c.2a and 3c.3a clades, as well as a very distant swine-like H3 sequence (A/Michigan/84/2016) based on bioinformatics analysis to select a set of maximally diverse H3N2 sequences from the same timeframe as A/Singapore/INFIMH-16-0019/2016.

For microneutralization (MN) assays, sera samples were diluted in receptor-destroying enzyme (Denka Seiken, 370013) and incubated overnight in a 37° C. water bath. Samples were heat-inactivated for 30-minutes at 56° C. then two-fold serial dilutions were run in duplicate in 96-well plates. An equal volume of virus at 100TCID$_{50}$ was added to the plates followed by a 1-hour incubation at 37° C. One-hundred microliters of sample/virus mixture was transferred to 96-well flat-bottom plates of MDCK cells (ATCC #CCL-34) containing TPCK-treated media and incubated for 48-hours at 37° C. with 5% $CO_2$. Plates were fixed with cold acetone then stained with biotin-conjugated anti-Influenza A NP (Millipore, MAB8258B) followed by incubation with DELFIA Europium-labeled streptavidin in Delfia assay buffer. Fluorescence was measured and endpoint titers reported.

At day 43, after the second immunization, NHPs vaccinated with Sing16HA-CL-059 and Sing16HA-CL017 developed neutralizing antibodies to homologous virus, A/Singapore/INFIMH-16-0019/2016 (H3N2), as noted in MN assay (FIG. 36 and FIG. 37). Further, in this model, MN titers were observed to hetero subtype viral panel including A/Shandoglaicheng/1763/2016, A/Louisiana/13/2017, A/Kenya/105/2017, A/Victoria/746/2017, and A/Aksaray/4048/2016 contrary to the IIV vaccine. The data indicates the said mRNA formulations have potential to provide greater breadth than IIV covering for hetero subtype strains of influenza.

The invention claimed is:

1. A pharmaceutical composition comprising a nucleic acid molecule encapsulated in a lipid nanoparticle (LNP), wherein the LNP comprises:
   a cationic lipid GL-HEPES-E3-E12-DS-4-E10 at a molar ratio between 35% and 45%,
   dimyristoyl-PEG2000 (DMG-PEG2000) at a molar ratio between 0.25% and 2.75%,
   cholesterol at a molar ratio between 20% and 35%, and
   1,2-dioleoyl-SN-glycero-3-phosphoethanolamine (DOPE) at a molar ratio of between 25% and 35%,
   wherein all the molar ratios are relative to the total lipid content of the LNP,
   wherein the nucleic acid molecule encodes an antigen derived from *Propionibacterium acnes*.

2. The composition of claim 1, wherein the LNP comprises:
   GL-HEPES-E3-E12-DS-4-E10 at a molar ratio of 40%,
   DMG-PEG2000 at a molar ratio of 1.5%,
   cholesterol at a molar ratio of 28.5%, and
   DOPE at a molar ratio of 30%.

3. The composition of claim 1, wherein the LNP has an average diameter of 30-200 nm.

4. The composition of claim 1, wherein the nucleic acid molecule(s) is an mRNA molecule comprising an open reading frame (ORF).

5. The composition of claim 4, wherein
   the LNP comprises two or more mRNA molecules, wherein each mRNA molecule encodes a different *Propionibacterium acnes* antigen.

6. The composition of claim 4, wherein
   the ORF is codon optimized.

7. The composition of claim 4, wherein the mRNA molecule comprises at least one 5' untranslated region (5' UTR), at least one 3' untranslated region (3' UTR), and at least one polyadenylation (poly(A)) sequence.

8. The composition of claim 4, wherein the mRNA comprises at least one chemical modification.

9. The composition of claim 4, wherein at least 20%, at least 30%, at least 40%, at least 50%, at least 60%, at least 70%, at least 80%, at least 85%, at least 90%, at least 95%, or 100% of the uracil nucleotides in the mRNA are chemically modified.

10. The composition of claim 8, wherein the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

11. The composition of claim 4, wherein the composition comprises two or more LNPs, wherein each LNP comprises an mRNA encoding a different *Propionibacterium acnes* antigen.

12. The composition of claim 1, wherein the composition is formulated for intramuscular injection.

13. The composition of claim 12, wherein the composition comprises a phosphate-buffer saline.

14. The composition of claim 12, wherein the composition comprises trehalose.

15. The composition of claim 14, wherein the trehalose is at 10% (w/v) of the composition.

16. A kit comprising a container comprising a single-use or multi-use dosage of the composition of claim 1.

17. The kit of claim 16, wherein the container is a vial or a pre-filled syringe or injector.

18. A method of preparing the composition of claim 1, comprising
   providing an aqueous buffered solution comprising the nucleic acid molecule,
   providing an amphiphilic solution comprising the cationic lipid, the PEGylated lipid, the cholesterol-based lipid, and the helper lipid, and
   mixing the aqueous buffered solution and the amphiphilic solution at a ratio of 5:1 to 3:1.

19. The method of claim 18, comprising mixing the aqueous buffered solution and the amphiphilic solution at a ratio of 4:1.

20. The method of claim 18, wherein the aqueous buffered solution is an acidic buffered solution.

21. The method of claim 20, wherein the aqueous buffered solution comprises 1 mM citrate and 150 mM sodium chloride with a pH of about 4.5.

22. The method of claim 18, wherein the amphiphilic solution is an ethanol solution.

23. A method of eliciting an immune response in a subject in need thereof, comprising administering to the subject a prophylactically effective amount of the composition of claim 1.

24. The method of claim 23 wherein the composition is administered intramuscularly, intranasally, intravenously, subcutaneously, or intradermally.

25. The method of claim 23, wherein the method comprises administering to the subject one or more doses of the composition, each dose comprising 1-250 µg of mRNA.

26. The method of claim 23, wherein the method comprises administering to the subject one or more doses of the composition, each dose comprising 2.5, 5, 15, 45, or 135 µg of mRNA.

27. The method of claim 23, wherein the method comprises administering to the subject two doses of the composition with an interval of 2-6 weeks.

28. The method of claim 23, wherein the method comprises administering to the subject two doses of the composition with an interval of 4 weeks.

29. A method of treating or preventing *Propionibacterium acnes* infections or reducing one or more symptoms of *Propionibacterium acnes* infections, comprising administering to the subject an effective amount of a pharmaceutical composition comprising a nucleic acid molecule encoding an antigen derived from *Propionibacterium acnes* encapsulated in a lipid nanoparticle (LNP), wherein the LNP comprises:
   a cationic lipid GL-HEPES-E3-E12-DS-4-E10 at a molar ratio between 35% and 45%,
   dimyristoyl-PEG2000 (DMG PEG2000) at a molar ratio between 0.25% and 2.75%,
   cholesterol at a molar ratio between 20% and 35%, and
   1,2-dioleoyl-SN-glycero-3-phosphoethanolamine (DOPE) at a molar ratio of between 25% and 35%,
   wherein all the molar ratios are relative to the total lipid content of the LNP.

30. The method of claim 29, wherein the composition is administered intramuscularly, intranasally, intravenously, subcutaneously, or intradermally.

31. The method of claim 29, wherein the LNP comprises:
GL-HEPES-E3-E12-DS-4-E10 at a molar ratio of 40%,
DMG-PEG2000 at a molar ratio of 1.5%,
cholesterol at a molar ratio of 28.5%, and
DOPE at a molar ratio of 30%.

32. The method of claim 29, wherein the LNP has an average diameter of 30-200 nm.

33. The method of claim 29, wherein the nucleic acid molecule(s) is an mRNA molecule comprising an open reading frame (ORF).

34. The method of claim 29, wherein
the LNP comprises two or more mRNA molecules, wherein each mRNA molecule encodes a different antigen.

35. The method of claim 33, wherein the ORF is codon optimized.

36. The method of claim 33, wherein the mRNA molecule comprises at least one 5' untranslated region (5' UTR), at least one 3' untranslated region (3' UTR), and at least one polyadenylation (poly(A)) sequence.

37. The method of claim 33, wherein the mRNA comprises at least one chemical modification.

38. The method of claim 37, wherein at least 20%, at least 30%, at least 40%, at least 50%, at least 60%, at least 70%, at least 80%, at least 85%, at least 90%, at least 95%, or 100% of the uracil nucleotides in the mRNA are chemically modified.

39. The method of claim 37, wherein the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

40. The method of claim 29, wherein the LNP has an average diameter of 80-150 nm.

41. The method of claim 29, wherein the composition comprises 1-10 mg/mL of the LNP.

42. The method of claim 29, wherein the composition comprises 1 mg/mL of the LNP.

43. The method of claim 29, wherein the LNP comprises 1-20 nucleic acid molecules.

44. The method of claim 29, wherein the LNP comprises 5-10 or 6-8 nucleic acid molecules.

45. The method of claim 29, wherein the composition comprises two or more LNPs, wherein each LNP comprises an mRNA encoding a different antigen.

* * * * *

SEQUENCE LISTING

```
Sequence total quantity: 26
SEQ ID NO: 1              moltype = AA  length = 566
FEATURE                   Location/Qualifiers
REGION                    1..566
                          note = source = /note="Description of Artificial Sequence:
                          Synthetic polypeptide"
source                    1..566
                          mol_type = protein
                          organism = synthetic construct
SEQUENCE: 1
MKTIIALSYI LCLVFAQKIP GNDNSTATLC LGHHAVPNGT IVKTITNDRI EVTNATELVQ   60
NSSIGEICDS PHQILDGENC TLIDALLGDP QCDGFQNKKW DLFVERSKAY SNCYPYDVPD  120
YASLRSLVAS SGTLEFKNES FNWTGVTQNG TSSACIRGSS SSFFSRLNWL THLNYTYPAL  180
NVTMPNKEQF DKLYIWGVHH PGTDKDQIFL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKHSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIESIRNE TYDHNVYRDE ALNNRFQIKG VELKSGYKDW ILWISFAISC  540
FLLCVALLGF IMWACQKGNI RCNICI                                      566

SEQ ID NO: 2              moltype = DNA  length = 1701
FEATURE                   Location/Qualifiers
misc_feature              1..1701
                          note = source = /note="Description of Artificial Sequence:
                          Synthetic polynucleotide"
source                    1..1701
                          mol_type = other DNA
                          organism = synthetic construct
SEQUENCE: 2
atgaaaacca taatcgcgct ctcatacata ctttgcctgg tctttgccca aaagatccct    60
ggcaacgaca actcaaccgc gacccttgc ctcggccatc acgccgtgcc gaacggcact   120
atcgtcaaga ccatcacaaa cgaccgcatc gaagtgacca acgcgactga gctagtgcag   180
aactccagca ttggagagat ttgcgattct ccacaccaaa tcctggacgg agagaattgt   240
accttgatcg acgcgctgct gggggatccg cagtgcgacg gattccagaa caagaaatgg   300
gacctttcg tggaacggag caaggcatac tcgaattgct accctacga tgtgcccgac   360
tacgcctcgc tgcggtcctt ggtcgcttcc tccgggaccc tggaattcaa aaacgagagc   420
tttaattgga ccggagtgac ccagaatggc acctcgagcg cctgcattcg gggctcctcc   480
tcgagcttct tcagccgcct gaactggctc actcacctca actacccta cccggcactg   540
aacgtgacca tgccgaacaa ggaacaattc gacaagctct catttgggg ggtgcatcac   600
ccgggtaccg ataaggacca gatcttcctc tacgcccaat cctcgggccg gatcaccgtg   660
tccactaagc gctcgcagca ggccgtgatc ccgaacattg gaagcagacc ccgcattcgc   720
gacattccat cgaggatctc gatctactgg acgattgtca agcctggcga catcctcctc   780
attaactcca ccgggaacct catcgcccct cggggttatt tcaagatccg cagcgggaag   840
tcctccatca tgagaagcga tgcccccatt ggaaagtgca agtccgagtg tatcacacct   900
aacggaagca ttcccaatga caagccattc cagaacgtga acagaattac ctacgagct   960
tgccctcgct acgtcaaaca ttcgaccctc aagttggcca ctggaatgcg caacgtgccg  1020
gagaagcaaa cccgggggat cttcggggct atcgcgggat tcatcgaaaa tggatgggaa  1080
ggaatggtcg atggttggta cggtttcaga caccagaact ccgaggggcg gggccaggcc  1140
gcagacctga agtccactca ggccgcgatt gaccagatca acggaaagct caacagactc  1200
attggaaaga ccaacgaaaa gttccaccaa atcgaaaagg aattctccga agtggaggc  1260
cgggtgcaag acctggagaa gtacgtggag gacactaaga tcgacctttg gagctataac  1320
```

```
gcagaactcc ttgtggccct ggaaaaccag cacaccatcg acctgaccga ttcagagatg   1380
aacaagctct tgagaaaac  taagaagcaa ctccgggaaa acgctgagga catgggaaat   1440
ggatgcttta agatctacca caagtgcgac aacgcctgca ttgagtccat acggaacgaa   1500
acttacgacc ataacgtcta ccgggatgaa gccctgaaca acagattcca gatcaagggc   1560
gtggagctga agtccggcta caaagattgg atcctgtgga tttccttcgc gatttcatgc   1620
ttcttgctct gcgtggccct cctgggattc ataatgtggg cctgtcagaa gggcaacatt   1680
aggtgcaaca tatgcatata a                                             1701

SEQ ID NO: 3          moltype = DNA  length = 1701
FEATURE               Location/Qualifiers
source                1..1701
                      mol_type = other DNA
                      organism = synthetic construct
SEQUENCE: 3
atgaagacta tcattgcttt gagctacatt ctatgtctgg ttttcgctca aaaaattcct   60
ggaaatgaca atagcacggc aacgctgtgc cttgggcacc atgcagtacc aaacggaacg   120
atagtgaaaa caatcacaaa tgaccgaatt gaagttacta atgctactga gttggttcag   180
aattcctcaa taggtgaaat atgcgacagt cctcatcaga tccttgatgg agagaactgc   240
acactaatag atgctctatt gggagacccc cagtgtgatg gctttcaaaa taagaaatgg   300
gacctttttg ttgaacgaag caaagcctac agcaactgtt acccttatga tgtgccggat   360
tatgcctccc ttaggtcact agttgcctca tccggcacac tggagtttaa aaatgaaagc   420
ttcaattgga ctggagtcac tcaaaacgga acaagttctg cttgcataag gggatctaaa   480
agtagtttct ttagtagatt aaattggttg acccacttaa actacacata tccagcattg   540
aacgtgacta tgccaaacaa ggaacaattt gacaaattgt acatttgggg ggttcaccac   600
ccgggtacga acaaggacca aatcttcctg tatgctcaat catcaggaag aatcacagta   660
tctaccaaaa gaagccaaca agctgtaatc ccaaatatcg gatctagacc cagaataagg   720
gatatcccta gcagaataag catctattgg acaatagtaa accgggagac atacttttg    780
attaacagca cagggaatct aattgctcct agggggttact tcaaaatacg aagtgggaaa   840
agctcaataa tgagatcaga tgcacccatt ggcaaatgca gtctgaatgc atcactcca    900
aatggaagca tttcccaatga caaaccattc caaaatgtaa acaggatcac atacggggcc   960
tgtcccagat atgttaagca tagcactctg aaattggcaa caggaatgcg aaatgtacca   1020
gagaaacaaa ctagaggcat atttggcgca atagcgggtt tcatagaaaa tggttgggag   1080
ggaatggtgg atggttggta cggtttcagg catcaaaatt ctgagggaag aggacaagca   1140
gcagatctca aaagcactca agcagcaatc gatcaaatca atgggaagct gaataggttg   1200
atcggaaaaa ccaacgagaa attccatcag attgaaaaag aattctcaga agtagaagga   1260
agagttcaag accttgagaa atatgttgag gacactaaaa tagatctctg gtcatacaac   1320
gcggagcttc ttgttgccct ggagaaccaa catacaattg atctaactga ctcagaaatg   1380
aacaaactgt ttgaaaaaac aaagaagcaa ctgagggaaa atgctgagga tatgggaaat   1440
ggttgtttca aaatataccac aaatgtgac aatgcctgca tagaatcaat aagaaatgaa   1500
acttatgacc acaatgtgta cagggatgaa gcattgaaca ccggttcca  gatcaaggga   1560
gttgagctga agtcaggata caaagattgg atcctatgga tttccttgc  catatcatgt   1620
tttttgcttt gtgttgcttt gttggggttc atcatgtggg cctgccaaaa gggcaacatt   1680
agatgcaaca tttgcatttg a                                             1701

SEQ ID NO: 4          moltype = AA  length = 469
FEATURE               Location/Qualifiers
REGION                1..469
                      note = source = /note="Description of Artificial Sequence:
                      Synthetic polypeptide"
source                1..469
                      mol_type = protein
                      organism = synthetic construct
SEQUENCE: 4
MNPNQKIITI GSVSLTISTI CFFMQIAILI TTVTLHFKQY EFNSPPNNQV MLCEPTIIER   60
NITEIVYLTN TTIEKEICPK LAEYRNWSKP QCDITGFAPF SKDNSIRLSA GGDIWVTREP   120
YVSCDPDKCY QFALGQGTTL NNVHSNNTVR DRTPYRTLLM NELGVPFHLG TKQVCIAWSS   180
SSCHDGKAWL HVCITGDDKN ATASFIYNGR LVDSVVSWSK EILRTQESEC VCINGTCTVV   240
MTDGSASGKA DTKILFIEEG KIVHTSTLSG SAQHVEECSC YPRYPGVRCV CRDNWKGSNR   300
PIVDINIKDH SIVSSYVCSG LVGDTPRKND SSSSSHCLDP NNEEGGHGVK GWAFDDGNDV   360
WMGRTISEKS RLGYETFKVI EGWSNPKSKL QINRQVIVDR GNRSGYSGIF SVEGKSCINR   420
CFYVELIRGR KEETEVLWTS NSIVVFCGTS GTYGTGSWPD GADINLMPI             469

SEQ ID NO: 5          moltype = AA  length = 469
FEATURE               Location/Qualifiers
REGION                1..469
                      note = source = /note="Description of Artificial Sequence:
                      Synthetic polypeptide"
source                1..469
                      mol_type = protein
                      organism = synthetic construct
SEQUENCE: 5
MNPNQKIITI GSICMTIGMA NLILQIGNII SIWVSHSIQI GNQSQIETCN QSVITYENNT   60
WVNQTYVNIS NTNFAAGQSV VSVKLAGNSS LCPVSGWAIY SKDNSVRIGS KGDVFVIREP   120
FISCSPLECR TFFLTQGALL NDKHSNGTIK DRSPYRTLMS CPIGEVPSPY NSRFESVAWS   180
ASACHDGINW LTIGISGPDS GAVAVLKYNG IITDTIKSWR NNILRTQESE CACVNGSCFT   240
IMTDGPSDGQ ASYKIFRIEK GKIIKSVEMK APNYHYEECS CYPDSSEITC VCRDNWHGSN   300
RPWVSFNQNL EYQMGYICSG VFGDNPRPND KTGSCGPVSS NGANGVKGFS FKYGNGVWIG   360
RTKSISSRKG FEMIWDPNGW TGTDNKFSIK QDIVGINEWS GYSGSFVQHP ELTGLDCIRP   420
CFWVELIRGR PEENTIWTSG SSISFCGVNS DTVGWSWPDG AELPFTIDK              469
```

```
SEQ ID NO: 6              moltype = AA   length = 566
FEATURE                   Location/Qualifiers
REGION                    1..566
                          note = source = /note="Description of Artificial Sequence:
                           Synthetic polypeptide"
source                    1..566
                          mol_type = protein
                          organism = synthetic construct
SEQUENCE: 6
MKTIIALSYI LCLVFAQKIP GNDNSTATLC LGHHAVPNGT IVKTITNDRI EVTNATELVQ   60
NSSIGEICDS PHQILDGENC TLIDALLGDP QCDGFQNKKW DLFVERSKAY SNCYPYDVPD  120
YASLRSLVAS SGTLEFKNES FNWTGVTQNG TSSACIRGSS SSFFSRLNWL THLNYTYPAL  180
NVTMPNKEQF DKLYIWGVHH PGTDKDQIFL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKHSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIESIRNE TYDHNVYRDE ALNNRFQIKG VELKSGYKDW ILWISFAISC  540
FLLCVALLGF IMWACQKGNI RCNICI                                      566

SEQ ID NO: 7              moltype = AA   length = 469
FEATURE                   Location/Qualifiers
REGION                    1..469
                          note = source = /note="Description of Artificial Sequence:
                           Synthetic polypeptide"
source                    1..469
                          mol_type = protein
                          organism = synthetic construct
SEQUENCE: 7
MNPNQKIITI GSVSLTISTI CFFMQIAILI TTVTLHFKQY EFNSPPNNQV MLCEPTIIER   60
NITEIVYLTN TTIEKEICPK PAEYRNWSKP QCGITGFAPF SKDNSIRLSA GGDIWVTREP  120
YVSCDPDKCY QFALGQGTTL NNVHSNNTVR DRTPYRTLLM NELGVPFHLG TKQVCIAWSS  180
SSCHDGKAWL HVCITGDDKN ATASFIYNGR LIDSVVSWSK DILRTQESEC VCINGTCTVV  240
MTDGNATGKA DTKILFIEEG KIVHTSKLSG SAQHVEECSC YPRYPGVRCV CRDNWKGSNR  300
PIVDINIKDH SIVSSYVCSG LVGDTPRKND SSSSSHCLNP NNEEGGHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GADLNLMHI              469

SEQ ID NO: 8              moltype = RNA   length = 1701
FEATURE                   Location/Qualifiers
misc_feature              1..1701
                          note = source = /note="Description of Artificial Sequence:
                           Synthetic polynucleotide"
source                    1..1701
                          mol_type = other RNA
                          organism = synthetic construct
SEQUENCE: 8
atgaaagcta tcctggtcgt cttgctgtat actttcgcca ctgccaacgc cgacaccctg    60
tgtatcggtt accacgcgaa caactccacc gacactgtgg acaccgtgct cgaaaagaac   120
gtgaccgtga ctcattctgt gaatctgctc gaggacaagc acaacggaaa gttgtgcaag   180
ctgcgcggag tggcaccgct gcaccttgga aagtgcaaca ttgccggatg gatcctggga   240
aacccggagt gcgaaagcct gagcaccgcg tcctcatggt cctacatcgt ggaaaccccg   300
tcctctgaca acggcacctg ttaccccggc gatttcatcg actacgaaga actgcgggag   360
cagctgtcct ccgtgtcctc gtttgaacgc ttcgagattt ccctaagac ctccagctgg   420
cctaatcacg atagcaacaa gggcgtgacg gcagcctgcc cgcacgccgg agcaaagtca   480
ttctacaaga atctgatttg gctcgtgaag aaagggaact catacccaa gctgtccaag   540
tcgtacatca acgacaaggg aaaggaagtg ctcgtgctct ggggggatcca ccacccatcc   600
acctccgccg accagcctga cctgtaccag aacgccgatg cttacgtgtt tgtgggttcc   660
agccggtact ccaagaagtt caagcctgaa atcgcgatca ggcctaaagt ccggaccgc    720
gagggccgca tgaactacta ctggactctc gtggagcctg agacaagat cacccttgag   780
gccaccggaa atccgtggt gccacgctac gctttcgcca tggaacgaa cgccggaagc   840
ggcatcatca ttagcgatac tcctgtgcat gactgtaaca ccacgtgcca gacacccaag   900
ggcgccatca acaccagcct gccgtttcaa aacatccatc ccattaccat tgggaagtga   960
cccaaatacg tcaagtccac caagctgagg ctggcgaccg gactgcgaa cattccgagc  1020
atccagtcga gaggcctgtt cggtgccatc gcgggattca tcgagggcgg ctggactgga  1080
atggtggacg gttggtacgg gtatcaccac caaaacgaac agggatcagg ctacgcggcc  1140
gatttgaagt ccacccagaa cgccattgat gaaatcacca acaaggtcaa ctccgtgatt  1200
gagaagatga atactcaatt caccgccgtg ggcaaagaat tcaatcacct ggagaagaa   1260
atagagaacc tgaacaagaa ggtcgacgac gggttcctcg acatctggac ctataacgcc  1320
gagttgctcg tgctgctgga aaacgaacgg accctggact atcacgactc gaacgtgaag  1380
aacctgtacg agaaagtccg ctcgcaactg aagaacaacg ccaaggaaat cggaaatggt  1440
tgcttcgagt tctaccataa gtgcgacaac acttgcatgg agtccgtgaa gaacggcact  1500
tacgattacc ccaagtactc cgaagaggct aaacttaccg gggaagagat cgatgaggtt  1560
aagctcgagt ccaccagaat ctaccagatt ctcgccatct actcgactgt ggcatcgagc  1620
ctcgtccttg tcgtgtccct gggggccatt tcattctgga tgtgctccaa cgggtccctg  1680
cagtgccgga tttgcatcta a                                           1701

SEQ ID NO: 9              moltype = RNA   length = 1410
```

```
FEATURE          Location/Qualifiers
misc_feature     1..1410
                 note = source = /note="Description of Artificial Sequence:
                 Synthetic polynucleotide"
source           1..1410
                 mol_type = other RNA
                 organism = synthetic construct
SEQUENCE: 9
atgaacccaa accagaaaat catcacgatt ggctcgattt gcatgaccat tggaatggcg    60
aaccttatcc tccaaattgg caacattatc tcgatctggg tcagccactc gatccagatc   120
ggcaaccaat cccagattga aacttgcaac cagagcgtga ttacttacga aaacaacacg   180
tgggtgaacc agacttacgt caatattagc aacactaact cgccgctgg gcagagcgtc    240
gtcagcgtga agctcgccgg aaattcctcg ctctgccccg tgtccggctg ggcgatctac   300
agcaaggata acagcgtccg gattggtagc aagggcgacg ttttcgtgat ccgcgaacct   360
ttcatatcat gctccccgct cgaatgtcgc acgttcttcc tgacccaagg cgccctgctg   420
aacgacaagc actccaatgg cactatcaag gatcggagcc cttaccggac cttgatgtcc   480
tgccctattg gagaagtgcc ttcaccatat aactcgcgct ttgaaagcgt ggcttggtca   540
gcctccgcct gccatgacgg gattaactgg ctgaccattg gcataagcgg ccccgattcc   600
ggcgccgtgg ccgtcctgaa gtacaacggg atcatcaccg acaccattaa gtcctggcgc   660
aacaacatcc tgaggaccca ggagtccgag tgcgcgtgcg tgaacgggtc ctgctttacc   720
atcatgaccg acggaccgtc cgacggtcaa gcctcgtaca agatcttccg gatcgagaaa   780
ggaaagatca tcaagagcgt ggagatgaag gccccgaact accactacga ggaatgttca   840
tgctatcccg actcgtccga gattacttgc gtgtgccgcg acaattggca cggatccaac   900
aggccgtggg tcagcttcaa ccagaaccct gaataccaga tgggatacat ttgcagcgga   960
gtgttcgggg acaaccctcg cccgaacgac aagaccggat cgtgtgggcc cgtgtcctcc  1020
aacggcgcaa acggcgtcaa gggattttcc ttcaaatacg gacacggggt ctggatcgga  1080
cggaccaaga gcatttcaag cagaaaggga ttcgagatga tttgggaccc gaacggctgg  1140
actggtaccg ataacaaatt cagcatcaag caggacatcg tggaattaa cgagtggtcc   1200
ggttactccg gagcttcgt gcagcatccc gaactcactg gactgactg cattcggccg    1260
tgcttttggg tggaattgat ccggggcaga cctgaggaga acacgatttg gacctccggc   1320
tcctcgatct cgttctgcgg agtgaactcc gacaccgtgg gatggtcctg gcccgacggt   1380
gcagagctgc ccttcaccat tgataagtaa                                    1410

SEQ ID NO: 10    moltype = RNA  length = 1701
FEATURE          Location/Qualifiers
misc_feature     1..1701
                 note = source = /note="Description of Artificial Sequence:
                 Synthetic polynucleotide"
source           1..1701
                 mol_type = other RNA
                 organism = synthetic construct
SEQUENCE: 10
atgaaaacca taatcgcgct ctcatacata ctttgcctgg tctttgccca aaagatccct    60
ggcaacgaca actcaaccgc gacccttttgc ctcggccatc acgccgtgcc gaacggcact   120
atcgtcaaga ccatcacaaa cgaccgcatc gaagtgacca acgcgactga gctagtgcag   180
aactccagca ttgagagat tgcgattct ccacaccaaa tcctgacgg agagaattgt       240
accttgatcg acgcgctgct gggggatccg cagtgcgacg gattccagaa caagaaatgg   300
gacctttttcg tggaacggag caaggcatac tcgaattgct accccctacga tgtgcccgac  360
tacgcctcgc tgccggtcctt ggtcgcttcc tccgggaccc tggaattcaa aaacgagagc   420
tttaattgga ccggagtgac ccagaatggc acctcgagcg cctgcattcg gggctcctcc   480
tcgagcttct tcagccgcct gaactggctc actcacctca actacaccta cccggcactg   540
aacgtgacca tgccgaacaa ggaacaattc gacaagctct acatttgggg ggtgcatcac   600
ccgggtaccg ataaggacca gatcttcctc tacgcccaat cctcgggccg gatcaccgtg   660
tccactaagc gctcgcagca ggccgtgatc ccgaacattg gaagcagacc ccgcattcgc   720
gacattccat cgaggatctc gatctactgg acgattgtca agcctggcga catcctcctc   780
attaactcca ccgggaacct catcgccctc cggggttatt tcaagatccg cagcgggaag   840
tcctccatca tgagaagcga tgcccccatt ggaaagtgca agtccgagtg tatcacacct   900
aacggaagca ttcccaatga caagccattc agaacgtga acagaattac ctacggagct    960
tgccctcgct acgtcaaaca ttcgacccctc aagttggcga ctggaatgcg caacgtgccg  1020
gagaagcaaa cccggggat cttcgggct atcgcggat tcatcgaaaa tggatgggaa     1080
ggaatggtcg atggttggta cggtttcaga caccagaact ccgaggggcg gggccaggcc  1140
gcagacctga gtccactca ggccgcgatt gaccagatca acggaaagct caacagactc   1200
attggaaaga ccaacgaaaa gttccaccaa atcgaaaagg aattctcga agtggaggc    1260
cgggtcgaag acctggagaa gtacgtggag gacactaaga tcgaccttg gagctataac  1320
gcagaactcc ttgtgccct ggaaaaccag cacaccatcg acctgaccga ttcagagatg   1380
aacaagctct tgagaaaac taagaagcaa ctccgggaaa acgctgagga catgggaaat   1440
ggatgcttta gatctacca caagtgcgac aacgcctgca ttgagtccat acggaacgaa  1500
acttacgacc ataacgtcta ccgggatgaa gccctgaaca acagattcca gatcaagggc   1560
gtggagtga agtccggcta caaagattgg atcctgtgga tttccttcgc gatttcatgc   1620
ttcttgctct gcgttggccct cctgggattc ataatgtggg cctgtcagaa gggcaacatt  1680
aggtgcaaca tatgcatata a                                             1701

SEQ ID NO: 11    moltype = RNA  length = 1410
FEATURE          Location/Qualifiers
misc_feature     1..1410
                 note = source = /note="Description of Artificial Sequence:
                 Synthetic polynucleotide"
source           1..1410
                 mol_type = other RNA
```

```
                        organism = synthetic construct
SEQUENCE: 11
atgaaccctaa accagaagat catcacaatt ggaagcgtgt ccctgaccat ttcgacgatt   60
tgcttcttca tgcaaatcgc gatcttgatt accaccgtca cctgcattt caagcaatac   120
gaattcaact ccccgccaaa caaccaagtc atgctctgcg agccaccat catcgaacgc   180
aacatcaccg agatcgtgta ccttaccaac actaccatcg aaaggagat ttgcccaag   240
ttggccgaat accggaactg gagcaagccc cagtgtgaca tcacgggatt tgcgccattc   300
agcaggata actcgatcag actttccgcc gggggcgaca tttgggtcac tcgggagcct   360
tacgtgagct gcgacccgga caagtgctac caattcgcac tcggacaggg taccaccctg   420
aacaacgtcc atagcaacaa caccgtgcgc gatagaaccc cgtaccgcac cctcctcatg   480
aacgaactgg gagtgccgtt ccacttggga accaaacaag tctgcattgc atggtcctcc   540
tcctcctgcc acgacggcaa agcctggctt cacgtttgca tcaccggcga cgacaagaat   600
gcgacggcct ccttcatata caatggtaga ctcgtggata gcgtggtgtc atggtccaag   660
gaaattctca ggactcagga gtcagagtgc gtgtgcataa acgggacttg cactgtcgtg   720
atgaccgacg gatcggcctc cggaaaggcc gacactaaga tcctcttcat cgaggaggga   780
aagatcgtgc acacttctac cctgagcggc tcggctcagc atgtcgaaga gtgctcgtgc   840
taccccggt atcccggggt ccgctgcgtg tgccgggaca attggaaagg ctcaaaccgc   900
cccatcgga acattaacat caaggaccac tccatcgtga gctcctacgt atgcagcgag   960
ctggtcgggg ataccccgcg gaagaacgat tcctcgtcct cctcccactg cctggaccct  1020
aacaacgaag agggaggcca cggagtgaag ggatgggctt ttgacgatgg caacgacgtg  1080
tggatgggca ggactatttc cgaaaagtcc cggctgggat acgaaccttt caaggtcatc  1140
gagggcctggt ccaacccgaa gtcaaagctc cagatcgcat cgtggatagg  1200
ggcaatagat ccggctactc cgggatcttc agcgtggaag ggaagtcctg cattaaccga  1260
tgcttctacg tggaactcat tcgggtcgg aaggaggaaa ccgaagtgct gtggacttcg  1320
aactcaatcg tggtgttttg tgggacctcc ggaacttacg gaactgggtc ctggcctgac  1380
ggtgccgaca tcaaccttat gccgatctaa                                  1410

SEQ ID NO: 12              moltype = RNA  length = 1701
FEATURE                    Location/Qualifiers
misc_feature               1..1701
                           note = source = /note="Description of Artificial Sequence:
                           Synthetic polynucleotide"
source                     1..1701
                           mol_type = other RNA
                           organism = synthetic construct
SEQUENCE: 12
atgaaagcca tccttgttgt catgctgtac acattcacca ccgcaaatgc ggataccctg    60
tgtatcggct accacgcaaa taattccacc gacaccgttg ataccgtcct ggaaaagaac   120
gtgacagtga ctcacagcgt caatctcctt gaggataaac ataatggcaa gctgtgcaag   180
ctgagaggcg tggctcccct gcatctggga aagtgcaaca tcgctggttg gatcctcggg   240
aacccagagt gtgagtccct ctcaaccgca cggtcttggt catacatcgt ggagactagc   300
aattcagaca acggcacatg ctaccccggt gacttcatta actacgagga gctgagagaa   360
cagctgagtt ccgtgtcatc cttcgagaga ttcgaaatct tccccaaaac ctcctcctgg   420
cccaatcatg actccgacaa tggagtgaca gccgcttgtc cccacgccgg tgccaagagt   480
ttctataaga acctcatctg gctggtgaaa aagggcaagt cctatcccaa aattaaccag   540
acctacatta acgataaggg gaagaagtc ctggtcctgt gggggataca ccaccccct    600
accatcgccg accagcagtc tctgtatcag aacgccgacg cctacgtgtt cgtgggtacc   660
agccgttata gtaaaaagtt caagccagaa attgccacca gacctaaggt gcgcgaccag   720
gagggccgca tgaactacta ctggaccctg gtgaacctgc gcgacaagat tacattcgag   780
gccactggga acctggtggc acccagatac gcctttaaca tggaacggga tgctgggagc   840
ggaatcatta tctccgatac ccctgtccac gactgcaata ctacctgtca gaccccagaa   900
ggcgctatca atacctctct gccttttcaa aacgtgcacc ctatcactat cgggaaatgt   960
cccaagtatg tgaaaagcac caaactcgcg ctggcaaccg gtctgagaaa tgtgcctcc   1020
atccagtccc gcgggcttgtt cggtgcaatc gctggctttta tcgagggtgg ctggactgga  1080
atggtcgatg gctggtacgg ctaccatcac cagaacgagc aggggtccgg gtatgctgcc  1140
gacctgaaaa gcactcagaa cgccatcgat aaaatcacta acaaggtgaa ctccgtgatc  1200
gaaaagatga acacacagtt cacagcagtt ggcaaggagt tcaaccaccl ggaaaaacgg  1260
atagagaacc tgaataagaa agtcgatgat ggctttctgg acatctggac ttacaatgcc  1320
gagctgctgg tgctcctgga aaacgagcgg acactggatt atcacgactc aaacgtgaag  1380
aacctgtatg aaaaggtgcg taaccagctg aaaaacaacg ccaaggaaat cggcaatggc  1440
tgtttcgaat tttaccacaa gtgtgataat acctgtatgg agagcgttaa gaacgggact  1500
tacgactacc caaatacag cgaggaggcc aagctgaacc gggagaagat cgacggcgtc  1560
aaactcgact ccactagaat ataccagatt ctcgccatct atagcacagt ggcatcaagt  1620
ctcgtcctgg tggtgtcact gggagccatc agcttttgga tgtgcagcaa tggatccctc  1680
cagtgtagga tctgcatcta a                                            1701

SEQ ID NO: 13              moltype = RNA  length = 1701
FEATURE                    Location/Qualifiers
misc_feature               1..1701
                           note = source = /note="Description of Artificial Sequence:
                           Synthetic polynucleotide"
source                     1..1701
                           mol_type = other RNA
                           organism = synthetic construct
SEQUENCE: 13
atgaagacca tcatcgctct gtcctacatc ctgtgcctgg tgtttgctca gaaaatcccc    60
gggaatgaca attccactgc cactctctgc ctgggccatc atgccgtgcc aaatggaacc   120
attgtcaaga ctataacaaa tgaccgcatc gaagtgacca cgctaccga gctggttcag   180
aacagcagta ttgagaaaat ctgcgattcc ccacaccaga tactggatgg cggcaactgc   240
```

```
accctgatcg acgcactgct gggtgaccct cagtgcgacg gatttcagaa taaggagtgg   300
gaccttttcg ttgagcgcag cagagccaat agcaactgct acccgtacga cgtgccggat   360
tacgccagtc ttcgaagcct ggtcgcatcc agcgggacac tggagtttaa gaatgagtcc   420
tttaattgga caggcgtgaa gcagaacggg actagcagcg catgcattcg gggcagtagc   480
tcatccttct ttagccgact gaactggctg acccacctca actacacata ccccgcactg   540
aatgtgacta tgccaaacaa agaacagttt gacaaactgt acatctgggg agtgcaccat   600
cctagcacag acaaggacca gatcagcctg tttgcccagc ccagcggcag gattaccgtg   660
tccacaaaac ggtcacagca agccgtgatc cctaatattg atcccgccc ccggataagg   720
gacatcccta gtcgcatcag tatctactgg accatcgtga agcccggaga tatcttgctc   780
atcaatagca ctggcaacct cattgccccc aggggctatt ttaagatcag aagcggcaag   840
tccagcatta tgcgcagcga cgcacccatt ggcaagtgca agtccgagtg catcactcct   900
aatgggtcca tcccaaacga caagccattc caaaatgtca acagaatcac ctacgggct   960
tgcccccgct acgtgaagca gagtacactg aaactggcca ccgggatgcg caacgtgccc  1020
gagaagcaaa ctagaggcat ctttggagct atcgctcgct tcattgagaa tggctgggag  1080
ggtatggtgg acggctggta cggattccgc caccagaata gcgaaggcag aggccaggca  1140
gcagacttga agtccaccca ggccgccatt gatcagatca acgcaaact gaatcggctt  1200
attggaaaaa caaacgagaa gttccatcag attgagaagg agtttagcga ggtggagggc  1260
cgcgtgcagg atctgaaaa gtacgttgaa gacaccaaga tcgacctgtg gtcatacaat  1320
gcagagctgc tcgttgccct ggaaaatcag cacacaattg accttacaga ctcccgaaatg  1380
aataagctct ttgaaaagac caagaagcag ctgcgcgaga acgccgagga tatgggaaac  1440
ggttgtttta agatctacca caagtgtgac aacgcctgca ttgggtccat ccgaaatgaa  1500
acatacgacc caacgtgta tagagatgag gccctgaaca accgattcca gattaaggga  1560
gtcgagctga agagtggcta taaggactgg atcctgtgga tctcattcgc catgtcatgc  1620
ttccttctgt gtattgctct gctcggcttc atcatgtggg cttgccagaa aggcaatatc  1680
cggtgcaaca tctgcatcta a                                             1701

SEQ ID NO: 14          moltype = RNA   length = 1749
FEATURE                Location/Qualifiers
misc_feature           1..1749
                       note = source = /note="Description of Artificial Sequence:
                       Synthetic polynucleotide"
source                 1..1749
                       mol_type = other RNA
                       organism = synthetic construct
SEQUENCE: 14
atgaaagcaa tcatagtgct gctgatggtg gtgactagca atgccgatcg gatctgcacc   60
ggcatcactt ccagtaacag ccctcatgtg gtcaaaaccg ccacacaggg cgaggtgaac  120
gtgaccggag tgattccact gacaactaca ccaacgaaga gtcacttcgc caacctgaag  180
ggcaccgaaa cacgaggcaa gctctgcccc aagtgtctga attgcaccga cctggacgtc  240
gctttgggcc gccctaaatg taccggcaaa atacctccg ccagagtgtc catcctgcac  300
gaggtgcgcc ccgtgacctc cgggtgtttt cccataatgc acgaccgcac taaaatccgc  360
cagctgccca atcttctgag ggggtacgaa catgtcaggc tgtccactca caacgtgatc  420
aacgcagaag acgcccccgg aaggccttat gagattgaa cagtgggtc ctgcccaaac  480
attaccaacg gcaacggctt cttcgccact atggcctggg ccgtgccaaa gaacaagacc  540
gccaccaacc cctgacaat tgaagtccct tacatctgca cagagggaga ggatcagatc  600
accgtgtggg ggtttcactc tgataacgaa actcagatgg ccaagctgta cggggattct  660
aaacccagaa agttcaccag tagcgctaac ggggtgaaca cccattatgt gtctcagatc  720
ggaggtttcc caaatcagac cgaggacggc ggactgcccc agtctggaag gatcgtagtg  780
gactatatgg tgcagaagag tggaaaaacc ggcaccatta cctatcagcg cggcatactg  840
ctgccacaga aggtgtggtg tgcttccggc aggtccaagg ttatcaaagg gtccctccc   900
ctgatcggcg aagcagattg tctgcacgag aagtacgacg gactgaataa gagcaaaccc   960
tactacaccg gagaacacgc taaggcaatt gggaattgtc cgatctgggt gaagacgccc  1020
ctgaaactgg ccaatggcac aaaatacgg ccccccgcta agctgctgaa ggaacggggg  1080
ttcttcggcg ccatagccgg ctttctggag ggaggctggg agggcatgat agccgggtgg  1140
cacggctaca cttcccatgg ggctcacggg gtggctggcg ccgccgacct gaagtctacg  1200
caggaagcta tcaacaaaat cactaagaac ctgaacagcc tgtcggaatt ggaggtcaag  1260
aatctgcagc ggctgagcgg cgccatggat gagctgcaca atgagatcct ggagcttgac  1320
gagaaggtcg atgatcttcg ggccgataca attagtagcc aaattgagtt ggccgtgctg  1380
ctcagcaacg aaggcataat caacgacgag gacgagcacc tcctggctct ggagagaaag  1440
ctgaagaaga tgctcggccc tagcgcagtt gagatcggaa acggctgctt cgaaaccaag  1500
cacaagtgca accagacctg cctggacagg atcgcggcag gaacattcga cgctggggaa  1560
ttcagcctcc ccaccttcga cagcctgaac atcacagccg ccagtctgaa tgatgacgga  1620
ctggataacc ataccatcct gctgtactac tctaccgctg cttcctccct ggccgtgaca  1680
ttgatgatcg caatctttgt ggttatatg gtgagccgag caacgtcag ttgcagtatc  1740
tgcctttaa                                                          1749

SEQ ID NO: 15          moltype = RNA   length = 1755
FEATURE                Location/Qualifiers
misc_feature           1..1755
                       note = source = /note="Description of Artificial Sequence:
                       Synthetic polynucleotide"
source                 1..1755
                       mol_type = other RNA
                       organism = synthetic construct
SEQUENCE: 15
atgaaagcca tcattgtgct gctgatggtg gttacaagca acgccgaccg catctgcacc   60
gggattacaa gcagcaatag ccctcacgtg gtgaagacag caacacaggg agaggtgaac  120
gtgaccggcg tgattccact gacaaccacc ccaactaaat cttactttgc aaaccctgaa  180
gggacacgga ccagaggaaa gctgtgccct gattgcctga attgcacaga cctggacgtg  240
```

-continued

```
gccctgggca gaccaatgtg cgtgggcact acaccaagcg ccaaggcctc catcctccat   300
gaggtgcggc ccgtgacttc tggatgtttc cccattatgc acgacagaac caagattaga   360
cagctgccaa acctgctccg cggctacgag aaaattcgcc tgtctacaca gaatgtgatc   420
gacgccgaga aggctccagg aggaccatac agactgggga cttctggcag ctgccctaac   480
gccacctcta agatcgggtt cttcgcaacc atggcttggg ccgtgcctaa agacaattac   540
aagaatgcca ccaatccact gactgtcgag gtgccatata tttgcacaga ggggaggac    600
cagatcactg tgtggggctt tcatagcgat aataagactc agatgaagtc tctctacggc   660
gactctaacc ctcagaagtt cacctcctct gccaacgggg tgacaacaca ctacgtgtcc   720
cagatcgggg actttcctga ccagaccgag gatggaggac tgcctcagtc tggacgcatc   780
gtggtggact atatgatgca gaagcctggg aagaccggca ctatcgtgta ccagaggggc   840
gtgctgctgc cccaaaaggt gtggtgtgcc tccggaagaa gcaaagtgat taagggatcc   900
ctgcctctga ttggggaggc cgattgcctg catgaagagt atggagggct gaacaagtcc   960
aagccatact atacaggaaa gcacgcaaaa gccatcggca actgtcccat ctgggtcaaa  1020
actcctctga agctggccaa cggcaccaaa taccgccctc cagccaagct gctgaaagaa  1080
cgcggattct tcggcgccat tgcagggttt ctggaaggag gctgggaggg catgattgct  1140
ggatggcacg gatataccte tcacggcgct cacggggtgg ccgtggccgc cgatctgaag  1200
tccacacagg aggcaattaa caagatcacc aagaatctga attcactgtc cgagctcgaa  1260
gtgaaaaacc tgcagcgcct gtccggcgcc atggacgagc tgcacaatga aatcctgaag  1320
ctggacgaga aggtggacga cctgcgggct gacactatca gcagccagat cgagctggca  1380
gtgctgctga gcaatgaggg catcatcaac tcagaagacg aacacctcct ggcactggaa  1440
aggaaactca agaagatgct gggccccctc gcagtgagtga ttgggaacgg ctgttttcgaa  1500
accaagcata agtgtaacca gacttgtctg gataggatcg cagcaggaac cttcaacgcc  1560
ggcgaattt ctctgccaac atttgactcc ctgaacatca cagctgcatc cctgaacgac  1620
gacggactgg acaatcacac catcctgctg tactactcta ctgccgctag ctccctggcc  1680
gtgaccctga tgctggccat cttcatcgtg tacatggttt ccagggataa cgtgtcttgt  1740
agcatttgcc tgtaa                                                   1755

SEQ ID NO: 16          moltype = AA   length = 534
FEATURE                Location/Qualifiers
REGION                 1..534
                       note = source = /note="Description of Artificial Sequence:
                       Synthetic polypeptide"
source                 1..534
                       mol_type = protein
                       organism = synthetic construct
SEQUENCE: 16
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMGSG NVGLGGAIAS GVAVSKVLHL   120
EGEVNKIKSA LLSTNKAVVS LSNGVSVLTF KVLDLKNYID KQLLPILNKQ SCSISNPETV   180
IEFQQKNNRL LEITREFSVN AGVTTPVSTY MLTNSELLSL INDMPITNDQ KKLMSNNVQI   240
VRQQSYSIMS IIKEEVLAYV VQLPLYGVID TPCWKLHTSP LCTTNTKNGS NICLTRTDRG   300
WYCDNAGNVS FFPQAETCKV QSNRVFCDTM NSRTLPSEVN LCNVDIFNPK YDCKIMTSKT   360
DVSSSVITSL GAIVSCYGKT KCTASNKNRG IIKTFSNGCD YVSNKGVDTV SVGNTLYYVN   420
KQEGKSLYVK GEPIINFYDP LVFPSDEFDA SISQVNELIN QSLAFINQSD ELLHNVNAGK   480
STTNIMITTI IIVIIVILLS LIAVGLLLYC KARSTPVTLS KDQLSGINNI AFSN         534

SEQ ID NO: 17          moltype = RNA   length = 1605
FEATURE                Location/Qualifiers
misc_feature           1..1605
                       note = source = /note="Description of Artificial Sequence:
                       Synthetic polynucleotide"
source                 1..1605
                       mol_type = other RNA
                       organism = synthetic construct
SEQUENCE: 17
atggaactgc tgatcctcaa agccaacgca atcaccacca ttctcaccgc tgtgaccttc    60
tgcttcgcat cggggcagaa catcactgaa gagttttacc agagcacttg cagcgcggtg   120
tcaaagggtt acctttccgc actgcggacc ggatggtaca cttccgtgat caccattgag   180
ctcagcaaca tcaaggaaaa caagtgcaat ggcaccgacg ccaaggtgaa gctgatcaaa   240
caagaactgg acaagtacaa gaacgccgtg acagaattgc agctcctgat gggatccgga   300
aacgtcggtc tgggcggagc catcgcgagt ggagtggctg tgtccaaggt cttgcacctc   360
gagggagaag tgaacaagat caagtccgcg ctgctgtcaa cgaacaaggc cgtggtgtcc   420
ctgtctaacg gcgtcagcgt gctgacgttc aaggtcctgg acctgaagaa ttacattgac   480
aagcagctgc tgcccatcct caacaagcaa tcctgctcca tctccaacc cgaaaccgtg   540
atcgagttcc agcagaagaa caaccgcctg ctggaaatta tcgcgagtt ctctgtgaat   600
gccggcgtga ccacccctgt gtccacctac atgctgacca actcgagct tctctccctt   660
atcaatgaca tgcctatcac gaacgaccag aagaagctga tgtcgaacaa cgtgcagatt   720
gtgcggcagc agtcatacag catcatgtcg atcatcaagg aagaagtgct ggcgtacgtg   780
gtgcaactcc cgctgtacgg cgtcatcgat accccgtgct ggaagctgca cacctcgcct   840
ttgtgtacca ccaacaccaa gaacggatcc aacatctgct taacccgac tgatcgggt    900
tggtactgcg acaacgccgg gaatgtttcg ttcttcccac aagccgagac ttgtaaagtg   960
cagtcaaaca gagtgttctg tgacaccatg aactcgagaa ccctgcccag cgaagtgaac  1020
ctgtgtaacg tcgacatctt taaccccaaa tacgattgca agattatgac cagcaaaacc  1080
gacgtgtcct cctccgtgat aacaagcctg ggggcgattg tgtcatgcta cggaaagact  1140
aagtgcaccg cctcgaacaa gaaccgcggc atcattaaga cttctctgaa tggttgcgac  1200
tatgtgtcca acaagggcgt ggatactgtg tcagtcggga atactcttta ctacgtgaac  1260
aagcaggagg ggaaaagcct ctacgtgaag ggagagccta ttatcaactt ttacgatccg  1320
ctggtgttcc cgtccgacga attcgacgcc agcatcagcc aagtcaacga gctgattaac  1380
cagtccctcg ccttcatcaa ccaatccgac gagctcctgc ataacgtgaa cgccggaaag  1440
```

```
tccaccacca acatcatgat cactactatt atcatcgtga tcatcgtcat cctgctgagc    1500
ctgattgctg tgggcctgtt gctgtattgc aaagccaggt ccaccccggt caccctgtcg    1560
aaggatcagc tgtccggaat caacaacatt gccttctcca actaa                    1605

SEQ ID NO: 18           moltype = DNA  length = 1605
FEATURE                 Location/Qualifiers
misc_feature            1..1605
                        note = source = /note="Description of Artificial Sequence:
                        Synthetic polynucleotide"
source                  1..1605
                        mol_type = other DNA
                        organism = synthetic construct
SEQUENCE: 18
atggaactgc tgatcctcaa agccaacgca atcaccacca ttctcaccgc tgtgaccttc      60
tgcttcgcat cggggcagaa catcactgaa gagttttacc agagcacttg cagcgcggtg     120
tcaaaggggtt accttcccgc actgcggacc ggatggtaca cttccgtgat caccattgag    180
ctcagcaaca tcaaggaaaa caagtgcaat ggcaccgacg ccaaggtcaa gctgatcaaa     240
caagaactgc acaagtacaa gaacgccgtg acagaattgc agctcctgat gggatccgga    300
aacgtcggtc tgggcggagc catcgcgagt ggagtggctg tgtccaaggt cttgcacctc    360
gagggagaag tgaacaagat caagtccgcg ctgctgtcaa cgaacaaggc cgtggtgtcc    420
ctgtctaacg gcgtcagcgt gctgacgttc aaggtcctgg acctgaagaa ttacattgac    480
aagcagctgc tgcccatcct caacaagcaa tcctgctcca tctccaaccc cgaaaccgtg    540
atcgagttcc agcagaagaa caaccgcctg ctggaaatta ctcgcgagtt ctctgtgaat    600
gccggcgtga ccacccctgt gtccacctac atgctgacca actccgagct tctctcccctt   660
atcaatgaca tgcctatcac gaacgaccag aagaagctga tgtcgaacaa cgtgcagatt    720
gtgcggcagc agtcatacag catcatgtcg atcatcaagg aagaagtgct gcgtacgtg     780
gtgcaactcc cgctgtacgg cgtcatcgat acccccgtgct ggaagctgca cacctcgcct   840
ttgtgtacca ccaacaccaa gaacggatcc aacatctgct taacccggac tgatcggggt   900
tggtactgcg acaacgccgg gaatgtttcg ttcttcccac aagccgagac ttgtaaagtg    960
cagtcaaaca gagtgttctg tgacaccatg aactcgaaa ccctgcccag cgaagtgaac   1020
ctgtctaacg tcgacatctt taacccaaaa tacgattgca agattatgac cagcaaaacc   1080
gacgtgtcct cctccgtgat aacaagcctg ggggcgattg tgtcatgcta cggaaagact   1140
aagtgcaccg cctcgaacaa gaaccgcggc atcattaaga ctttctcgaa tggttgcgac   1200
tatgtgtcca acaagggcgt ggatactgtg tcagtcggga atactcttta ctacgtgaac   1260
aagcaggagg ggaaaagcct ctacgtgaag ggagagccta ttatcaactt ttacgatccg   1320
ctggtgttcc cgtccgacga attcgacgcc agcatcagcc aagtcaacga gctgattaac   1380
cagtccctcg ccttcatcaa ccaatccgac gagctcctgc ataacgtgaa cgccggaaag   1440
tccaccacca acatcatgat cactactatt atcatcgtga tcatcgtcat cctgctgagc   1500
ctgattgctg tgggcctgtt gctgtattgc aaagccaggt ccaccccggt caccctgtcg   1560
aaggatcagc tgtccggaat caacaacatt gccttctcca actaa                   1605

SEQ ID NO: 19           moltype = RNA  length = 140
FEATURE                 Location/Qualifiers
misc_feature            1..140
                        note = source = /note="Description of Artificial Sequence:
                        Synthetic polynucleotide"
source                  1..140
                        mol_type = other RNA
                        organism = synthetic construct
SEQUENCE: 19
ggacagatcg cctggagacg ccatccacgc tgttttgacc tccatagaag acaccgggac      60
cgatccagcc tccgcggccg ggaacggtgc attggaacgc ggattccccg tgccaagagt    120
gactcaccgt ccttgacacg                                                140

SEQ ID NO: 20           moltype = RNA  length = 100
FEATURE                 Location/Qualifiers
misc_feature            1..100
                        note = source = /note="Description of Artificial Sequence:
                        Synthetic polynucleotide"
source                  1..100
                        mol_type = other RNA
                        organism = synthetic construct
SEQUENCE: 20
cgggtggcat ccctgtgacc cctccccagt gcctctcctg gccctggaag ttgccactcc      60
agtgcccacc agccttgtcc taataaaatt aagttgcatc                          100

SEQ ID NO: 21           moltype = RNA  length = 1845
FEATURE                 Location/Qualifiers
misc_feature            1..1845
                        note = source = /note="Description of Artificial Sequence:
                        Synthetic polynucleotide"
source                  1..1845
                        mol_type = other RNA
                        organism = synthetic construct
SEQUENCE: 21
ggacagatcg cctggagacg ccatccacgc tgttttgacc tccatagaag acaccgggac      60
cgatccagcc tccgcggccg ggaacggtgc attggaacgc ggattccccg tgccaagagt    120
gactcaccgt ccttgacacg atggaactgc tgatcctcaa agccaacgca atcaccacca    180
ttctcaccgc tgtgaccttc tgcttcgcat cggggcagaa catcactgaa gagttttacc    240
```

```
agagcacttg cagcgcggtg tcaaagggtt acctttccgc actgcggacc ggatggtaca    300
cttccgtgat caccattgag ctcagcaaca tcaaggaaaa caagtgcaat ggcaccgacg    360
ccaaggtcaa gctgatcaaa caagaactgg acaagtacaa gaacgccgtg acagaattgc    420
agctcctgat gggatccgga aacgtcggtc tgggcggagc catcgcgagt ggagtggctg    480
tgtccaaggt cttgcacctc gagggagaag tgaacaagat caagtccgcg ctgctgtcaa    540
cgaacaaggc cgtggtgtcc ctgtctaacg gcgtcagcgt gctgacgttc aaggtcctga    600
acctgaagaa ttacattgac aagcagctgc tgcccatcct caacaagcaa tcctgctcca    660
tctccaaccc cgaaaccgtg atcgagttcc agcagaagaa caaccgcctg ctggaaatta    720
ctcgcgagtt ctctgtgaat gccggcgtga ccacccctgt gtccacctac atgctgacca    780
actccgagct tctctcccct atcaatgaca tgcctatcga gaacgaccag aagaagctga    840
tgtcgaacaa cgtgcagatt gtgcggcagc agtcatacag catcatgtcg atcatcaagg    900
aagaagtgct ggcgtacgtg gtgcaactcc cgctgtacgg cgtcatcgat ccccgtgct   960
ggaagctgca cacctcgcct ttgtgtacca ccaacaccaa gaacggatcc aacatctgct   1020
taacccggac tgatcggggt tggtactgcg acaacgccgg gaatgtttcg ttcttcccac   1080
aagccgagac ttgtaaagtg cagtcaaaca gagtgttctg tgacaccatg aactcgagaa   1140
ccctgcccag cgaagtgaac ctgtgtaacg tcgacatctt taacccaaaa tacgattgca   1200
agattatgac cagcaaaacc gacgtgtcct cctccgtgat aacaagcctg ggggcgattg   1260
tgtcatgcta cggaaagact aagtgcaccg cctcgaacaa gaaccgcggc atcattaaga   1320
ctttctcgaa tggttgcgac tatgtgtcca acaagggcgt ggatactgtg tcagtcggga   1380
atactctta ctacgtgaac aagcaggagg ggaaaagcct ctacgtgaag ggagagccta   1440
ttatcaactt ttacgatccg ctggtgttcc cgtccgacga attcgacgcc agcatcagcc   1500
aagtcaacga gctgattaac cagtccctcg ccttcatcaa ccaatccgag gagctcctgc   1560
ataacgtgaa cgccggaaag tccaccacca catcatgat cactactatt atcatcgtga   1620
tcatcgtcat cctgctgagc ctgattgctg tgggccgtgtt gctgtattgc aaagccaggt   1680
ccaccccggt caccctgtcg aaggatcagc tgtccggaat caacaacatt gccttctcca   1740
actaacgggt ggcatccctg tgaccccctcc ccagtgcctc tcctggccct ggaagttgcc   1800
actccagtgc ccaccagcct tgtcctaata aaattaagtt gcatc                   1845

SEQ ID NO: 22           moltype = RNA   length = 11
FEATURE                 Location/Qualifiers
misc_feature            1..11
                        note = source = /note="Description of Artificial Sequence:
                        Synthetic oligonucleotide"
source                  1..11
                        mol_type = other RNA
                        organism = synthetic construct
SEQUENCE: 22
gggatcctac c                                                          11

SEQ ID NO: 23           moltype = RNA   length = 110
FEATURE                 Location/Qualifiers
misc_feature            1..110
                        note = source = /note="Description of Artificial Sequence:
                        Synthetic polynucleotide"
source                  1..110
                        mol_type = other RNA
                        organism = synthetic construct
SEQUENCE: 23
aaaaaaaaaa aaaaaaaaaa aaaaaaaaaa gcatatgact aaaaaaaaaa aaaaaaaaaa     60
aaaaaaaaaa aaaaaaaaaa aaaaaaaaaa aaaaaaaaaa aaaaaaaaaa               110

SEQ ID NO: 24           moltype = AA    length = 566
FEATURE                 Location/Qualifiers
REGION                  1..566
                        note = source = /note="Description of Artificial Sequence:
                        Synthetic polypeptide"
source                  1..566
                        mol_type = protein
                        organism = synthetic construct
SEQUENCE: 24
MKAILVVLLY TFATANADTL CIGYHANNST DTVDTVLEKN VTVTHSVNLL EDKHNGKLCK     60
LRGVAPLHLG KCNIAGWILG NPECESLSTA SSWSYIVETP SSDNGTCYPG DFIDYEELRE    120
QLSSVSSFER FEIFPKTSSW PNHDSNKGVT AACPHAGAKS FYKNLIWLVK KGNSYPKLSK    180
SYINDKGKEV LVLWGIHHPS TSADQQSLYQ NADAYVFVGS SRYSKKFKPE IAIRPKVRDR    240
EGRMNYYWTL VEPGDKITFE ATGNLVVPRY AFAMERNAGS GIIISDTPVH DCNTTCQTPK    300
GAINTSLPFQ NIHPITIGKC PKYVKSTKLR LATGLRNIPS IQSRGLFGAI AGFIEGGWTG    360
MVDGWYGYHH QNEQGSGYAA DLKSTQNAID EITNKVNSVI EKMNTQFTAV GKEFNHLEKR    420
IENLNKKVDD GFLDIWTYNA ELLVLLENER TLDYHDSNVK NLYEKVRSQL KNNAKEIGNG    480
CFEFYHKCDN TCMESVKNGT YDYPKYSEEA KLNREEIDGV KLESTRIYQI LAIYSTVASS    540
LVLVVSLGAI SFWMCSNGSL QCRICI                                         566

SEQ ID NO: 25           moltype = DNA   length = 1701
FEATURE                 Location/Qualifiers
misc_feature            1..1701
                        note = source = /note="Description of Artificial Sequence:
                        Synthetic polynucleotide"
source                  1..1701
                        mol_type = other DNA
                        organism = synthetic construct
```

```
SEQUENCE: 25
atgaaaacca taatcgcgct ctcatacata ctttgcctgg tctttgccca aaagatccct    60
ggcaacgaca actcaaccgc gacccttgc ctcggccatc acgccgtgcc gaacggcact    120
atcgtcaaga ccatcacaaa cgaccgcatc gaagtgacca acgcgactga gctagtgcag   180
aactccagca ttggagagat ttgcgattct ccacaccaaa tcctggacgg agagaattgt   240
accttgatcg acgcgctgct gggggatccg cagtgcgacg gattccagaa caagaaatgg   300
gaccttttcg tggaacggag caaggcatac tcgaattgct accccctacga tgtgcccgac   360
tacgcctcgc tgcggtcctt ggtcgcttcc tccgggaccc tggaattcaa aaacgagagc   420
tttaattgga ccggagtgac ccagaatggc acctcgagcg cctgcattcg gggctcctcc   480
tcgagcttct tcagccgcct gaactggctc actcacctca actacaccta cccggcactg   540
aacgtgacca tgccgaacaa ggaacaattc gacaagctct catttgggg ggtgcatcac   600
ccgggtaccg ataaggacca gatcttcctc tacgcccaat cctcgggccg gatcaccgtg   660
tccactaagc gctcgcagca ggccgtgatc ccgaacattg gaagcagacc ccgcattcgc   720
gacattccat cgaggatctc gatctactgg acgattgtca agcctggcga catcctcctc   780
attaactcca ccgggaacct catcgcccct cggggttatt tcaagatccg cagcgggaag   840
tcctccatca tgagaagcga tgcccccatt ggaaagtgca agtccgagtg tatcacacct   900
aacggaagca ttcccaatga caagccattc cagaacgtga acagaattac ctacggagct   960
tgccctcgct acgtcaaaca ttcgaccctc aagttggcga ctggaatgcg caacgtgccg  1020
gagaagcaaa cccgggggat cttcggggct atcgcgggat tcatcgaaaa tggatgggaa  1080
ggaatggtcg atggttggta cggtttcaga caccagaact ccgaggggcg gggccaggcc  1140
gcagacctga agtccactca ggccgcgatt gaccagatca acggaaagct caacagactc  1200
attggaaaga ccaacgaaaa gttccaccaa atcgaaaagg aattctccga agtggagggc  1260
cgggtgcaag acctggagaa gtacgtggag gacactaaga tcgacctttg gagctataac  1320
gcagaactcc ttgtggccct ggaaaaccag cacaccatcg acctgaccga ttcagagatg  1380
aacaagctct tgagaaaaac taagaagcaa ctccgggaaa acgctgagga catgggaaat  1440
ggatgcttta agatctacca caagtgcgac aacgcctgca ttgagtccat acggaacgaa  1500
acttacgacc ataacgtcta ccgggatgaa gccctgaaca acagattcca gatcaagggc  1560
gtggagctga agtccggcta caaagattgg atcctgtgga tttccttcgc gatttcatgc  1620
ttcttgctct gcgtggccct cctgggattc ataatgtggg cctgtcagaa gggcaacatt  1680
aggtgcaaca tatgcatata a                                              1701

SEQ ID NO: 26          moltype = RNA   length = 1941
FEATURE                Location/Qualifiers
misc_feature           1..1941
                       note = source = /note="Description of Artificial Sequence:
                       Synthetic polynucleotide"
source                 1..1941
                       mol_type = other RNA
                       organism = synthetic construct
SEQUENCE: 26
ggacagatcg cctggagacg ccatccacgc tgttttgacc tccatagaag acaccgggac    60
cgatccagcc tccgcggccg ggaacggtgc attggaacgc ggattccccg tgccaagagt   120
gactcaccgt ccttgacacg atgaaaacca taatcgcgct ctcatacata ctttgcctgg   180
tctttgccca aaagatccct ggcaacgaca actcaaccgc gacccttgc ctcggccatc    240
acgccgtgcc gaacgcact atcgtcaaga ccatcacaaa cgaccgcatc gaagtgacca   300
acgcgactga gctagtgcag aactccagca ttggagagat ttgcgattct ccacaccaaa   360
tcctggacgg agagaattgt accttgatcg acgcgctgct gggggatccg cagtgcgacg   420
gattccagaa caagaaatgg gaccttttcg tggaacggag caaggcatac tcgaattgct   480
accccctacga tgtgcccgac tacgcctcgc tgcggtcctt ggtcgcttcc tccgggaccc   540
tggaattcaa aaacgagagc tttaattgga ccggagtgac ccagaatggc acctcgagcg   600
cctgcattcg gggctcctcc tcgagcttct tcagccgcct gaactggctc actcacctca   660
actacaccta cccggcactg aacgtgacca tgccgaacaa ggaacaattc gacaagctct   720
catttgggg ggtgcatcac ccgggtaccg ataaggacca gatcttcctc tacgcccaat   780
cctcgggccg gatcaccgtg tccactaagc gctcgcagca ggccgtgatc ccgaacattg   840
gaagcagacc ccgcattcgc gacattccat cgaggatctc gatctactgg acgattgtca   900
agcctggcga catcctcctc attaactcca ccgggaacct catcgcccct cggggttatt   960
tcaagatccg cagcgggaag tcctccatca tgagaagcga tgcccccatt ggaaagtgca  1020
agtccgagtg tatcacacct aacggaagca ttcccaatga caagccattc cagaacgtga  1080
acagaattac ctacggagct tgccctcgct acgtcaaaca ttcgaccctc aagttggcga  1140
ctggaatgcg caacgtgccg gagaagcaaa cccgggggat cttcggggct atcgcgggat  1200
tcatcgaaaa tggatgggaa ggaatggtcg atggttggta cggtttcaga caccagaact  1260
ccgaggggcg gggccaggcc gcagacctga agtccactca ggccgcgatt gaccagatca  1320
acggaaagct caacagactc attggaaaga ccaacgaaaa gttccaccaa atcgaaaagg  1380
aattctccga agtggagggc cgggtgcaag acctggagaa gtacgtggag gacactaaga  1440
tcgacctttg gagctataac gcagaactcc ttgtggccct ggaaaaccag cacaccatcg  1500
acctgaccga ttcagagatg aacaagctct tgagaaaaac taagaagcaa ctccgggaaa  1560
acgctgagga catgggaaat ggatgcttta agatctacca caagtgcgac aacgcctgca  1620
ttgagtccat acggaacgaa acttacgacc ataacgtcta ccgggatgaa gccctgaaca  1680
acagattcca gatcaagggc gtggagctga agtccggcta caaagattgg atcctgtgga  1740
tttccttcgc gatttcatgc ttcttgctct gcgtggccct cctgggattc ataatgtggg  1800
cctgtcagaa gggcaacatt aggtgcaaca tatgcatata acgggtggca tccctgtgac  1860
ccctcccag tgcctctcct ggccctgaa gttgccactc cagtgccac cagccttgtc   1920
ctaataaaat taagttgcat c                                             1941
```